United States Patent
Hahn et al.

(10) Patent No.: US 7,202,073 B2
(45) Date of Patent: Apr. 10, 2007

(54) HUMAN ANALOGS OF MURINE DEUBIQUITINATING PROTEASES

(75) Inventors: Chang Hahn, Princeton, NJ (US); Hong Liu, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 339 days.

(21) Appl. No.: 10/371,905

(22) Filed: Feb. 20, 2003

(65) Prior Publication Data

US 2003/0224969 A1 Dec. 4, 2003

Related U.S. Application Data

(60) Provisional application No. 60/358,873, filed on Feb. 22, 2002, provisional application No. 60/358,875, filed on Feb. 22, 2002, provisional application No. 60/363,020, filed on Mar. 8, 2002.

(30) Foreign Application Priority Data

Apr. 12, 2002 (GB) ................................. 0208404.4

(51) Int. Cl.
*C12N 9/64* (2006.01)
(52) U.S. Cl. .................................... 435/226
(58) Field of Classification Search ............... None
See application file for complete search history.

(56) References Cited

OTHER PUBLICATIONS

Burrows et al, DUB-3, a cytokine-inducible deubiquitinating enzyme that blocks proliferation. J Biol Chem. Apr. 2, 2004;279(14):13993-4000.*

UniProt_03 database Accession No. Q6R6M4 Jul. 5, 2004 Burrows et al. Alignment with Seq ID No. 2.*

Baek Kwang-Hyun et al., *DUB-2*A, a New Member of the *DUB* Subfamily of Hematopoietic Deubiquitinating Enzymes, Blood, Aug. 1, 2001, vol. 98, No. 3, pp. 636-642.

Jaster Robert et al., *JAK2* Is Required for Induction of the Murine *DUB-1* Gene, Molecular and Cellular Biology, Jun. 1997, pp. 3364-3372.

Migone Thi-Sau et al., The Deubiquitinating Enzyme *DUB-2* Prolongs Cytokine-induced Signal Transducers and Activators of Transcription Activation and Suppresses Apoptosis Following Cytokine Withdrawal, Blood, Sep. 15, 2001, vol. 98, No. 6.

Jaster Robert et al., Analysis of *cis*-acting sequences and *trans*-acting factors regulating the interleukin-3 response element of the *DUB-1* gene, Biochimica et Biophysica Acta vol. 1446, 1999, pp. 308-316.

Zhu Yuan et al., *DUB-1*, a Deubiquitinating Enzyme with Growth-suppressing Activity, Proc. Natl. Acad. Sci. USA, vol. 93, pp. 3275-3279, Apr. 1996.

Zhu Yuan et al., *DUB-2* is a Member of a Novel Family of Cytokine-inducible Deubiquitinating Enzymes, The Journal of Biological Chemistry, Journal of Biological Chemistry, vol. 272, No. 1, Jan. 3, 1997, pp. 51-57.

Zhu Yuan et al., The Murine *DUB-1* Gene is Specifically Induced by the Bc Subunit of he Interleukin-3 Receptor, Molecular and Cellular Biology, Sep. 1996, pp. 4808-4817.

Heinemeyer T. et al., Expanding the TRANSFAC database towards an expert system of regulatory molecular mechanisms, Nucleic Acids Research, vol. 27, No. 1, 1999, pp. 318-322.

* cited by examiner

*Primary Examiner*—Sheridan Swope
(74) *Attorney, Agent, or Firm*—Xuhong Sunny Wang

(57) ABSTRACT

The present invention is directed to human analogs of murine hematopoetic-specific, cytokine-inducible deubiquinating proteases ("DUBs") clustered on chromosomes 4 and 8 and their respective regulatory regions. The nucleotides or proteins encoded thereby my be used in assays to identify inhibitors of human DUBs.

1 Claim, 1 Drawing Sheet

HUMAN ANALOGS OF MURINE DEUBIQUITINATING PROTEASES

BACKGROUND OF THE INVENTION

The role of ubiquitin in protein degradation was discovered and the main enzymatic reactions of this system elucidated in biochemical studies in a cell-free system from reticulocytes. In this system, proteins are targeted for degradation by covalent ligation to ubiquitin, a 76-amino-acid-residue protein. Briefly, ubiquitin-protein ligation requires the sequential action of three enzymes. The C-terminal Gly residue of ubiquitin is activated in an ATP-requiring step by a specific activating enzyme, E1 (Step 1). This step consists of an intermediate formation of ubiquitin adenylate, with the release of $PP_i$, followed by the binding of ubiquitin to a Cys residue of E1 in a thiolester linkage, with the release of AMP. Activated ubiquitin is next transferred to an active site Cys residue of a ubiquitin-carrier protein, E2 (Step 2). In the third step catalyzed by a ubiquitin-protein ligase or E3 enzyme, ubiquitin is linked by its C-terminus in an amide isopeptide linkage to an -amino group of the substrate protein's Lys residues (Step 3).

Proteins ligated to polyubiquitin chains are usually degraded by the 26S proteasome complex that requires ATP hydrolysis for its action. The 26S proteasome is formed by an ATP-dependent assembly of a 20S proteasome, a complex that contains the protease catalytic sites, with 19S "cap" or regulatory complexes. The 19S complexes contain several ATPase subunits and other subunits that are presumably involved in the specific action of the 26S proteasome on ubiquitinylated proteins. The roles of ATP in the assembly of the 26S proteasome complex and in its proteolytic action are not understood. The action of the 26S proteasome presumably generates several types of products: free peptides, short peptides still linked to ubiquitin via their Lys residues, and polyubiquitin chains (Step 4). The latter two products are converted to free and reusable ubiquitin by the action of ubiquitin-C-terminal hydrolases or isopeptidases (Steps 5 and 6). Some isopeptidases may also disassemble certain ubiquitin-protein conjugates (Step 7) and thus prevent their proteolysis by the 26S proteasome. The latter type of isopeptidase action may have a correction function to salvage incorrectly ubiquitinylated proteins or may have a regulatory role. Short peptides formed by the above processes can be further degraded to free amino acids by cytosolic peptidases (Step 8).

Ubiquitin-mediated degradation of protein is involved in various biological processes. The selective and programmed degradation of cell-cycle regulatory proteins, such as cyclins, inhibitors of cyclin-dependent kinases, and anaphase inhibitors are essential events in cell-cycle progression. Cell growth and proliferation are further controlled by ubiquitin-mediated degradation of tumor suppressors, protooncogenes, and components of signal transduction systems. The rapid degradation of numerous transcriptional regulators is involved in a variety of signal transduction processes and responses to environmental cues. The ubiquitin system is clearly involved in endocytosis and down-regulation of receptors and transporters, as well as in the degradation of resident or abnormal proteins in the endoplasmic reticulum. There are strong indications for roles of the ubiquitin system in development and apoptosis, although the target proteins involved in these cases have not been identified. Dysfunction in several ubiquitin-mediated processes causes pathological conditions, including malignant transformation.

Our knowledge of different signals in proteins that mark them for ubiquitinylation is also limited. Recent reports indicate that many proteins are targeted for degradation by phosphorylation. It was observed previously that many rapidly degraded proteins contain PEST elements, regions enriched in Pro, Glu, Ser, and Thr residues. More recently, it was pointed out that PEST elements are rich in S/TP sequences, which are minimum consensus phosphorylation sites for Cdks and some other protein kinases. Indeed, it now appears that in several (though certainly not all) instances, PEST elements contain phosphorylation sites necessary for degradation. Thus multiple phosphorylations within PEST elements are required for the ubiquitinylation and degradation of the yeast G1 cyclins Cln3 and Cln2, as well as the Gcn4 transcriptional activator. Other proteins, such as the mammalian G1 regulators cyclin E and cyclin D1, are targeted for ubiquitinylation by phosphorylation at specific, single sites. In the case of the IkBα inhibitor of the NF-kB transcriptional regulator, phosphorylation at two specific sites, Ser-32 and Ser-36, is required for ubiquitin ligation. β-cateinin, which is targeted for ubiquitin-mediated degradation by phosphorylation, has a sequence motif similar to that of IkBα around these phosphorylation sites. However, the homology in phosphorylation patterns of these two proteins is not complete, because phosphorylation of other sites of β-catenin is also required for its degradation. Other proteins targeted for degradation by phosphorylation include the Cdk inhibitor Sic1p and the STAT1 transcription factor. Though different patterns of phosphorylation target different proteins for degradation, a common feature appears to be that the initial regulatory event is carried out by a protein kinase, while the role of a ubiquitin ligase would be to recognize the phosphorylated form of the protein substrate. It further appears that different ubiquitin ligases recognize different phosphorylation patterns as well as additional motifs in the various protein substrates. However, the identity of such E3s is unknown, except for some PULC-type ubiquitin ligases that act on some phosphorylated cell-cycle regulators in the budding yeast. The multiplicity of signals that target proteins for ubiquitin-mediated degradation (and of ligases that have to recognize such signals) is underscored by observations that the phosphorylation of some proteins actually prevents their degradation. Thus the phosphorylation of the c-Mos protooncogene on Ser3 and the multiple phosphorylations of c-Fos and c-Jun protooncogenes at multiple sites by MAP kinases suppress their ubiquitinylation and degradation.

In addition to the families of enzymes involved in conjugation of ubiquitin, a very large family of deubiquitinating enzymes has recently been identified from various organisms. These enzymes have several possible functions. First, they may have peptidase activity and cleave the products of ubiquitin genes. Ubiquitin is encoded by two distinct classes of genes. One is a polyubiquitin gene, which encodes a linear polymer of ubiquitins linked through peptide bonds between the C-terminal Gly and N-terminal Met of contiguous ubiquitin molecules. Each copy of ubiquitin must be released by precise cleavage of the peptide bond between Gly-76-Met-1 of successive ubiquitin moieties. The other class of ubiquitin genes encodes ubiquitin C-terminal extension proteins, which are peptide bond fusions between the C-terminal Gly of ubiquitin and N-terminal Met of the extension protein. To date, the extensions described are ribosomal proteins consisting of 52 or 76–80 amino acids. These ubiquitin fusion proteins are processed to yield ubiquitin and the corresponding C-terminal extension proteins. Second, deubiquitinating enzymes may have isopeptidase activities. When a target protein is degraded, deubiquitinating enzymes can cleave the polyubiquitin chain from the target protein or its remnants. The polyubiquitin chain must also be disassembled by deubiquitinating enzymes during or after proteolysis by the 26 S proteasome, regenerating free monomeric ubiquitin. In this way, deubiquitinating enzymes can facilitate the ability of the 26 S proteasome to degrade ubiquitinated proteins. Third, deubiquitinating enzymes may hydrolyze ester, thiolester, and amide linkages to the carboxyl group of Gly-76 of ubiquitin. Such nonfunctional linkages may arise from reactions between small intracellular compounds such as glutathione and the E1-, E2-, or E3-ubiquitin thiolester intermediates. Fourth, deubiquitinating enzymes may compete with the conjugating system by removing ubiquitin from protein substrates, thereby rescuing them from degradation or any other function mediated by ubiquitination. Thus generation of ubiquitin by deubiquitinating enzymes from the linear polyubiquitin and ubiquitin fusion proteins and from the branched polyubiquitin ligated to proteins should be essential for maintaining a sufficient pool of free ubiquitin. Many deubiquitinating enzymes exist, suggesting that these deubiquitinating enzymes recognize distinct substrates and are therefore involved in specific cellular processes. Although there is recent evidence to support such specificity of these deubiquitinating enzymes, the structure-function relationships of these enzymes remain poorly studied.

Deubiquitinating enzymes can be divided broadly on the basis of sequence homology into two classes, the ubiquitin-specific processing protease (UBP or USP, also known as type 2 ubiquitin C-terminal hydrolase (type 2 UCH)) and the UCH, also known as type 1 UCH). UCH (type 1 UCH) enzymes hydrolyze primarily C-terminal esters and amides of ubiquitin but may also cleave ubiquitin gene products and disassemble polyubiquitin chains. They have in common a 210-amino acid catalytic domain, with four highly conserved blocks of sequences that identify these enzymes. They contain two very conserved motifs, the CYS and HIS boxes. Mutagenesis studies revealed that the two boxes play important roles in catalysis. Some UCH enzymes have significant C-terminal extensions. The functions of the C-terminal extensions are still unknown but appear to be involved in proper localization of the enzyme. The active site of these UCH enzymes contains a catalytic triad consisting of cysteine, histidine, and aspartate and utilizes a chemical mechanism similar to that of papain. The crystal structure of one of these, UCH-L3, has been solved at 1.8 Å resolution. The enzyme comprises a central antiparallel β-sheet flanked on both sides by helices. The β-sheet and one of the helices are similar to those observed in the thiol protease cathepsin B. The similarity includes the three amino acid residues that comprise the active site, $Cys^{95}$, $His^{169}$, and $Asp^{184}$. The active site appears to fit the binding of ubiquitin that may anchor also at an additional site. The catalytic site in the free enzyme is masked by two different segments of the molecule that limit nonspecific hydrolysis and must undergo conformational rearrangement after substrate binding.

UBP (type 2 UCH) enzymes are capable of cleaving the ubiquitin gene products and disassembling polyubiquitin chains after hydrolysis. It appears that there is a core region of about 450 amino acids delimited by CYS and HIS boxes. Many of these isoforms have N-terminal extensions and a few have C-terminal extensions. In addition, there are variable sequences in the core region of many of the isoforms. The functions of these divergent sequences remain poorly characterized. Another interesting function of specific UBPs is the regulation of cell proliferation. It was observed that cytokines induced in T-cells specific deubiquitinating enzymes (DUBs), termed DUB-1 and DUB-2 DUB-1 is induced by stimulation of the cytokine receptors for IL-3, IL-5, and GM-CSF, suggesting a role in its induction for the β-common (betac) subunit of the interleukin receptors. Overexpression of a dominant negative mutant of JAK2 inhibits cytokine induction of DUB-1, suggesting that the regulation of the enzyme is part of the cell response to the JAK/STAT signal transduction pathway. Continued expression of DUB-1 arrests cells at $G_1$; therefore, the enzyme appears to regulate cellular growth via control of the $G_0$–$G_1$ transition. The catalytic conserved Cys residue of the enzyme is required for its activity. DUB-2 is induced by IL-2 as an immediate early (IE) gene that is down-regulated shortly after the initiation of stimulation. The function of this enzyme is also obscure. It may stimulate or inhibit the degradation of a critical cell-cycle regulator.

Cytokines, such as interleukin-2 (IL-2), activate intracellular signaling pathways via rapid tyrosine phosphorylation of their receptors, resulting in the activation of many genes involved in cell growth and survival. The deubiquitinating enzyme DUB-2 is induced in response to IL-2 and is expressed in human T-cell lymphotropic virus-I (HTLV-1)-transformed T cells that exhibit constitutive activation of the IL-2 JAK/STAT (signal transducers and activators of transcription) pathway, and when expressed in Ba/F3 cells DUB-2 markedly prolonged IL-2-induced STAT5 phosphorylation. Although DUB-2 does not enhance IL-2-mediated proliferation, when withdrawn from growth factor, cells expressing DUB-2 had sustained STAT5 phosphorylation and enhanced expression of IL-2-induced genes cis and c-myc. DUB-2 expression markedly inhibited apoptosis induced by cytokine withdrawal allowing cells to survive. Therefore, DUB-2 has a role in enhancing signaling through the JAK/STAT pathway, prolonging lymphocyte survival, and, when constitutively expressed, may contribute to the activation of the JAK/STAT pathway observed in some transformed cells. (Migone, T.-S., et al., *Blood.* 2001;98: 1935–1941).

Protein ubiquitination is an important regulator of cytokine-activated signal transduction pathways and hematopoietic cell growth. Protein ubiquitination is controlled by the coordinate action of ubiquitin-conjugating enzymes and deubiquitinating enzymes. Recently a novel family of genes encoding growth-regulatory deubiquitinating enzymes (DUB-1 and DUB-2) has been identified. DUBs are immediate-early genes and are induced rapidly and transiently in response to cytokine stimuli. By means of polymerase chain reaction amplification with degenerate primers for the DUB-2 complementary DNA, 3 murine bacterial artificial chromosome (BAC) clones that contain DUB gene sequences were isolated. One BAC contained a novel DUB gene (DUB-2A) with extensive homology to DUB-2. Like DUB-1 and DUB-2, the DUB-2A gene consists of 2 exons. The predicted DUB-2A protein is highly related to other DUBs throughout the primary amino acid sequence, with a hypervariable region at its C-terminus. In vitro, DUB-2A had functional deubiquitinating activity; mutation of its conserved amino acid residues abolished this activity. The 5' flanking sequence of the DUB-2A gene has a hematopoietic-specific functional enhancer sequence. It is proposed that there are at least 3 members of the DUB subfamily (DUB-1, DUB-2, and DUB-2A) and that different hematopoietic cytokines induce specific DUB genes, thereby initiating a cytokine-specific growth response. (Baek , K.-H., et al, *Blood.* 2001;98:636–642).

Protein ubiquitination also serves regulatory functions in the cell that do not involve proteasome-mediated degradation. For example, Hicke and Riezman have recently demonstrated ligand-inducible ubiquitination of the Ste2 receptor in yeast. Ubiquitination of the Ste2 receptor triggers receptor endocytosis and receptor targeting to vacuoles, not proteasomes. Also, Chen et al. have demonstrated that activation of the IB kinase requires a rapid, inducible ubiquitination event. This ubiquitination event is a prerequisite for the specific phosphorylation of IB and does not result in subsequent proteolysis of the kinase complex. The ubiquitination of Ste2 and IB kinase appears reversible, perhaps resulting from the action of a specific deubiquitinating enzyme.

A large superfamily of genes encoding deubiquitinating enzymes, or UBPs, has recently been identified. UBPs are ubiquitin-specific thiol-proteases that cleave either linear ubiquitin precursor proteins or post-translationally modified proteins containing isopeptide ubiquitin conjugates. The large number of UBPs suggests that protein ubiquitination, like protein phosphorylation, is a highly reversible process that is regulated in the cell.

Interestingly, UBPs vary greatly in length and structural complexity, suggesting functional diversity. While there is little amino acid sequence similarity throughout their coding region, sequence comparison reveals two conserved domains. The Cys domain contains a cysteine residue that serves as the active enzymatic nucleophile. The His domain contains a histidine residue that contributes to the enzyme's active site. More recent evidence demonstrates six homology domains contained by all members of the ubp superfamily. Mutagenesis of conserved residues in the Cys and His domains has identified several residues that are essential for UBP activity.

Recently, a growth regulatory deubiquitinating enzyme, DUB-1, that is rapidly induced in response to cytokine receptor stimulation was identified. DUB-1 is specifically induced by the receptors for IL-3, granulocyte macrophage-colony-stimulating factor, and IL-5, suggesting a specific role for the c subunit shared by these receptors. In the process of cloning the DUB-1 gene, a family of related, cross-hybridizing DUB genes was identified. From this, other DUB genes might be induced by different growth factors. Using this approach, an IL-2-inducible DUB enzyme, DUB-2 and closely related DUB-2a were identified. DUB-1 and DUB-2 are more related to each other than to other members of the ubp superfamily and thereby define a novel subfamily of deubiquitinating enzymes.

Hematopoietic-specific, cytokine induced DUBs in murine system have shown to prolong cytokine receptor, see Migone, T. S., et al. (2001). The deubiquitinating enzyme DUB-2 prolongs cytokine-induced signal transducers and activators of transcription activation and suppresses apoptosis following cytokine withdrawal, *Blood* 98, 1935–41; Zhu, Y., et al., (1997). DUB-2 is a member of a novel family of cytokine-inducible deubiquitinating enzymes, *J Biol Chem* 272, 51–7 and Zhu, Y., et al., (1996). The murine DUB-1 gene is specifically induced by the betac subunit of interleukin-3 receptor, *Mol Cell Biol* 16, 4808–17.). These effects are likely due to the deubiquitination of receptors or other signaling intermediates by DUB-1 or DUB-2, murine analogs of hDUBs. Inhibition of hDUBs may achieve down-regulation of specific cytokine receptor signaling, thus modulating specific immune responses.

Cytokines regulate cell growth by inducing the expression of specific target genes. A recently identified a cytokine-inducible, immediate-early gene, DUB-1, encodes a deubiquitinating enzyme with growth regulatory activity. In addition, a highly related gene, DUB-2, that is induced by interleukin-2 was identified. The DUB-2 mRNA was induced in T cells as an immediate-early gene and was rapidly down-regulated. Like DUB-1, the DUB-2 protein had deubiquitinating activity in vitro. When a conserved cysteine residue of DUB-2, required for ubiquitin-specific thiol protease activity, was mutated to serine (C60S), deubiquitinating activity was abolished. DUB-1 and DUB-2 proteins are highly related throughout their primary amino acid sequence except for a hypervariable region at their COOH terminus. Moreover, the DUB genes co-localize to a region of mouse chromosome 7, suggesting that they arose by a tandem duplication of an ancestral DUB gene. Additional DUB genes co-localize to this region, suggesting a larger family of cytokine-inducible DUB enzymes. We propose that different cytokines induce specific DUB genes. Each induced DUB enzyme thereby regulates the degradation or the ubiquitination state of an unknown growth regulatory factor, resulting in a cytokine-specific growth response.

On the basis of these structural criteria, additional members of the DUB subfamily can be identified in the GenBank™. The highest degree of homology is in the Cys and His domains. Additionally, this putative human DUB protein contains a Lys domain (amino acids 400–410) and a hypervariable region (amino acids 413–442).

Murine DUB (mDUB) subfamily members differ from other UBPs by functional criteria as well. mDUB subfamily members are cytokine-inducible, immediate-early genes and may therefore play regulatory roles in cellular growth or differentiation. Also, DUB proteins are unstable and are rapidly degraded by ubiquitin-mediated proteolysis shortly after their induction.

mDUB reports demonstrate that specific cytokines, such as IL-2 and IL-3, induce specific deubiquitinating enzymes (DUBs). The DUB proteins may modify the ubiquitin-proteolytic pathway and thereby mediate specific cell growth or differentiation signals. These modifications are temporally regulated. The DUB-2 protein, for instance, is rapidly but transiently induced by IL-2. Interference of DUB enzymes with specific isopeptidase inhibitors may block specific cytokine signaling events.

Defensins constitute a major family of antimicrobial peptides in mammals. Depending on the distribution of the cysteines and the linkages of the disulfide bonds, human defensins can be divided into two categories: α-defensins, which can be found in granulocytes and in epithelial cells of the small intestine, and β-defensins, which are expressed by epithelial cells and leukocytes including macrophages. Some defensins are expressed constitutive manner in granulocytes and epithelial cells where as others are induces by either exposure to microbial pathogens or pro-inflammatory cytokines such as IL-1β, TNF-α and interferon-γ. The genes coding for human defensins are clustered within 1 Mb segment on chromosome 8P23, and it has been suggested that β-defensins may predate the a-defensin family during recent gene amplification since α-defensin cannot be detected even in many mammalians including cow. Cow has at least 13 β-defensins but no α-defensin. β-defensins contribute to early host defense against several bacterial and fungal pathogens, as an important mechanism of innate immune response. Beside this antimicrobial activity, a chemoattractant activity on both immature dentritic cells and memory T cells, as well as monocytes, has been recently described, demonstrating that β-defensins may promote both innate and adaptive immune response.

SUMMARY OF THE INVENTION

Figure 1:
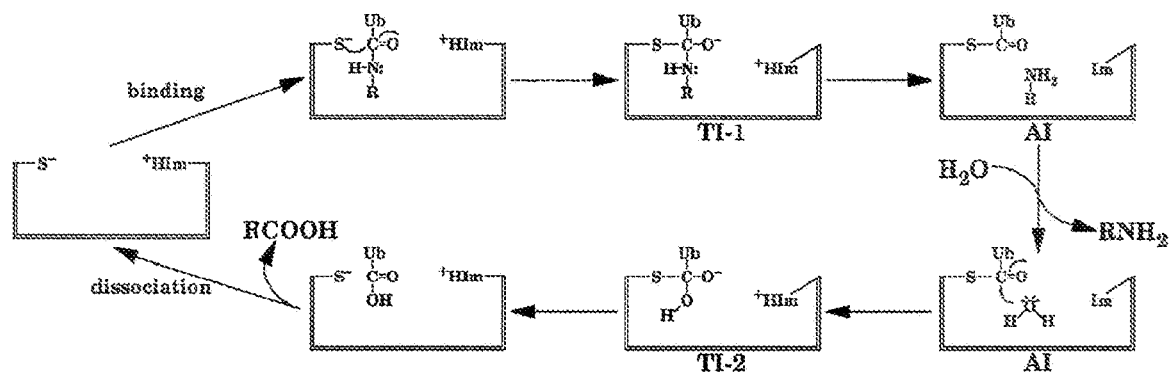
FIG. 1: Proposed enzyme reaction mechanism of DUB-.

The present invention is directed to analogs of murine DUBs, hematopoietic-specific, cytokine-inducible deubiquitinating proteases found as a cluster of genes on chromosomes 4 and 8 and respective regulatory regions. Eleven novel human DUBs and four potential genes that express truncated form of DUBs not previously reported in public databases were identified by searching human genome database using murine DUB-1 and DUB-2 sequences. These genes share open reading frames (ORFs) that are 88 to 99% amino acid identity to each other, when gaps caused by deletion and N-terminal and/or C-terminal extension was not counted as mismatch, and exhibit approximately 50% identity to murine DUBs. Eight of eleven ORFs generate a protein of 530 amino acids. Two ORFs (hDUB8.3 and hDUB8.11) have internal in-frame deletions such that the genes are capable of generating 497 and 417 amino acid long polypeptides, respectively. One ORF (hDUB4.5) exhibits extension at both 5' and 3' end of the ORF so that the gene is capable of expressing 574 amino acid long polypeptide. Surprisingly, this 5' extension results in specific propolypeptide sequence that can direct polypeptide targeting to the mitochondria. Furthermore, the respective regulatory regions, putative promoters, of these genes also share close to 90% identity each other suggesting that their expression is coordinated. In addition, we found that two of these genes can be expressed under the control of separate promoters that can be controlled independently and expressing potentially distinctive protein products.

Manipulation of these gene products by small molecular compounds can (1) reduce inflammation by regulating proinflammatory cytokine signaling, (2) modulate autoimmune diseases by regulating cytokine receptor signaling that are critical for lymphocytes proliferation, and (3) immune over-reaction during infection using above mechanisms.

Two of cluster genes (hDUB4.1 and hDUB4.2) possesses two distinctive promoter domains in front of their ORFs such that they can be regulated independently in their transcription potential. The longer transcripts of these ORFs (called hDUB4.1a and hDUB4.2a) has 12 and 4 exons respectively and capable of generating 1016 and 1021 amino acid long polypeptides, respectively. These polypeptides share C-terminal 530 amino acids with their shorter form that can be expressed separately from independent promoters (called hDUB4.1b and hDUB4.2b, respectively). In addition, two other ORFs are capable of generating longer than 530 amino acid polypeptides (hDUB4.10 and hDUB4.11). Remarkably, these two deduced polypeptides shares significant homology within portion of N-terminal portions (I added alignment file of these at the end of sequence file). Three of the ORFs (hDUB4.5, 4.8, and 8.2) has N-terminal insertion that is typical for mitochondria targeting sequence. An alignment of these sequences is provide in the Tables. The promoter sequences defined as upstream of initiation ATG of the ORF exhibit remarkable level of homology each other except that of hDUB4.1a. The sequence identity among all promoter sequences except that of hDUB4.1a is approximately 90% in 2000 base pair span upstream of initiation ATG. Two of the promoter sequences (hDUB8.3 and 8.11) have 334 nucleotides insertion at approximately 1000 base pair upstream of initiation ATG. Interestingly, hDUB8.3 and hDUB8.11 are the only ones with shorter ORFs due to the internal deletions. In addition to these ORFs, there are 5 ORFs that are capable of expressing polypeptides (hDUB4.4, hDUB4.9, hDUB8.2, hDUB8.9, and hDUB8.10) that share initiation codon with other 530 amino acid long polypeptides but terminate prematurely due to the in frame termination sequences. These also shares significant homology upstream of ATG initiation codon suggesting they may expressed as truncated proteins, potential regulatory functions. All 11 hDUB8 genes are clustered with the defensin clusters within 2 Mb region in 8P23, implying that both acquisition and amplification are relatively recent event, perhaps during mammalian evolution. It is of interest that hDUB4 gene cluster is also in highly amplified cluster region of chromosome 4P16 that is yet to be assigned in chromosome location. These data suggest that hDUB4s and hDUB8s are within very dynamic region of the human chromosomes (both 4p16 and 8p23) that are undergoing volatile amplifications. The data also suggest that expression of hDUB8 may also be coordinated in conjunction with defensins that are critical components of innate immune response and inflammation.

Search Methods for Identifying Human Analogs of mDUBs:

In order to identify human analogs of mDUB1, -2, -2A, mDUB1 (U41636), mDUB2 (NM_010089), and mDUB2A (AF393637) DNA sequences were used to search against Ensembl entire "golden path" (as contigs) using Ensembl blast search engine (http://www.ensembl.org/perl/blastview). All three mDUBs have significant alignments with contig AC083981, AF252831, AF228730, AF252830, AC068974 on chromosome 8 with the high score above 2000 and the probability less than e-87. In order to find all the homolog genes in the genome, exhaust search was performed using genomic aligned sequence to search against the "golden path" contigs. Two more contigs were found to have significant alignment that has probability less than e-100: one is AC074340 on chromosome 8 and the other is AC022770 on chromosome 4.

DNA sequences for contig AC083981, AF252831, AF228730, AF252830, AC068974, AC074340 and AC022770 were downloaded from Ensembl and gene annotation for each contig was performed using GenScan gene annotation program. Genes having homolog with mDUBs were named in sequence based on their locations on chromosomes. For example, hDUB8.1 was derived from AF228730, 8.2, 8.3 were derived from AF252830, 8.5 were derived from AC074340, 8.6 were derived from AF252831, 8.7, 8.8 and 8.9 were derived from AC083981, and 8.10 and 8.11 were derived from AC068974. hDUB4.1, 4.2, 4.3, 4.4, 4.5 were derived from AC022770 on chromosome 4.

Using these hDUB4s and hDUB8s, both Ensemble and NCBI blast search was performed. Further contig NT_028165 that covers chromosome 4 was identified. From this and already assembled chromosome 4p16.1 region, further annotation was performed using GenScan gene annotation program. From this we identified hDUB4.6, 4.7, 4.8, 4.9, 4.10, and 4.11.

Analysis of the hDUB gene clusters in chromosome 4 reveals that at least five ORFs in an unmapped cOntig (AC022770) were identified by nucleotide homology search with murine DUB1 and 2. At least four out of five ORFs share core 530 amino acid sequences. Two ORFs (hDUB4.1 and hDUB4.2) are multi-exon ORFs that extend N-terminal part of polypeptides that shares minimal sequence identity. However, there is a conserved putative promoter sequences that encompass over 2,000 bases in the intron region proximal to the last exon that is conserved among all 5 genes. Three of the ORFs (hDUB4.5, 4.8, and 8.2) has N-terminal insertion that is typical for mitochondria targeting sequence. The hDUB genes cluster in 4P16 of the human chromosome, which is an unmapped part of the human chromosome.

Analysis of the hDUB gene clusters in chromosome 8 reveals that at least eleven ORFs in six different contigs (AC068974, AC074340, AC083981, AF228730, AF252830, and AF252831) were identified by nucleotide homology search with murine DUB1 and 2. At least seven out of eleven ORFs share significant identities with similar length. There are conserved putative promoter sequences that encompass over 2,000 bases in all 11 genes. The hDUB genes cluster in 8P23.1 of the human chromosome and clustered with defensin molecules (at lease 9 defensins are clustered with hDUB8s) and the whole domain belongs the olfactory GPCR cluster.

Analysis of the deduced amino acid sequences of the hDUBs reveals polypeptides consistent with mDUBs, which contain highly conserved Cys and His domains that are likely to form the enzyme's active site. The putative active site nucleophile of mDUB-2 is a cysteine residue ($Cys^{-60}$) in the Cys domain. Both mDUB-1 and mDUB-2 have a lysine rich region (Lys domain; amino acids 374–384 of mDUB-2) and a short hypervariable region (amino acids 385–451 of mDUB-2), in which the mDUB-1 and mDUB-2 sequences diverge considerably. The hypervariable (HV) region of mDUB-2 contains a duplication of the eight-amino acid sequence: PQEQNHQK (Seq ID No. 55).

The protein and nucleotide sequences named in this invention and their Sequence ID NOs are set forth as following:

Nucleotide Sequence for hDUB4.1a: Seq ID No. 3
hDUB4.1a deduced polypeptide sequence: Seq ID No. 4
Nucleotide Sequence for hDUB4.1b: Seq ID No. 5
hDUB4.1b deduced polypeptide sequence: Seq ID No. 6
Nucleotide Sequence for hDUB4.2a: Seq ID No. 7
hDUB4.2a deduced polypeptide sequence: Seq ID No. 8
Nucleotide Sequence for hDUB4.2b: Seq ID No. 9
hDUB4.2b deduced polypeptide sequence: Seq ID No. 10
Nucleotide Sequence for hDUB4.3: Seq ID No. 11
hDUB4.3 deduced polypeptide sequence: Seq ID No. 12
Nucleotide Sequence for hDUB4.5: Seq ID No. 13
hDUB4.5 deduced polypeptide sequence: Seq ID No. 14
Nucleotide Sequence for hDUB4.6: Seq ID No. 15
hDUB4.6 deduced polypeptide sequence: Seq ID No. 16
Nucleotide Sequence for hDUB4.7: Seq ID No. 17
hDUB4.7 deduced polypeptide sequence: Seq ID No. 18
Nucleotide Sequence for hDUB4.8: Seq ID No. 19
hDUB4.8 deduced polypeptide sequence: Seq ID No. 20
Nucleotide Sequence for hDUB4.10: Seq ID No.21
hDUB4.10 deduced polypeptide sequence: Seq ID No. 22
Nucleotide Sequence for hDUB4.11: Seq ID No. 23
hDUB4.11 deduced polypeptide sequence: Seq ID No. 24
Nucleotide Sequence for hDUB8.1: Seq ID No. 25
hDUB8.1 deduced polypeptide sequence: Seq ID No. 26
Nucleotide Sequence for hDUB8.3: Seq ID No. 27
hDUB8.3 deduced polypeptide sequence: Seq ID No. 28
Nucleotide Sequence for hDUB8.5: Seq ID No. 29
hDUB8.5 deduced polypeptide sequence: Seq ID No. 30
Nucleotide Sequence for hDUB8.6: Seq ID No. 31
hDUB8.6 deduced polypeptide sequence: Seq ID No. 32
Nucleotide Sequence for hDUB8.7: Seq ID No. 33
hDUB8.7 deduced polypeptide sequence: Seq ID No. 34
Nucleotide Sequence for hDUB8.8: Seq ID No. 35
hDUB8.8 deduced polypeptide sequence: Seq ID No. 36
Nucleotide Sequence for hDUB8.11: Seq ID No. 37
hDUB8.11 deduced polypeptide sequence: Seq ID No. 38
Nucleotide Sequence for hDUB4.4: Seq ID No. 39
hDUB4.4 deduced polypeptide sequence: Seq ID No. 40
Nucleotide Sequence for hDUB4.9: Seq ID No. 41
hDUB4.9 deduced polypeptide sequence: Seq ID No. 42
Nucleotide Sequence for hDUB8.2: Seq ID No. 43
hDUB8.2 deduced polypeptide sequence: Seq ID No. 44
Nucleotide Sequence for hDUB8.9: Seq ID No. 45
hDUB8.9 deduced polypeptide sequence: Seq ID No. 46
Nucleotide Sequence for hDUB8.10: Seq ID No. 47
hDUB8.10 deduced polypeptide sequence: Seq ID No. 48
Promoter sequence for hDUB4.6: Seq ID No. 49
Promoter sequence for hDUB4.7: Seq ID No. 50
Promoter sequence for hDUB4.8: Seq ID No. 51
Promoter sequence for hDUB4.9: Seq ID No. 52
Promoter sequence for hDUB4.10: Seq ID No. 53
Promoter sequence for hDUB4.11: Seq ID No. 54

TaqMan Real Time PCR Analysis of Expression of hDUB4s and hDUB8s in Human Immunocytes upon Various Stimulation Protocol of Reverse Transcription (RT) from Total Cellular RNA using Random Hexamer as Primer (using TaqMan Reverse Transcription Reagents Cat# N808-0234)

1 ug of total RNA preparation in 100 ul of 1×TaqMan RT Buffer Mix, 5.5 mM $MgCl_2$, 0.5 mM dNTPs, 2.5 uM Random Hexamers, 40 U RNAse inhibitor, 125 U Multiscribe Reverse Transcriptase. Mix by pipeting up and down. Incubate 25° C. for 10 minutes (annealing step), 48° C. for 30 minutes (reverse transcription), and 95° C. for 5 minutes (heat killing of the enzyme). The samples can be left at the machine at 4° C., or alternatively, can be stored at −20° C. Yield of cDNA synthesis can be measured by incorporation of small portion of radioactive dATP (or dCTP). Average efficiency for this protocol is between 60–80% of conversion of RNA to cDNA.

Protocol of TaqMan Real-Time Quantitative PCR 1 ul of TaqMan RT product in 12.5 ul of 1× master Mix (Applied Biosystems Cat# 4304437) containing all necessary reaction components except primers and probes, 0.9 uM forward primer, 0.9 uM reverse primer, 0.2 uM probe. Mix by pipetting up and down. Samples containing GADPH primer pair and probe were also prepared as control. Thermal cycling and detection of the real-time amplification were performed using the ABI PRISM 7900HT Sequuence Detection System. The quantity of target gene is given relative to the GADPH control based on $C_t$ values determined during the exponential phase of PCR.

Primer-probe Sets used and their Specificities:

Primer 4.1 is unique for hDUB 4.1
Primer 4.2 covers hDUB 4.2, 4.3, 4.5 and 8.1
Primer 8.3 covers hDUB 8.3 and 8.11
Primer 8.5 is unique for hDUB 8.5
Primer 8.6 covers hDUB 8.6, 8.7 and 8.8

TABLE 1

Expression of hDUBs in PBMC stimulated with LPS (100 ng/ml) and PHA (5 ug/ml) for 7 hours.

| | Donor 1 | | Donor 2 | |
| --- | --- | --- | --- | --- |
| Primer | Fold-Upregulation upon stimulation | Relative expression | Fold-Upregulation upon stimulation | Relative expression |
| 4.1 | 2.2 | 1 | 3.8 | 1 |
| 4.2 | 2.0 | 21000 | 2.0 | 16400 |
| 8.3 | 1.8 | 5560 | 1.8 | 5500 |
| 8.5 | 2.1 | 80 | 3.1 | 310 |
| 8.6 | 2.6 | 19200 | 3.0 | 23000 |

TABLE 2

Expression of hDUBs in PBMC stimulated with LPS (100 ng/ml) for 1.5, 7 and 24 hours (Donor 3)

| | 1.5 hours | | 7 hours | | 24 hours | |
|---|---|---|---|---|---|---|
| | Fold-Upregulation upon stimulation | Relative expression | Fold-Upregulation upon stimulation | Relative expression | Fold-Upregulation upon stimulation | Relative expression |
| 4.2 | 2.4 | 64 | 336 | 35.2 | 1.8 | 12.5 |
| 8.3 | 0.4 | 1 | 13.1 | 1 | 1.7 | 1 |
| 8.5 | 1.6 | 11 | 65.9 | 4.8 | 1.5 | 1.8 |

TABLE 3

Expression of DUBs in PBMC stimulated with LPS (100 ng/ml) and/or PHA (5 ug/ml) for 1.5, 7, 24 hours (donor 4)

| | | 1.5 hours | | 7 hours | | 24 hours | |
|---|---|---|---|---|---|---|---|
| | Primer | Fold-Upregulation upon stimulation | Relative expression | Fold-Upregulation upon stimulation | Relative expression | Fold-Upregulation upon stimulation | Relative expression |
| LPS | 4.2 | 0.4 | 39 | 2.5 | 54 | 1.6 | 48 |
| | 8.3 | 0.5 | 5 | 1.6 | 6 | 1.1 | 7 |
| | 8.5 | 0.9 | 1 | 1.5 | 1.7 | 1.4 | 2 |
| | 8.6 | 0.6 | 26 | 1.7 | 57 | 1.0 | 21 |
| PHA | 4.2 | 3.5 | 367 | 4.4 | 94 | 0.9 | 26 |
| | 8.3 | 1.5 | 13 | 1.7 | 6 | 0.7 | 5 |
| | 8.5 | 1.9 | 2 | 0.9 | 1 | 0.7 | 1 |
| | 8.6 | 2.3 | 103 | 2.5 | 23 | 0.8 | 17 |
| LPS + PHA | 4.2 | 1.2 | 129 | 3.4 | 73 | 0.8 | 23 |
| | 8.3 | 1.0 | 9 | 2.2 | 8 | 0.7 | 5 |
| | 8.5 | 1.0 | 1 | 0.9 | 1.3 | 0.9 | 1.2 |
| | 8.6 | 1.3 | 56 | 2.5 | 33 | 0.8 | 18 |

There is no increase of expression in T lymphocytes (donor 5) and B lymphocytes (donor 6) when stimulated with anti-CD4/CD28 and anti-CD40/IL-4, respectively.

TABLE 4

Expression of hDUB 4.2, 4.3, 4.5 and 8.1 examined by primer 4.2 in different human organ panel by TaqMan analysis.

| Tissue Type | Mean | β 2 Mean | ∂∂ Ct | Expression |
|---|---|---|---|---|
| Adrenal Gland | 29.72 | 20.00 | 10.08 | 0.92 |
| Bone marrow | 34.02 | 20.49 | 13.89 | 0.07 |
| Brain | 26.92 | 22.73 | 4.54 | 42.84 |
| Colon | 32.03 | 19.97 | 12.42 | 0.18 |
| Fetal Brain | 27.59 | 24.23 | 3.71 | 76.15 |
| Fetal Liver | 33.22 | 22.58 | 10.99 | 0.49 |
| Heart | 33.09 | 21.60 | 11.85 | 0.27 |
| Kidney | 29.93 | 21.97 | 8.32 | 3.13 |
| Lung | 32.10 | 19.31 | 13.15 | 0.11 |
| Mammary Gland | 30.00 | 21.74 | 8.61 | 2.56 |
| Pancreas | 34.83 | 24.07 | 11.11 | 0.45 |
| Placenta | 36.60 | 23.77 | 13.19 | 0.00 |
| Prostate | 29.14 | 20.93 | 8.55 | 2.66 |
| Salivary Gland | 32.11 | 21.39 | 11.07 | 0.46 |
| Skeletal Muscle | 28.27 | 20.44 | 8.18 | 3.45 |
| Small Intestine | 34.33 | 21.00 | 13.69 | 0.08 |
| Spinal Cord | 27.04 | 21.91 | 5.47 | 22.48 |
| Spleen | 32.45 | 19.02 | 13.78 | 0.07 |
| Stomach | 32.15 | 21.66 | 10.84 | 0.55 |
| Testis | 28.57 | 23.07 | 5.87 | 17.16 |
| Thymus | 31.01 | 20.68 | 10.69 | 0.61 |
| Thyroid | 28.84 | 20.80 | 8.39 | 2.97 |
| Trachea | 31.39 | 19.63 | 12.11 | 0.23 |
| Uterus | 30.37 | 21.09 | 9.64 | 1.25 |
| PBMC/Control | 33.98 | 18.82 | 15.52 | 0.02 |
| PBMC/PMA | 33.62 | 18.81 | 15.17 | 0.03 |
| PBMC/PHA | 34.20 | 18.77 | 15.78 | 0.02 |
| PBMC/HDM | 34.23 | 17.81 | 16.77 | 0.01 |
| A549 Cells | 31.98 | 21.57 | 10.77 | 0.57 |
| THP-1 | 35.48 | 20.75 | 15.09 | 0.00 |
| Ovary | 31.84 | 21.55 | 10.65 | 0.62 |
| (+ve) Positive Control | 29.61 | 21.86 | 8.11 | 3.62 |

TABLE 5

Expression of hDUB 4.2, 4.3, 4.5 and 8.1 examined by primer 4.2 in human immunocytes panel:

| Cell Type and stimulation condition | Mean | β 2 Mean | ∂∂ Ct | Expression |
|---|---|---|---|---|
| Granulocyte resting | 34.18 | 17.22 | 17.50 | 0.005 |
| Granulocyte TNF-β 4/24 hr | 32.39 | 17.16 | 15.76 | 0.018 |
| CD19 (tonsillar-CD40L) | 28.7 | 19.92 | 9.32 | 1.565 |
| CD19 (tonsillar-LPS) | 31.14 | 20.67 | 11.00 | 0.488 |
| FLS-REST | 34.67 | 20.43 | 14.78 | 0.036 |
| FLS-IL1 4/24 hr | 34.26 | 20.41 | 14.38 | 0.047 |
| FLS-TNF-β 4/24 hr | 34.91 | 20.15 | 15.31 | 0.025 |
| Monocyte resting (pool 1.5, 7, 24 hr) | 33.63 | 18.29 | 15.89 | 0.017 |
| Monocyte LPS (pool 1.5, 7, 24 hr) | 34.55 | 18.03 | 17.06 | 0.007 |
| Monocyte INF-g (pool 1.5, 7, 24 hr) | 34.62 | 17.27 | 17.88 | 0.004 |
| Monocyte LPS & IFN-β (pool 1.5, 7, 24 hr) | 34.87 | 17.38 | 18.03 | 0.004 |
| DCs progenitors (CD14+) | 35.87 | 19.73 | 16.67 | 0.000 |
| DCs immature | 35.48 | 18.18 | 17.84 | 0.000 |
| DCs mature | 37.46 | 17.92 | 20.07 | 0.000 |
| TH0 resting | 31.11 | 17.63 | 14.02 | 0.060 |
| TH0 activated | 31.29 | 18.23 | 13.60 | 0.081 |
| Th1 resting | 33.88 | 18.27 | 16.15 | 0.014 |
| Th1 CD28/CD3 | 32.15 | 19.31 | 13.38 | 0.094 |
| Th2 resting | 33.94 | 18.07 | 16.40 | 0.012 |
| Th2 CD28/CD3 | 33.27 | 18.78 | 15.02 | 0.030 |
| BSMC | 35.33 | 21.64 | 14.22 | 0.000 |
| BSMC IL-4 + TNF-β 24 hr | 36.44 | 21.52 | 15.45 | 0.000 |

TABLE 5-continued

Expression of hDUB 4.2, 4.3, 4.5 and 8.1 examined by primer 4.2 in human immunocytes panel:

| Cell Type and stimulation condition | Mean | β 2 Mean | ∂∂ Ct | Expression |
|---|---|---|---|---|
| BSMC IL-13 + TNF-β 24 hr | 35.94 | 21.41 | 15.07 | 0.000 |
| BSMC IL-4 + IL-13 | 36.28 | 22.09 | 14.73 | 0.000 |
| NHBE d0 | 36.63 | 22.24 | 14.92 | 0.000 |
| NHBE IL-4 + TNF-β d0 | 35.72 | 21.42 | 14.83 | 0.000 |
| NHBE IL-13 + TNF-βd0 | 36.35 | 21.37 | 15.52 | 0.000 |
| NHBE resting d7 + d14 | 34.89 | 22.41 | 13.01 | 0.121 |
| NHBE IL-4 + TNF-β d7 + d14 | 38.59 | 22.02 | 17.11 | 0.000 |
| NHBE IL-13 + TNF-β d7 + d14 | 37.62 | 21.93 | 16.23 | 0.000 |
| CD8 T cell O hour | 30.15 | 19.52 | 11.16 | 0.437 |
| CD8 T cell a-CD3/CD28 4 hour | 32.08 | 19.6 | 13.01 | 0.121 |
| CD8 T cell a-CD3/CD28 24 hour | 30.94 | 18.64 | 12.84 | 0.137 |
| HMVEC resting | 35.09 | 20.25 | 15.38 | 0.000 |
| HMVEC TNF-β + IL-4 24 hr | 35.91 | 20.86 | 15.59 | 0.000 |
| HMVEC TNF-β 24 hr | 35.57 | 21.06 | 15.05 | 0.000 |
| HMVEC TNF-β + IL-13 24 hr | 36.38 | 20.61 | 16.31 | 0.000 |
| Normal synovium pool | 34.92 | 21.16 | 14.3 | 0.050 |
| RA synovium pool | 33.65 | 20.88 | 13.3 | 0.099 |
| Normal colon | 32.5 | 21.68 | 11.36 | 0.381 |
| Colitis Colon | 33.17 | 21.32 | 12.39 | 0.187 |
| Crohns colon pooled | 32.91 | 22.06 | 11.39 | 0.374 |
| Normal Lung | 31.01 | 20.5 | 11.05 | 0.472 |
| COPD Lung | 35.09 | 22.14 | 13.49 | 0.000 |
| Positive control | 28.4 | 22.29 | 6.64 | 9.992 |

Cloning of hDUB4,8s by PCR

Following promer set was used to clone 530 amino acid open reading frame portion of single exon hDUB4s and 8s from human genomic DNA:

```
N-terminal primer:
5'-atggaggacgactcactct-3'      (Seq ID No. 1)

C-terminal primer:
5'-ctggcacacaagcaga-3'         (Seq ID No. 2)
```

Underlined triplet nucleotides in each primer represent translational initiation and termination codon. This primer set can amplify most of hDUB4s and hDUB8s as well as potentially yet to be identified hDUBs that are similar enough to hDUB4s and hDUB8s due to the high homology in nucleotide sequences in this part of the ORF. 1593 base pair fragment was successfully amplified from genomic DNA from two healthy human subjects and cloned into pCR2.1 vector and transformed into TOP10 strain of *E coli*. Over 300 independent clones with appropriate size insert were obtained and sequences are obtained by ABI automated DNA sequencers.

Deubiquitination Assay

Confirmation that the DUB is a deubiquitinating enzyme may be shown using previously identified deubiquitination assay of ubiquitin-galactosidase fusion proteins, as described previously in the literature. Briefly, a fragment of the DUB, of approximately 1,500 nucleotides, based on the wild-type DUB cDNA (corresponding to amino acids 1 to about 500) and a cDNA containing a missense mutation are generated by PCR and inserted, in frame, into pGEX (Pharmacia), downstream of the glutathione S-transferase (GST) coding element. Ub-Met-gal is expressed from a pACYC184-based plasmid. Plasmids are co-transformed as indicated into MC1061 *Escherichia coli*. Plasmid-bearing *E. coli* MC1061 cells are lysed and analyzed by immunoblotting with a rabbit anti-gal antiserum (Cappel), a rabbit anti-GST antiserum (Santa Cruz), and the ECL system (Amersham Corp.). in vitro deubiquitinating enzyme activity may be shown from purified hDUB fusion protein using commercial polyubiquitinated protein as substrate.

HDUB4s and hDUB8s are Potential Inflamatory Cytokins Specific Immediate-early Genes mDUB-1 was originally cloned as an IL-3-inducible immediate-early gene. Similarly, mDUB-2 was cloned as an IL-2-inducible immediate-early gene. We examined inducibility as well as cell-type specific expression of these genes using multiple TaqMan analysis from human organ RNA samples and human immunocytes RNA samples. Our data suggest that expression of hDUBs are not apparent in lymphocytes and granulocytes but high in fresh human PBMC from several donor. This strongly suggest that expression may be limited to the monocytes/macrophages and potentially NK cells. hDUB4s and hDUB8s are upregulated in PBMC stimulated with stimuli (LPS and/or PHA) that is known to upregulate various inflammatory cytokines such as TNF-alpha, IL-1 beta etc. This increase of expression is almost completely disappeared 20 to 24 hours after stimulation suggesting this is an early gene. The fact that there is only weak expression upregulation at 1.5 hours after stimulation suggests that stimuli by themselves may not upregulate hDUB4s and hDUB8s, but cytokines that are upregulated within couple of hours after stimulation may be responsible for upregulation of the hDUB4s and hDUB8s.

The DUB Subfamily of the ubp Superfamily

From these data we propose that hDUB4s and hDUB8s are members of a discrete subfamily of deubiquitinating enzymes that shows the strongest similarity to mDUB subfamily including mDUB1, mDUB2, and mDUB2A, called the DUB subfamily. DUB subfamily members contain distinct structural features that distinguish them from other ubps. First, DUB subfamily members are comparatively small enzymes of approximately 500–550 amino acids. Second, DUB subfamily members share amino acid similarity not only in the Cys and His domains but also throughout their primary amino acid sequence. For instance, DUB proteins contain a lysine-rich region (Lys domain) and a HV domain near their carboxyl terminus.

The regulatory regions, or promoter regions, of each of the DUBs was analyzed for putative transcription factor binding motifs using TRANSFACFind, a dynamic programming method, see Heinemeyer, T., et al., "Expanding the TRANSFAC database towards an expert system of regulatory molecular mechanisms" *Nucleic Acids Res.* 27, 318–322, (1999). The Transfac database provides eukaryotic cis- and trans-acting regulatory elements.

TABLE 6 putative transcription factor binding motifs within the DUB regulatory or promoter, region of hDUB 4.1a. The position is indicated by nucleotides.

| Transfac | Position(Score) | Name | Description |
|---|---|---|---|
| M00271 | 729 . . . 724(100) | AML-1a | runt-factor AML-1 |
| M00148 | 296 . . . 302(100) | SRY | sex-determining region Y gene product |
|  | 1016 . . . 1010(96) | | |
|  | 958 . . . 964(94) | | |
|  | 474 . . . 480(94) | | |
|  | 1982 . . . 1988(92) | | |
|  | 129 . . . 123(90) | | |
|  | 857 . . . 863(90) | | |
|  | 776 . . . 782(90) | | |
|  | 1919 . . . 1913(90) | | |
|  | 1227 . . . 1233(90) | | |
|  | 276 . . . 282(90) | | |
|  | 1741 . . . 1735(90) | | |
|  | 193 . . . 199(90) | | |
|  | 105 . . . 111(90) | | |
| M00240 | 1600 . . . 1606(100) | Nkx-2.5 | homeo domain factor Nkx-2.5/Csx, tinman homolog |
|  | 700 . . . 694(100) | | |
| M00083 | 892 . . . 899(100) | MZF1 | MZF1 |
| M00101 | 162 . . . 156(100) | CdxA | CdxA |
|  | 1008 . . . 1002(100) | | |
|  | 423 . . . 429(100) | | |
|  | 153 . . . 147(99) | | |
|  | 359 . . . 353(98) | | |
|  | 1388 . . . 1394(98) | | |
|  | 1644 . . . 1650(97) | | |
|  | 1702 . . . 1696(97) | | |
|  | 250 . . . 256(97) | | |
|  | 231 . . . 237(97) | | |
|  | 617 . . . 611(94) | | |
|  | 509 . . . 503(93) | | |
|  | 432 . . . 426(92) | | |
|  | 307 . . . 313(92) | | |
|  | 153 . . . 159(92) | | |
|  | 1832 . . . 1838(92) | | |
|  | 1366 . . . 1372(92) | | |
|  | 494 . . . 500(92) | | |
|  | 1450 . . . 1456(91) | | |
|  | 1456 . . . 1450(91) | | |
|  | 722 . . . 716(90) | | |
|  | 991 . . . 985(90) | | |
|  | 986 . . . 992(90) | | |
|  | 1646 . . . 1640(90) | | |
| M00253 | 1142 . . . 1149(97) | cap | cap signal for transcription initiation |
|  | 1344 . . . 1351(96) | | |
|  | 639 . . . 632(95) | | |
|  | 1313 . . . 1320(94) | | |
|  | 1872 . . . 1879(93) | | |
|  | 269 . . . 262(92) | | |
|  | 257 . . . 250(91) | | |
|  | 1103 . . . 1110(91) | | |
|  | 745 . . . 752(91) | | |
|  | 1589 . . . 1596(90) | | |
| M00099 | 978 . . . 993(96) | S8 | S8 |
|  | 1637 . . . 1652(94) | | |
|  | 995 . . . 980(93) | | |
| M00100 | 162 . . . 156(96) | CdxA | CdxA |
|  | 1008 . . . 1002(96) | | |
|  | 423 . . . 429(96) | | |
|  | 1774 . . . 1768(96) | | |
|  | 415 . . . 421(92) | | |
|  | 860 . . . 854(91) | | |
|  | 1026 . . . 1020(91) | | |
|  | 494 . . . 500(91) | | |
|  | 94 . . . 100(91) | | |
| M00285 | 725 . . . 713(95) | TCF11 | TCF11/KCR-F1/Nrf1 homodimers |
|  | 982 . . . 970(92) | | |
| M00347 | 531 . . . 522(95) | GATA-1 | GATA-binding factor 1 |
| M00135 | 1642 . . . 1660(95) | Oct-1 | octamer factor 1 |
| M00075 | 217 . . . 226(94) | GATA-1 | GATA-binding factor 1 |
| M00278 | 530 . . . 522(94) | Lmo2 | complex of Lmo2 bound to Tal-1, E2A proteins, and GATA-1, half-site 2 |
|  | 900 . . . 908(90) | | |

TABLE 6-continued putative transcription factor binding motifs within the DUB regulatory or promoter, region of hDUB 4.1a. The position is indicated by nucleotides.

| Transfac | Position(Score) | Name | Description |
|---|---|---|---|
| M00157 | 990 . . . 978(94) | RORalpha2 | RAR-related orphan receptor alpha2 |
| M00127 | 533 . . . 520(93) | GATA-1 | GATA-binding factor 1 |
| M00109 | 1933 . . . 1920(93) | C/EBPbeta | CCAAT/enhancer binding protein beta |
| M00190 | 1656 . . . 1643(93) | C/EBP | CCAAT/enhancer binding factor |
| M00137 | 1193 . . . 1205(93) | Oct-1 | octamer factor 1 |
|  | 248 . . . 260(90) |  |  |
|  | 1652 . . . 1640(90) |  |  |
| M00302 | 1501 . . . 1512(92) | NF-AT | Nuclear factor of activated T-cells |
| M00077 | 900 . . . 908(91) | GATA-3 | GATA-binding factor 3 |
|  | 530 . . . 522(90) |  |  |
| M00126 | 533 . . . 520(91) | GATA-1 | GATA-binding factor 1 |
| M00159 | 1231 . . . 1219(91) | C/EBP | CCAAT/enhancer binding protein |
| M00074 | 1280 . . . 1292(91) | c-Ets-1(p54) | c-Ets-1(p54) |
| M00042 | 192 . . . 201(91) | Sox-5 | Sox-5 |
| M00241 | 1650 . . . 1643(91) | Nkx-2.5 | homeo domain factor Nkx-2.5/Csx, tinman homolog |
| M00116 | 138 . . . 125(91) | C/EBPalpha | CCAAT/enhancer binding protein alpha |
| M00138 | 1640 . . . 1662(91) | Oct-1 | octamer factor 1 |
| M00128 | 532 . . . 520(90) | GATA-1 | GATA-binding factor 1 |
| M00248 | 1645 . . . 1656(90) | Oct-1 | octamer factor 1 |
| M00289 | 1009 . . . 1021(90) | HFH-3 | HNF-3/Fkh Homolog 3 (= Freac-6) |

TABLE 7 transcription factor binding motifs within the DUB regulatory or promoter, region of hDUB 4.1b (SEQ ID NO: 6). The position is indicated by nucleotides.

| Transfac | Position(Score) | Name | Description |
|---|---|---|---|
| M00254 | 1831 . . . 1820(99) | CCAAT | cellular and viral CCAAT box |
| M00101 | 832 . . . 826(98) | CdxA | CdxA |
|  | 727 . . . 721(92) |  |  |
|  | 70 . . . 64(92) |  |  |
|  | 570 . . . 564(92) |  |  |
|  | 523 . . . 529(92) |  |  |
|  | 425 . . . 431(92) |  |  |
|  | 1682 . . . 1688(91) |  |  |
|  | 1409 . . . 1415(91) |  |  |
|  | 1415 . . . 1409(91) |  |  |
|  | 1688 . . . 1682(91) |  |  |
| M00054 | 470 . . . 461(97) | NF-kappaB | NF-kappaB |
|  | 643 . . . 634(95) |  |  |
| M00148 | 946 . . . 940(96) | SRY | sex-determining region Y gene product |
|  | 1564 . . . 1570(92) |  |  |
|  | 1528 . . . 1534(92) |  |  |
|  | 1092 . . . 1098(92) |  |  |
|  | 1048 . . . 1054(90) |  |  |
|  | 708 . . . 714(90) |  |  |
|  | 655 . . . 661(90) |  |  |
|  | 1360 . . . 1354(90) |  |  |
|  | 1824 . . . 1818(90) |  |  |
|  | 396 . . . 390(90) |  |  |
|  | 749 . . . 743(90) |  |  |
|  | 1016 . . . 1010(90) |  |  |
|  | 302 . . . 308(90) |  |  |
| M00053 | 470 . . . 461(95) | c-Rel | c-Rel |
|  | 643 . . . 634(94) |  |  |
| M00285 | 1734 . . . 1746(95) | TCF11 | TCF11/KCR-F1/Nrf1 homodimers |
|  | 1111 . . . 1123(91) |  |  |
|  | 17 . . . 5(90) |  |  |
| M00052 | 470 . . . 461(95) | NF-kappaB | NF-kappaB (p65) |
|  | 643 . . . 634(94) |  |  |
| M00077 | 1933 . . . 1941(95) | GATA-3 | GATA-binding factor 3 |
| M00253 | 485 . . . 492(95) | cap | cap signal for transcription initiation |
|  | 1893 . . . 1886(95) |  |  |
|  | 749 . . . 756(94) |  |  |
|  | 834 . . . 841(93) |  |  |
|  | 1484 . . . 1477(92) |  |  |
|  | 511 . . . 504(92) |  |  |
|  | 1194 . . . 1201(91) |  |  |

TABLE 7-continued transcription factor binding motifs within the DUB regulatory or promoter, region of hDUB 4.1b (SEQ ID NO: 6). The position is indicated by nucleotides.

| Transfac | Position(Score) | Name | Description |
|---|---|---|---|
| | 163 ... 170(91) | | |
| | 321 ... 328(91) | | |
| | 340 ... 347(91) | | |
| | 1815 ... 1808(90) | | |
| | 563 ... 570(90) | | |
| M00096 | 652 ... 660(95) | Pbx-1 | Pbx-1 |
| M00194 | 472 ... 459(95) | NF-kappaB | NF-kappaB |
| M00209 | 1818 ... 1831(94) | NF-Y | NF-Y binding site |
| M00116 | 1238 ... 1225(94) | C/EBPalpha | CCAAT/enhancer binding protein alpha |
| M00203 | 1699 ... 1689(94) | GATA-X | GATA binding site |
| | 1227 ... 1217(90) | | |
| M00241 | 535 ... 542(94) | Nkx-2.5 | homeo domain factor Nkx-2.5/Csx, tinman homolog |
| M00033 | 759 ... 746(94) | p300 | p300 |
| | 333 ... 320(90) | | |
| M00127 | 1703 ... 1690(93) | GATA-1 | GATA-binding factor 1 |
| M00158 | 323 ... 310(93) | COUP-TF | COUP/HNF-4 heterodimer |
| M00075 | 1889 ... 1898(93) | GATA-1 | GATA-binding factor 1 |
| | 142 ... 133(90) | | |
| | 1736 ... 1745(90) | | |
| M00286 | 963 ... 976(93) | GKLF | gut-enriched Krueppel-like factor |
| M00278 | 1933 ... 1941(93) | Lmo2 | complex of Lmo2 bound to Tal-1, E2A proteins, and GATA-1, half-site 2 |
| M00076 | 1932 ... 1941(93) | GATA-2 | GATA-binding factor 2 |
| | 983 ... 992(92) | | |
| M00208 | 471 ... 460(93) | NF-kappaB | NF-kappaB binding site |
| M00185 | 1829 ... 1819(92) | NF-Y | nuclear factor Y (Y-box binding factor) |
| M00302 | 232 ... 243(92) | NF-AT | Nuclear factor of activated T-cells |
| M00348 | 98 ... 107(92) | GATA-2 | GATA-binding factor 2 |
| M00134 | 308 ... 326(92) | HNF-4 | hepatic nuclear factor 4 |
| M00223 | 548 ... 540(92) | STATx | signal transducers and activators of transcription |
| M00039 | 1046 ... 1039(92) | CREB | cAMP-responsive element binding protein |
| M00271 | 1955 ... 1960(92) | AML-1a | runt-factor AML-1 |
| M00074 | 231 ... 243(91) | c-Ets-1(p54) | c-Ets-1(p54) |
| | 252 ... 264(91) | | |
| M00289 | 385 ... 397(91) | HFH-3 | HNF-3/Fkh Homolog 3 (= Freac-6) |
| M00199 | 1722 ... 1714(91) | AP-1 | AP-1 binding site |
| M00032 | 254 ... 263(91) | c-Ets-1(p54) | c-Ets-1(p54) |
| M00147 | 782 ... 773(91) | HSF2 | heat shock factor 2 |
| M00100 | 1101 ... 1095(91) | CdxA | CdxA |
| M00042 | 650 ... 659(90) | Sox-5 | Sox-5 |
| M00183 | 1026 ... 1035(90) | c-Myb | c-Myb |
| M00240 | 963 ... 957(90) | Nkx-2.5 | homeo domain factor Nkx-2.5/Csx, tinman homolog |
| | 1272 ... 1266(90) | | |
| M00190 | 1238 ... 1225(90) | C/EBP | CCAAT/enhancer binding factor |
| M00083 | 49 ... 42(90) | MZF1 | MZF1 |
| M00184 | 275 ... 284(90) | MyoD | myoblast determining factor |
| M00087 | 980 ... 991(90) | Ik-2 | Ikaros 2 |
| M00221 | 1860 ... 1850(90) | SREBP-1 | sterol regulatory element-binding protein 1 |
| M00137 | 1388 ... 1376(90) | Oct-1 | octamer factor 1 |

TABLE 8 putative transcription factor binding motifs within the DUB regulatory or promoter, region of hDUB 4.2a. The position is indicated by nucleotides.

| Transfac | Position(Score) | Name | Description |
|---|---|---|---|
| M00148 | 992 ... 986(100) | SRY | sex-determining region Y gene product |
| | 942 ... 948(100) | | |
| | 919 ... 913(96) | | |
| | 1544 ... 1550(92) | | |
| | 1505 ... 1511(92) | | |
| | 815 ... 809(90) | | |
| | 1068 ... 1074(90) | | |
| | 1196 ... 1190(90) | | |
| | 1337 ... 1331(90) | | |
| | 680 ... 686(90) | | |
| | 1697 ... 1691(90) | | |
| | 1802 ... 1796(90) | | |

TABLE 8-continued putative transcription factor binding motifs within the DUB regulatory or promoter, region of hDUB 4.2a. The position is indicated by nucleotides.

| Transfac | Position(Score) | Name | Description |
|---|---|---|---|
|  | 368 . . . 362(90) |  |  |
|  | 721 . . . 715(90) |  |  |
|  | 274 . . . 280(90) |  |  |
| M00100 | 1077 . . . 1071(100) | CdxA | CdxA |
| M00271 | 1933 . . . 1938(100) | AML-1a | runt-factor AML-1 |
|  | 2204 . . . 2209(92) |  |  |
| M00101 | 1077 . . . 1071(99) | CdxA | CdxA |
|  | 805 . . . 799(98) |  |  |
|  | 699 . . . 693(92) |  |  |
|  | 1384 . . . 1390(92) |  |  |
|  | 936 . . . 942(92) |  |  |
|  | 495 . . . 501(92) |  |  |
|  | 1660 . . . 1666(91) |  |  |
|  | 1666 . . . 1660(91) |  |  |
| M00076 | 716 . . . 707(98) | GATA-2 | GATA-binding factor 2 |
|  | 1910 . . . 1919(95) |  |  |
|  | 959 . . . 968(92) |  |  |
|  | 1679 . . . 1670(91) |  |  |
| M00285 | 1712 . . . 1724(96) | TCF11 | TCF11/KCR-F1/Nrf1 homodimers |
|  | 1087 . . . 1099(91) |  |  |
| M00272 | 1242 . . . 1251(96) | p53 | tumor suppressor p53 |
| M00253 | 135 . . . 142(96) | cap | cap signal for transcription initiation |
|  | 457 . . . 464(95) |  |  |
|  | 1871 . . . 1864(95) |  |  |
|  | 721 . . . 728(94) |  |  |
|  | 1461 . . . 1454(92) |  |  |
|  | 312 . . . 319(92) |  |  |
|  | 1989 . . . 1996(92) |  |  |
|  | 1855 . . . 1848(91) |  |  |
|  | 770 . . . 777(90) |  |  |
|  | 1793 . . . 1786(90) |  |  |
|  | 295 . . . 302(90) |  |  |
|  | 1274 . . . 1281(90) |  |  |
| M00106 | 627 . . . 636(95) | CDP | cut-like homeodomain protein |
|  | 634 . . . 625(93) |  |  |
| M00116 | 1215 . . . 1202(95) | C/EBPalpha | CCAAT/enhancer binding protein alpha |
| M00254 | 1809 . . . 1798(95) | CCAAT | cellular and viral CCAAT box |
| M00249 | 1117 . . . 1105(95) | CHOP-C/EBPalpha | heterodimers of CHOP and C/EBPalpha |
| M00054 | 442 . . . 433(95) | NF-kappaB | NF-kappaB |
| M00147 | 2182 . . . 2173(94) | HSF2 | heat shock factor 2 |
|  | 2173 . . . 2182(92) |  |  |
|  | 754 . . . 745(91) |  |  |
|  | 141 . . . 132(90) |  |  |
| M00104 | 634 . . . 625(94) | CDP | cut-like homeodomain protein |
|  | 2 . . . 11(92) |  |  |
| M00134 | 280 . . . 298(94) | HNF-4 | hepatic nuclear factor 4 |
| M00052 | 442 . . . 433(94) | NF-kappaB | NF-kappaB (p65) |
| M00053 | 442 . . . 433(94) | c-Rel | c-Rel |
|  | 785 . . . 794(90) |  |  |
| M00033 | 731 . . . 718(94) | p300 | p300 |
| M00158 | 295 . . . 282(93) | COUP-TF | COUP/HNF-4 heterodimer |
| M00032 | 225 . . . 216(93) | c-Ets-1(p54) | c-Ets-1(p54) |
|  | 226 . . . 235(93) |  |  |
| M00172 | 1851 . . . 1861(92) | AP-1 | activator protein 1 |
| M00223 | 520 . . . 512(92) | STATx | signal transducers and activators of transcription |
| M00075 | 1679 . . . 1670(92) | GATA-1 | GATA-binding factor 1 |
|  | 1867 . . . 1876(91) |  |  |
|  | 716 . . . 707(91) |  |  |
|  | 316 . . . 307(90) |  |  |
| M00184 | 1463 . . . 1472(91) | MyoD | myoblast determining factor |
|  | 1472 . . . 1463(91) |  |  |
|  | 247 . . . 256(90) |  |  |
|  | 2057 . . . 2048(90) |  |  |
| M00289 | 357 . . . 369(91) | HFH-3 | HNF-3/Fkh Homolog 3 (= Freac-6) |
| M00109 | 1202 . . . 1215(91) | C/EBPbeta | CCAAT/enhancer binding protein beta |
|  | 2036 . . . 2023(90) |  |  |
| M00268 | 937 . . . 950(91) | XFD-2 | Xenopus fork head domain factor 2 |
| M00208 | 443 . . . 432(90) | NF-kappaB | NF-kappaB binding site |
| M00173 | 1851 . . . 1861(90) | AP-1 | activator protein 1 |
| M00183 | 1002 . . . 1011(90) | c-Myb | c-Myb |
|  | 2020 . . . 2011(90) |  |  |
| M00240 | 217 . . . 211(90) | Nkx-2.5. | homeo domain factor Nkx-2.5/Csx, tinman homolog |
| M00188 | 1851 . . . 1861(90) | AP-1 | activator protein 1 |

TABLE 8-continued putative transcription factor binding motifs within the DUB regulatory or promoter, region of hDUB 4.2a. The position is indicated by nucleotides.

| Transfac | Position(Score) | Name | Description |
| --- | --- | --- | --- |
| M00099 | 1086 . . . 1101(90) | S8 | S8 |
| M00302 | 813 . . . 802(90) | NF-AT | Nuclear factor of activated T-cells |
| M00083 | 21 . . . 14(90) | MZF1 | MZF1 |
| M00190 | 1215 . . . 1202(90) | C/EBP | CCAAT/enhancer binding factor |
| M00221 | 1838 . . . 1828(90) | SREBP-1 | sterol regulatory element-binding protein 1 |
| M00294 | 949 . . . 937(90) | HFH-8 | HNF-3/Fkh Homolog-8 |
| M00137 | 1365 . . . 1353(90) | Oct-1 | octamer factor 1 |
| M00077 | 1911 . . . 1919(90) | GATA-3 | GATA-binding factor 3 |
| M00194 | 444 . . . 431(90) | NF-kappaB | NF-kappaB |

TABLE 9 putative transcription factor binding motifs within the DUB regulatory or promoter, region of hDUB 4.2b. The position is indicated by nucleotides.

| Transfac | Position(Score) | Name | Description |
| --- | --- | --- | --- |
| M00100 | 1102 . . . 1096(100) | CdxA | CdxA |
| M00148 | 1017 . . . 1011(100) | SRY | sex-determining region Y gene product |
| | 967 . . . 973(100) | | |
| | 944 . . . 938(96) | | |
| | 1566 . . . 1572(92) | | |
| | 1530 . . . 1536(92) | | |
| | 840 . . . 834(90) | | |
| | 1093 . . . 1099(90) | | |
| | 705 . . . 711(90) | | |
| | 1362 . . . 1356(90) | | |
| | 1719 . . . 1713(90) | | |
| | 1824 . . . 1818(90) | | |
| | 393 . . . 387(90) | | |
| | 746 . . . 740(90) | | |
| | 299 . . . 305(90) | | |
| M00253 | 1120 . . . 1127(99) | cap | cap signal for transcription initiation |
| | 160 . . . 167(96) | | |
| | 482 . . . 489(95) | | |
| | 1893 . . . 1886(95) | | |
| | 746 . . . 753(94) | | |
| | 1486 . . . 1479(92) | | |
| | 337 . . . 344(92) | | |
| | 1877 . . . 1870(91) | | |
| | 795 . . . 802(90) | | |
| | 1815 . . . 1808(90) | | |
| | 320 . . . 327(90) | | |
| | 1299 . . . 1306(90) | | |
| M00101 | 1102 . . . 1096(99) | CdxA | CdxA |
| | 830 . . . 824(98) | | |
| | 1231 . . . 1225(98) | | |
| | 1409 . . . 1415(92) | | |
| | 724 . . . 718(92) | | |
| | 520 . . . 526(92) | | |
| | 1682 . . . 1688(91) | | |
| | 1688 . . . 1682(91) | | |
| M00076 | 741 . . . 732(98) | GATA-2 | GATA-binding factor 2 |
| | 1932 . . . 1941(95) | | |
| | 984 . . . 993(92) | | |
| | 1701 . . . 1692(91) | | |
| M00285 | 1734 . . . 1746(96) | TCF11 | TCF11/KCR-F1/Nrf1 homodimers |
| | 1112 . . . 1124(91) | | |
| M00272 | 1267 . . . 1276(96) | p53 | tumor suppressor p53 |
| M00106 | 652 . . . 661(95) | CDP | cut-like homeodomain protein |
| | 659 . . . 650(93) | | |
| M00116 | 1240 . . . 1227(95) | C/EBPalpha | CCAAT/enhancer binding protein alpha |
| M00254 | 1831 . . . 1820(95) | CCAAT | cellular and viral CCAAT box |
| M00249 | 1142 . . . 1130(95) | CHOP-C/EBPalpha | heterodimers of CHOP and C/EBPalpha |
| M00054 | 467 . . . 458(95) | NF-kappaB | NF-kappaB |
| M00104 | 659 . . . 650(94) | CDP | cut-like homeodomain protein |
| | 27 . . . 36(92) | | |
| M00134 | 305 . . . 323(94) | HNF-4 | hepatic nuclear factor 4 |
| M00052 | 467 . . . 458(94) | NF-kappaB | NF-kappaB (p65) |
| M00053 | 467 . . . 458(94) | c-Rel | c-Rel |

TABLE 9-continued putative transcription factor binding motifs within the DUB regulatory or promoter, region of hDUB 4.2b. The position is indicated by nucleotides.

| Transfac | Position(Score) | Name | Description |
|---|---|---|---|
| M00033 | 756 . . . 743(94) | p300 | p300 |
| M00158 | 320 . . . 307(93) | COUP-TF | COUP/HNF-4 heterodimer |
| M00075 | 1889 . . . 1898(93) | GATA-1 | GATA-binding factor 1 |
|  | 1701 . . . 1692(92) |  |  |
|  | 741 . . . 732(91) |  |  |
|  | 341 . . . 332(90) |  |  |
|  | 641 . . . 632(90) |  |  |
| M00160 | 965 . . . 976(93) | SRY | sex-determining region Y gene product |
| M00032 | 250 . . . 241(93) | c-Ets- | c-Ets-1(p54) |
|  | 251 . . . 260(93) | 1(p54) |  |
| M00172 | 1873 . . . 1883(92) | AP-1 | activator protein 1 |
| M00223 | 545 . . . 537(92) | STATx | signal transducers and activators of transcription |
| M00271 | 1955 . . . 1960(92) | AML-1a | runt-factor AML-1 |
| M00184 | 1488 . . . 1497(91) | MyoD | myoblast determining factor |
|  | 1497 . . . 1488(91) |  |  |
|  | 272 . . . 281(90) |  |  |
| M00289 | 382 . . . 394(91) | HFH-3 | HNF-3/Fkh Homolog 3 (= Freac-6) |
| M00109 | 1227 . . . 1240(91) | C/EBPbeta | CCAAT/enhancer binding protein beta |
| M00147 | 779 . . . 770(91) | HSF2 | heat shock factor 2 |
|  | 166 . . . 157(90) |  |  |
| M00208 | 468 . . . 457(90) | NF-kappaB | NF-kappaB binding site |
| M00183 | 1027 . . . 1036(90) | c-Myb | c-Myb |
| M00173 | 1873 . . . 1883(90) | AP-1 | activator protein 1 |
| M00240 | 242 . . . 236(90) | Nkx-2.5 | homeo domain factor Nkx-2.5/Csx, tinman homolog |
| M00188 | 1873 . . . 1883(90) | AP-1 | activator protein 1 |
| M00302 | 838 . . . 827(90) | NF-AT | Nuclear factor of activated T-cells |
| M00083 | 46 . . . 39(90) | MZF1 | MZF1 |
| M00190 | 1240 . . . 1227(90) | C/EBP | CCAAT/enhancer binding factor |
| M00096 | 1115 . . . 1123(90) | Pbx-1 | Pbx-1 |
| M00221 | 1860 . . . 1850(90) | SREBP-1 | sterol regulatory element-binding protein 1 |
| M00194 | 469 . . . 456(90) | NF-kappaB | NF-kappaB |
| M00077 | 1933 . . . 1941(90) | GATA-3 | GATA-binding factor 3 |

TABLE 10 putative transcription factor binding motifs within the DUB regulatory or promoter, region of hDUB 4.3. The position is indicated by nucleotides.

| Transfac | Position(Score) | Name | Description |
|---|---|---|---|
| M00148 | 1015 . . . 1009(100) | SRY | sex-determining region Y gene product |
|  | 965 . . . 971(100) |  |  |
|  | 942 . . . 936(96) |  |  |
|  | 1566 . . . 1572(92) |  |  |
|  | 1528 . . . 1534(92) |  |  |
|  | 838 . . . 832(90) |  |  |
|  | 1091 . . . 1097(90) |  |  |
|  | 1219 . . . 1213(90) |  |  |
|  | 703 . . . 709(90) |  |  |
|  | 1360 . . . 1354(90) |  |  |
|  | 1719 . . . 1713(90) |  |  |
|  | 1824 . . . 1818(90) |  |  |
|  | 391 . . . 385(90) |  |  |
|  | 744 . . . 738(90) |  |  |
|  | 297 . . . 303(90) |  |  |
| M00100 | 1100 . . . 1094(100) | CdxA | CdxA |
| M00101 | 1100 . . . 1094(99) | CdxA | CdxA |
|  | 828 . . . 822(98) |  |  |
|  | 1407 . . . 1413(92) |  |  |
|  | 722 . . . 716(92) |  |  |
|  | 959 . . . 965(92) |  |  |
|  | 518 . . . 524(92) |  |  |
|  | 1682 . . . 1688(91) |  |  |
|  | 1688 . . . 1682(91) |  |  |
| M00076 | 739 . . . 730(98) | GATA-2 | GATA-binding factor 2 |
|  | 1932 . . . 1941(95) |  |  |
|  | 982 . . . 991(92) |  |  |
|  | 1701 . . . 1692(91) |  |  |
| M00285 | 1734 . . . 1746(96) | TCF11 | TCF11/KCR-F1/Nrf1 homodimers |
|  | 1110 . . . 1122(91) |  |  |

TABLE 10-continued putative transcription factor binding motifs within the DUB regulatory or promoter, region of hDUB 4.3. The position is indicated by nucleotides.

| Transfac | Position(Score) | Name | Description |
| --- | --- | --- | --- |
| M00272 | 1265 . . . 1274(96) | p53 | tumor suppressor p53 |
| M00253 | 158 . . . 165(96) | cap | cap signal for transcription initiation |
|  | 480 . . . 487(95) |  |  |
|  | 1893 . . . 1886(95) |  |  |
|  | 744 . . . 751(94) |  |  |
|  | 1484 . . . 1477(92) |  |  |
|  | 335 . . . 342(92) |  |  |
|  | 1877 . . . 1870(91) |  |  |
|  | 793 . . . 800(90) |  |  |
|  | 318 . . . 325(90) |  |  |
|  | 1297 . . . 1304(90) |  |  |
| M00106 | 650 . . . 659(95) | CDP | cut-like homeodomain protein |
|  | 657 . . . 648(93) |  |  |
| M00116 | 1238 . . . 1225(95) | C/EBPalpha | CCAAT/enhancer binding protein alpha |
| M00254 | 1831 . . . 1820(95) | CCAAT | cellular and viral CCAAT box |
| M00249 | 1140 . . . 1128(95) | CHOP-C/EBPalpha | heterodimers of CHOP and C/EBPalpha |
| M00054 | 465 . . . 456(95) | NF-kappaB | NF-kappaB |
| M00104 | 657 . . . 648(94) | CDP | cut-like homeodomain protein |
|  | 25 . . . 34(92) |  |  |
| M00134 | 303 . . . 321(94) | HNF-4 | hepatic nuclear factor 4 |
| M00052 | 465 . . . 456(94) | NF-kappaB | NF-kappaB (p65) |
| M00053 | 465 . . . 456(94) | c-Rel | c-Rel |
| M00033 | 754 . . . 741(94) | p300 | p300 |
| M00158 | 318 . . . 305(93) | COUP-TF | COUP/HNF-4 heterodimer |
| M00075 | 1889 . . . 1898(93) | GATA-1 | GATA-binding factor 1 |
|  | 1701 . . . 1692(92) |  |  |
|  | 739 . . . 730(91) |  |  |
|  | 339 . . . 330(90) |  |  |
| M00160 | 963 . . . 974(93) | SRY | sex-determining region Y gene product |
| M00032 | 248 . . . 239(93) | c-Ets-1(p54) | c-Ets-1(p54) |
|  | 249 . . . 258(93) |  |  |
| M00172 | 1873 . . . 1883(92) | AP-1 | activator protein 1 |
| M00223 | 543 . . . 535(92) | STATx | signal transducers and activators of transcription |
| M00271 | 1955 . . . 1960(92) | AML-1a | runt-factor AML-1 |
| M00173 | 1873 . . . 1883(91) | AP-1 | activator protein 1 |
| M00184 | 1486 . . . 1495(91) | MyoD | myoblast determining factor |
|  | 1495 . . . 1486(91) |  |  |
|  | 270 . . . 279(90) |  |  |
| M00289 | 380 . . . 392(91) | HFH-3 | HNF-3/Fkh Homolog 3 (= Freac-6) |
| M00109 | 1225 . . . 1238(91) | C/EBPbeta | CCAAT/enhancer binding protein beta |
| M00147 | 777 . . . 768(91) | HSF2 | heat shock factor 2 |
|  | 164 . . . 155(90) |  |  |
| M00208 | 466 . . . 455(90) | NF-kappaB | NF-kappaB binding site |
| M00183 | 1025 . . . 1034(90) | c-Myb | c-Myb |
| M00240 | 240 . . . 234(90) | Nkx-2.5 | homeo domain factor Nkx-2.5/Csx, tinman homolog |
| M00099 | 1109 . . . 1124(90) | S8 | S8 |
| M00302 | 836 . . . 825(90) | NF-AT | Nuclear factor of activated T-cells |
| M00083 | 44 . . . 37(90) | MZF1 | MZF1 |
| M00190 | 1238 . . . 1225(90) | C/EBP | CCAAT/enhancer binding factor |
| M00221 | 1860 . . . 1850(90) | SREBP-1 | sterol regulatory element-binding protein 1 |
| M00174 | 1873 . . . 1883(90) | AP-1 | activator protein 1 |
| M00077 | 1933 . . . 1941(90) | GATA-3 | GATA-binding factor 3 |
| M00194 | 467 . . . 454(90) | NF-kappaB | NF-kappaB |

TABLE 11 putative transcription factor binding motifs within the DUB regulatory or promoter, region of hDUB 4.4. The position is indicated by nucleotides.

| Transfac | Position(Score) | Name | Description |
| --- | --- | --- | --- |
| M00100 | 1101 . . . 1095(100) | CdxA | CdxA |
| M00148 | 1016 . . . 1010(100) | SRY | sex-determining region Y gene product |
|  | 966 . . . 972(100) |  |  |
|  | 944 . . . 938(96) |  |  |
|  | 1566 . . . 1572(92) |  |  |
|  | 1529 . . . 1535(92) |  |  |
|  | 840 . . . 834(90) |  |  |
|  | 1092 . . . 1098(90) |  |  |

TABLE 11-continued putative transcription factor binding motifs within the DUB regulatory or promoter, region of hDUB 4.4. The position is indicated by nucleotides.

| Transfac | Position(Score) | Name | Description |
|---|---|---|---|
| | 705 ... 711(90) | | |
| | 1361 ... 1355(90) | | |
| | 1719 ... 1713(90) | | |
| | 1824 ... 1818(90) | | |
| | 393 ... 387(90) | | |
| | 746 ... 740(90) | | |
| | 299 ... 305(90) | | |
| M00101 | 1101 ... 1095(99) | CdxA | CdxA |
| | 830 ... 824(98) | | |
| | 1230 ... 1224(98) | | |
| | 1408 ... 1414(92) | | |
| | 724 ... 718(92) | | |
| | 520 ... 526(92) | | |
| | 1682 ... 1688(91) | | |
| | 1688 ... 1682(91) | | |
| M00076 | 741 ... 732(98) | GATA-2 | GATA-binding factor 2 |
| | 1932 ... 1941(95) | | |
| | 983 ... 992(92) | | |
| | 1701 ... 1692(91) | | |
| M00350 | 876 ... 867(96) | GATA-3 | GATA-binding factor 3 |
| M00285 | 1734 ... 1746(96) | TCF11 | TCF11/KCR-F1/Nrf1 homodimers |
| | 1111 ... 1123(91) | | |
| M00272 | 1266 ... 1275(96) | p53 | tumor suppressor p53 |
| M00253 | 160 ... 167(96) | cap | cap signal for transcription initiation |
| | 482 ... 489(95) | | |
| | 1893 ... 1886(95) | | |
| | 746 ... 753(94) | | |
| | 1485 ... 1478(92) | | |
| | 337 ... 344(92) | | |
| | 1877 ... 1870(91) | | |
| | 795 ... 802(90) | | |
| | 1815 ... 1808(90) | | |
| | 320 ... 327(90) | | |
| | 1298 ... 1305(90) | | |
| M00106 | 652 ... 661(95) | CDP | cut-like homeodomain protein |
| | 659 ... 650(93) | | |
| M00116 | 1239 ... 1226(95) | C/EBPalpha | CCAAT/enhancer binding protein alpha |
| M00254 | 1831 ... 1820(95) | CCAAT | cellular and viral CCAAT box |
| M00249 | 1141 ... 1129(95) | CHOP-C/EBPalpha | heterodimers of CHOP and C/EBPalpha |
| M00349 | 876 ... 867(95) | GATA-2 | GATA-binding factor 2 |
| M00054 | 467 ... 458(95) | NF-kappaB | NF-kappaB |
| M00104 | 659 ... 650(94) | CDP | cut-like homeodomain protein |
| | 27 ... 36(92) | | |
| M00134 | 305 ... 323(94) | HNF-4 | hepatic nuclear factor 4 |
| M00052 | 467 ... 458(94) | NF-kappaB | NF-kappaB (p65) |
| M00053 | 467 ... 458(94) | c-Rel | c-Rel |
| M00033 | 756 ... 743(94) | p300 | p300 |
| M00348 | 876 ... 867(93) | GATA-2 | GATA-binding factor 2 |
| M00158 | 320 ... 307(93) | COUP-TF | COUP/HNF-4 heterodimer |
| M00075 | 1889 ... 1898(93) | GATA-1 | GATA-binding factor 1 |
| | 1701 ... 1692(92) | | |
| | 741 ... 732(91) | | |
| | 341 ... 332(90) | | |
| M00160 | 964 ... 975(93) | SRY | sex-determining region Y gene product |
| M00347 | 876 ... 867(93) | GATA-1 | GATA-binding factor 1 |
| M00032 | 250 ... 241(93) | c-Ets-1(p54) | c-Ets-1(p54) |
| | 251 ... 260(93) | | |
| M00172 | 1873 ... 1883(92) | AP-1 | activator protein 1 |
| M00223 | 545 ... 537(92) | STATx | signal transducers and activators of transcription |
| M00271 | 1955 ... 1960(92) | AML-1a | runt-factor AML-1 |
| M00184 | 1487 ... 1496(91) | MyoD | myoblast determining factor |
| | 1496 ... 1487(91) | | |
| | 272 ... 281(90) | | |
| M00289 | 382 ... 394(91) | HFH-3 | HNF-3/Fkh Homolog 3 (= Freac-6) |
| M00109 | 1226 ... 1239(91) | C/EBPbeta | CCAAT/enhancer binding protein beta |
| M00208 | 468 ... 457(90) | NF-kappaB | NF-kappaB binding site |
| M00183 | 1026 ... 1035(90) | c-Myb | c-Myb |
| M00173 | 1873 ... 1883(90) | AP-1 | activator protein 1 |
| M00240 | 242 ... 236(90) | Nkx-2.5 | homeo domain factor Nkx-2.5/Csx, tinman homolog |
| M00188 | 1873 ... 1883(90) | AP-1 | activator protein 1 |
| M00099 | 1110 ... 1125(90) | S8 | S8 |
| M00302 | 838 ... 827(90) | NF-AT | Nuclear factor of activated T-cells |

TABLE 11-continued putative transcription factor binding motifs within the DUB regulatory or promoter, region of hDUB 4.4. The position is indicated by nucleotides.

| Transfac | Position(Score) | Name | Description |
| --- | --- | --- | --- |
| M00083 | 46 . . . 39(90) | MZF1 | MZF1 |
| M00190 | 1239 . . . 1226(90) | C/EBP | CCAAT/enhancer binding factor |
| M00147 | 166 . . . 157(90) | HSF2 | heat shock factor 2 |
| M00080 | 874 . . . 864(90) | Evi-1 | ectopic viral integration site 1 encoded factor |
| M00082 | 874 . . . 864(90) | Evi-1 | ectopic viral integration site 1 encoded factor |
| M00221 | 1860 . . . 1850(90) | SREBP-1 | sterol regulatory element-binding protein 1 |
| M00194 | 469 . . . 456(90) | NF-kappaB | NF-kappaB |
| M00077 | 1933 . . . 1941(90) | GATA-3 | GATA-binding factor 3 |

TABLE 12 putative transcription factor binding motifs within the DUB regulatory or promoter, region of hDUB 4.5. The position is indicated by nucleotides.

| Transfac | Position(Score) | Name | Description |
| --- | --- | --- | --- |
| M00148 | 963 . . . 969(100) | SRY | sex-determining region Y gene product |
|  | 1013 . . . 1007(100) |  |  |
|  | 940 . . . 934(96) |  |  |
|  | 1526 . . . 1532(92) |  |  |
|  | 1089 . . . 1095(90) |  |  |
|  | 836 . . . 830(90) |  |  |
|  | 701 . . . 707(90) |  |  |
|  | 1358 . . . 1352(90) |  |  |
|  | 1720 . . . 1714(90) |  |  |
|  | 1825 . . . 1819(90) |  |  |
|  | 389 . . . 383(90) |  |  |
|  | 742 . . . 736(90) |  |  |
|  | 295 . . . 301(90) |  |  |
| M00100 | 1098 . . . 1092(100) | CdxA | CdxA |
| M00101 | 1098 . . . 1092(99) | CdxA | CdxA |
|  | 826 . . . 820(98) |  |  |
|  | 1405 . . . 1411(92) |  |  |
|  | 720 . . . 714(92) |  |  |
|  | 957 . . . 963(92) |  |  |
|  | 516 . . . 522(92) |  |  |
|  | 1683 . . . 1689(91) |  |  |
|  | 1689 . . . 1683(91) |  |  |
| M00076 | 737 . . . 728(98) | GATA-2 | GATA-binding factor 2 |
|  | 980 . . . 989(92) |  |  |
|  | 1702 . . . 1693(91) |  |  |
|  | 1299 . . . 1308(90) |  |  |
| M00285 | 1735 . . . 1747(96) | TCF11 | TCF11/KCR-F1/Nrf1 homodimers |
|  | 1108 . . . 1120(91) |  |  |
| M00272 | 1263 . . . 1272(96) | p53 | tumor suppressor p53 |
| M00253 | 156 . . . 163(96) | cap | cap signal for transcription initiation |
|  | 478 . . . 485(95) |  |  |
|  | 742 . . . 749(94) |  |  |
|  | 1482 . . . 1475(92) |  |  |
|  | 333 . . . 340(92) |  |  |
|  | 791 . . . 798(90) |  |  |
|  | 1816 . . . 1809(90) |  |  |
|  | 316 . . . 323(90) |  |  |
| M00106 | 648 . . . 657(95) | CDP | cut-like homeodomain protein |
|  | 655 . . . 646(93) |  |  |
| M00116 | 1236 . . . 1223(95) | C/EBPalpha | CCAAT/enhancer binding protein alpha |
| M00254 | 1832 . . . 1821(95) | CCAAT | cellular and viral CCAAT box |
| M00249 | 1138 . . . 1126(95) | CHOP-C/EBPalpha | heterodimers of CHOP and C/EBPalpha |
| M00054 | 463 . . . 454(95) | NF-kappaB | NF-kappaB |
| M00183 | 1493 . . . 1484(94) | c-Myb | c-Myb |
|  | 1023 . . . 1032(90) |  |  |
| M00104 | 655 . . . 646(94) | CDP | cut-like homeodomain protein |
|  | 23 . . . 32(92) |  |  |
| M00134 | 301 . . . 319(94) | HNF-4 | hepatic nuclear factor 4 |
| M00052 | 463 . . . 454(94) | NF-kappaB | NF-kappaB (p65) |
| M00053 | 463 . . . 454(94) | c-Rel | c-Rel |
|  | 806 . . . 815(90) |  |  |
| M00033 | 752 . . . 739(94) | p300 | p300 |
| M00158 | 316 . . . 303(93) | COUP-TF | COUP/HNF-4 heterodimer |
| M00032 | 246 . . . 237(93) | c-Ets- | c-Ets-1(p54) |

TABLE 12-continued putative transcription factor binding motifs within the DUB regulatory or promoter, region of hDUB 4.5. The position is indicated by nucleotides.

| Transfac | Position(Score) | Name | Description |
|---|---|---|---|
|  | 247 . . . 256(93) | 1(p54) |  |
| M00278 | 1300 . . . 1308(92) | Lmo2 | complex of Lmo2 bound to Tal-1, E2A proteins, and GATA-1, half-site 2 |
| M00223 | 541 . . . 533(92) | STATx | signal transducers and activators of transcription |
| M00075 | 1702 . . . 1693(92) | GATA-1 | GATA-binding factor 1 |
|  | 737 . . . 728(91) |  |  |
|  | 337 . . . 328(90) |  |  |
| M00077 | 1300 . . . 1308(91) | GATA-3 | GATA-binding factor 3 |
| M00289 | 378 . . . 390(91) | HFH-3 | HNF-3/Fkh Homolog 3 (= Freac-6) |
| M00109 | 1223 . . . 1236(91) | C/EBPbeta | CCAAT/enhancer binding protein beta |
| M00268 | 958 . . . 971(91) | XFD-2 | Xenopus fork head domain factor 2 |
| M00147 | 775 . . . 766(91) | HSF2 | heat shock factor 2 |
|  | 162 . . . 153(90) |  |  |
| M00208 | 464 . . . 453(90) | NF-kappaB | NF-kappaB binding site |
| M00240 | 238 . . . 232(90) | Nkx-2.5 | homeo domain factor Nkx-2.5/Csx, tinman homolog |
| M00099 | 1107 . . . 1122(90) | S8 | S8 |
| M00302 | 834 . . . 823(90) | NF-AT | Nuclear factor of activated T-cells |
| M00083 | 42 . . . 35(90) | MZF1 | MZF1 |
| M00184 | 268 . . . 277(90) | MyoD | myoblast determining factor |
| M00190 | 1236 . . . 1223(90) | C/EBP | CCAAT/enhancer binding factor |
| M00221 | 1861 . . . 1851(90) | SREBP-1 | sterol regulatory element-binding protein 1 |
| M00294 | 970 . . . 958(90) | HFH-8 | HNF-3/Fkh Homolog-8 |
| M00137 | 1386 . . . 1374(90) | Oct-1 | octamer factor 1 |
| M00194 | 465 . . . 452(90) | NF-kappaB | NF-kappaB |

TABLE 13 putative transcription factor binding motifs within the DUB regulatory or promoter, region of hDUB 8.1. The position is indicated by nucleotides.

| Transfac | Position(Score) | Name | Description |
|---|---|---|---|
| M00148 | 1015 . . . 1009(100) | SRY | sex-determining region Y gene product |
|  | 965 . . . 971(100) |  |  |
|  | 942 . . . 936(96) |  |  |
|  | 1544 . . . 1550(92) |  |  |
|  | 838 . . . 832(90) |  |  |
|  | 702 . . . 708(90) |  |  |
|  | 1719 . . . 1713(90) |  |  |
|  | 1824 . . . 1818(90) |  |  |
|  | 390 . . . 384(90) |  |  |
|  | 1384 . . . 1390(90) |  |  |
|  | 1356 . . . 1350(90) |  |  |
|  | 296 . . . 302(90) |  |  |
|  | 63 . . . 69(90) |  |  |
| M00100 | 1100 . . . 1094(100) | CdxA | CdxA |
|  | 724 . . . 730(96) |  |  |
|  | 1547 . . . 1541(91) |  |  |
| M00349 | 93 . . . 102(100) | GATA-2 | GATA-binding factor 2 |
| M00350 | 93 . . . 102(100) | GATA-3 | GATA-binding factor 3 |
| M00241 | 1800 . . . 1807(100) | Nkx-2.5 | homeo domain factor Nkx-2.5/Csx, tinman homolog |
| M00348 | 93 . . . 102(100) | GATA-2 | GATA-binding factor 2 |
| M00101 | 1100 . . . 1094(99) | CdxA | CdxA |
|  | 828 . . . 822(98) |  |  |
|  | 1229 . . . 1223(98) |  |  |
|  | 1203 . . . 1209(94) |  |  |
|  | 721 . . . 715(92) |  |  |
|  | 959 . . . 965(92) |  |  |
|  | 1386 . . . 1380(92) |  |  |
|  | 65 . . . 59(92) |  |  |
|  | 517 . . . 523(92) |  |  |
|  | 419 . . . 425(92) |  |  |
|  | 1682 . . . 1688(91) |  |  |
|  | 1688 . . . 1682(91) |  |  |
| M00203 | 95 . . . 105(98) | GATA-X | GATA binding site |
| M00347 | 93 . . . 102(97) | GATA-1 | GATA-binding factor 1 |
| M00075 | 1838 . . . 1847(97) | GATA-1 | GATA-binding factor 1 |
|  | 1701 . . . 1692(95) |  |  |
|  | 137 . . . 128(92) |  |  |
|  | 1483 . . . 1492(92) |  |  |
|  | 1889 . . . 1898(91) |  |  |

TABLE 13-continued putative transcription factor binding motifs within the DUB regulatory or promoter, region of hDUB 8.1. The position is indicated by nucleotides.

| Transfac | Position(Score) | Name | Description |
|---|---|---|---|
|  | 1736 ... 1745(90) |  |  |
| M00158 | 317 ... 304(96) | COUP-TF | COUP/HNF-4 heterodimer |
| M00253 | 158 ... 165(96) | cap | cap signal for transcription initiation |
|  | 1794 ... 1801(95) |  |  |
|  | 479 ... 486(95) |  |  |
|  | 1297 ... 1304(93) |  |  |
|  | 337 ... 344(93) |  |  |
|  | 48 ... 55(93) |  |  |
|  | 1484 ... 1477(92) |  |  |
|  | 1324 ... 1317(91) |  |  |
|  | 557 ... 564(91) |  |  |
|  | 1893 ... 1886(91) |  |  |
|  | 1877 ... 1870(91) |  |  |
|  | 793 ... 800(90) |  |  |
|  | 1356 ... 1363(90) |  |  |
|  | 1815 ... 1808(90) |  |  |
|  | 317 ... 324(90) |  |  |
| M00285 | 1734 ... 1746(95) | TCF11 | TCF11/KCR-F1/Nrf1 homodimers |
|  | 1110 ... 1122(91) |  |  |
|  | 13 ... 1(90) |  |  |
| M00134 | 302 ... 320(95) | HNF-4 | hepatic nuclear factor 4 |
| M00077 | 1933 ... 1941(95) | GATA-3 | GATA-binding factor 3 |
| M00096 | 1827 ... 1819(95) | Pbx-1 | Pbx-1 |
| M00141 | 451 ... 459(94) | Lyf-1 | LyF-1 |
| M00199 | 1797 ... 1789(94) | AP-1 | AP-1 binding site |
|  | 1789 ... 1797(91) |  |  |
| M00174 | 1788 ... 1798(94) | AP-1 | activator protein 1 |
| M00076 | 1483 ... 1492(93) | GATA-2 | GATA-binding factor 2 |
|  | 1932 ... 1941(93) |  |  |
|  | 1701 ... 1692(92) |  |  |
|  | 982 ... 991(92) |  |  |
| M00278 | 1933 ... 1941(93) | Lmo2 | complex of Lmo2 bound to Tal-1, E2A proteins, and GATA-1, half-site 2 |
| M00099 | 1813 ... 1798(92) | S8 | S8 |
|  | 1109 ... 1124(90) |  |  |
| M00294 | 1551 ... 1539(92) | HFH-8 | HNF-3/Fkh Homolog-8 |
| M00223 | 542 ... 534(92) | STATx | signal transducers and activators of transcription |
| M00073 | 36 ... 46(92) | deltaEF1 | deltaEF1 |
| M00271 | 1955 ... 1960(92) | AML-1a | runt-factor AML-1 |
|  | 132 ... 127(92) |  |  |
| M00137 | 335 ... 323(91) | Oct-1 | octamer factor 1 |
| M00042 | 644 ... 653(91) | Sox-5 | Sox-5 |
|  | 1829 ... 1820(90) |  |  |
| M00289 | 379 ... 391(91) | HFH-3 | HNF-3/Fkh Homolog 3 (= Freac-6) |
| M00183 | 1025 ... 1034(90) | c-Myb | c-Myb |
| M00240 | 239 ... 233(90) | Nkx-2.5 | homeo domain factor Nkx-2.5/Csx, tinman homolog |
| M00188 | 1788 ... 1798(90) | AP-1 | activator protein 1 |
| M00302 | 836 ... 825(90) | NF-AT | Nuclear factor of activated T-cells |
| M00128 | 92 ... 104(90) | GATA-1 | GATA-binding factor 1 |
| M00184 | 269 ... 278(90) | MyoD | myoblast determining factor |
| M00147 | 164 ... 155(90) | HSF2 | heat shock factor 2 |
| M00087 | 979 ... 990(90) | Ik-2 | Ikaros 2 |
| M00172 | 1788 ... 1798(90) | AP-1 | activator protein 1 |
| M00221 | 1860 ... 1850(90) | SREBP-1 | sterol regulatory element-binding protein 1 |

TABLE 14 putative transcription factor binding motifs within the DUB regulatory or promoter, region of hDUB 8.2. The position is indicated by nucleotides.

| Transfac | Position(Score) | Name | Description |
|---|---|---|---|
| M00241 | 1804 ... 1811(100) | Nkx-2.5 | homeo domain factor Nkx-2.5/Csx, tinman homolog |
| M00240 | 556 ... 562(100) | Nkx-2.5 | homeo domain factor Nkx-2.5/Csx, tinman homolog |
|  | 1354 ... 1360(90) |  |  |
|  | 301 ... 307(90) |  |  |
| M00096 | 1342 ... 1350(100) | Pbx-1 | Pbx-1 |
|  | 1831 ... 1823(96) |  |  |
| M00271 | 702 ... 707(100) | AML-1a | runt-factor AML-1 |
|  | 1955 ... 1960(92) |  |  |

TABLE 14-continued putative transcription factor binding motifs within the DUB regulatory or promoter, region of hDUB 8.2. The position is indicated by nucleotides.

| Transfac | Position(Score) | Name | Description |
|---|---|---|---|
|  | 170 . . . 175(92) |  |  |
| M00050 | 104 . . . 111(100) | E2F | E2F |
| M00148 | 1271 . . . 1277(100) | SRY | sex-determining region Y gene product |
|  | 1572 . . . 1578(92) |  |  |
|  | 1345 . . . 1351(90) |  |  |
|  | 1719 . . . 1713(90) |  |  |
|  | 1828 . . . 1822(90) |  |  |
|  | 1634 . . . 1628(90) |  |  |
| M00272 | 472 . . . 463(97) | p53 | tumor suppressor p53 |
|  | 463 . . . 472(97) |  |  |
|  | 295 . . . 286(91) |  |  |
| M00075 | 1842 . . . 1851(97) | GATA-1 | GATA-binding factor 1 |
|  | 1893 . . . 1902(93) |  |  |
|  | 1380 . . . 1371(92) |  |  |
|  | 1740 . . . 1749(90) |  |  |
| M00253 | 1072 . . . 1065(96) | cap | cap signal for transcription initiation |
|  | 1798 . . . 1805(95) |  |  |
|  | 1897 . . . 1890(95) |  |  |
|  | 769 . . . 776(92) |  |  |
|  | 1701 . . . 1708(92) |  |  |
|  | 1881 . . . 1874(91) |  |  |
|  | 497 . . . 504(90) |  |  |
|  | 1819 . . . 1812(90) |  |  |
|  | 21 . . . 28(90) |  |  |
| M00285 | 1738 . . . 1750(95) | TCF11 | TCF11/KCR-F1/Nrf1 homodimers |
|  | 366 . . . 378(93) |  |  |
| M00077 | 1933 . . . 1941(95) | GATA-3 | GATA-binding factor 3 |
| M00147 | 148 . . . 139(94) | HSF2 | heat shock factor 2 |
|  | 139 . . . 148(92) |  |  |
| M00199 | 1801 . . . 1793(94) | AP-1 | AP-1 binding site |
|  | 1037 . . . 1029(94) |  |  |
|  | 1793 . . . 1801(91) |  |  |
|  | 1029 . . . 1037(90) |  |  |
| M00174 | 1792 . . . 1802(94) | AP-1 | activator protein 1 |
|  | 1038 . . . 1028(92) |  |  |
| M00074 | 1247 . . . 1259(93) | c-Ets-1(p54) | c-Ets-1(p54) |
| M00211 | 702 . . . 710(93) | Poly | Retroviral Poly A downstream element |
|  | 1531 . . . 1539(91) |  |  |
| M00124 | 1339 . . . 1353(93) | Pbx1b | homeo domain factor Pbx-1 |
| M00278 | 1933 . . . 1941(93) | Lmo2 | complex of Lmo2 bound to Tal-1, E2A proteins, and GATA-1, half-site 2 |
| M00052 | 1261 . . . 1252(93) | NF-kappaB | NF-kappaB (p65) |
| M00076 | 1932 . . . 1941(93) | GATA-2 | GATA-binding factor 2 |
|  | 837 . . . 828(90) |  |  |
| M00099 | 1817 . . . 1802(92) | S8 | S8 |
| M00101 | 987 . . . 981(92) | CdxA | CdxA |
| M00042 | 1635 . . . 1626(92) | Sox-5 | Sox-5 |
| M00254 | 1835 . . . 1824(91) | CCAAT | cellular and viral CCAAT box |
| M00008 | 252 . . . 243(91) | Sp1 | stimulating protein 1 |
|  | 1323 . . . 1314(91) |  |  |
| M00227 | 933 . . . 941(90) | v-Myb | v-Myb |
| M00141 | 1328 . . . 1320(90) | Lyf-1 | LyF-1 |
| M00183 | 1033 . . . 1042(90) | c-Myb | c-Myb |
| M00001 | 654 . . . 665(90) | MyoD | myoblast determination gene product |
| M00188 | 1792 . . . 1802(90) | AP-1 | activator protein 1 |
| M00184 | 23 . . . 14(90) | MyoD | myoblast determining factor |
| M00172 | 1792 . . . 1802(90) | AP-1 | activator protein 1 |
| M00221 | 1864 . . . 1854(90) | SREBP-1 | sterol regulatory element-binding protein 1 |
| M00037 | 871 . . . 861(90) | NF-E2 | NF-E2 p45 |
| M00053 | 1261 . . . 1252(90) | c-Rel | c-Rel |
| M00249 | 823 . . . 835(90) | CHOP-C/EBPalpha | heterodimers of CHOP and C/EBPalpha |
| M00302 | 1248 . . . 1259(90) | NF-AT | Nuclear factor of activated T-cells |

TABLE 15 putative transcription factor binding motifs within the DUB regulatory or promoter, region of hDUB 8.3. The position is indicated by nucleotides.

| Transfac | Position(Score) | Name | Description |
|---|---|---|---|
| M00348 | 71 ... 80(100) | GATA-2 | GATA-binding factor 2 |
| M00349 | 71 ... 80(100) | GATA-2 | GATA-binding factor 2 |
| M00148 | 990 ... 984(100) | SRY | sex-determining region Y gene product |
|  | 1654 ... 1648(100) |  |  |
|  | 813 ... 807(96) |  |  |
|  | 917 ... 911(96) |  |  |
|  | 1848 ... 1854(92) |  |  |
|  | 1840 ... 1846(92) |  |  |
|  | 1826 ... 1832(92) |  |  |
|  | 1504 ... 1498(92) |  |  |
|  | 1391 ... 1397(90) |  |  |
|  | 680 ... 686(90) |  |  |
|  | 2094 ... 2088(90) |  |  |
|  | 368 ... 362(90) |  |  |
|  | 721 ... 715(90) |  |  |
|  | 1002 ... 996(90) |  |  |
|  | 1900 ... 1894(90) |  |  |
|  | 274 ... 280(90) |  |  |
| M00350 | 71 ... 80(100) | GATA-3 | GATA-binding factor 3 |
| M00100 | 595 ... 589(100) | CdxA | CdxA |
|  | 1400 ... 1394(100) |  |  |
| M00101 | 595 ... 589(99) | CdxA | CdxA |
|  | 1400 ... 1394(99) |  |  |
|  | 803 ... 797(98) |  |  |
|  | 1527 ... 1521(98) |  |  |
|  | 1705 ... 1711(92) |  |  |
|  | 699 ... 693(92) |  |  |
|  | 934 ... 940(92) |  |  |
|  | 43 ... 37(92) |  |  |
|  | 495 ... 501(92) |  |  |
|  | 397 ... 403(92) |  |  |
| M00141 | 1274 ... 1266(98) | Lyf-1 | LyF-1 |
| M00347 | 71 ... 80(97) | GATA-1 | GATA-binding factor 1 |
| M00272 | 1563 ... 1572(96) | p53 | tumor suppressor p53 |
| M00253 | 1128 ... 1135(96) | cap | cap signal for transcription initiation |
|  | 136 ... 143(96) |  |  |
|  | 2064 ... 2071(95) |  |  |
|  | 457 ... 464(95) |  |  |
|  | 2163 ... 2156(95) |  |  |
|  | 721 ... 728(94) |  |  |
|  | 660 ... 653(94) |  |  |
|  | 1782 ... 1775(92) |  |  |
|  | 312 ... 319(92) |  |  |
|  | 1622 ... 1615(91) |  |  |
|  | 535 ... 542(91) |  |  |
|  | 2085 ... 2078(91) |  |  |
|  | 2147 ... 2140(91) |  |  |
|  | 1350 ... 1357(91) |  |  |
|  | 768 ... 775(90) |  |  |
|  | 295 ... 302(90) |  |  |
| M00285 | 2004 ... 2016(95) | TCF11 | TCF11/KCR-F1/Nrf1 homodimers |
|  | 1410 ... 1422(91) |  |  |
| M00254 | 2101 ... 2090(95) | CCAAT | cellular and viral CCAAT box |
| M00130 | 1647 ... 1658(95) | HFH-2 | HNF-3/Fkh Homolog 2 |
| M00054 | 442 ... 433(95) | NF-kappaB | NF-kappaB |
| M00077 | 2203 ... 2211(95) | GATA-3 | GATA-binding factor 3 |
| M00052 | 442 ... 433(94) | NF-kappaB | NF-kappaB (p65) |
| M00203 | 73 ... 83(94) | GATA-X | GATA binding site |
| M00199 | 2067 ... 2059(94) | AP-1 | AP-1 binding site |
|  | 2059 ... 2067(91) |  |  |
|  | 1984 ... 1992(90) |  |  |
| M00174 | 2058 ... 2068(94) | AP-1 | activator protein 1 |
| M00075 | 895 ... 886(94) | GATA-1 | GATA-binding factor 1 |
|  | 2159 ... 2168(93) |  |  |
|  | 1082 ... 1073(93) |  |  |
|  | 1971 ... 1962(92) |  |  |
|  | 2006 ... 2015(90) |  |  |
| M00053 | 442 ... 433(94) | c-Rel | c-Rel |
| M00241 | 2070 ... 2077(94) | Nkx-2.5 | homeo domain factor Nkx-2.5/Csx, tinman homolog |
| M00076 | 716 ... 707(94) | GATA-2 | GATA-binding factor 2 |
|  | 1599 ... 1608(92) |  |  |
|  | 957 ... 966(92) |  |  |
|  | 895 ... 886(91) |  |  |
|  | 1971 ... 1962(91) |  |  |

TABLE 15-continued putative transcription factor binding motifs within the DUB regulatory or promoter, region of hDUB 8.3. The position is indicated by nucleotides.

| Transfac | Position(Score) | Name | Description |
| --- | --- | --- | --- |
| M00106 | 627 ... 636(94) | CDP | cut-like homeodomain protein |
| M00033 | 731 ... 718(94) | p300 | p300 |
| M00227 | 2139 ... 2131(94) | v-Myb | v-Myb |
| M00158 | 295 ... 282(93) | COUP-TF | COUP/HNF-4 heterodimer |
| M00162 | 2070 ... 2083(93) | Oct-1 | octamer-binding factor 1 |
| M00134 | 280 ... 298(93) | HNF-4 | hepatic nuclear factor 4 |
| M00032 | 226 ... 235(93) | c-Ets-1(p54) | c-Ets-1(p54) |
| M00117 | 1080 ... 1067(92) | C/EBPbeta | CCAAT/enhancer binding protein beta |
| M00223 | 520 ... 512(92) | STATx | signal transducers and activators of transcription |
| M00042 | 1901 ... 1892(92) | Sox-5 | Sox-5 |
|  | 622 ... 631(91) |  |  |
| M00073 | 13 ... 23(92) | deltaEF1 | deltaEF1 |
| M00099 | 2083 ... 2068(91) | S8 | S8 |
|  | 2066 ... 2081(90) |  |  |
|  | 1409 ... 1424(90) |  |  |
| M00289 | 1647 ... 1659(91) | HFH-3 | HNF-3/Fkh Homolog 3 (= Freac-6) |
|  | 357 ... 369(91) |  |  |
| M00147 | 752 ... 743(91) | HSF2 | heat shock factor 2 |
|  | 142 ... 133(90) |  |  |
| M00208 | 443 ... 432(90) | NF-kappaB | NF-kappaB binding site |
| M00217 | 115 ... 108(90) | USF | USF binding site |
| M00183 | 1325 ... 1334(90) | c-Myb | c-Myb |
| M00240 | 217 ... 211(90) | Nkx-2.5 | homeo domain factor Nkx-2.5/Csx, tinman homolog |
| M00188 | 2058 ... 2068(90) | AP-1 | activator protein 1 |
| M00184 | 1955 ... 1964(90) | MyoD | myoblast determining factor |
|  | 247 ... 256(90) |  |  |
| M00087 | 954 ... 965(90) | Ik-2 | Ikaros 2 |
| M00128 | 70 ... 82(90) | GATA-1 | GATA-binding factor 1 |
| M00172 | 2058 ... 2068(90) | AP-1 | activator protein 1 |
| M00145 | 1339 ... 1354(90) | Brn-2 | POU factor Brn-2 |
| M00062 | 1217 ... 1205(90) | IRF-1 | interferon regulatory factor 1 |
| M00194 | 444 ... 431(90) | NF-kappaB | NF-kappaB |

TABLE 16 putative transcription factor binding motifs within the DUB regulatory or promoter, region of hDUB 8.4. The position is indicated by nucleotides.

| Transfac | Position(Score) | Name | Description |
| --- | --- | --- | --- |
| M00100 | 1105 ... 1099(100) | CdxA | CdxA |
| M00241 | 1800 ... 1807(100) | Nkx-2.5 | homeo domain factor Nkx-2.5/Csx, tinman homolog |
| M00148 | 1020 ... 1014(100) | SRY | sex-determining region Y gene product |
|  | 970 ... 976(100) |  |  |
|  | 947 ... 941(96) |  |  |
|  | 1550 ... 1556(92) |  |  |
|  | 843 ... 837(90) |  |  |
|  | 707 ... 713(90) |  |  |
|  | 1362 ... 1356(90) |  |  |
|  | 1719 ... 1713(90) |  |  |
|  | 1824 ... 1818(90) |  |  |
|  | 395 ... 389(90) |  |  |
|  | 748 ... 742(90) |  |  |
|  | 300 ... 306(90) |  |  |
| M00101 | 1105 ... 1099(99) | CdxA | CdxA |
|  | 833 ... 827(98) |  |  |
|  | 1385 ... 1379(98) |  |  |
|  | 1409 ... 1415(92) |  |  |
|  | 964 ... 970(92) |  |  |
|  | 726 ... 720(92) |  |  |
|  | 424 ... 430(92) |  |  |
| M00075 | 1838 ... 1847(97) | GATA-1 | GATA-binding factor 1 |
|  | 1889 ... 1898(93) |  |  |
|  | 925 ... 916(93) |  |  |
|  | 1736 ... 1745(90) |  |  |
| M00272 | 1267 ... 1276(96) | p53 | tumor suppressor p53 |
| M00253 | 161 ... 168(96) | cap | cap signal for transcription initiation |
|  | 1794 ... 1801(95) |  |  |
|  | 484 ... 491(95) |  |  |
|  | 1893 ... 1886(95) |  |  |
|  | 1452 ... 1459(94) |  |  |

TABLE 16-continued putative transcription factor binding motifs within the DUB regulatory or promoter, region of hDUB 8.4. The position is indicated by nucleotides.

| Transfac | Position(Score) | Name | Description |
|---|---|---|---|
|  | 798 . . . 805(94) |  |  |
|  | 748 . . . 755(94) |  |  |
|  | 957 . . . 964(94) |  |  |
|  | 1486 . . . 1479(92) |  |  |
|  | 338 . . . 345(92) |  |  |
|  | 1697 . . . 1704(92) |  |  |
|  | 562 . . . 569(91) |  |  |
|  | 1877 . . . 1870(91) |  |  |
|  | 1815 . . . 1808(90) |  |  |
|  | 321 . . . 328(90) |  |  |
|  | 1326 . . . 1319(90) |  |  |
|  | 1299 . . . 1306(90) |  |  |
| M00096 | 1827 . . . 1819(96) | Pbx-1 | Pbx-1 |
| M00285 | 1734 . . . 1746(95) | TCF11 | TCF11/KCR-F1/Nrf1 homodimers |
|  | 1115 . . . 1127(91) |  |  |
| M00077 | 1933 . . . 1941(95) | GATA-3 | GATA-binding factor 3 |
| M00054 | 469 . . . 460(95) | NF-kappaB | NF-kappaB |
| M00141 | 456 . . . 464(94) | Lyf-1 | LyF-1 |
| M00134 | 306 . . . 324(94) | HNF-4 | hepatic nuclear factor 4 |
| M00052 | 469 . . . 460(94) | NF-kappaB | NF-kappaB (p65) |
| M00199 | 1797 . . . 1789(94) | AP-1 | AP-1 binding site |
|  | 1789 . . . 1797(91) |  |  |
| M00174 | 1788 . . . 1798(94) | AP-1 | activator protein 1 |
| M00053 | 469 . . . 460(94) | c-Rel | c-Rel |
| M00033 | 758 . . . 745(94) | p300 | p300 |
|  | 808 . . . 795(92) |  |  |
| M00158 | 321 . . . 308(93) | COUP-TF | COUP/HNF-4 heterodimer |
| M00278 | 1933 . . . 1941(93) | Lmo2 | complex of Lmo2 bound to Tal-1, E2A proteins, and GATA-1, half-site 2 |
| M00076 | 1932 . . . 1941(93) | GATA-2 | GATA-binding factor 2 |
|  | 1303 . . . 1312(92) |  |  |
|  | 743 . . . 734(92) |  |  |
|  | 987 . . . 996(92) |  |  |
|  | 925 . . . 916(90) |  |  |
| M00099 | 1813 . . . 1798(92) | S8 | S8 |
|  | 1114 . . . 1129(90) |  |  |
| M00104 | 28 . . . 37(92) | CDP | cut-like homeodomain protein |
| M00223 | 547 . . . 539(92) | STATx | signal transducers and activators of transcription |
| M00271 | 1955 . . . 1960(92) | AML-1a | runt-factor AML-1 |
| M00254 | 1831 . . . 1820(91) | CCAAT | cellular and viral CCAAT box |
| M00042 | 649 . . . 658(91) | Sox-5 | Sox-5 |
| M00289 | 384 . . . 396(91) | HFH-3 | HNF-3/Fkh Homolog 3 (= Freac-6) |
| M00302 | 1384 . . . 1395(91) | NF-AT | Nuclear factor of activated T-cells |
|  | 841 . . . 830(90) |  |  |
| M00155 | 367 . . . 382(91) | ARP-1 | apolipoprotein AI regulatory protein 1 |
| M00208 | 470 . . . 459(90) | NF-kappaB | NF-kappaB binding site |
| M00183 | 1030 . . . 1039(90) | c-Myb | c-Myb |
| M00240 | 243 . . . 237(90) | Nkx-2.5 | homeo domain factor Nkx-2.5/Csx, tinman homolog |
|  | 1454 . . . 1448(90) |  |  |
| M00188 | 1788 . . . 1798(90) | AP-1 | activator protein 1 |
| M00083 | 47 . . . 40(90) | MZF1 | MZF1 |
| M00184 | 273 . . . 282(90) | MyoD | myoblast determining factor |
| M00147 | 167 . . . 158(90) | HSF2 | heat shock factor 2 |
| M00087 | 984 . . . 995(90) | Ik-2 | Ikaros 2 |
| M00172 | 1788 . . . 1798(90) | AP-1 | activator protein 1 |
| M00221 | 1860 . . . 1850(90) | SREBP-1 | sterol regulatory element-binding protein 1 |
| M00194 | 471 . . . 458(90) | NF-kappaB | NF-kappaB |

TABLE 17 putative transcription factor binding motifs within the DUB regulatory or promoter, region of hDUB 8.5. The position is indicated by nucleotides.

| Transfac | Position(Score) | Name | Description |
|---|---|---|---|
| M00100 | 1105 . . . 1099(100) | CdxA | CdxA |
| M00241 | 1800 . . . 1807(100) | Nkx-2.5 | homeo domain factor Nkx-2.5/Csx, tinman homolog |
| M00271 | 27 . . . 32(100) | AML-1a | runt-factor AML-1 |
|  | 1955 . . . 1960(92) |  |  |
| M00148 | 1020 . . . 1014(100) | SRY | sex-determining region Y gene product |
|  | 970 . . . 976(100) |  |  |

TABLE 17-continued putative transcription factor binding motifs within the DUB regulatory or promoter, region of hDUB 8.5. The position is indicated by nucleotides.

| Transfac | Position(Score) | Name | Description |
|---|---|---|---|
| | 947 ... 941(96) | | |
| | 1553 ... 1559(92) | | |
| | 100 ... 106(92) | | |
| | 141 ... 135(90) | | |
| | 843 ... 837(90) | | |
| | 1365 ... 1359(90) | | |
| | 1719 ... 1713(90) | | |
| | 1824 ... 1818(90) | | |
| M00101 | 1105 ... 1099(99) | CdxA | CdxA |
| | 833 ... 827(98) | | |
| | 1234 ... 1228(98) | | |
| | 1388 ... 1382(98) | | |
| | 1300 ... 1294(93) | | |
| | 1412 ... 1418(92) | | |
| | 964 ... 970(92) | | |
| | 1682 ... 1688(91) | | |
| | 1688 ... 1682(91) | | |
| M00278 | 618 ... 610(98) | Lmo2 | complex of Lmo2 bound to Tal-1, E2A proteins, and GATA-1, half-site 2 |
| | 1933 ... 1941(93) | | |
| M00075 | 1838 ... 1847(97) | GATA-1 | GATA-binding factor 1 |
| | 619 ... 610(97) | | |
| | 1701 ... 1692(95) | | |
| | 1889 ... 1898(93) | | |
| | 903 ... 894(91) | | |
| | 1736 ... 1745(90) | | |
| M00054 | 442 ... 451(96) | NF-kappaB | NF-kappaB |
| | 451 ... 442(91) | | |
| M00253 | 175 ... 168(96) | cap | cap signal for transcription initiation |
| | 1794 ... 1801(95) | | |
| | 1893 ... 1886(95) | | |
| | 1455 ... 1462(94) | | |
| | 798 ... 805(94) | | |
| | 629 ... 636(94) | | |
| | 1489 ... 1482(92) | | |
| | 433 ... 426(92) | | |
| | 1329 ... 1322(91) | | |
| | 1877 ... 1870(91) | | |
| | 921 ... 928(91) | | |
| | 957 ... 964(90) | | |
| | 1815 ... 1808(90) | | |
| | 1302 ... 1309(90) | | |
| M00272 | 1270 ... 1279(96) | p53 | tumor suppressor p53 |
| M00096 | 1827 ... 1819(96) | Pbx-1 | Pbx-1 |
| M00285 | 1734 ... 1746(95) | TCF11 | TCF11/KCR-F1/Nrf1 homodimers |
| | 1115 ... 1127(91) | | |
| | 1490 ... 1478(91) | | |
| M00076 | 619 ... 610(95) | GATA-2 | GATA-binding factor 2 |
| | 1932 ... 1941(93) | | |
| | 1701 ... 1692(92) | | |
| | 1306 ... 1315(92) | | |
| | 987 ... 996(92) | | |
| M00077 | 1933 ... 1941(95) | GATA-3 | GATA-binding factor 3 |
| | 618 ... 610(92) | | |
| M00199 | 1797 ... 1789(94) | AP-1 | AP-1 binding site |
| | 1789 ... 1797(91) | | |
| M00174 | 1788 ... 1798(94) | AP-1 | activator protein 1 |
| M00083 | 566 ... 559(93) | MZF1 | MZF1 |
| M00099 | 1813 ... 1798(92) | S8 | S8 |
| | 1114 ... 1129(90) | | |
| M00208 | 441 ... 452(92) | NF-kappaB | NF-kappaB binding site |
| M00033 | 808 ... 795(92) | p300 | p300 |
| M00227 | 1677 ... 1669(91) | v-Myb | v-Myb |
| M00254 | 1831 ... 1820(91) | CCAAT | cellular and viral CCAAT box |
| M00183 | 166 ... 157(91) | c-Myb | c-Myb |
| | 1030 ... 1039(90) | | |
| M00267 | 102 ... 89(91) | XFD-1 | Xenopus fork head domain factor 1 |
| M00240 | 1457 ... 1451(90) | Nkx-2.5 | homeo domain factor Nkx-2.5/Csx, tinman homolog |
| | 296 ... 302(90) | | |
| M00188 | 1788 ... 1798(90) | AP-1 | activator protein 1 |
| M00302 | 841 ... 830(90) | NF-AT | Nuclear factor of activated T-cells |
| M00087 | 984 ... 995(90) | Ik-2 | Ikaros 2 |
| M00172 | 1788 ... 1798(90) | AP-1 | activator protein 1 |

TABLE 17-continued putative transcription factor binding motifs within the DUB regulatory or promoter, region of hDUB 8.5. The position is indicated by nucleotides.

| Transfac | Position(Score) | Name | Description |
|---|---|---|---|
| M00003 | 965 . . . 956(90) | v-Myb | v-Myb |
| M00221 | 1860 . . . 1850(90) | SREBP-1 | sterol regulatory element-binding protein 1 |
| M00053 | 441 . . . 450(90) | c-Rel | c-Rel |

TABLE 18 putative transcription factor binding motifs within the DUB regulatory or promoter, region of hDUB 8.6. The position is indicated by nucleotides.

| Transfac | Position(Score) | Name | Description |
|---|---|---|---|
| M00100 | 1105 . . . 1099(100) | CdxA | CdxA |
| M00241 | 1800 . . . 1807(100) | Nkx-2.5 | homeo domain factor Nkx-2.5/Csx, tinman homolog |
| M00148 | 1020 . . . 1014(100) | SRY | sex-determining region Y gene product |
| | 970 . . . 976(100) | | |
| | 947 . . . 941(96) | | |
| | 1550 . . . 1556(92) | | |
| | 843 . . . 837(90) | | |
| | 707 . . . 713(90) | | |
| | 1362 . . . 1356(90) | | |
| | 1719 . . . 1713(90) | | |
| | 1824 . . . 1818(90) | | |
| | 395 . . . 389(90) | | |
| | 748 . . . 742(90) | | |
| | 300 . . . 306(90) | | |
| M00101 | 1105 . . . 1099(99) | CdxA | CdxA |
| | 833 . . . 827(98) | | |
| | 1385 . . . 1379(98) | | |
| | 1409 . . . 1415(92) | | |
| | 964 . . . 970(92) | | |
| | 726 . . . 720(92) | | |
| | 424 . . . 430(92) | | |
| M00075 | 1838 . . . 1847(97) | GATA-1 | GATA-binding factor 1 |
| | 1889 . . . 1898(93) | | |
| | 925 . . . 916(93) | | |
| | 1736 . . . 1745(90) | | |
| M00272 | 1267 . . . 1276(96) | p53 | tumor suppressor p53 |
| M00253 | 161 . . . 168(96) | cap | cap signal for transcription initiation |
| | 1794 . . . 1801(95) | | |
| | 484 . . . 491(95) | | |
| | 1893 . . . 1886(95) | | |
| | 1452 . . . 1459(94) | | |
| | 798 . . . 805(94) | | |
| | 748 . . . 755(94) | | |
| | 957 . . . 964(94) | | |
| | 1486 . . . 1479(92) | | |
| | 338 . . . 345(92) | | |
| | 1697 . . . 1704(92) | | |
| | 562 . . . 569(91) | | |
| | 1877 . . . 1870(91) | | |
| | 1815 . . . 1808(90) | | |
| | 321 . . . 328(90) | | |
| | 1326 . . . 1319(90) | | |
| | 1299 . . . 1306(90) | | |
| M00096 | 1827 . . . 1819(96) | Pbx-1 | Pbx-1 |
| M00285 | 1734 . . . 1746(95) | TCF11 | TCF11/KCR-F1/Nrf1 homodimers |
| | 1115 . . . 1127(91) | | |
| M00077 | 1933 . . . 1941(95) | GATA-3 | GATA-binding factor 3 |
| M00054 | 469 . . . 460(95) | NF-kappaB | NF-kappaB |
| M00141 | 456 . . . 464(94) | Lyf-1 | LyF-1 |
| M00134 | 306 . . . 324(94) | HNF-4 | hepatic nuclear factor 4 |
| M00052 | 469 . . . 460(94) | NF-kappaB | NF-kappaB (p65) |
| M00199 | 1797 . . . 1789(94) | AP-1 | AP-1 binding site |
| | 1789 . . . 1797(91) | | |
| M00174 | 1788 . . . 1798(94) | AP-1 | activator protein 1 |
| M00053 | 469 . . . 460(94) | c-Rel | c-Rel |
| M00033 | 758 . . . 745(94) | p300 | p300 |
| | 808 . . . 795(92) | | |
| M00158 | 321 . . . 308(93) | COUP-TF | COUP/HNF-4 heterodimer |
| M00278 | 1933 . . . 1941(93) | Lmo2 | complex of Lmo2 bound to Tal-1, E2A proteins, |

TABLE 18-continued putative transcription factor binding motifs within the DUB regulatory or promoter, region of hDUB 8.6. The position is indicated by nucleotides.

| Transfac | Position(Score) | Name | Description |
|---|---|---|---|
|  |  |  | and GATA-1, half-site 2 |
| M00076 | 1932 . . . 1941(93) | GATA-2 | GATA-binding factor 2 |
|  | 1303 . . . 1312(92) |  |  |
|  | 743 . . . 734(92) |  |  |
|  | 987 . . . 996(92) |  |  |
|  | 925 . . . 916(90) |  |  |
| M00099 | 1813 . . . 1798(92) | S8 | S8 |
|  | 1114 . . . 1129(90) |  |  |
| M00104 | 28 . . . 37(92) | CDP | cut-like homeodomain protein |
| M00223 | 547 . . . 539(92) | STATx | signal transducers and activators of transcription |
| M00271 | 1955 . . . 1960(92) | AML-1a | runt-factor AML-1 |
| M00254 | 1831 . . . 1820(91) | CCAAT | cellular and viral CCAAT box |
| M00042 | 649 . . . 658(91) | Sox-5 | Sox-5 |
| M00289 | 384 . . . 396(91) | HFH-3 | HNF-3/Fkh Homolog 3 (= Freac-6) |
| M00302 | 1384 . . . 1395(91) | NF-AT | Nuclear factor of activated T-cells |
|  | 841 . . . 830(90) |  |  |
| M00155 | 367 . . . 382(91) | ARP-1 | apolipoprotein AI regulatory protein 1 |
| M00208 | 470 . . . 459(90) | NF-kappaB | NF-kappaB binding site |
| M00183 | 1030 . . . 1039(90) | c-Myb | c-Myb |
| M00240 | 243 . . . 237(90) | Nkx-2.5 | homeo domain factor Nkx-2.5/Csx, tinman homolog |
|  | 1454 . . . 1448(90) |  |  |
| M00188 | 1788 . . . 1798(90) | AP-1 | activator protein 1 |
| M00083 | 47 . . . 40(90) | MZF1 | MZF1 |
| M00184 | 273 . . . 282(90) | MyoD | myoblast determining factor |
| M00147 | 167 . . . 158(90) | HSF2 | heat shock factor 2 |
| M00087 | 984 . . . 995(90) | Ik-2 | Ikaros 2 |
| M00172 | 1788 . . . 1798(90) | AP-1 | activator protein 1 |
| M00221 | 1860 . . . 1850(90) | SREBP-1 | sterol regulatory element-binding protein 1 |
| M00194 | 471 . . . 458(90) | NF-kappaB | NF-kappaB |

TABLE 19 putative transcription factor binding motifs within the DUB regulatory or promoter, region of hDUB 8.7. The position is indicated by nucleotides.

| Transfac | Position(Score) | Name | Description |
|---|---|---|---|
| M00349 | 94 . . . 103(100) | GATA-2 | GATA-binding factor 2 |
| M00348 | 94 . . . 103(100) | GATA-2 | GATA-binding factor 2 |
| M00241 | 1800 . . . 1807(100) | Nkx-2.5 | homeo domain factor Nkx-2.5/Csx, tinman homolog |
| M00100 | 1102 . . . 1096(100) | CdxA | CdxA |
| M00148 | 1017 . . . 1011(100) | SRY | sex-determining region Y gene product |
|  | 967 . . . 973(100) |  |  |
|  | 704 . . . 710(100) |  |  |
|  | 944 . . . 938(96) |  |  |
|  | 1550 . . . 1556(92) |  |  |
|  | 840 . . . 834(90) |  |  |
|  | 1362 . . . 1356(90) |  |  |
|  | 1719 . . . 1713(90) |  |  |
|  | 1824 . . . 1818(90) |  |  |
|  | 392 . . . 386(90) |  |  |
|  | 745 . . . 739(90) |  |  |
|  | 298 . . . 304(90) |  |  |
| M00350 | 94 . . . 103(100) | GATA-3 | GATA-binding factor 3 |
| M00101 | 1102 . . . 1096(99) | CdxA | CdxA |
|  | 830 . . . 824(98) |  |  |
|  | 1231 . . . 1225(98) |  |  |
|  | 1385 . . . 1379(98) |  |  |
|  | 1297 . . . 1291(93) |  |  |
|  | 1409 . . . 1415(92) |  |  |
|  | 723 . . . 717(92) |  |  |
|  | 961 . . . 967(92) |  |  |
|  | 66 . . . 60(92) |  |  |
|  | 421 . . . 427(92) |  |  |
|  | 1682 . . . 1688(91) |  |  |
|  | 1688 . . . 1682(91) |  |  |
| M00203 | 96 . . . 106(98) | GATA-X | GATA binding site |
| M00347 | 94 . . . 103(97) | GATA-1 | GATA-binding factor 1 |
| M00075 | 1838 . . . 1847(97) | GATA-1 | GATA-binding factor 1 |
|  | 1701 . . . 1692(95) |  |  |

TABLE 19-continued putative transcription factor binding motifs within the DUB regulatory or promoter, region of hDUB 8.7. The position is indicated by nucleotides.

| Transfac | Position(Score) | Name | Description |
|---|---|---|---|
|  | 1889 . . . 1898(93) |  |  |
|  | 900 . . . 891(91) |  |  |
|  | 138 . . . 129(90) |  |  |
|  | 1736 . . . 1745(90) |  |  |
| M00158 | 319 . . . 306(96) | COUP-TF | COUP/HNF-4 heterodimer |
| M00272 | 1267 . . . 1276(96) | p53 | tumor suppressor p53 |
| M00134 | 304 . . . 322(96) | HNF-4 | hepatic nuclear factor 4 |
| M00096 | 1827 . . . 1819(96) | Pbx-1 | Pbx-1 |
| M00285 | 1734 . . . 1746(95) | TCF11 | TCF11/KCR-F1/Nrf1 homodimers |
|  | 1112 . . . 1124(91) |  |  |
|  | 1487 . . . 1475(91) |  |  |
|  | 13 . . . 1(90) |  |  |
| M00077 | 1933 . . . 1941(95) | GATA-3 | GATA-binding factor 3 |
| M00253 | 1794 . . . 1801(95) | cap | cap signal for transcription initiation |
|  | 481 . . . 488(95) |  |  |
|  | 1893 . . . 1886(95) |  |  |
|  | 1452 . . . 1459(94) |  |  |
|  | 795 . . . 802(94) |  |  |
|  | 656 . . . 649(93) |  |  |
|  | 1486 . . . 1479(92) |  |  |
|  | 1326 . . . 1319(91) |  |  |
|  | 559 . . . 566(91) |  |  |
|  | 1877 . . . 1870(91) |  |  |
|  | 745 . . . 752(91) |  |  |
|  | 918 . . . 925(91) |  |  |
|  | 954 . . . 961(90) |  |  |
|  | 1815 . . . 1808(90) |  |  |
|  | 1299 . . . 1306(90) |  |  |
| M00054 | 466 . . . 457(95) | NF-kappaB | NF-kappaB |
| M00146 | 165 . . . 156(94) | HSF1 | heat shock factor 1 |
| M00147 | 165 . . . 156(94) | HSF2 | heat shock factor 2 |
|  | 156 . . . 165(94) |  |  |
| M00141 | 453 . . . 461(94) | Lyf-1 | LyF-1 |
| M00052 | 466 . . . 457(94) | NF-kappaB | NF-kappaB (p65) |
| M00199 | 1797 . . . 1789(94) | AP-1 | AP-1 binding site |
|  | 1789 . . . 1797(91) |  |  |
| M00174 | 1788 . . . 1798(94) | AP-1 | activator protein 1 |
| M00053 | 466 . . . 457(94) | c-Rel | c-Rel |
| M00278 | 1933 . . . 1941(93) | Lmo2 | complex of Lmo2 bound to Tal-1, E2A proteins, and GATA-1, half-site 2 |
| M00076 | 1932 . . . 1941(93) | GATA-2 | GATA-binding factor 2 |
|  | 1701 . . . 1692(92) |  |  |
|  | 1303 . . . 1312(92) |  |  |
|  | 984 . . . 993(92) |  |  |
| M00099 | 1813 . . . 1798(92) | S8 | S8 |
|  | 1111 . . . 1126(90) |  |  |
| M00184 | 271 . . . 280(92) | MyoD | myoblast determining factor |
| M00223 | 544 . . . 536(92) | STATx | signal transducers and activators of transcription |
| M00073 | 36 . . . 46(92) | deltaEF1 | deltaEF1 |
| M00033 | 805 . . . 792(92) | p300 | p300 |
| M00271 | 1955 . . . 1960(92) | AML-1a | runt-factor AML-1 |
| M00254 | 1831 . . . 1820(91) | CCAAT | cellular and viral CCAAT box |
| M00277 | 281 . . . 270(91) | Lmo2 | complex of Lmo2 bound to Tal-1, E2A proteins, and GATA-1, half-site 1 |
| M00289 | 381 . . . 393(91) | HFH-3 | HNF-3/Fkh Homolog 3 (= Freac-6) |
| M00208 | 467 . . . 456(90) | NF-kappaB | NF-kappaB binding site |
| M00183 | 1027 . . . 1036(90) | c-Myb | c-Myb |
| M00240 | 241 . . . 235(90) | Nkx-2.5 | homeo domain factor Nkx-2.5/Csx, tinman homolog |
|  | 1454 . . . 1448(90) |  |  |
| M00188 | 1788 . . . 1798(90) | AP-1 | activator protein 1 |
| M00302 | 838 . . . 827(90) | NF-AT | Nuclear factor of activated T-cells |
| M00128 | 93 . . . 105(90) | GATA-1 | GATA-binding factor 1 |
| M00087 | 981 . . . 992(90) | Ik-2 | Ikaros 2 |
| M00172 | 1788 . . . 1798(90) | AP-1 | activator protein 1 |
| M00042 | 69 . . . 78(90) | Sox-5 | Sox-5 |
| M00003 | 962 . . . 953(90) | v-Myb | v-Myb |
| M00221 | 1860 . . . 1850(90) | SREBP-1 | sterol regulatory element-binding protein 1 |
| M00194 | 468 . . . 455(90) | NF-kappaB | NF-kappaB |

TABLE 20 putative transcription factor binding motifs within the DUB regulatory or promoter, region of hDUB 8.8. The position is indicated by nucleotides.

| Transfac | Position(Score) | Name | Description |
|---|---|---|---|
| M00148 | 1020 . . . 1014(100) | SRY | sex-determining region Y gene product |
| | 970 . . . 976(100) | | |
| | 947 . . . 941(96) | | |
| | 1550 . . . 1556(92) | | |
| | 843 . . . 837(90) | | |
| | 707 . . . 713(90) | | |
| | 1362 . . . 1356(90) | | |
| | 1719 . . . 1713(90) | | |
| | 1824 . . . 1818(90) | | |
| | 395 . . . 389(90) | | |
| | 748 . . . 742(90) | | |
| | 300 . . . 306(90) | | |
| M00241 | 1800 . . . 1807(100) | Nkx-2.5 | homeo domain factor Nkx-2.5/Csx, tinman homolog |
| M00100 | 1105 . . . 1099(100) | CdxA | CdxA |
| M00101 | 1105 . . . 1099(99) | CdxA | CdxA |
| | 833 . . . 827(98) | | |
| | 1385 . . . 1379(98) | | |
| | 1409 . . . 1415(92) | | |
| | 964 . . . 970(92) | | |
| | 726 . . . 720(92) | | |
| | 424 . . . 430(92) | | |
| M00075 | 1838 . . . 1847(97) | GATA-1 | GATA-binding factor 1 |
| | 1889 . . . 1898(93) | | |
| | 925 . . . 916(93) | | |
| | 1736 . . . 1745(90) | | |
| M00272 | 1267 . . . 1276(96) | p53 | tumor suppressor p53 |
| M00253 | 161 . . . 168(96) | cap | cap signal for transcription initiation |
| | 1794 . . . 1801(95) | | |
| | 484 . . . 491(95) | | |
| | 1893 . . . 1886(95) | | |
| | 1452 . . . 1459(94) | | |
| | 798 . . . 805(94) | | |
| | 748 . . . 755(94) | | |
| | 957 . . . 964(94) | | |
| | 1486 . . . 1479(92) | | |
| | 338 . . . 345(92) | | |
| | 1697 . . . 1704(92) | | |
| | 562 . . . 569(91) | | |
| | 1877 . . . 1870(91) | | |
| | 1815 . . . 1808(90) | | |
| | 321 . . . 328(90) | | |
| | 1326 . . . 1319(90) | | |
| | 1299 . . . 1306(90) | | |
| M00096 | 1827 . . . 1819(96) | Pbx-1 | Pbx-1 |
| M00285 | 1734 . . . 1746(95) | TCF11 | TCF11/KCR-F1/Nrf1 homodimers |
| | 1115 . . . 1127(91) | | |
| M00077 | 1933 . . . 1941(95) | GATA-3 | GATA-binding factor 3 |
| M00054 | 469 . . . 460(95) | NF-kappaB | NF-kappaB |
| M00141 | 456 . . . 464(94) | Lyf-1 | LyF-1 |
| M00134 | 306 . . . 324(94) | HNF-4 | hepatic nuclear factor 4 |
| M00052 | 469 . . . 460(94) | NF-kappaB | NF-kappaB (p65) |
| M00199 | 1797 . . . 1789(94) | AP-1 | AP-1 binding site |
| | 1789 . . . 1797(91) | | |
| M00174 | 1788 . . . 1798(94) | AP-1 | activator protein 1 |
| M00053 | 469 . . . 460(94) | c-Rel | c-Rel |
| M00033 | 758 . . . 745(94) | p300 | p300 |
| | 808 . . . 795(92) | | |
| M00158 | 321 . . . 308(93) | COUP-TF | COUP/HNF-4 heterodimer |
| M00278 | 1933 . . . 1941(93) | Lmo2 | complex of Lmo2 bound to Tal-1, E2A proteins, and GATA-1, half-site 2 |
| M00076 | 1932 . . . 1941(93) | GATA-2 | GATA-binding factor 2 |
| | 1303 . . . 1312(92) | | |
| | 743 . . . 734(92) | | |
| | 925 . . . 916(90) | | |
| M00099 | 1813 . . . 1798(92) | S8 | S8 |
| | 1114 . . . 1129(90) | | |
| M00104 | 28 . . . 37(92) | CDP | cut-like homeodomain protein |
| M00223 | 547 . . . 539(92) | STATx | signal transducers and activators of transcription |
| M00271 | 1955 . . . 1960(92) | AML-1a | runt-factor AML-1 |
| M00254 | 1831 . . . 1820(91) | CCAAT | cellular and viral CCAAT box |
| M00042 | 649 . . . 658(91) | Sox-5 | Sox-5 |
| M00289 | 384 . . . 396(91) | HFH-3 | HNF-3/Fkh Homolog 3 (= Freac-6) |
| M00302 | 1384 . . . 1395(91) | NF-AT | Nuclear factor of activated T-cells |
| | 841 . . . 830(90) | | |

TABLE 20-continued putative transcription factor binding motifs within the DUB regulatory or promoter, region of hDUB 8.8. The position is indicated by nucleotides.

| Transfac | Position(Score) | Name | Description |
|---|---|---|---|
| M00155 | 367 . . . 382(91) | ARP-1 | apolipoprotein AI regulatory protein 1 |
| M00208 | 470 . . . 459(90) | NF-kappaB | NF-kappaB binding site |
| M00183 | 1030 . . . 1039(90) | c-Myb | c-Myb |
| M00240 | 243 . . . 237(90) | Nkx-2.5 | homeo domain factor Nkx-2.5/Csx, tinman homolog |
| | 1454 . . . 1448(90) | | |
| M00188 | 1788 . . . 1798(90) | AP-1 | activator protein 1 |
| M00083 | 47 . . . 40(90) | MZF1 | MZF1 |
| M00184 | 273 . . . 282(90) | MyoD | myoblast determining factor |
| M00147 | 167 . . . 158(90) | HSF2 | heat shock factor 2 |
| M00172 | 1788 . . . 1798(90) | AP-1 | activator protein 1 |
| M00221 | 1860 . . . 1850(90) | SREBP-1 | sterol regulatory element-binding protein 1 |
| M00194 | 471 . . . 458(90) | NF-kappaB | NF-kappaB |

TABLE 21 putative transcription factor binding motifs within the DUB regulatory or promoter, region of hDUB 8.9. The position is indicated by nucleotides.

| Transfac | Position(Score) | Name | Description |
|---|---|---|---|
| M00148 | 991 . . . 997(100) | SRY | sex-determining region Y gene product |
| | 1040 . . . 1034(100) | | |
| | 967 . . . 961(96) | | |
| | 1576 . . . 1582(92) | | |
| | 1550 . . . 1556(92) | | |
| | 1385 . . . 1379(90) | | |
| | 1824 . . . 1818(90) | | |
| | 13 . . . 19(90) | | |
| | 415 . . . 409(90) | | |
| | 727 . . . 733(90) | | |
| M00101 | 1125 . . . 1119(100) | CdxA | CdxA |
| | 1254 . . . 1248(98) | | |
| | 1167 . . . 1161(97) | | |
| | 542 . . . 548(97) | | |
| | 884 . . . 878(94) | | |
| | 1432 . . . 1438(93) | | |
| | 743 . . . 737(92) | | |
| | 89 . . . 83(92) | | |
| | 592 . . . 586(92) | | |
| | 1280 . . . 1286(92) | | |
| | 444 . . . 450(92) | | |
| | 1682 . . . 1688(91) | | |
| | 1688 . . . 1682(91) | | |
| M00083 | 779 . . . 772(100) | MZF1 | MZF1 |
| | 68 . . . 61(90) | | |
| M00241 | 1800 . . . 1807(100) | Nkx-2.5 | homeo domain factor Nkx-2.5/Csx, tinman homolog |
| M00272 | 1290 . . . 1299(96) | p53 | tumor suppressor p53 |
| M00253 | 182 . . . 189(96) | cap | cap signal for transcription initiation |
| | 1794 . . . 1801(95) | | |
| | 1893 . . . 1886(95) | | |
| | 1475 . . . 1482(94) | | |
| | 768 . . . 775(94) | | |
| | 1506 . . . 1499(93) | | |
| | 1349 . . . 1342(91) | | |
| | 582 . . . 589(91) | | |
| | 351 . . . 358(90) | | |
| | 1815 . . . 1808(90) | | |
| | 342 . . . 349(90) | | |
| | 1877 . . . 1870(90) | | |
| | 504 . . . 511(90) | | |
| | 1322 . . . 1329(90) | | |
| M00100 | 1125 . . . 1119(96) | CdxA | CdxA |
| M00042 | 742 . . . 751(96) | Sox-5 | Sox-5 |
| | 669 . . . 678(92) | | |
| | 726 . . . 735(92) | | |
| M00096 | 1827 . . . 1819(96) | Pbx-1 | Pbx-1 |
| M00077 | 1933 . . . 1941(95) | GATA-3 | GATA-binding factor 3 |
| M00045 | 1877 . . . 1888(95) | E4BP4 | E4BP4 |
| M00054 | 489 . . . 480(95) | NF-kappaB | NF-kappaB |
| M00141 | 476 . . . 484(94) | Lyf-1 | LyF-1 |
| M00052 | 489 . . . 480(94) | NF-kappaB | NF-kappaB (p65) |

TABLE 21-continued putative transcription factor binding motifs within the DUB regulatory or promoter, region of hDUB 8.9. The position is indicated by nucleotides.

| Transfac | Position(Score) | Name | Description |
|---|---|---|---|
| M00199 | 1797 . . . 1789(94) | AP-1 | AP-1 binding site |
|  | 1789 . . . 1797(91) |  |  |
| M00174 | 1788 . . . 1798(94) | AP-1 | activator protein 1 |
| M00053 | 489 . . . 480(94) | c-Rel | c-Rel |
| M00278 | 1933 . . . 1941(93) | Lmo2 | complex of Lmo2 bound to Tal-1, E2A proteins, and GATA-1, half-site 2 |
| M00076 | 1932 . . . 1941(93) | GATA-2 | GATA-binding factor 2 |
|  | 1007 . . . 1016(92) |  |  |
|  | 1701 . . . 1692(91) |  |  |
| M00285 | 1734 . . . 1746(92) | TCF11 | TCF11/KCR-F1/Nrf1 homodimers |
|  | 1135 . . . 1147(91) |  |  |
| M00099 | 1813 . . . 1798(92) | S8 | S8 |
|  | 1134 . . . 1149(90) |  |  |
| M00104 | 49 . . . 58(92) | CDP | cut-like homeodomain protein |
| M00223 | 567 . . . 559(92) | STATx | signal transducers and activators of transcription |
| M00075 | 1701 . . . 1692(92) | GATA-1 | GATA-binding factor 1 |
|  | 161 . . . 152(90) |  |  |
|  | 1736 . . . 1745(90) |  |  |
| M00348 | 316 . . . 325(92) | GATA-2 | GATA-binding factor 2 |
| M00109 | 873 . . . 886(91) | C/EBPbeta | CCAAT/enhancer binding protein beta |
| M00254 | 1831 . . . 1820(91) | CCAAT | cellular and viral CCAAT box |
| M00203 | 318 . . . 328(91) | GATA-X | GATA binding site |
| M00350 | 316 . . . 325(91) | GATA-3 | GATA-binding factor 3 |
| M00289 | 404 . . . 416(91) | HFH-3 | HNF-3/Fkh Homolog 3 (= Freac-6) |
| M00113 | 833 . . . 822(90) | CREB | cAMP-responsive element binding protein |
| M00249 | 1165 . . . 1153(90) | CHOP-C/EBPalpha | heterodimers of CHOP and C/EBPalpha |
| M00208 | 490 . . . 479(90) | NF-kappaB | NF-kappaB binding site |
| M00190 | 1263 . . . 1250(90) | C/EBP | CCAAT/enhancer binding factor |
| M00349 | 316 . . . 325(90) | GATA-2 | GATA-binding factor 2 |
| M00116 | 1263 . . . 1250(90) | C/EBPalpha | CCAAT/enhancer binding protein alpha |
| M00183 | 1050 . . . 1059(90) | c-Myb | c-Myb |
| M00240 | 263 . . . 257(90) | Nkx-2.5 | homeo domain factor Nkx-2.5/Csx, tinman homolog |
|  | 1477 . . . 1471(90) |  |  |
| M00188 | 1788 . . . 1798(90) | AP-1 | activator protein 1 |
| M00302 | 1407 . . . 1418(90) | NF-AT | Nuclear factor of activated T-cells |
| M00184 | 293 . . . 302(90) | MyoD | myoblast determining factor |
| M00147 | 188 . . . 179(90) | HSF2 | heat shock factor 2 |
| M00087 | 1004 . . . 1015(90) | Ik-2 | Ikaros 2 |
| M00172 | 1788 . . . 1798(90) | AP-1 | activator protein 1 |
| M00221 | 1860 . . . 1850(90) | SREBP-1 | sterol regulatory element-binding protein 1 |
| M00033 | 778 . . . 765(90) | p300 | p300 |
| M00194 | 491 . . . 478(90) | NF-kappaB | NF-kappaB |

TABLE 22 putative transcription factor binding motifs within the DUB regulatory or promoter, region of hDUB 8.10. The position is indicated by nucleotides.

| Transfac | Position(Score) | Name | Description |
|---|---|---|---|
| M00148 | 1038 . . . 1032(100) | SRY | sex-determining region Y gene product |
|  | 965 . . . 959(96) |  |  |
|  | 1550 . . . 1556(92) |  |  |
|  | 725 . . . 731(90) |  |  |
|  | 1382 . . . 1376(90) |  |  |
|  | 310 . . . 316(90) |  |  |
|  | 1715 . . . 1709(90) |  |  |
|  | 1824 . . . 1818(90) |  |  |
|  | 12 . . . 18(90) |  |  |
|  | 413 . . . 407(90) |  |  |
|  | 1630 . . . 1624(90) |  |  |
|  | 319 . . . 325(90) |  |  |
| M00241 | 1800 . . . 1807(100) | Nkx-2.5 | homeo domain factor Nkx-2.5/Csx, tinman homolog |
| M00100 | 1123 . . . 1117(100) | CdxA | CdxA |
| M00240 | 1240 . . . 1234(100) | Nkx-2.5 | homeo domain factor Nkx-2.5/Csx, tinman homolog |
|  | 262 . . . 256(90) |  |  |
| M00141 | 474 . . . 482(100) | Lyf-1 | LyF-1 |
| M00101 | 1123 . . . 1117(99) | CdxA | CdxA |
|  | 540 . . . 546(97) |  |  |
|  | 1429 . . . 1435(94) |  |  |

TABLE 22-continued putative transcription factor binding motifs within the DUB regulatory or promoter, region of hDUB 8.10. The position is indicated by nucleotides.

| Transfac | Position(Score) | Name | Description |
| --- | --- | --- | --- |
|  | 982 ... 988(92) |  |  |
|  | 88 ... 82(92) |  |  |
|  | 741 ... 735(92) |  |  |
|  | 442 ... 448(92) |  |  |
| M00075 | 1838 ... 1847(97) | GATA-1 | GATA-binding factor 1 |
|  | 1889 ... 1898(93) |  |  |
|  | 1736 ... 1745(90) |  |  |
| M00253 | 766 ... 773(96) | cap | cap signal for transcription initiation |
|  | 181 ... 188(96) |  |  |
|  | 1794 ... 1801(95) |  |  |
|  | 1893 ... 1886(95) |  |  |
|  | 1210 ... 1217(94) |  |  |
|  | 816 ... 823(94) |  |  |
|  | 1506 ... 1499(92) |  |  |
|  | 357 ... 364(92) |  |  |
|  | 1697 ... 1704(92) |  |  |
|  | 1090 ... 1097(91) |  |  |
|  | 1346 ... 1339(91) |  |  |
|  | 1877 ... 1870(91) |  |  |
|  | 71 ... 78(90) |  |  |
|  | 580 ... 587(90) |  |  |
|  | 1815 ... 1808(90) |  |  |
|  | 340 ... 347(90) |  |  |
|  | 502 ... 509(90) |  |  |
|  | 1319 ... 1326(90) |  |  |
| M00096 | 1827 ... 1819(96) | Pbx-1 | Pbx-1 |
| M00285 | 1734 ... 1746(95) | TCF11 | TCF11/KCR-F1/Nrf1 homodimers |
|  | 1133 ... 1145(91) |  |  |
|  | 35 ... 23(91) |  |  |
|  | 1089 ... 1101(90) |  |  |
| M00134 | 325 ... 343(94) | HNF-4 | hepatic nuclear factor 4 |
| M00199 | 1797 ... 1789(94) | AP-1 | AP-1 binding site |
|  | 1789 ... 1797(91) |  |  |
| M00174 | 1788 ... 1798(94) | AP-1 | activator protein 1 |
| M00042 | 740 ... 749(94) | Sox-5 | Sox-5 |
|  | 1631 ... 1622(92) |  |  |
|  | 667 ... 676(91) |  |  |
| M00106 | 672 ... 681(94) | CDP | cut-like homeodomain protein |
| M00158 | 340 ... 327(93) | COUP-TF | COUP/HNF-4 heterodimer |
| M00076 | 761 ... 752(93) | GATA-2 | GATA-binding factor 2 |
|  | 1323 ... 1332(92) |  |  |
|  | 1005 ... 1014(92) |  |  |
| M00099 | 1813 ... 1798(92) | S8 | S8 |
|  | 1132 ... 1147(90) |  |  |
| M00104 | 48 ... 57(92) | CDP | cut-like homeodomain protein |
| M00223 | 565 ... 557(92) | STATx | signal transducers and activators of transcription |
| M00033 | 826 ... 813(92) | p300 | p300 |
| M00271 | 1955 ... 1960(92) | AML-1a | runt-factor AML-1 |
| M00254 | 1831 ... 1820(91) | CCAAT | cellular and viral CCAAT box |
| M00289 | 402 ... 414(91) | HFH-3 | HNF-3/Fkh Homolog 3 (= Freac-6) |
| M00217 | 160 ... 153(90) | USF | USF binding site |
| M00183 | 1048 ... 1057(90) | c-Myb | c-Myb |
| M00188 | 1788 ... 1798(90) | AP-1 | activator protein 1 |
| M00083 | 67 ... 60(90) | MZF1 | MZF1 |
| M00184 | 292 ... 301(90) | MyoD | myoblast determining factor |
| M00147 | 187 ... 178(90) | HSF2 | heat shock factor 2 |
| M00087 | 1002 ... 1013(90) | Ik-2 | Ikaros 2 |
| M00172 | 1788 ... 1798(90) | AP-1 | activator protein 1 |
| M00221 | 1860 ... 1850(90) | SREBP-1 | sterol regulatory element-binding protein 1 |

TABLE 23 putative transcription factor binding motifs within the DUB regulatory or promoter, region of hDUB 8.11. The position is indicated by nucleotides.

| Transfac | Position(Score) | Name | Description |
| --- | --- | --- | --- |
| M00348 | 71 ... 80(100) | GATA-2 | GATA-binding factor 2 |
| M00350 | 71 ... 80(100) | GATA-3 | GATA-binding factor 3 |
| M00349 | 71 ... 80(100) | GATA-2 | GATA-binding factor 2 |
| M00148 | 990 ... 984(100) | SRY | sex-determining region Y gene product |

TABLE 23-continued putative transcription factor binding motifs within the DUB regulatory or promoter, region of hDUB 8.11. The position is indicated by nucleotides.

| Transfac | Position(Score) | Name | Description |
|---|---|---|---|
|  | 1664 ... 1658(100) |  |  |
|  | 813 ... 807(96) |  |  |
|  | 917 ... 911(96) |  |  |
|  | 1858 ... 1864(92) |  |  |
|  | 1850 ... 1856(92) |  |  |
|  | 1836 ... 1842(92) |  |  |
|  | 1399 ... 1405(90) |  |  |
|  | 1514 ... 1508(90) |  |  |
|  | 680 ... 686(90) |  |  |
|  | 2104 ... 2098(90) |  |  |
|  | 368 ... 362(90) |  |  |
|  | 721 ... 715(90) |  |  |
|  | 1002 ... 996(90) |  |  |
|  | 1910 ... 1904(90) |  |  |
|  | 274 ... 280(90) |  |  |
| M00100 | 595 ... 589(100) | CdxA | CdxA |
|  | 1408 ... 1402(100) |  |  |
|  | 1474 ... 1480(96) |  |  |
| M00101 | 595 ... 589(99) | CdxA | CdxA |
|  | 1408 ... 1402(99) |  |  |
|  | 803 ... 797(98) |  |  |
|  | 1537 ... 1531(98) |  |  |
|  | 1715 ... 1721(92) |  |  |
|  | 699 ... 693(92) |  |  |
|  | 934 ... 940(92) |  |  |
|  | 43 ... 37(92) |  |  |
|  | 495 ... 501(92) |  |  |
| M00141 | 1282 ... 1274(98) | Lyf-1 | LyF-1 |
| M00347 | 71 ... 80(97) | GATA-1 | GATA-binding factor 1 |
| M00272 | 1573 ... 1582(96) | p53 | tumor suppressor p53 |
| M00253 | 1137 ... 1144(96) | cap | cap signal for transcription initiation |
|  | 136 ... 143(96) |  |  |
|  | 2074 ... 2081(95) |  |  |
|  | 457 ... 464(95) |  |  |
|  | 2173 ... 2166(95) |  |  |
|  | 721 ... 728(94) |  |  |
|  | 1444 ... 1437(94) |  |  |
|  | 660 ... 653(94) |  |  |
|  | 1792 ... 1785(92) |  |  |
|  | 312 ... 319(92) |  |  |
|  | 1632 ... 1625(91) |  |  |
|  | 535 ... 542(91) |  |  |
|  | 2095 ... 2088(91) |  |  |
|  | 1358 ... 1365(91) |  |  |
|  | 768 ... 775(90) |  |  |
|  | 295 ... 302(90) |  |  |
|  | 2157 ... 2150(90) |  |  |
| M00096 | 2107 ... 2099(96) | Pbx-1 | Pbx-1 |
| M00285 | 2014 ... 2026(95) | TCF11 | TCF11/KCR-F1/Nrf1 homodimers |
|  | 1418 ... 1430(91) |  |  |
| M00130 | 1657 ... 1668(95) | HFH-2 | HNF-3/Fkh Homolog 2 |
| M00077 | 2213 ... 2221(95) | GATA-3 | GATA-binding factor 3 |
| M00054 | 442 ... 433(95) | NF-kappaB | NF-kappaB |
| M00052 | 442 ... 433(94) | NF-kappaB | NF-kappaB (p65) |
| M00203 | 73 ... 83(94) | GATA-X | GATA binding site |
| M00199 | 2077 ... 2069(94) | AP-1 | AP-1 binding site |
|  | 2069 ... 2077(91) |  |  |
|  | 1994 ... 2002(90) |  |  |
| M00174 | 2068 ... 2078(94) | AP-1 | activator protein 1 |
|  | 1436 ... 1446(90) |  |  |
| M00075 | 895 ... 886(94) | GATA-1 | GATA-binding factor 1 |
|  | 2169 ... 2178(93) |  |  |
|  | 1091 ... 1082(93) |  |  |
|  | 1981 ... 1972(92) |  |  |
|  | 2016 ... 2025(90) |  |  |
| M00053 | 442 ... 433(94) | c-Rel | c-Rel |
| M00241 | 2080 ... 2087(94) | Nkx-2.5 | homeo domain factor Nkx-2.5/Csx, tinman homolog |
| M00076 | 716 ... 707(94) | GATA-2 | GATA-binding factor 2 |
|  | 2212 ... 2221(93) |  |  |
|  | 1609 ... 1618(92) |  |  |
|  | 957 ... 966(92) |  |  |
|  | 895 ... 886(91) |  |  |
|  | 1981 ... 1972(91) |  |  |
| M00106 | 627 ... 636(94) | CDP | cut-like homeodomain protein |

TABLE 23-continued putative transcription factor binding motifs within the DUB regulatory or promoter, region of hDUB 8.11. The position is indicated by nucleotides.

| Transfac | Position(Score) | Name | Description |
|---|---|---|---|
| M00033 | 731 ... 718(94) | p300 | p300 |
| M00227 | 2149 ... 2141(94) | v-Myb | v-Myb |
| M00158 | 295 ... 282(93) | COUP-TF | COUP/HNF-4 heterodimer |
| M00162 | 2080 ... 2093(93) | Oct-1 | octamer-binding factor 1 |
| M00278 | 2213 ... 2221(93) | Lmo2 | complex of Lmo2 bound to Tal-1, E2A proteins, and GATA- 1, half-site 2 |
| M00134 | 280 ... 298(93) | HNF-4 | hepatic nuclear factor 4 |
| M00032 | 226 ... 235(93) | c-Ets-1(p54) | c-Ets-1(p54) |
| M00172 | 1436 ... 1446(92) 2068 ... 2078(90) | AP-1 | activator protein 1 |
| M00117 | 1089 ... 1076(92) | C/EBPbeta | CCAAT/enhancer binding protein beta |
| M00223 | 520 ... 512(92) | STATx | signal transducers and activators of transcription |
| M00042 | 1911 ... 1902(92) 622 ... 631(91) | Sox-5 | Sox-5 |
| M00073 | 13 ... 23(92) | deltaEF1 | deltaEF1 |
| M00188 | 1436 ... 1446(91) 2068 ... 2078(90) | AP-1 | activator protein 1 |
| M00254 | 2111 ... 2100(91) | CCAAT | cellular and viral CCAAT box |
| M00099 | 2093 ... 2078(91) 2076 ... 2091(90) 1417 ... 1432(90) | S8 | S8 |
| M00289 | 1657 ... 1669(91) 357 ... 369(91) | HFH-3 | HNF-3/Fkh Homolog 3 (=Freac-6) |
| M00147 | 752 ... 743(91) 142 ... 133(90) | HSF2 | heat shock factor 2 |
| M00208 | 443 ... 432(90) | NF-kappaB | NF-kappaB binding site |
| M00217 | 115 ... 108(90) | USF | USF binding site |
| M00183 | 1333 ... 1342(90) | c-Myb | c-Myb |
| M00173 | 1436 ... 1446(90) | AP-1 | activator protein 1 |
| M00240 | 217 ... 211(90) | Nkx-2.5 | homeo domain factor Nkx-2.5/Csx, tinman homolog |
| M00184 | 1965 ... 1974(90) 247 ... 256(90) | MyoD | myoblast determining factor |
| M00087 | 954 ... 965(90) | Ik-2 | Ikaros 2 |
| M00128 | 70 ... 82(90) | GATA-1 | GATA-binding factor 1 |
| M00145 | 1347 ... 1362(90) | Brn-2 | POU factor Brn-2 |
| M00194 | 444 ... 431(90) | NF-kappaB | NF-kappaB |

REFERENCES

1. Baek, K. H., Mondoux, M. A., Jaster, R., Fire-Levin, E., and D'Andrea, A. D. (2001). DUB-2A, a new member of the DUB subfamily of hematopoietic deubiquitinating enzymes, Blood 98, 636–42.
2. Jaster, R., Baek, K. H., and D'Andrea, A. D. (1999). Analysis of cis-acting sequences and trans-acting factors regulating the interleukin-3 response element of the DUB-1 gene, Biochim Biophys Acta 1446, 308–16.
3. Jaster, R., Zhu, Y., Pless, M., Bhattacharya, S., Mathey-Prevot, B., and D'Andrea, A. D. (1997). JAK2 is required for induction of the murine DUB-1 gene, Mol Cell Biol 17, 3364–72.
4. Migone, T. S., Humbert, M., Rascle, A., Sanden, D., D'Andrea, A., Johnston, J. A., Baek, K. H., Mondoux, M. A., Jaster, R., Fire-Levin, E., et al. (2001). The deubiquitinating enzyme DUB-2 prolongs cytokine-induced signal transducers and activators of transcription activation and suppresses apoptosis following cytokine withdrawal, Blood 98, 1935–41.
5. Zhu, Y., Carroll, M., Papa, F. R., Hochstrasser, M., and D'Andrea, A. D. (1996a). DUB-1, a deubiquitinating enzyme with growth-suppressing activity, Proc Natl Acad Sci USA 93, 3275–9.
6. Zhu, Y., Lambert, K., Corless, C., Copeland, N. G., Gilbert, D. J., Jenkins, N. A., and D'Andrea, A. D. (1997). DUB-2 is a member of a novel family of cytokine-inducible deubiquitinating enzymes, J Biol Chem 272, 51–7.
7. Zhu, Y., Pless, M., Inhorn, R., Mathey-Prevot, B., and D'Andrea, A. D. (1996b). The murine DUB-1 gene is specifically induced by the betac subunit of interleukin-3 receptor, Mol Cell Biol 16, 4808–17.

TABLE 24

Deduced Amino acid alignment of hDUB4.10 (Seq ID NO. 22) and hDUB4.11 (Seq ID NO. 24).

```
hDUB4.10 MCIRTGSPCDVCENYSVMSMTGRQLIDWAPLKIGYEHSSTPMPREHVHFRQHYNFGTKCA    60
hDUB4.11 MCIRTGSPCDVCENYSVMSMTGRQLIDWAPLKIGYEHSSTPMPRT-LYIRHRK-------    52
         ********************************************  ::*::

hDUB4.10 NCNSTIQCVTGNGGNIADPERSMRESRICTAYFGLFPLKQGPVLKMVISLGQRINRLNVE   120
hDUB4.11 ---------PSDGAHLAHEK------------------------------------TRE    66
```

TABLE 24-continued

Deduced Amino acid alignment of hDUB4.10 (Seq ID NO. 22) and hDUB4.11 (Seq ID NO. 24).

```
                ..:*.::*. :                                                    . *
hDUB4.10 RLSLEGKKIRCAKYYTSLTILRSESALSTSCPSVAERMMAAAKRIASFCNLRSQQKNLVI 180
hDUB4.11 RNGAKGKKIRCAKYYTSLTILRSESALSSSCPSVAERMMAAAK----------------- 109
         *  . :****************** :************ hDUB4.10 LVPVDMEDDSLYLGGEWQFNHFSKLTSSRPDAAFAEIQRTSLPEKSPLSCETRVDLCDDL 240
hDUB4.11 ---IDMEDDSLYLGGEWQFNHFSKLTSSRPDAAFAEIQRTSLPEKSPLS--------YDL 158
            :*******************************************          ** hDUB4.10 APVARQLAPREKLPLSSRRPAAVGAGLQNMGNTCYVNASLQCLTYTTPLANYMLSREHSQ 300
hDUB4.11 APVARQLAPREKLPLSSRRPAAVGAGLQNMGNTCYVNASLQCLTYTPPLANYMLSREHSQ 218
         ********************************************.********** hDUB4.10 TCHRHKGCMLCTMQAHITRALHNPGHVIQPSQALAAGFHRGKQEDAHEFLMFTVDAMKKA 360
hDUB4.11 TCHRHKGCMLCTMQAHITRALHNPGHVIQPSQALAAGFHRGKQEDAHEFLMFTVDAMKKA 278
         ************************************************************ hDUB4.10 CLPGHKQVDHHSKDTTLIHQIFGGYWRSQIKCLHCHGISDTFDPYLDIALDIQAAQSVQQ 420
hDUB4.11 CLPRHKQVDHHSKDTTLIHQIFGGYWRSQIKCLHCHGISDTFDPYLDIALDIQAAQSVQQ 338
         * ****************************************************** hDUB4.10 ALEQLVKPEELNGENAYHSGVCLQRAPASKTLTLHTSAKVLILVLKRFSDVTGNKIAKNV 480
hDUB4.11 ALEQLVKPEELNGENAYHCGVCLQRAPASKTLTLHTSAKVLILVLKRFSDVTGNKIAKNV 398
         **************** .************************************** hDUB4.10 QYPECLDMQPYMSQQNTGPLVYVLYAVLVHAGWSCHNGHYFSYVKAQEGQWYKMDDAEVT 540
hDUB4.11 QYPECLDMQPYMSQQNTGPLVYVLYAVLVHAEWSCHNGHYFSYVKAQEGQWYKMDDAEVT 458
         ***************************** ************************** hDUB4.10 AASITSALSQQAYVLFYIQKSEWERHSESVSRGREPRALGTEDTDRRATQGELKRDHPCL 600
hDUB4.11 AASITSVLSQQAYVLFYIQKSEWERHSESVSRGREPRALGAEDTDRRATQGELKRDHPCL 518
         ****.****************************:****************** hDUB4.10 QAPELDEHLVERATQESTLDHWKFLQEQNKTKPEFNVRKVEGTLPPDVLVIHQSKYKCGM 660
hDUB4.11 QAPELDEHLVERATQESTLDHWKFLQEQNKTKPEFNVRKVKGTLPPDVLVIHQSKYKCGM 578
         **************************************:***************** hDUB4.10 KNHHPEQQSSLLNLSSSTPTHQESMNTGTLASLRGRARRSKGKNKHSKRALLVCQ 715
hDUB4.11 KNHHPEQQSSLLNLSSSTPTHQESMNTGTLASLRGRARRSKGKNKHSKRALLVC- 632
         ****************************************************** 
```

TABLE 25

Nucleotide sequence alignment of hDUB4.5 (Seq ID NO. 13), hDUB4.8 (Seq ID NO. 19) and hDUB8.2 (Seq ID NO. 43). In frame termination codons in hDUB8.2 are underlined

```
hDUB4.5  ATGCG-CCAGAGAGCTCGTCATTTGAAGACTCTCTCGGAAGGGATAGCGTCTTTCTGCAA 59
hDUB4.8  ATGCG-CCAGAGAGCTCGTCATTTGAAGACTCTCTCGGAACGGATAGCGTCTTGCTGCAA 59
hDUB8.2  ATGCGGCCAGAGAGCCCGTCATTTGAAGA----CTCGGAAGAGATAGCGTCTTTCTGCAA 56
         *** ***** ********     *** ******** **** hDUB4.5  CCTGCGGTCCCAGCAGAAAAACCTTGTGATCCTTGTTCCAGTCGACATGGAGGAAGACTC 119
hDUB4.8  ACTGCGGTCCCAGCAGAAAAACCTTGTGATCCTTGTTCCAGTCGACATGGAGGACGACTC 119
hDUB8.2  CCTGCGGTCCCAGCCGAAAAACCTTGTGATCCTTGTTCCGGGCGACATGGAGGACGACTC 116
          *********** ********************* *  ********** *** hDUB4.5  ACTCTACTTGGGAGGTGAGTGGCAGTTCAACCACTTTTCAAAACTCACATCTTCTCGGCC 179
hDUB4.8  ACTCTACTTGGGAGGTGAGTGGCAGTTCAACCACTTTTCAAAACTCACATCTTCTCGGCC 179
hDUB8.2  ACTCTACTTGGGAGGTGAGTGGCAGTTCAACCACTTTTCAAAACTCACATCTTCTCGGCC 176
         ************************************************************ hDUB4.5  CGATGCAGCTTTTGCTGAAATCCAGCGGACTTCTCTCCCTGAGAAGTCACCACTCTCATG 239
hDUB4.8  CGATGCAGCTTTTGCTGAAATCCAGCGGACTTCTCTCCCTGAGAAGTCACCACTCTCATG 239
hDUB8.2  AGATGCAGCTTTTGCTGAAATCCAGCGGACTTCTCTCTCTGAAGAAGTCATCACTCTCATC 236
          **********************************  *  ******* hDUB4.5  TGAGACCCGTGTCGACCTCTGTGATGATTTGGCTCCTGTGGCAAGACAGCTTGCTCCCAG 299
hDUB4.8  TGAGACCCGTGTCGACCTCTGTGATGATTTGGCTCCTGTGGCAAGACAGCTTGCTCCCAG 299
hDUB8.2  TGAGACCCGCGTCGACCTCTGTGATGATTTGGCTCCTGTGGCAAGACAGCTCGCTCCCAG 296
         ********* ***************************************** *******
```

TABLE 25-continued

Nucleotide sequence alignment of hDUB4.5 (Seq ID NO. 13), hDUB4.8 (Seq ID NO. 19) and hDUB8.2 (Seq ID NO. 43). In frame termination codons in hDUB8.2 are underlined

```
hDUB4.5   GGAGAAGCTTCCTCTGAGTAACAGGAGACCTGCTGCGGTGGGGGCTGGGCTCCAGAATAT   359
hDUB4.8   GGAGAAGCTTCCTCTGAGTAGCAGGAGACCTGCTGCGGTGGGGGCTGGGCTCCAGAATAT   359
hDUB8.2   GGAGAAGCTTCCTCTGAGTAGCAGGAGACCTGCTGCGGTGGGGGCTGGGCTCCAGAATAT   356
          ****************** ************************************* hDUB4.5   GGGAAATACCTGCTACGTGAACGCTTCCTTGCAGTGCCTGACATACACACCGCCCCTTGC   419
hDUB4.8   GGGAAATACCTGCTACGTGAACGCTTCCTTGCAGTGCCTGACATACACACCGCCCCTTGC   419
hDUB8.2   GGGAAATACCTGCTACGTGAACGCTTCCCTGCAGTGCCTGACATACACACCGCCCCTTGC   416
          **************************  **************************** hDUB4.5   CAACTACATGCTGTCCCGGGAGCACTCTCAAACGTGTCATCGTCACAAGGGCTGCATGCT   479
hDUB4.8   CAACTACATGCTGTCCCGGGAGCACTCTCAAACGTGTCATCGTCACAAGGGCTGCATGCT   479
hDUB8.2   CAACTACATGCTGTCCCGGGAGCACTCTCAAACGTGTCATCGTCACAAGTGCTGCATGCT   476
          ***********************************************  ******* hDUB4.5   CTGTACGATGCAAGCTCACATCACACGGGCCCTCCACAATCCTGGCCACGTCATCCAGCC   539
hDUB4.8   CTGTACGATGCAAGCTCACATCACACGGGCCCTCCACAATCCTGGCCACGTCATCCAGCC   539
hDUB8.2   CTGTACTATGCAAGCTCACATCACATGGCCCCTCCACAGTCCTGGCCATGTCATCCAGCC   536
          ****  *************   ******  ****  ******** hDUB4.5   CTCACAGGCATTGGCTGCTGGCTTCCATAGAGGCAAGCAGGAAGATGCCCATGAATTTCT   599
hDUB4.8   CTCACAGGCATTGGCTGCTGGCTTCCATAGAGGCAAGCAGGAAGATGCCCATGAATTTCT   599
hDUB8.2   CTCACAGGTGTTGGCTGCTGGCTTCCATAGAGGCGAGCAGGAAGATGCCCATGAATTTCT   596
          ******  ******************** *********************** hDUB4.5   CATGTTCACTGTGGATGCCATGAAAAAGGCATGCCTTCCCGGGCACAAGCAGGTGGATCA   659
hDUB4.8   CATGTTCACTGTGGATGCCATGAAAAAGGCATGCCTTCCCGGGCACAAGCAGGTAGATCA   659
hDUB8.2   CATGTTCACTGTGGATGCCATGAAAAAGGCATTCCTTCCCGGGCACAAGCATTTAGATAA   656
          ******************************  *************   * * hDUB4.5   TCACTCTAAGGACACCACCCTCATCCACCAAATATTTGGAGGCTACTGGAGATCTCAAAT   719
hDUB4.8   TCACTCTAAGGACACCACCCTCATCCACCAAATATTTGGAGGCTACTGGAGATCTCAAAT   719
hDUB8.2   TCACTCTAAGGACACCACCCTCATCCACCAAATATTTGGAGGGTACTGGAGATCTCACAT   716
          ****************************************  ********* hDUB4.5   CAAGTGTCTCCACTGCCACGGCATTTCAGACACTTTTGACCCTTACCTGGACATCGCCCT   779
hDUB4.8   CAAGTGTCTCCACTGCCACGGCATTTCAGACACTTTTGACCCTTACCTGGACATCGCCCT   779
hDUB8.2   CAACTGTTTCCACTGCCACGGGATTTCAGACACCTTTGACCCTTACCTGGACATCGCCCT   776
          * *  ********** ******* ************************ hDUB4.5   GGATATCCAGGCAGCTCAGAGTGTCCAGCAAGCTTTGGAACAGTTGGTGAAGCCCGAAGA   839
hDUB4.8   GGATATCCAGGCAGCTCAGAGTGTCCAGCAAGCTTTGGAACAGTTGGTGAAGCCCCAAGA   839
hDUB8.2   GGATATCCAGGCAGCTCAGAGTGTCAAGCAAGCTTTGTAACAGTTGGTGAAGCCCGAAGA   836
          *********************** *******  ************  * hDUB4.5   ACTCAATGGAGAGAATGCCTATCATTGTGGTGTTTGTCTCCAGAGGGCGCCGGCCTCCAA   899
hDUB4.8   ACTCAATGGAGAGAATGCCTATCATTGTGGTGTTTGTCTCCAGAGGGCGCCGGCCTCCAA   899
hDUB8.2   ACTCAATGGATAAAATGCCTATCATTGTGGTCTTTGTCTCCAGAAGGCGCCTGCCTCCAG   896
          ********** * **************** ******** *** ***** hDUB4.5   GACGTTAACTTTACACACCTCTGCCAAGGTCCTCATCCTTGTATTGAAGAGATTCTCCGA   959
hDUB4.8   GACGTTAACTTTACACACCTCTGCCAAGGTCCTCATCCTTGTATTGAAGAGATTCTCCGA   959
hDUB8.2   GACGTTAACTTTACACACTTCTGCCAAGGTCCTCATCCTTGTATTGAAGAGATTCTCTGA   956
          **************** ********************************** hDUB4.5   TGTCACAGGCAACAAGATTGACAAGAATGTGCAATATCCTGAGTGCCTTGACATGAAGCT   1019
hDUB4.8   TGTGACAGGCAACAAGATTGCCAAGAATGTGCAATATCCTGAGTGCCTTGACATGCAGCC   1019
hDUB8.2   GGTCACAGGCAACAAACTTGCCAAGAATGTGCAATATCCTGAGTGCCTTGACATGCAGCC   1016
           *******   *****************************  * hDUB4.5   ATACATGTCTCAGACGAACTCAGGACCTCTCGTCTATGTCCTCTATGCTGTGCTGGTCCA   1079
hDUB4.8   ATACATGTCTCAGCAGAACACAGGACCTCTTGTCTATGTCCTCTATGCTGTGCTGGTCCA   1079
hDUB8.2   ATACATGTCTCAGCAGAACACAGGACCTCTTGTCTATGTCCTCTATGCTGTGCTGGTCCA   1076
          ***********   ****** *************************** hDUB4.5   CGCTGGGTGGAGTTGTCACAACGGACATTACTTCTCTTATGTCAAAGCTCAAGAAGGCCA   1139
hDUB4.8   CGCTGGGTGGAGTTGTCACAACGGACATTACTTCTCTTATGTCAAAGCTCAAGAAGGCCA   1139
hDUB8.2   CGCTGGGTGGAGTTGTCACAACGGACATTACTTATCTTATGTCAAA-CTCAAGAAGGCCA   1135
          ******************************* *******  *********** hDUB4.5   GTGGTATAAAATGGATGATGCCGAGGTCACCGCCTCTAGCATCACTTCTGTCCTGAGTCA   1199
hDUB4.8   ATGGTATAAAATGGATGATGCCGAGGTCACCGCCGCTAGCATCACTTCTGTCCTGAGTCA   1199
hDUP8.2   TTGGTATAAAATGGATGATGCCGAGGTCACTGCCTCCGGTATCACTTCTGTCCTGAGTCA   1195
            *****************************  ***  *  *******************
```

TABLE 25-continued

Nucleotide sequence alignment of hDUB4.5 (Seq ID NO. 13),
hDUB4.8 (Seq ID NO. 19) and hDUB8.2 (Seq ID NO. 43).
In frame termination codons in hDUB8.2 are underlined

```
hDUB4.5    ACAGGCCTACGTCCTCTTTTACATCCAGAAGAGTGAATGGGAAAGACACAGTGAGAGTGT  1259
hDUB4.8    ACAGGCCTACGTCCTCTTTTACATCCAGAAGAGTGAATGGGAAAGACACAGTGAGAGTGT  1259
hDUB8.2    ACAGGCCTATGTCCTCTTTTACATCCAGAAGAATGAATTTGGAAGACCCAGTTACAGTGT  1255
           ****** ******************* ***  * *** ** * ***** hDUB4.5    GTCAAGAGGCAGGGAACCAAGAGCCCTTGGCGCAGAAGACACAGACAGGCGAGCAACGCA  1319
hDUB4.8    GTCAAGAGGCAGGGAACCAAGAGCCCTTGGCGCAGAAGACACAGACAGGCGAGCAACGCA  1319
hDUB8.2    GTCCATAGGCAGGCAACCAAGAGCTCTTTGCGTGAAGGCAAGTGAATTGTGTGTGAAATA  1315
           *** * *********** * *  *  *         *   *  *  * hDUB4.5    AGGAGAGCTCAAGAGAGACCCACCCCTGCCTCCAGGCCCCCGAGTTGGACGAGCACTTGGT  1379
hDUB4.8    AGGAGAGCTCAAGAGAGACCCACCCCTGCCTCCAGGCCCCCGAGTTGGACGAGCACTTGGT  1379
hDUB8.2    AAATG---TCATGA---ATAAATCTTGCAGTGGAGTATTT-ATTTGTCTCACTTTGTAAT  1368
            *   *   *      *    * ***    *    *     *  ***    *   * hDUB4.5    GGAAAGAGCCACTCAGGAAAGCACCTTAGACCACTGGAAATTCCTTCAAGAGCAAAACAA  1439
hDUB4.8    GGAAAGAGCCACTCAGGAAAGCACCTTAGACCACTGGAAATTCCTTCAAGAGCAAAACAA  1439
hDUB8.2    CAGTGAATGAGCTTTAACCAATATCAATGCCTAGTGCCTACCCCCAGAGATAAGAACTT   1428
             * *    * **         *  *     * * **    * *  *** * *  * ** hDUB4.5    AACGAAGCCTGAGTTCAACGTCAGAAAAGTCGAAGGTACCCTGCCTCCCGACGTACTTGT  1499
hDUB4.8    AACGAAGCCTGAGTTCAACGTCAGAAAAGTCGAAGGTACCCTGCCTCCCGACGTACTTGT  1499
hDUB8.2    CCACTCTCTTATGTGTAAC--CATGGCCTCTGGATTGCTTATGACTCTGAAGATAATTCT  1486
             *    *  **      * *        * *   *   *  ** * * hDUB4.5    GATTCATCAATCAAAATACAAGTGTGGGATGAAGAACCATCATCCTG-AACAGCAAAGCT  1558
hDUB4.8    GATTCATCAATCAAAATACAAGTGTGGGATGAAGAACCATCATCCTG-AACAGCAAAGCT  1558
hDUB8.2    CCTT--TCCCCCAACGTTTCAGAATCACTTCAGGTGGTGGTAACAGATAACACATCAGTC  1544
                  ***  *   **  *   **  *  *    *  **     *   * hDUB4.5    CCCTGCTAAACCTCTCTTCGACGACCCCGACACATCAGGAGTCCATGAACACTGGCACAC  1618
hDUB4.8    CCCTGCTAAACCTCTCTTCGTCGACCCCGACACATCAGGAGTCCATGAACACTGGCACAC  1618
hDUB8.2    CCTTTCTCTCTCTTTTCTCTTCACTCAGGAAAACTCTCACTGAGACAAAGGAAAATCCTA  1604
           ** * *   *      *  ** *    *                  * hDUB4.5    TCGCTTCCCTGCGAGGGAGGGC-----CAGGAGATCCAAAGGGAAGAACAAACACAGCAA  1673
hDUB4.8    TCGCTTCCCTGCGAGGGAGGGC-----CAGGAGATCCAAAGGGAAGAACAAACACAGCAA  1673
hDUB8.2    TGGTTTACTGGGGAGGAAGAATTCCCTCAGGAGTGAAATTGGTGGCTCCTTCCTCCCTGT  1664
           * * ** * * * ***  *          ******   * *   *     *    * * hDUB4.5    GAGGGCTCTGCTTGTGTG----CCAGTGGTCTCAGTGGAAGTACCGACCCACA         1722
hDUB4.8    GAGGGCTCTGCTTGTGTG----CCAGTGA-----------------------         1698
hDUB8.2    CAAGTCTCTTCCTCAGGATTGCCCCTTTGTCTCTTCAGGACT-----------         1706
            * * **** * * * *** *      ** *  *
```

TABLE 26

Deduced amino acid alignment of hDUB4.5 (Seq ID NO. 14),
hDUB4.8 (Seq ID NO. 20) and hDUB8.2 (Seq ID NO. 44).
N-terminal potential mitochondrial targeting sequences are underlined.

```
hDUB4.5    MRQRARHLKTLSEGIASFCNLRSQQKNLVILVPVDMEEDSLYLGGEWQFNHFSKLTSSRP   60
hDUB4.8    MRQRARHLKTLSEGIASCCKLRSQQKNLVILVPVDMEDDSLYLGGEWQFNHFSKLTSSRP   60
hDUB8.2    MRPESPSFED-SEEIASFCNLRSQPKNLVILVPGDMEDDSLYLGGEWQFNHFSKLTSSRP   59
            .:  ::    * ***.********************** hDUB4.5    DAAFAEIQRTSLPEKSPLSCETRVDLCDDLAPVARQLAPREKLPLSNRRPAAVGAGLQNM  120
hDUB4.8    DAAFAEIQRTSLPEKSPLSCETRVDLCDDLAPVARQLAPREKLPLSSRRPAAVGAGLQNM  120
hDUB8.2    DAAFAEIQRTSLSEKSSLSSETRVDLCDDLAPVARQLAPREKLPLSSRRPAAVGAGLQNM  119
           **********.*..*******************:.*********** hDUB4.5    GNTCYVNASLQCLTYTPPLANYMLSREHSQTCHRHKGCMLCTMQAHITRALHNPGHVIQP  180
hDUB4.8    GNTCYVNASLQCLTYTPPLANYMLSREHSQTCHRHKGCMLCTMQAHITRALHNPGHVIQP  180
hDUB8.2    GNTCYVNASLQCLTYTPPLANYMLSREHSQTCHRHKCCMLCTMQAHITWPLHSPGHVIQP  179
           ********************************** ******* . ****** hDUB4.5    SQALAAGFHRGKQEDAHEFLMFTVDAMKKACLPGHKQVDHHSKDTTLIHQIFGGYWRSQI  240
hDUB4.8    SQALAAGFHRGKQEDAHEFLMFTVDAMKKACLPGHKQVDHHSKDTTLIHQIFGGYWRSQI  240
hDUB8.2    SQVLAAGFHRGEQEDAHEFLMFTVDAMKKAFLPGHKHLDNHSKDTTLIHQIFGGYWRSHI  239
           .****:*************.*:: :***************:* hDUB4.5    KCLHCHGISDTFDPYLDIALDIQAAQSVQQALEQLVKPEELNGENAYHCGVCLQRAPASK  300
```

TABLE 26-continued

Deduced amino acid alignment of hDUB4.5 (Seq ID NO. 14),
hDUB4.8 (Seq ID NO. 20) and hDUB8.2 (Seq ID NO. 44).
N-terminal potential mitochondrial targeting sequences are underlined.

```
hDUB4.8  KCLHCHGISDTFDPYLDIALDIQAAQSVQQALEQLVKPEELNGENAYHCGVCLQRAPASK  300
hDUB8.2  NCFHCHGISDTFDPYLDIALDIQAAQSVKQAL----------------------------  271
         :*:**********************:* hDUB4.5  TLTLHTSAKVLILVLKRFSDVTGNKIDKNVQYPECLDMKLYMSQTNSGPLVYVLYAVLVH  360
hDUB4.8  TLTLHTSAKVLILVLKRFSDVTGNKIAKNVQYPECLDMQPYMSQQNTGPLVYVLYAVLVH  360
hDUB8.2  ------------------------------------------------------------ hDUB4.5  AGWSCHNGHYFSYVKAQEGQWYKMDDAEVTASSITSVLSQQAYVLFYIQKSEWERHSESV  420
hDUB4.8  AGWSCHNGHYFSYVKAQEGQWYKMDDAEVTAASITSVLSQQAYVLFYIQKSEWERHSESV  420
hDUB8.2  ------------------------------------------------------------ hDUB4.5  SRGREPRALGAEDTDRRATQGELKRDHPCLQAPELDEHLVERATQESTLDHWKFLQEQNK  480
hDUB4.8  SRGREPRALGAEDTDRRATQGELKRDHPCLQAPELDEHLVERATQESTLDHWKFLQEQNK  480
hDUB8.2  ------------------------------------------------------------ hDUB4.5  TKPEFNVRKVEGTLPPDVLVIHQSKYKCGMKNHHPEQQSSLLNLSSTTPTHQESMNTGTL  540
hDUB4.8  TKPEFNVRKVEGTLPFDVLVIHQSKYKCGMKNHHPEQQSSLLNLSSSTPTHQESMNTGTL  540
hDUB8.2  ------------------------------------------------------------ hDUB4.5  ASLRGRARRSKGKNKHSKRALLVCQWSQWKYRPT  574
hDUB4.8  ASLRGRARRSKGKNKHSKRALLVCQ---------  565
hDUB8.2  ----------------------------------
```

TABLE 27

Upstream of initiation codon nucleotide sequence
(putative promoter region) alignment of
hDUB4.5 (Seq ID NO. 13), hDUB4.8 (Seq ID NO. 19)
and hDUB8.2 (Seq ID NO. 43).
Numbering is initiated from initiation ATG.

```
hDUB4.5  CACACGAACACAATCACACACACACACTCACACGGTTTCCTACGTAAAGATTTCTTCCCT  -276
hDUB4.8  CACACGAACACAATCACACACACACACTCACACGGTTTCCTACGTAAAGATTTCTTCCCT  -276
hDUB8.2  GGGAGAAAAACACACACACACACACACACGGTTTCATAGGTAAAGATTTCTTCCCT      -276
         *   *  ********** *******  ***************** hDUB4.5  GCCATTGCTTTACCTAAAATAAGGCAACTGTGTGGCCACTGTCCCAACCCGGTTACACTC  -216
hDUB4.8  GCCATTGCTTTACCTAAAATAAGGCAACTGTGTGGCCACTGTCCCAACCCGGTTACACTC  -216
hDUB8.2  GACATTGTTTTACCTAAAATAAGGCAACTGTGTGGCCACTGTCCCAACCCGGTTACACTC  -216
         * ***  ************************************************* hDUB4.5  CTATTATATGTGCCTATCATCCTGAGGAGTAATTTGATTCAGGTGTTCTGGAAGTCATGC  -156
hDUB4.8  CTATTATATGTGCCTATCATCCTGAGGAGTAATTTGATTCAGGTGTTCTGGAAGTCATGC  -156
hDUB8.2  ATATTACATGTGTCTATCAGCCTGAGGAGTAGTTTGATTCAGGTGTTCTAGAAGTCATGA  -156
         *** ** ** ****** ************* ******** hDUB4.5  TGTGGGCTGTGTCTGTTGAATTCCCAGCGATGCAAGGGGACACACCCTGTGACTCCTTCC  -96
hDUB4.8  TGTGGGCTGTGTCTGTTGAATACCCAGCGATGCAAGGGGACACACCCTGTGACTCCTTCC  -96
hDUB8.2  TGTGGGCCGTGTCTGTTGAATTCCCAGCGATGCAAGGGGACACACCCTGTGACTCATTCC  -96
         ***** ********* ****************************** * ** hDUB4.5  TGAATTGAGTGCTGATATTTGATTGGCTTATCGCGCACCTGATGAGTGAGTGGGGTGTTC  -36
hDUB4.8  TGAATTGAGTGCTGATATTTGATTGGCTTATCGCGCACCTGATGAGTGAGTGGGGTGTTC  -36
hDUB8.2  TTAATTGAGTGCTGATATTTGATTGGTTTATCGCGCACCTGATGGGTGGGTGGGGTGTTC  -36
         * ********************** ************* * ********** hDUB4.5  GCGGTTGGTGGGGTTGACTTACAGAAGGGCTGATG  0
hDUB4.8  GCGGTTGGTGGGGTGACTTACAGAAGGGCTGATG   0
hDUB8.2  GCGGTTGGTGGGGGTGAGTTATATAAGGGCTGATG  0
         ************  *** *** * **********
```

TABLE 28

CLUSTAL W (1.81) multiple sequence alignment
of core amino acids of hDUBs (8.5: Seq ID NO. 30; 8.7: Seq
ID NO. 34; 8.1: Seq ID NO. 26; 4.2: Seq ID NO. 10; 4.3: Seq
ID NO. 12; 4.5: Seq ID NO. 14; 4.1: Seq ID NO. 6; 8.3: Seq
ID NO. 28; 8.11: Seq ID NO. 38; 8.8: Seq ID NO. 36;
8.6: Seq ID NO. 32).

```
8.5   MEDDSLYLGGEWQFNHFSKLTSSRPDAAFAEIQRTSLPEKSPLSSEARVDLCDDLAPVAR  60
8.7   MEDDSLYLGGEWQFNHFSKLTSSRPDAAFAEIQRTSLPEKSPLSSEARVDLCDDLAPVAR  60
8.1   MGDDSLYLGGEWQFNHFSKLTSSRPDAAFAEIQRTSLPEKSPLSSETRVDLCDDLAPVAR  60
4.2   MEDDSLYLGGEWQFNHFSKLTSSRPDAAFAEIQRTSLPEKSPLSCETRVDLCDDLAPVAR  60
4.3   MEDDSLYLGGEWQFNHFSKLTSSRPDAAFAEIQRTSLPEKSPLSCETRVDLCDDLAPVAR  60
4.5   MEEDSLYLGGEWQFNHFSKLTSSRPDAAFAEIQRTSLPEKSPLSCETRVDLCDDLAPVAR  60
4.1   MEDDSLYLGGEWQFNHFSKLTSSRPDAAFAEIQRTSLPEKSPLSCETRVDLCDDLAPVAR  60
8.3   MEDDSLYLGGEWQFNHFSKLTSSRPDAAFAEIQRTSLPEKSQLSTETRVDFCDDLAPVAR  60
8.11  MEDDSLYLGGEWQFNHFSKLTSSRPDAAFAEIQRTSLPEKSQLSTETRVDFCDDLAAVAR  60
8.8   MEDDSLYLGGDWQFNHFSKLTSSRLDAAFAEIQRTSLSEKSPLSSETRFDLCDDLAPVAR  60
8.6   MEDDSLYLGGDWQFNHFSKLTSSRLDAAFAEIQRTSLSEKSPLSSETRFDLCDDLAPVAR  60
      * :**********:********** ************.*** ** *:*.*:*****.***

8.5   QLAPRKKLPLSSRRPAAVGAGLQNMGNTCYENASLQCLTYTPPLANYMLSREHSQTCQRP  120
8.7   QLAPRKKLPLSSRRPAAVGAGLQNMGNTCYENASLQCLTYTPPLANYMLSREHSQTCQRP  120
8.1   QLAPREKLPLSSRRPAAVGAGLQNMGNTCYENASLQCLTYTLPLANYMLSREHSQTCQRP  120
4.2   QLAPREKLPLSSRRPAAVGAGLQNMGNTCYVNASLQCLTYTTPPLANYMLSREHSQTCHRH  120
4.3   QLAPREKLPLSSRRPAAVGAGLQNMGNTCYVNASLQCLTYTPPLANYMLSREHSQTCHRH  120
4.5   QLAPREKLPLSNRRPAAVGAGLQNMGNTCYVNASLQCLTYTPPLANYMLSREHSQTCHRH  120
4.1   QLAPREKPPLSSRRPAAVGAGLQNMGNTCYVNASLQCLTYKPPLANYMLFREHSQTCHRH  120
8.3   QLAPREKLPLSSRRPAAVGAGLQNMGNTCYVNASQQCLTYTPPLANYMLSREHSQTCHRH  120
8.11  QLAPREKLPLSSRRPAAVGAGLQNMGNTCYVNASQQCLTYIPPLANYMLSREHSQTCHRH  120
8.8   QLAPREKLPLSSRRPAAVGAGLQKIGNTFYVNVSLQCLTYTLPLSNYMLSREDSQTCHLH  120
8.6   QLAPREKLPLSSRRPAAVGAGLQKIGNTFYVNVSLQCLTYTLPLSNYMLSREDSQTCHLH  120
      *****:* ***.*************::*** * *.* *****  **:**** **.****:

8.5   KCCMLCTMQAHITWALHSPGHVIQPSQALAAGFHRGKQEDAHEFLMFTVDAMKKACLPGH  180
8.7   KCCMLCTMQAHITWALHSPGHVIQPSQALAAGFHRGKQEDAHEFLMFTVDAMKKACLPGH  180
8.1   KCCMLCTMQAHITWALHSPGHVIQPSQALAAGFHRGKQEDVHEFLMFTVDAMKKACLPGH  180
4.2   KGCMLCTMQAHITRALHNPGHVIQPSQALAAGFHRGKQEDAHEFLMFTVDAMKKACLPGH  180
4.3   KGCMLCTMQAHITRALHNPGHVIQPSQALAAGFHRGKQEDAHEFLMFTVDAMKKACLPGH  180
4.5   KGCMLCTMQAHITRALHNPGHVIQPSQALAAGFHRGKQEDAHEFLMFTVDAMKKACLPGH  180
4.1   KGCMLCTMQAHITRALHIPGHVIQPSQALAAGFHRGKQEDAHEFLMFTVDAMRKACLPGH  180
8.3   KCCMLCTMEAHITWPLHIPGHVIQPSQALAAGFHRGKQEAALEFLMFTVDAMKKACLPGH  180
8.11  KCCMLCTMEAHITWPLHIPGHVIQPSQALAAGFHRGKQEAALEFLMFTVDAMKKACLPGH  180
8.8   KCCMFCTMQAHITWALYRPGHVIQPSQVLAAGFHRGEQEDAHEFLMFTVDAMKKACLPGH  180
8.6   KCCMFCTMQAHITWALYRPGHVIQPSQVLAAGFHRGEQEDAHEFLMFTVDAMKKACLPGH  180
      * **:***:**** .*: *********.********:**  .**********:*******

8.5   KQVDHHSKDTTLIHQIFGGCWRSQIKCLHCHGISDTFDPYLDIALDIQAAQSVKQALEQL  240
8.7   KQVDHHSKDTTLIHQIFGGCWRSQIKCLHCHGISDTFDPYLDIALDIQAAQSVKQALEQL  240
8.1   KQVDHHCKDTTLIHQIFGGCWRSQIKCLHCHGISDTFDPYLDIALDIQAAQSVKQALEQL  240
4.2   KQVDHHSKDTTLIHQIFGGYWRSQIKCLHCHGISDTFDPYLDIALDIQAAQSVQQALEQL  240
4.3   KQVDHHSKDTTLIHQIFGGYWRSQIKCLHCHGISDTFDPYLDIALDIQAAQSVQQALEQL  240
4.5   KQVDHHSKDTTLIHQIFGGYWRSQIKCLHCHGISDTFDPYLDIALDIQAAQSVQQALEQL  240
4.1   KQVDRHSKDTTLIHQIFGGYWRSQIKCLHCHGISDTFDPYLDIALDIQAAQSVQQALEQL  240
8.3   KQVDHHSKDTTLIHQIFGGYWRSQIKCLHCHGISDTFGPYLDIALDIQEAQSVKQALEQL  240
8.11  K-------------------QILILVWKRFSDVTG-----------------------  196
8.8   KQLDHHSKDTTLIHQIFGAYWRSQIKYLHCHGISDTFDPYLDIALDIQAAQSVKQALEQL  240
8.6   KQLDHHSKDTTLIHQIFGAYWRSQIKYLHCHGISDTFDPYLDIALDIQAAQSVKQALEQL  240
      *                   ** *  : :**. .

8.5   VKPEELNGENAYHCGLCLQRAPVSKTLTLHTFAKERILETQRPWVVTRHKLAKSVQYAES  300
8.7   VKPEELNGENAYHCGLCLQRAPASKTLTLHTSAKVLILVLKRFSDVTGNKLAKNVQYPEC  300
8.1   VKPEELNGENAYHCGLCLQRAPSNTLTLHTSAKVLILVLKRFSDVAGNKLAKNVQYPEC  300
4.2   VKPEELNGENAYHSGVCLQRAPASKTLTLHTSAKVLILVLKRFSDVTGNKIAKNVQYPEC  300
4.3   VKPEELNGENAYHCGVCLQRAPASKTLTLHTSAKVLILVLKRFSDVTGNKIAKNVQYPEC  300
4.5   VKPEELNGENAYHCGVCLQRAPASKTLTLHTSAKVLILVLKRFSDVTGNKIDKNVQYPEC  300
4.1   VKPEELNGENAYHCGVCLQRAPASKTLTLHNSAKVLILVLKRFPDVTGNKIAKNVQYPEC  300
8.3   VKPEELNGENAYHC-------------------------GNKIAKNVQYPEC  267
8.11  ----------------------------------------NKIAKNVQYPEC  208
8.8   VKPKELNGENAYHCGLCLQKAPASKTLTLPTSAKVLILVLKRFSDVTGNKLAKNVQYPKC  300
8.6   VKPKELNGENAYHCGLCLQKAPASKTLTLPTSAKVLILVLKRFSDVTGNKLAKNVQYPKC  300
                                              :*: *.***.:.

8.5   LDMQPYMSQQNTGPLVYVLYAVLVHAGWSCHDGHYFSYVKAQEGQWYKMDDAKVTACSIT  360
8.7   LDMQPYMSQQNTGPLVYVLYAVLVHAGWSCHDGHYFSYVKAQEGQWYKMDDAKVTACSIT  360
8.1   LDMQPYMSQQNTGPLVYVLYAVLVHAGWSCHDGHYFSYVKAQEGVQWYKMDDAEVTVCSII  360
4.2   LDMQPYMSQQNTGPLVYVLYAVLVHAGWSCHNGHYFSYVKAQEGQWYKMDDAEVTAASIT  360
4.3   LDMQPYMSQQNTGPLVYVLYAVLVHAGWSCHNGHYFSYVKAQEGQWYKMDDAEVTAASIT  360
4.5   LDMKLYMSQTNSGPLVYVLYAVLVHAGWSCHNGHYFSYVKAQEGQWYKMDDAEVTASSIT  360
4.1   LDMQPYMSQQNTGPLVYVLYAVLVHAGWSCHNGHYSSYVKAQEGQWYKMDDAEVTASSIT  360
```

TABLE 28-continued

CLUSTAL W (1.81) multiple sequence alignment
of core amino acids of hDUBs (8.5: Seq ID NO. 30; 8.7: Seq
ID NO. 34; 8.1: Seq ID NO. 26; 4.2: Seq ID NO. 10; 4.3: Seq
ID NO. 12; 4.5: Seq ID NO. 14; 4.1: Seq ID NO. 6; 8.3: Seq
ID NO. 28; 8.11: Seq ID NO. 38; 8.8: Seq ID NO. 36;
8.6: Seq ID NO. 32).

```
8.3   LDMQPYMSQQNTGPLVYVLYAVLVHAGWSCHNGHYFSYVKVQEGQWYKMDDAEVTASGIT 327
8.11  LDMQPYMSQQNTGPLVYVLYAVLVHAGWSCHNGHYFSYVKVQEGQWYKMDDAE------- 261
8.8   RDMQPYMSQQNTGPLVYVLYAVLVHAGWSCHNGHYFSYVKAQEGQWYKMDDAEVTASGIT 360
8.6   RDMQPYMSQQNTGPLVYVLYAVLVHAGWSCHNGHYFSYVKAQEGQWYKMDDAEVTASGIT 360
       **: **** *:******************:*** ****.** ********:

8.5   SVLSQQAYVLFYIQKSEWERHSESVSRGREPRALGAEDTDRRATQGELKRDHPCLQAPEL 420
8.7   SVLSQQAYVLFYIQKSEWERHSESVSRGREPRALGAEDTDRRATQGELKRDHPCLQAPEL 420
8.1   SVLSQQAYVLFYIQKSEWERHSESVSRGREPRALGAEDTDRRAKQGELKRDHPCLQAPEL 420
4.2   SALSQQAYVLFYIQKSEWERHSESVSRGREPRALGTEDTDRRATQGELKRDHPCLQAPEL 420
4.3   SVLSQQAYVLFYIQKSEWERHSESVSRGREPRALGAEDTDRRATQGELKRDHPCLQAPEL 420
4.5   SVLSQQAYVLFYIQKSEWERHSESVSRGREPRALGAEDTDRRATQGELKRDHPCLQAPEL 420
4.1   SVLSQQAYVLFYIQKSEWERHSESVSRGREPRALGVEDTDRRATQGELKRDHPCLQAPEL 420
8.3   SVLSQQAYVLFYIHKSEWERHSESVSRGREPRALGAEDTDRRATQGELKRDYPCLQVPEL 387
8.11  ---------------KSEWERHSESVSRGREPRALGAEDTDRRATQGELKRDYPCLQVPEL 307
8.8   SVLSQQAYVLFYIQKSEWERHSESVSRGREPRALGAEDTDRPATQGELKRDHPCLQVPEL 420
8.6   SVLSQQAYVLFYIQKSEWERHSESVSRGREPRALGAEDTDRPATQGELKRDHPCLQVPEL 420
                      ********************.***** *.********:****.***

8.5   DERLVERATQESTLDHWRFPQEQNKTKPEFNVRKVEGTLPPNVLVIHQSKYKCGMKNHHP 480
8.7   DERLVERATQESTLDHWRFPQEQNKTKPEFNVRKVEGTLPPNVLVIHQSKYKCGMKNHHP 480
8.1   DEHLVERATQESTLDHWKFLQEQNKTKPEFNVGKVEGTLPPDVLVIHQSKYKCGMKNHHP 480
4.2   DEHLVERATQESTLDHWKFLQEQNKTKPEFNVRKVEGTLPPDVLVIHQSKYKCGMKNHHP 480
4.3   DEHLVERATQESTLDRWKFLQEQNKTKPEFNVRKVEGTLPPDVLVIHQSKYKCGMKNHHP 480
4.5   DEHLVERATQESTLDHWKFLQEQNKTKPEFNVRKVEGTLPPDVLVIHQSKYKCGMKNHHP 480
4.1   DEHLVERATQESTLDHWKFLQEQNKTKPEFNVRRVEGTVPPDVLVIHQSKYKCRMKNHHP 480
8.3   DEHLVERATQESTLDHWKFLQEQNKTKPEFNVRKLEGTLPPNVLVIHQSKYKCGMKNHHP 447
8.11  DEHLVERATQESTLDHWKFLQEQNKTKPEFNVRKLEGTLPPNVLVIHQSKYKCGMKNHHP 367
8.8   DEHLVERATQESTLDHWKFPQKQNKTKPEFNVRKVEGTLPPNVLVIHQSKYKCGMKNHHP 480
8.6   DEHLVERATQESTLDHWKFPQKQNKTKPEFNVRKVEGTLPPNVLVIHQSKYKCGMKNHHP 480
       **:************:*:* *:********** ::***:**:.********** ******

8.5   EQQSSLLNLSSTTRTDQESVNTGTLASLQGRTRRSKGKNKHSKRALLVCQ 530
8.7   EQQSSLLNLSSTTRTDQESVNTGTLASLQGRTRRSKGKNKHSKRALLVCQ 530
8.1   EQQSSLLNLSSTTRTDQESMNTGTLASLQGRTRRAKGKNKHSKRALLVCQ 530
4.2   EQQSSLLNLSSSTPTHQESMNTGTLASLRGRARRSKGKNKHSKRALLVCQ 530
4.3   EQQSSLLNLSSSTPTHQESMNTGTLASLRGRARRSKGKNKHSKRALLVCQ 530
4.5   EQQSSLLNLSSTTPTHQESMNTGTLASLRGRARRSKGKNKHSKRALLVCQ 530
4.1   EQQSSLLNLSSTTPTDQESMNTGTLASLRGRTRRSKGKNKHSKRALLVCQ 530
8.3   EQQSSLLNLSSTNPTDQESMNTGTLASLQGRTRRAKGKNKHCKRALLVCQ 497
8.11  EQQSSLLNLSSTNPTDQESMNTGTLASLQGRTRRSKGKNKHCKRALLVCQ 417
8.8   EQQSSVLNLSSTKPTDQESMNTGTLASLQGSTRRSKGNNKHSKRSLLVCQ 530
8.6   EQQSSLLNLSSTKPTDQESMNTGTLASLQGSTRRSKGNNKHSKRSLLVCQ 530
       *****:*****:. *.***:*******:* :**:**:***.**:*****
```

What is claimed is:

1. An isolated polypeptide comprising the human deubiquitinating protease hDUB4.1b (SEQ ID NO: 6).

\* \* \* \* \*

SEQUENCE LISTING

<160> NUMBER OF SEQ IDS NOS: 54

<210> SEQ ID NO 1
<211> LENGTH: 19
<212> TYPE: DNA
<213> ORGANISM: Homo sapiens

<400> SEQUENCE: 1
atggaggacg actcactct                                          19

<210> SEQ ID NO 2
<211> LENGTH: 16
<212> TYPE: DNA
<213> ORGANISM: Homo sapiens

<400> SEQUENCE: 2

-continued ctggcacaca agcaga                                              16

<210> SEQ ID NO 3
<211> LENGTH: 3051
<212> TYPE: DNA
<213> ORGANISM: Homo sapiens
<220> FEATURE:
<221> NAME/KEY: misc_feature
<223> OTHER INFORMATION: human DUB4.1a

<400> SEQUENCE: 3

| | | | | | |
|---|---|---|---|---|---|
| atgaccctgc | aacagagcat | gcccttctgc | attgagcatg | caatcatgaa | tcacaggcgg | 60 |
| aggaactgcg | agagtgccta | cgttagccca | aggcctgacc | cgacgatccc | agggaccctc | 120 |
| gacctaactg | gccccgcctc | ccgggcccca | acccggact | cggccccccc | gaagctccgg | 180 |
| atcctggggc | ccgcccctgg | ccccgcgtcg | gaagaccatg | ggctcgctcc | tgggccttcc | 240 |
| tcaaaccctc | cgcagtccag | gcccggcttc | ctccaggtct | ccaggcaacg | ctgcggctcc | 300 |
| gcccacgtca | tggcgcccga | ggagaacgcg | gggacagaac | tctggctgca | gggtttcgag | 360 |
| cgccgcttcc | tggcggcgcg | ctcactgcgc | tccttcccct | ggcagagctt | agaggcaaag | 420 |
| ttaagagact | catcagattc | tgagctgctg | cgggatattt | gcagaagac | tgtgaagcat | 480 |
| cccgtgtgtg | tgaagcaccc | gccatcagtc | aagtatgccc | ggtgctttct | ctcagaactc | 540 |
| atcaaaaagg | gtgcatctgt | ggtcaccagc | agcacgaggc | tgtccacac | ggagcctttg | 600 |
| gacgagctgt | acgaggtgct | ggcggagact | ctgatggcca | aggagtccac | ccagggccac | 660 |
| cggagctatt | tgctgccctc | gggaggctcg | ttcacacttt | ccgagatcac | agccatcatc | 720 |
| tcccatggta | ctacaggcct | ggtcacatgg | gacgccaccc | tctaccttgc | agaatgggcc | 780 |
| atcgagaacc | cagcagcctt | cactaacagg | ggtgtcctag | agcttggcag | tggcgctggc | 840 |
| ctcacaggcc | tggccatctg | caagatgtgt | cgcccccagg | catacatctt | cagcgactgt | 900 |
| cacagccggg | tcctcgagca | gctccgaggg | aatgtccttc | tcaatggcct | ctcattagag | 960 |
| gcagacatca | ctgccaactt | agacgcccca | ggagaccaca | ggagaaaaac | aaccacttct | 1020 |
| gggacgagga | cagggccctt | gagaaaaggt | ggtgtttggc | tgggccaccg | aaaacccctc | 1080 |
| accctgcca | gcacactcag | tccctctct | ggtggaacag | agctctgcct | gtggccctgg | 1140 |
| gtcccagccc | tgaaacccac | aggtccagcg | gtggccaggg | acacaggccc | acccctgcaa | 1200 |
| gccagcagac | caaacggcag | acacctgaaa | caagaagttc | acgacgtgct | gtattgccca | 1260 |
| gaagccatcg | tgtcactggt | cggggtcctg | cggaggctgg | ctgcctgccg | ggagcacaag | 1320 |
| caggctcctg | aggtctacct | ggcctttacc | gtccgcaacc | cagagacgtg | ccagctgttc | 1380 |
| accaccgagc | tagagatagc | gtctttctgc | aacctgcggt | cccagcagaa | aaaccttgtg | 1440 |
| atccttgttc | cagtcgacat | ggaggacgac | tcactctact | gggaggtga | gtggcagttc | 1500 |
| aaccactttt | caaaactcac | atcttctcgg | ccagatgcag | cttttgctga | atccagcgt | 1560 |
| acttctctcc | ctgagaagtc | accactctca | tgtgagaccc | gtgtcgacct | ctgtgatgat | 1620 |
| ttggctcctg | tggcaagaca | gcttgctccc | agggagaagc | ctcctctgag | tagcaggaga | 1680 |
| cctgctgcgg | tggggctgg | gctccagaat | atgggaaata | cctgctacgt | gaacgcttcc | 1740 |
| ctgcagtgcc | tgacatacaa | accgccactt | gccaactaca | tgctgttccg | ggagcactct | 1800 |
| caaacgtgtc | atcgtcacaa | gggctgcatg | ctctgtacta | tgcaagctca | catcacaagg | 1860 |
| gccctccaca | ttcctggcca | tgtcatccag | ccctcacagg | cattggctgc | tggcttccat | 1920 |
| agaggcaagc | aggaagatgc | ccatgaattt | ctcatgttca | ctgtggatgc | catgagaaag | 1980 |

-continued

```
gcatgccttc ccgggcacaa gcaggtagat cgtcactcta aggacaccac cctcatccac      2040
caaatatttg gaggctactg gagatctcaa atcaagtgtc tccactgcca cggcatttca      2100 gcacttttg  accettacct ggacatcgcc ctggatatcc aggcagctca gagtgtccag      2160
caagctttgg aacagttggt gaagcccgaa gaactcaatg gagagaatgc ctatcattgt      2220 ggtgttttgtc tccagagggc gccggcctcc aagacgttaa ctttacacaa ctctgccaag    2280
gtcctcatcc ttgtattgaa gagattcccc gatgtcacag caacaaaat  tgccaagaat     2340 gtgcaatatc ctgagtgcct tgacatgcag ccatacatgt ctcagcagaa cacaggacct     2400
ctcgtctatg tcctctatgc tgtgctggtc cacgctgggt ggagttgtca caacggacat     2460
tactcctctt atgtcaaagc tcaagaaggc cagtggtata aaatggatga tgccgaggtc     2520
accgcctcta gcatcacttc tgtcctgagt caacaggcct acgtcctctt ttacatccag     2580
aagagtgaat gggaaagaca cagtgagagt gtgtcaagag gcagggaacc aagagccctt     2640
ggcgtagaag acacagacag gcgagcaacg caaggagagc tcaagagaga ccaccctgc     2700 ctccaggccc ccgagttgga cgagcacttg gtggaaagag ccactcagga agcaccttta    2760
gaccactgga aattccttca agagcaaaac aaaacgaagc ctgagttcaa cgtcagaaga    2820
gtcgaaggta cggtgcctcc cgacgtactt gtgattcatc aatcaaaata caagtgtcgg    2880
atgaagaacc atcatcctga acagcaaagc tccctgctaa acctctcttc gacgaccccg    2940
acagatcagg agtccatgaa cactggcaca ctcgcttccc tacgagggag gaccaggaga    3000
tccaaaggga agaacaaaca cagcaagagg gctctgcttg tgtgccagtg a              3051
```

<210> SEQ ID NO 4
<211> LENGTH: 1016
<212> TYPE: PRT
<213> ORGANISM: Homo sapiens
<220> FEATURE:
<221> NAME/KEY: MISC_FEATURE
<223> OTHER INFORMATION: human DUB4.1a

<400> SEQUENCE: 4

```
Met Thr Leu Gln Gln Ser Met Pro Phe Cys Ile Glu His Ala Ile Met
1               5                   10                  15

Asn His Arg Arg Arg Asn Cys Glu Ser Ala Tyr Val Ser Pro Arg Pro
            20                  25                  30

Asp Pro Thr Ile Pro Gly Thr Leu Asp Leu Thr Gly Pro Ala Ser Arg
        35                  40                  45

Ala Pro Asn Pro Asp Ser Ala Pro Pro Lys Leu Arg Ile Leu Gly Pro
    50                  55                  60

Ala Gly Pro Ala Ser Glu Asp His Gly Leu Ala Pro Gly Pro Ser
65                  70                  75                  80

Ser Asn Pro Pro Gln Ser Arg Pro Gly Phe Leu Gln Val Ser Arg Gln
                85                  90                  95

Arg Cys Gly Ser Ala His Val Met Ala Pro Glu Glu Asn Ala Gly Thr
            100                 105                 110

Glu Leu Trp Leu Gln Gly Phe Glu Arg Phe Leu Ala Ala Arg Ser
        115                 120                 125

Leu Arg Ser Phe Pro Trp Gln Ser Leu Glu Ala Lys Leu Arg Asp Ser
    130                 135                 140

Ser Asp Ser Glu Leu Leu Arg Asp Ile Leu Gln Lys Thr Val Lys His
145                 150                 155                 160

Pro Val Cys Val Lys His Pro Pro Ser Val Lys Tyr Ala Arg Cys Phe
                165                 170                 175
```

```
Leu Ser Glu Leu Ile Lys Lys Gly Ala Ser Val Val Thr Ser Ser Thr
            180                 185                 190

Arg Ala Val His Thr Glu Pro Leu Asp Glu Leu Tyr Glu Val Leu Ala
            195                 200                 205

Glu Thr Leu Met Ala Lys Glu Ser Thr Gln Gly His Arg Ser Tyr Leu
            210                 215                 220

Leu Pro Ser Gly Gly Ser Phe Thr Leu Ser Glu Ile Thr Ala Ile Ile
225                 230                 235                 240

Ser His Gly Thr Thr Gly Leu Val Thr Trp Asp Ala Thr Leu Tyr Leu
            245                 250                 255

Ala Glu Trp Ala Ile Glu Asn Pro Ala Ala Phe Thr Asn Arg Gly Val
            260                 265                 270

Leu Glu Leu Gly Ser Gly Ala Gly Leu Thr Gly Leu Ala Ile Cys Lys
            275                 280                 285

Met Cys Arg Pro Gln Ala Tyr Ile Phe Ser Asp Cys His Ser Arg Val
            290                 295                 300

Leu Glu Gln Leu Arg Gly Asn Val Leu Leu Asn Gly Leu Ser Leu Glu
305                 310                 315                 320

Ala Asp Ile Thr Ala Asn Leu Asp Ala Pro Gly Asp His Arg Arg Lys
            325                 330                 335

Thr Thr Thr Ser Gly Thr Arg Thr Gly Pro Leu Arg Lys Gly Gly Val
            340                 345                 350

Trp Leu Gly His Arg Lys Pro Leu Thr Pro Ala Ser Thr Leu Ser Pro
            355                 360                 365

Leu Ser Gly Gly Thr Glu Leu Cys Leu Trp Pro Trp Val Pro Ala Leu
370                 375                 380

Lys Pro Thr Gly Pro Ala Val Ala Arg Asp Thr Gly Pro Pro Leu Gln
385                 390                 395                 400

Ala Ser Arg Pro Asn Gly Arg His Leu Lys Gln Glu Val His Asp Val
            405                 410                 415

Leu Tyr Cys Pro Glu Ala Ile Val Ser Leu Val Gly Val Leu Arg Arg
            420                 425                 430

Leu Ala Ala Cys Arg Glu His Lys Gln Ala Pro Glu Val Tyr Leu Ala
            435                 440                 445

Phe Thr Val Arg Asn Pro Glu Thr Cys Gln Leu Phe Thr Thr Glu Leu
            450                 455                 460

Glu Ile Ala Ser Phe Cys Asn Leu Arg Ser Gln Gln Lys Asn Leu Val
465                 470                 475                 480

Ile Leu Val Pro Val Asp Met Glu Asp Ser Leu Tyr Leu Gly Gly
            485                 490                 495

Glu Trp Gln Phe Asn His Phe Ser Lys Leu Thr Ser Ser Arg Pro Asp
            500                 505                 510

Ala Ala Phe Ala Glu Ile Gln Arg Thr Ser Leu Pro Glu Lys Ser Pro
            515                 520                 525

Leu Ser Cys Glu Thr Arg Val Asp Leu Cys Asp Asp Leu Ala Pro Val
530                 535                 540

Ala Arg Gln Leu Ala Pro Arg Glu Lys Pro Pro Leu Ser Ser Arg Arg
545                 550                 555                 560

Pro Ala Ala Val Gly Ala Gly Leu Gln Asn Met Gly Asn Thr Cys Tyr
            565                 570                 575

Val Asn Ala Ser Leu Gln Cys Leu Thr Tyr Lys Pro Pro Leu Ala Asn
            580                 585                 590
```

-continued

```
Tyr Met Leu Phe Arg Glu His Ser Gln Thr Cys His Arg His Lys Gly
            595                 600                 605

Cys Met Leu Cys Thr Met Gln Ala His Ile Thr Arg Ala Leu His Ile
            610                 615                 620

Pro Gly His Val Ile Gln Pro Ser Gln Ala Leu Ala Ala Gly Phe His
625                 630                 635                 640

Arg Gly Lys Gln Glu Asp Ala His Glu Phe Leu Met Phe Thr Val Asp
                645                 650                 655

Ala Met Arg Lys Ala Cys Leu Pro Gly His Lys Gln Val Asp Arg His
            660                 665                 670

Ser Lys Asp Thr Thr Leu Ile His Gln Ile Phe Gly Tyr Trp Arg
            675                 680                 685

Ser Gln Ile Lys Cys Leu His Cys His Gly Ile Ser Asp Thr Phe Asp
            690                 695                 700

Pro Tyr Leu Asp Ile Ala Leu Asp Ile Gln Ala Ala Gln Ser Val Gln
705                 710                 715                 720

Gln Ala Leu Glu Gln Leu Val Lys Pro Glu Glu Leu Asn Gly Glu Asn
                725                 730                 735

Ala Tyr His Cys Gly Val Cys Leu Gln Arg Ala Pro Ala Ser Lys Thr
            740                 745                 750

Leu Thr Leu His Asn Ser Ala Lys Val Leu Ile Leu Val Leu Lys Arg
            755                 760                 765

Phe Pro Asp Val Thr Gly Asn Lys Ile Ala Lys Asn Val Gln Tyr Pro
770                 775                 780

Glu Cys Leu Asp Met Gln Pro Tyr Met Ser Gln Gln Asn Thr Gly Pro
785                 790                 795                 800

Leu Val Tyr Val Leu Tyr Ala Val Leu Val His Ala Gly Trp Ser Cys
                805                 810                 815

His Asn Gly His Tyr Ser Ser Tyr Val Lys Ala Gln Glu Gly Gln Trp
            820                 825                 830

Tyr Lys Met Asp Asp Ala Glu Val Thr Ala Ser Ser Ile Thr Ser Val
            835                 840                 845

Leu Ser Gln Gln Ala Tyr Val Leu Phe Tyr Ile Gln Lys Ser Glu Trp
850                 855                 860

Glu Arg His Ser Glu Ser Val Ser Arg Gly Arg Glu Pro Arg Ala Leu
865                 870                 875                 880

Gly Val Glu Asp Thr Asp Arg Arg Ala Thr Gln Gly Glu Leu Lys Arg
                885                 890                 895

Asp His Pro Cys Leu Gln Ala Pro Glu Leu Asp Glu His Leu Val Glu
            900                 905                 910

Arg Ala Thr Gln Glu Ser Thr Leu Asp His Trp Lys Phe Leu Gln Glu
            915                 920                 925

Gln Asn Lys Thr Lys Pro Glu Phe Asn Val Arg Arg Val Glu Gly Thr
            930                 935                 940

Val Pro Pro Asp Val Leu Val Ile His Gln Ser Lys Tyr Lys Cys Arg
945                 950                 955                 960

Met Lys Asn His His Pro Glu Gln Gln Ser Ser Leu Leu Asn Leu Ser
                965                 970                 975

Ser Thr Thr Pro Thr Asp Gln Glu Ser Met Asn Thr Gly Thr Leu Ala
            980                 985                 990

Ser Leu Arg Gly Arg Thr Arg Arg  Ser Lys Gly Lys Asn  Lys His Ser
            995                 1000                1005

Lys Arg  Ala Leu Leu Val Cys  Gln
```

<210> SEQ ID NO 5
<211> LENGTH: 1593
<212> TYPE: DNA
<213> ORGANISM: Homo sapiens
<220> FEATURE:
<221> NAME/KEY: misc_feature
<223> OTHER INFORMATION: human DUB4.1b

<400> SEQUENCE: 5

| | | | | | |
|---|---|---|---|---|---|
| atggaggacg | actcactcta | cttgggaggt | gagtggcagt | tcaaccactt | ttcaaaactc | 60 |
| acatcttctc | ggccagatgc | agcttttgct | gaaatccagc | gtacttctct | ccctgagaag | 120 |
| tcaccactct | catgtgagac | ccgtgtcgac | ctctgtgatg | atttggctcc | tgtggcaaga | 180 |
| cagcttgctc | ccagggagaa | gcctcctctg | agtagcagga | gacctgctgc | ggtgggggct | 240 |
| gggctccaga | atatgggaaa | tacctgctac | gtgaacgctt | ccctgcagtg | cctgacatac | 300 |
| aaaccgccac | ttgccaacta | catgctgttc | cgggagcact | ctcaaacgtg | tcatcgtcac | 360 |
| aagggctgca | tgctctgtac | tatgcaagct | cacatcacaa | gggcccctcca | cattcctggc | 420 |
| catgtcatcc | agccctcaca | ggcattggct | gctggcttcc | atagaggcaa | gcaggaagat | 480 |
| gcccatgaat | ttctcatgtt | cactgtggat | gccatgagaa | aggcatgcct | tcccgggcac | 540 |
| aagcaggtag | atcgtcactc | taaggacacc | accctcatcc | accaaatatt | tggaggctac | 600 |
| tggagatctc | aaatcaagtg | tctccactgc | cacggcattt | cagacacttt | tgacccttac | 660 |
| ctggacatcg | ccctggatat | ccaggcagct | cagagtgtcc | agcaagcttt | ggaacagttg | 720 |
| gtgaagcccg | aagaactcaa | tggagagaat | gcctatcatt | gtggtgtttg | tctccagagg | 780 |
| gcgccggcct | ccaagacgtt | aactttacac | aactctgcca | aggtcctcat | ccttgtattg | 840 |
| aagagattcc | ccgatgtcac | aggcaacaaa | attgccaaga | atgtgcaata | tcctgagtgc | 900 |
| cttgacatgc | agccatacat | gtctcagcag | aacacaggac | tctcgtcta | tgtcctctat | 960 |
| gctgtgctgg | tccacgctgg | gtggagttgt | cacaacggac | attactcctc | ttatgtcaaa | 1020 |
| gctcaagaag | gccagtggta | taaaatggat | gatgccgagg | tcaccgcctc | tagcatcact | 1080 |
| tctgtcctga | gtcaacaggc | ctacgtcctc | ttttacatcc | agaagagtga | atgggaaaga | 1140 |
| cacagtgaga | gtgtgtcaag | aggcagggaa | ccaagagccc | ttggcgtaga | agacacagac | 1200 |
| aggcgagcaa | cgcaaggaga | gctcaagaga | gaccacccct | gcctccaggc | cccgagttg | 1260 |
| gacgagcact | tggtggaaag | agccactcag | gaaagcacct | tagaccactg | gaaattcctt | 1320 |
| caagagcaaa | acaaaacgaa | gcctgagttc | aacgtcagaa | gagtcgaagg | tacggtgcct | 1380 |
| cccgacgtac | ttgtgattca | tcaatcaaaa | tacaagtgtc | ggatgaagaa | ccatcatcct | 1440 |
| gaacagcaaa | gctccctgct | aaacctctct | tcgacgaccc | cgacagatca | ggagtccatg | 1500 |
| aacactggca | cactcgcttc | cctacgaggg | aggaccagga | gatccaaagg | gaagaacaaa | 1560 |
| cacagcaaga | gggctctgct | tgtgtgccag | tga | | | 1593 |

<210> SEQ ID NO 6
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB4.1b

<400> SEQUENCE: 6

Met Glu Asp Asp Ser Leu Tyr Leu Gly Gly Glu Trp Gln Phe Asn His

-continued

```
1               5                   10                  15
Phe Ser Lys Leu Thr Ser Ser Arg Pro Asp Ala Ala Phe Ala Glu Ile
            20                  25                  30

Gln Arg Thr Ser Leu Pro Glu Lys Ser Pro Leu Ser Cys Glu Thr Arg
            35                  40                  45

Val Asp Leu Cys Asp Asp Leu Ala Pro Val Ala Arg Gln Leu Ala Pro
 50                  55                  60

Arg Glu Lys Pro Pro Leu Ser Ser Arg Arg Pro Ala Ala Val Gly Ala
 65                  70                  75                  80

Gly Leu Gln Asn Met Gly Asn Thr Cys Tyr Val Asn Ala Ser Leu Gln
                85                  90                  95

Cys Leu Thr Tyr Lys Pro Pro Leu Ala Asn Tyr Met Leu Phe Arg Glu
                100                 105                 110

His Ser Gln Thr Cys His Arg His Lys Gly Cys Met Leu Cys Thr Met
                115                 120                 125

Gln Ala His Ile Thr Arg Ala Leu His Ile Pro Gly His Val Ile Gln
                130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Arg Lys Ala Cys
                165                 170                 175

Leu Pro Gly His Lys Gln Val Asp Arg His Ser Lys Asp Thr Thr Leu
                180                 185                 190

Ile His Gln Ile Phe Gly Gly Tyr Trp Arg Ser Gln Ile Lys Cys Leu
                195                 200                 205

His Cys His Gly Ile Ser Asp Thr Phe Asp Pro Tyr Leu Asp Ile Ala
                210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Cys Gly Val
                245                 250                 255

Cys Leu Gln Arg Ala Pro Ala Ser Lys Thr Leu Thr Leu His Asn Ser
                260                 265                 270

Ala Lys Val Leu Ile Leu Val Leu Lys Arg Phe Pro Asp Val Thr Gly
                275                 280                 285

Asn Lys Ile Ala Lys Asn Val Gln Tyr Pro Glu Cys Leu Asp Met Gln
                290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Ser
                325                 330                 335

Ser Tyr Val Lys Ala Gln Glu Gly Gln Trp Tyr Lys Met Asp Asp Ala
                340                 345                 350

Glu Val Thr Ala Ser Ser Ile Thr Ser Val Leu Ser Gln Gln Ala Tyr
                355                 360                 365

Val Leu Phe Tyr Ile Gln Lys Ser Glu Trp Glu Arg His Ser Glu Ser
                370                 375                 380

Val Ser Arg Gly Arg Glu Pro Arg Ala Leu Gly Val Glu Asp Thr Asp
385                 390                 395                 400

Arg Arg Ala Thr Gln Gly Glu Leu Lys Arg Asp His Pro Cys Leu Gln
                405                 410                 415

Ala Pro Glu Leu Asp Glu His Leu Val Glu Arg Ala Thr Gln Glu Ser
                420                 425                 430
```

```
Thr Leu Asp His Trp Lys Phe Leu Gln Glu Gln Asn Lys Thr Lys Pro
        435                 440                 445

Glu Phe Asn Val Arg Arg Val Glu Gly Thr Val Pro Pro Asp Val Leu
    450                 455                 460

Val Ile His Gln Ser Lys Tyr Lys Cys Arg Met Lys Asn His His Pro
465                 470                 475                 480

Glu Gln Gln Ser Ser Leu Leu Asn Leu Ser Ser Thr Thr Pro Thr Asp
                485                 490                 495

Gln Glu Ser Met Asn Thr Gly Thr Leu Ala Ser Leu Arg Gly Arg Thr
            500                 505                 510

Arg Arg Ser Lys Gly Lys Asn Lys His Ser Lys Arg Ala Leu Leu Val
        515                 520                 525

Cys Gln
    530

<210> SEQ ID NO 7
<211> LENGTH: 3066
<212> TYPE: DNA
<213> ORGANISM: Homo sapiens
<220> FEATURE:
<221> NAME/KEY: misc_feature
<223> OTHER INFORMATION: human DUB4.2a

<400> SEQUENCE: 7
atgggaaata cctgctacgt gaacgcttcc ttgcagtgcc tgacatacac accgccctt      60 gccaactaca tgctgtcccg ggagcactct caaacgtgtc atcgtcacaa gggctgcatg   120
ctctgtacta tgcaagctca catcacacgg gccctccaca tcctggcca cgtcatccag    180 ccctcacagg cattggctgc tggcttccat agaggcaagc aggaagatgc ccatgaattt   240
ctcatgttca ctgtggatgc catgaaaaag gcatgccttc ccaggcacaa gcaggtagat   300
catcactcta aggacaccac cctcatccac caaatatttg gaggctactg agatctcaa    360 atcaagtgtc tccactgcca cggcattttca cactttttg accctttacct ggacatcgcc  420 ctggatatcc aggcagctca gagtgtccag caagctttgg aacagttggt gaagcccgaa   480
gaactcaatg agagaatgc ctatcattgt ggtgtttgtc tccagagggc gccggcctcc    540
aagacgttaa ctttacacac ctctgccaag gtcctcatcc ttgtattgaa gagattctcc   600
gatgtcacag gcaacaagat tgccaagaat gtgcaatatc ctgagtgcct tgacatgcag   660
ccatacatgt ctcagcagaa cacaggacct cttgtctatg tcctctatgc tgtgctggtc   720
cacgctgagt ggagttgtca acggacat tacttctctt atgtcaaagc tcaagaaggc    780
cagtggtata aatggatga tgccgaggtc accgccgcta gcatcacttc tgtcctgagt   840
caacaggcct acgtcctctt ttacatccag aagagtgaat gggaaagaca tagtgagagt   900
gtgtcaagag gcagggaacc aagagccctt ggcgcagaag acacagacag gcgagcaacg   960
caaggagagc tcaagagaga ccaccctgc ctccaggccc ccgagttgga cgagcacttg   1020
gtggaaagag ccactcagga agcaccttta gaccactgga aattccttca agagcaaaac   1080
aaaacgaagc ctgagttcaa cgtcagaaaa gtcaaaggta cagtgatcaa agttgaccag   1140
ccccagagga aagctgccca gggcacaact cagggctccg tagaaccaca gaatcttggg   1200
cgcaaccctg ctcaagcacc caaatgtgca tacgaacagg tctccgtgt gacggaacat   1260 gtccactttc ggcagcatta caattttggc accaaatgtg ctaactgcaa ttccaccata   1320
caatgcgtaa ctggaaatgg aggcaacatc gccgatcctg aacgatcgat gcgagaatcc   1380
```

-continued

```
aggatatgca cggcttattt tggccttttc ccactgaaac aagggccagt attaaaaatg   1440
cagaaaaacc ttgtgatcct cgttccagtc gacatggagg acgactcact ctacttggga   1500
ggtgagtggc agttcaacca cttttcaaaa ctcacatctt ctcggcccga tgcagctttt   1560
gctgaaatcc agcggacttc tctccctgag aagtcaccac tctcatgtga gacccgtgtc   1620
gacctctgtg atgatttggc tcctgtggca agacagcttg ctcccaggga gaagcttcct   1680
ctgagtagca ggagacctgc tgcggtgggg gctgggctcc agaatatggg aaatacctgc   1740
tacgtgaacg cttccttgca gtgcctgaca tacacaacgc cccttgccaa ctacatgctg   1800
tcccgggagc actctcaaac gtgtcatcgt cacaagggct gcatgctctg tactatgcaa   1860
gctcacatca cacgggccct ccacaatcct ggccacgtca tccagccctc acaggcattg   1920
gctgctggct tccatagagg caagcaggaa gatgcccatg aatttctcat gttcactgtg   1980
gatgccatga aaaggcatg ccttcccggg cacaagcagg tagatcatca ctctaaggac   2040
accaccctca tccaccaaat atttggaggc tactggagat ctcaaatcaa gtgtctccac   2100
tgccacggca tttcagacac ttttgaccct tacctggaca tcgccctaga tatccaggca   2160
gctcagagtg tccagcaagc tttggaacag ttggtgaagc ccgaagaact caatggagag   2220
aatgcctatc attctggtgt ttgtctccag agggcgccgg cctccaagac gttaacttta   2280
cacacctctg ccaaggtcct catccttgta ttgaagagat tctccgatgt cacaggcaac   2340
aagattgcca gaatgtgca atatcctgag tgccttgaca tgcagccata catgtctcag   2400
cagaacacag gacctcttgt ctatgtcctc tatgctgtgc tggtccacgc tgggtgggagt   2460
tgtcacaacg gacattactt ctcttatgtc aaagctcaag aaggccagtg gtataaaatg   2520
gatgatgccg aggtcaccgc cgctagcatc acttctgccc tgagtcaaca ggcctacgtc   2580
ctcttttaca tccagaagag tgaatgggaa agacacagtg agagtgtgtc aagaggcagg   2640
gaaccaagag cccttggcac agaagacaca gacaggcgag caacgcaagg agagctcaag   2700
agagaccacc cctgcctcca ggcccccgag ttggacgagc acttggtgga agagccact   2760
caggaaagca ccttagacca ctggaaattc cttcaagagc aaaacaaaac gaagcctgag   2820
ttcaacgtca gaaaagtcga aggtaccctg cctcccgacg tacttgtgat tcatcaatca   2880
aaatacaagt gtgggatgaa gaaccatcat cctgaacagc aaagctccct gctaaacctc   2940
tcttcgtcga ccccgacaca tcaggagtcc atgaacactg gcacactcgc ttccctgcga   3000
gggagggcca ggagatccaa agggaagaac aaacacagca agagggctct gcttgtgtgc   3060
cagtga                                                             3066
```

<210> SEQ ID NO 8
<211> LENGTH: 1021
<212> TYPE: PRT
<213> ORGANISM: Homo sapiens
<220> FEATURE:
<221> NAME/KEY: MISC_FEATURE
<223> OTHER INFORMATION: human DUB4.2a

<400> SEQUENCE: 8

Met Gly Asn Thr Cys Tyr Val Asn Ala Ser Leu Gln Cys Leu Thr Tyr
1               5                   10                  15

Thr Pro Pro Leu Ala Asn Tyr Met Leu Ser Arg Glu His Ser Gln Thr
            20                  25                  30

Cys His Arg His Lys Gly Cys Met Leu Cys Thr Met Gln Ala His Ile
        35                  40                  45

Thr Arg Ala Leu His Asn Pro Gly His Val Ile Gln Pro Ser Gln Ala

```
                50                  55                  60
Leu Ala Ala Gly Phe His Arg Gly Lys Gln Glu Asp Ala His Glu Phe
65                  70                  75                  80

Leu Met Phe Thr Val Asp Ala Met Lys Lys Ala Cys Leu Pro Arg His
                85                  90                  95

Lys Gln Val Asp His His Ser Lys Asp Thr Thr Leu Ile His Gln Ile
                100                 105                 110

Phe Gly Gly Tyr Trp Arg Ser Gln Ile Lys Cys Leu His Cys His Gly
                115                 120                 125

Ile Ser Asp Thr Phe Asp Pro Tyr Leu Asp Ile Ala Leu Asp Ile Gln
130                 135                 140

Ala Ala Gln Ser Val Gln Gln Ala Leu Glu Gln Leu Val Lys Pro Glu
145                 150                 155                 160

Glu Leu Asn Gly Glu Asn Ala Tyr His Cys Gly Val Cys Leu Gln Arg
                165                 170                 175

Ala Pro Ala Ser Lys Thr Leu Thr Leu His Thr Ser Ala Lys Val Leu
                180                 185                 190

Ile Leu Val Leu Lys Arg Phe Ser Asp Val Thr Gly Asn Lys Ile Ala
                195                 200                 205

Lys Asn Val Gln Tyr Pro Glu Cys Leu Asp Met Gln Pro Tyr Met Ser
210                 215                 220

Gln Gln Asn Thr Gly Pro Leu Val Tyr Val Leu Tyr Ala Val Leu Val
225                 230                 235                 240

His Ala Glu Trp Ser Cys His Asn Gly His Tyr Phe Ser Tyr Val Lys
                245                 250                 255

Ala Gln Glu Gly Gln Trp Tyr Lys Met Asp Asp Ala Glu Val Thr Ala
                260                 265                 270

Ala Ser Ile Thr Ser Val Leu Ser Gln Gln Ala Tyr Val Leu Phe Tyr
                275                 280                 285

Ile Gln Lys Ser Glu Trp Glu Arg His Ser Glu Ser Val Ser Arg Gly
                290                 295                 300

Arg Glu Pro Arg Ala Leu Gly Ala Glu Asp Thr Asp Arg Arg Ala Thr
305                 310                 315                 320

Gln Gly Glu Leu Lys Arg Asp His Pro Cys Leu Gln Ala Pro Glu Leu
                325                 330                 335

Asp Glu His Leu Val Glu Arg Ala Thr Gln Glu Ser Thr Leu Asp His
                340                 345                 350

Trp Lys Phe Leu Gln Glu Gln Asn Lys Thr Lys Pro Glu Phe Asn Val
                355                 360                 365

Arg Lys Val Lys Gly Thr Val Ile Lys Val Asp Gln Pro Gln Arg Lys
                370                 375                 380

Ala Ala Gln Gly Thr Thr Gln Gly Ser Val Glu Pro Gln Asn Leu Gly
385                 390                 395                 400

Arg Asn Pro Ala Gln Ala Pro Lys Cys Ala Tyr Glu Gln Gly Leu Arg
                405                 410                 415

Val Thr Glu His Val His Phe Arg Gln His Tyr Asn Phe Gly Thr Lys
                420                 425                 430

Cys Ala Asn Cys Asn Ser Thr Ile Gln Cys Val Thr Gly Asn Gly Gly
                435                 440                 445

Asn Ile Ala Asp Pro Glu Arg Ser Met Arg Glu Ser Arg Ile Cys Thr
450                 455                 460

Ala Tyr Phe Gly Leu Phe Pro Leu Lys Gln Gly Pro Val Leu Lys Met
465                 470                 475                 480
```

```
Gln Lys Asn Leu Val Ile Leu Val Pro Val Asp Met Glu Asp Asp Ser
            485                 490                 495
Leu Tyr Leu Gly Gly Glu Trp Gln Phe Asn His Phe Ser Lys Leu Thr
            500                 505                 510
Ser Ser Arg Pro Asp Ala Ala Phe Ala Glu Ile Gln Arg Thr Ser Leu
            515                 520                 525
Pro Glu Lys Ser Pro Leu Ser Cys Glu Thr Arg Val Asp Leu Cys Asp
            530                 535                 540
Asp Leu Ala Pro Val Ala Arg Gln Leu Ala Pro Arg Glu Lys Leu Pro
545                 550                 555                 560
Leu Ser Ser Arg Arg Pro Ala Ala Val Gly Ala Gly Leu Gln Asn Met
            565                 570                 575
Gly Asn Thr Cys Tyr Val Asn Ala Ser Leu Gln Cys Leu Thr Tyr Thr
            580                 585                 590
Thr Pro Leu Ala Asn Tyr Met Leu Ser Arg Glu His Ser Gln Thr Cys
            595                 600                 605
His Arg His Lys Gly Cys Met Leu Cys Thr Met Gln Ala His Ile Thr
            610                 615                 620
Arg Ala Leu His Asn Pro Gly His Val Ile Gln Pro Ser Gln Ala Leu
625                 630                 635                 640
Ala Ala Gly Phe His Arg Gly Lys Gln Glu Asp Ala His Glu Phe Leu
            645                 650                 655
Met Phe Thr Val Asp Ala Met Lys Lys Ala Cys Leu Pro Gly His Lys
            660                 665                 670
Gln Val Asp His His Ser Lys Asp Thr Thr Leu Ile His Gln Ile Phe
            675                 680                 685
Gly Gly Tyr Trp Arg Ser Gln Ile Lys Cys Leu His Cys His Gly Ile
            690                 695                 700
Ser Asp Thr Phe Asp Pro Tyr Leu Asp Ile Ala Leu Asp Ile Gln Ala
705                 710                 715                 720
Ala Gln Ser Val Gln Gln Ala Leu Glu Gln Leu Val Lys Pro Glu Glu
            725                 730                 735
Leu Asn Gly Glu Asn Ala Tyr His Ser Gly Val Cys Leu Gln Arg Ala
            740                 745                 750
Pro Ala Ser Lys Thr Leu Thr Leu His Thr Ser Ala Lys Val Leu Ile
            755                 760                 765
Leu Val Leu Lys Arg Phe Ser Asp Val Thr Gly Asn Lys Ile Ala Lys
770                 775                 780
Asn Val Gln Tyr Pro Glu Cys Leu Asp Met Gln Pro Tyr Met Ser Gln
785                 790                 795                 800
Gln Asn Thr Gly Pro Leu Val Tyr Val Leu Tyr Ala Val Leu Val His
            805                 810                 815
Ala Gly Trp Ser Cys His Asn Gly His Tyr Phe Ser Tyr Val Lys Ala
            820                 825                 830
Gln Glu Gly Gln Trp Tyr Lys Met Asp Asp Ala Glu Val Thr Ala Ala
            835                 840                 845
Ser Ile Thr Ser Ala Leu Ser Gln Gln Ala Tyr Val Leu Phe Tyr Ile
            850                 855                 860
Gln Lys Ser Glu Trp Glu Arg His Ser Glu Ser Val Ser Arg Gly Arg
865                 870                 875                 880
Glu Pro Arg Ala Leu Gly Thr Glu Asp Thr Asp Arg Arg Ala Thr Gln
            885                 890                 895
```

```
Gly Glu Leu Lys Arg Asp His Pro Cys Leu Gln Ala Pro Glu Leu Asp
            900                 905                 910

Glu His Leu Val Glu Arg Ala Thr Gln Glu Ser Thr Leu Asp His Trp
        915                 920                 925

Lys Phe Leu Gln Glu Gln Asn Lys Thr Lys Pro Glu Phe Asn Val Arg
    930                 935                 940

Lys Val Glu Gly Thr Leu Pro Pro Asp Val Leu Val Ile His Gln Ser
945                 950                 955                 960

Lys Tyr Lys Cys Gly Met Lys Asn His His Pro Glu Gln Gln Ser Ser
                965                 970                 975

Leu Leu Asn Leu Ser Ser Ser Thr Pro Thr His Gln Glu Ser Met Asn
            980                 985                 990

Thr Gly Thr Leu Ala Ser Leu Arg  Gly Arg Ala Arg Arg  Ser Lys Gly
        995                 1000                1005

Lys Asn  Lys His Ser Lys Arg  Ala Leu Leu Val Cys  Gln
    1010                1015                1020
```

<210> SEQ ID NO 9
<211> LENGTH: 1593
<212> TYPE: DNA
<213> ORGANISM: Homo sapiens
<220> FEATURE:
<221> NAME/KEY: misc_feature
<223> OTHER INFORMATION: human DUB4.2b

<400> SEQUENCE: 9

```
atggaggacg actcactcta cttgggaggt gagtggcagt tcaaccactt ttcaaaactc      60
acatcttctc ggcccgatgc agcttttgct gaaatccagc ggacttctct ccctgagaag     120
tcaccactct catgtgagac ccgtgtcgac ctctgtgatg atttggctcc tgtggcaaga     180
cagcttgctc ccaggagaa gcttcctctg agtagcagga gacctgctgc ggtgggggct     240
gggctccaga atatgggaaa tacctgctac gtgaacgctt ccttgcagtg cctgacatac     300
acaacgcccc ttgccaacta catgctgtcc cgggagcact ctcaaacgtg tcatcgtcac     360
aagggctgca tgctctgtac tatgcaagct cacatcacac gggccctcca caatcctggc     420
cacgtcatcc agccctcaca ggcattggct gctggcttcc atagaggcaa gcaggaagat     480
gcccatgaat ttctcatgtt cactgtggat gccatgaaaa aggcatgcct tcccgggcac     540
aagcaggtag atcatcactc taaggacacc accctcatcc accaaatatt tggaggctac     600
tggagatctc aaatcaagtg tctccactgc cacggcattt cagacacttt tgacccttac     660
ctggacatcg ccctagatat ccaggcagct cagagtgtcc agcaagcttt ggaacagttg     720
gtgaagcccg aagaactcaa tggagagaat gcctatcatt ctggtgtttg tctccagagg     780
gcgccggcct ccaagacgtt aactttacac acctctgcca aggtcctcat ccttgtattg     840
aagagattct ccgatgtcac aggcaacaag attgccaaga atgtgcaata tcctgagtgc     900
cttgacatgc agccatacat gtctcagcag aacacaggac ctcttgtcta tgtcctctat     960
gctgtgctgg tccacgctgg gtggagttgt acaacggac attacttctc ttatgtcaaa    1020
gctcaagaag gccagtggta taaatggat gatgccgagg tcaccgccgc tagcatcact    1080
tctgccctga tcaacaggc ctacgtcctc ttttacatcc agaagagtga atgggaaaga    1140
cacagtgaga gtgtgtcaag aggcagggaa ccaagagccc ttggcacaga agacacagac    1200
aggcgagcaa cgcaaggaga gctcaagaga gaccacccct gcctccaggc ccccgagttg    1260
gacgagcact tggtggaaag agccactcag gaaagcacct tagaccactg gaaattcctt    1320
```

```
caagagcaaa acaaaacgaa gcctgagttc aacgtcagaa aagtcgaagg taccctgcct    1380
cccgacgtac ttgtgattca tcaatcaaaa tacaagtgtg ggatgaagaa ccatcatcct    1440
gaacagcaaa gctccctgct aaacctctct tcgtcgaccc cgacacatca ggagtccatg    1500
aacactggca cactcgcttc cctgcgaggg agggccagga gatccaaagg gaagaacaaa    1560
cacagcaaga gggctctgct tgtgtgccag tga                                  1593
```

<210> SEQ ID NO 10
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB4.2b

<400> SEQUENCE: 10

```
Met Glu Asp Asp Ser Leu Tyr Leu Gly Gly Glu Trp Gln Phe Asn His
1               5                   10                  15

Phe Ser Lys Leu Thr Ser Ser Arg Pro Asp Ala Ala Phe Ala Glu Ile
            20                  25                  30

Gln Arg Thr Ser Leu Pro Glu Lys Ser Pro Leu Ser Cys Glu Thr Arg
        35                  40                  45

Val Asp Leu Cys Asp Asp Leu Ala Pro Val Ala Arg Gln Leu Ala Pro
50                  55                  60

Arg Glu Lys Leu Pro Leu Ser Ser Arg Arg Pro Ala Ala Val Gly Ala
65                  70                  75                  80

Gly Leu Gln Asn Met Gly Asn Thr Cys Tyr Val Asn Ala Ser Leu Gln
                85                  90                  95

Cys Leu Thr Tyr Thr Thr Pro Leu Ala Asn Tyr Met Leu Ser Arg Glu
            100                 105                 110

His Ser Gln Thr Cys His Arg His Lys Gly Cys Met Leu Cys Thr Met
        115                 120                 125

Gln Ala His Ile Thr Arg Ala Leu His Asn Pro Gly His Val Ile Gln
130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His His Ser Lys Asp Thr Thr Leu
            180                 185                 190

Ile His Gln Ile Phe Gly Gly Tyr Trp Arg Ser Gln Ile Lys Cys Leu
        195                 200                 205

His Cys His Gly Ile Ser Asp Thr Phe Asp Pro Tyr Leu Asp Ile Ala
210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Ser Gly Val
                245                 250                 255

Cys Leu Gln Arg Ala Pro Ala Ser Lys Thr Leu Thr Leu His Thr Ser
            260                 265                 270

Ala Lys Val Leu Ile Leu Val Leu Lys Arg Phe Ser Asp Val Thr Gly
        275                 280                 285

Asn Lys Ile Ala Lys Asn Val Gln Tyr Pro Glu Cys Leu Asp Met Gln
290                 295                 300

Pro Tyr Met Ser Gln Gln Asn Thr Gly Pro Leu Val Tyr Val Leu Tyr
```

-continued

```
            305                 310                 315                 320
        Ala Val Leu Val His Ala Gly Trp Ser Cys His Asn Gly His Tyr Phe
                    325                 330                 335

Ser Tyr Val Lys Ala Gln Glu Gly Gln Trp Tyr Lys Met Asp Asp Ala
                    340                 345                 350

Glu Val Thr Ala Ala Ser Ile Thr Ser Ala Leu Ser Gln Gln Ala Tyr
                    355                 360                 365

Val Leu Phe Tyr Ile Gln Lys Ser Glu Trp Glu Arg His Ser Glu Ser
                    370                 375                 380

Val Ser Arg Gly Arg Glu Pro Arg Ala Leu Gly Thr Glu Asp Thr Asp
        385                 390                 395                 400

Arg Arg Ala Thr Gln Gly Glu Leu Lys Arg Asp His Pro Cys Leu Gln
                    405                 410                 415

Ala Pro Glu Leu Asp Glu His Leu Val Glu Arg Ala Thr Gln Glu Ser
                    420                 425                 430

Thr Leu Asp His Trp Lys Phe Leu Gln Glu Gln Asn Lys Thr Lys Pro
                    435                 440                 445

Glu Phe Asn Val Arg Lys Val Glu Gly Thr Leu Pro Pro Asp Val Leu
                    450                 455                 460

Val Ile His Gln Ser Lys Tyr Lys Cys Gly Met Lys Asn His His Pro
        465                 470                 475                 480

Glu Gln Gln Ser Ser Leu Leu Asn Leu Ser Ser Ser Thr Pro Thr His
                    485                 490                 495

Gln Glu Ser Met Asn Thr Gly Thr Leu Ala Ser Leu Arg Gly Arg Ala
                    500                 505                 510

Arg Arg Ser Lys Gly Lys Asn Lys His Ser Lys Arg Ala Leu Leu Val
                    515                 520                 525

Cys Gln
            530

<210> SEQ ID NO 11
<211> LENGTH: 1593
<212> TYPE: DNA
<213> ORGANISM: Homo sapiens
<220> FEATURE:
<221> NAME/KEY: misc_feature
<223> OTHER INFORMATION: human DUB4.3

<400> SEQUENCE: 11
atggaggacg actcactcta cttgggaggt gagtggcagt tcaaccactt ttcaaaactc          60
acatcttctc ggcccgatgc agcttttgct gaaatccagc ggacttctct ccctgagaag        120
tcaccactct catgtgagac ccgtgtcgac ctctgtgatg atttggctcc tgtggcaaga        180
cagcttgctc ccagggagaa gcttcctctg agtagcagga gacctgctgc ggtgggggct        240
gggctccaga atatgggaaa tacctgctac gtgaacgctt ccttgcagtg cctgacatac        300
acaccgcccc ttgccaacta catgctgtcc cgggagcact ctcaaacgtg tcatcgtcac        360
aagggctgca tgctctgtac gatgcaagct cacatcacac gggccctcca caatcctggc        420
cacgtcatcc agccctcaca ggcattggct gctggcttcc atagaggcaa gcaggaagat        480
gcccatgaat ttctcatgtt cactgtggat gccatgaaaa aggcatgcct tcccgggcac        540
aagcaggtag atcatcactc taaggacacc accctcatcc accaaatatt tggaggctac        600
tggagatctc aaatcaagtg tctccactgc cacggcattt cagacacttt tgacccttac        660
ctggacatcg ccctggatat ccaggcagct cagagtgtcc agcaagcttt ggaacagttg        720
```

```
gtgaagcccg aagaactcaa tggagagaat gcctatcatt gtggtgtttg tctccagagg    780
gcgccggcct ccaagacgtt aactttacac acctctgcca aggtcctcat ccttgtattg    840
aagagattct ccgatgtgac aggcaacaag attgccaaga atgtgcaata tcctgagtgc    900
cttgacatgc agccatacat gtctcagcag aacacaggac ctcttgtcta tgtcctctat    960
gctgtgctgg tccacgctgg gtggagttgt cacaacggac attacttctc ttatgtcaaa   1020
gctcaagaag gccaatggta taaaatggat gatgccgagg tcaccgccgc tagcatcact   1080
tctgtcctga gtcaacaggc ctacgtcctc ttttacatcc agaagagtga atgggaaaga   1140
cacagtgaga gtgtgtcaag aggcagggaa ccaagagccc ttggcgcaga agacacagac   1200
aggcgagcaa cgcaaggaga gctcaagaga gaccacccct gcctccaggc ccccgagttg   1260
gacgagcact tggtggaaag agccactcag gaaagcacct tagaccgctg gaaattcctt   1320
caagagcaaa acaaaacgaa gcctgagttc aacgtcagaa aagtcgaagg taccctgcct   1380
cccgacgtac ttgtgattca tcaatcaaaa tacaagtgtg ggatgaagaa ccatcatcct   1440
gaacagcaaa gctccctgct aaacctctct tcgtcgaccc cgacacatca ggagtccatg   1500
aacactggca cactcgcttc cctgcgaggg agggccagga gatccaaagg gaagaacaaa   1560
cacagcaaga gggctctgct tgtgtgccag tga                                 1593
```

<210> SEQ ID NO 12
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB4.3

<400> SEQUENCE: 12

```
Met Glu Asp Asp Ser Leu Tyr Leu Gly Gly Glu Trp Gln Phe Asn His
 1               5                  10                  15

Phe Ser Lys Leu Thr Ser Ser Arg Pro Asp Ala Ala Phe Ala Glu Ile
                20                  25                  30

Gln Arg Thr Ser Leu Pro Glu Lys Ser Pro Leu Ser Cys Glu Thr Arg
            35                  40                  45

Val Asp Leu Cys Asp Asp Leu Ala Pro Val Ala Arg Gln Leu Ala Pro
        50                  55                  60

Arg Glu Lys Leu Pro Leu Ser Ser Arg Arg Pro Ala Ala Val Gly Ala
    65                  70                  75                  80

Gly Leu Gln Asn Met Gly Asn Thr Cys Tyr Val Asn Ala Ser Leu Gln
                85                  90                  95

Cys Leu Thr Tyr Thr Pro Pro Leu Ala Asn Tyr Met Leu Ser Arg Glu
            100                 105                 110

His Ser Gln Thr Cys His Arg His Lys Gly Cys Met Leu Cys Thr Met
        115                 120                 125

Gln Ala His Ile Thr Arg Ala Leu His Asn Pro Gly His Val Ile Gln
    130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His His Ser Lys Asp Thr Thr Leu
            180                 185                 190

Ile His Gln Ile Phe Gly Gly Tyr Trp Arg Ser Gln Ile Lys Cys Leu
        195                 200                 205
```

His Cys His Gly Ile Ser Asp Thr Phe Asp Pro Tyr Leu Asp Ile Ala
    210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Cys Gly Val
                245                 250                 255

Cys Leu Gln Arg Ala Pro Ala Ser Lys Thr Leu Thr Leu His Thr Ser
            260                 265                 270

Ala Lys Val Leu Ile Leu Val Leu Lys Arg Phe Ser Asp Val Thr Gly
        275                 280                 285

Asn Lys Ile Ala Lys Asn Val Gln Tyr Pro Glu Cys Leu Asp Met Gln
    290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Met Asp Asp Ala
            340                 345                 350

Glu Val Thr Ala Ala Ser Ile Thr Ser Val Leu Ser Gln Gln Ala Tyr
        355                 360                 365

Val Leu Phe Tyr Ile Gln Lys Ser Glu Trp Glu Arg His Ser Glu Ser
    370                 375                 380

Val Ser Arg Gly Arg Glu Pro Arg Ala Leu Gly Ala Glu Asp Thr Asp
385                 390                 395                 400

Arg Arg Ala Thr Gln Gly Glu Leu Lys Arg Asp His Pro Cys Leu Gln
                405                 410                 415

Ala Pro Glu Leu Asp Glu His Leu Val Glu Arg Ala Thr Gln Glu Ser
            420                 425                 430

Thr Leu Asp Arg Trp Lys Phe Leu Gln Glu Gln Asn Lys Thr Lys Pro
        435                 440                 445

Glu Phe Asn Val Arg Lys Val Glu Gly Thr Leu Pro Pro Asp Val Leu
    450                 455                 460

Val Ile His Gln Ser Lys Tyr Lys Cys Gly Met Lys Asn His His Pro
465                 470                 475                 480

Glu Gln Gln Ser Ser Leu Leu Asn Leu Ser Ser Thr Pro Thr His
                485                 490                 495

Gln Glu Ser Met Asn Thr Gly Thr Leu Ala Ser Leu Arg Gly Arg Ala
            500                 505                 510

Arg Arg Ser Lys Gly Lys Asn Lys His Ser Lys Arg Ala Leu Leu Val
        515                 520                 525

Cys Gln
    530

<210> SEQ ID NO 13
<211> LENGTH: 1722
<212> TYPE: DNA
<213> ORGANISM: Homo sapiens
<220> FEATURE:
<221> NAME/KEY: misc_feature
<223> OTHER INFORMATION: human DUB4.5

<400> SEQUENCE: 13
atgcgccaga gagctcgtca tttgaagact ctctcggaag ggatagcgtc tttctgcaac    60
ctgcggtccc agcagaaaaa ccttgtgatc cttgttccag tcgacatgga ggaagactca   120

-continued

```
ctctacttgg gaggtgagtg gcagttcaac cacttttcaa aactcacatc ttctcggccc      180
gatgcagctt ttgctgaaat ccagcggact tctctccctg agaagtcacc actctcatgt      240
gagacccgtg tcgacctctg tgatgatttg gctcctgtgg caagacagct tgctcccagg      300
gagaagcttc ctctgagtaa caggagacct gctgcggtgg gggctgggct ccagaatatg      360
ggaaatacct gctacgtgaa cgcttccttg cagtgcctga catacacacc gccccttgcc      420
aactacatgc tgtcccggga gcactctcaa acgtgtcatc gtcacaaggg ctgcatgctc      480
tgtacgatgc aagctcacat cacacgggcc ctccacaatc ctggccacgt catccagccc      540
tcacaggcat tggctgctgg cttccataga ggcaagcagg aagatgccca tgaatttctc      600
atgttcactg tggatgccat gaaaaaggca tgccttcccg gcacaagca ggtggatcat       660
cactctaagg acaccaccct catccaccaa atatttggag ctactggag atctcaaatc       720
aagtgtctcc actgccacgg catttcagac acttttgacc cttacctgga catcgccctg      780
gatatccagg cagctcagag tgtccagcaa gctttggaac agttggtgaa gcccgaagaa      840
ctcaatggag agaatgccta tcattgtggt gtttgtctcc agagggcgcc ggcctccaag      900
acgttaactt tacacacctc tgccaaggtc ctcatccttg tattgaagag attctccgat      960
gtcacaggca acaagattga caagaatgtg caatatcctg agtgccttga catgaagcta     1020
tacatgtctc agacgaactc aggacctctc gtctatgtcc tctatgctgt gctggtccac     1080
gctgggtgga gttgtcacaa cggacattac ttctcttatg tcaaagctca agaaggccag     1140
tggtataaaa tggatgatgc cgaggtcacc gcctctagca tcacttctgt cctgagtcaa     1200
caggcctacg tcctctttta catccagaag agtgaatggg aaagacacag tgagagtgtg     1260
tcaagaggca gggaaccaag agcccttggc gcagaagaca cagacaggcg agcaacgcaa     1320
ggagagctca agagagacca ccctgcctc caggcccccg agttggacga gcacttggtg      1380
gaaagagcca ctcaggaaag caccttagac cactggaaat ccttcaagaa gcaaaacaaa     1440
acgaagcctg agttcaacgt cagaaaagtc gaaggtaccc tgcctcccga cgtacttgtg     1500
attcatcaat caaatacaa gtgtgggatg aagaaccatc atcctgaaca gcaaagctcc      1560
ctgctaaacc tctcttcgac gaccccgaca catcaggagt ccatgaacac tggcacactc     1620
gcttccctgc agggagggc caggagatcc aaagggaaga acaaacacag caagagggct      1680
ctgcttgtgt gccagtggtc tcagtggaag taccgaccca ca                        1722
```

<210> SEQ ID NO 14
<211> LENGTH: 574
<212> TYPE: PRT
<213> ORGANISM: Homo sapiens
<220> FEATURE:
<221> NAME/KEY: MISC_FEATURE
<223> OTHER INFORMATION: human DUB4.5

<400> SEQUENCE: 14

```
Met Arg Gln Arg Ala Arg His Leu Lys Thr Leu Ser Glu Gly Ile Ala
1               5                   10                  15

Ser Phe Cys Asn Leu Arg Ser Gln Gln Lys Asn Leu Val Ile Leu Val
            20                  25                  30

Pro Val Asp Met Glu Glu Asp Ser Leu Tyr Leu Gly Gly Glu Trp Gln
        35                  40                  45

Phe Asn His Phe Ser Lys Leu Thr Ser Ser Arg Pro Asp Ala Ala Phe
    50                  55                  60

Ala Glu Ile Gln Arg Thr Ser Leu Pro Glu Lys Ser Pro Leu Ser Cys
65                  70                  75                  80
```

```
Glu Thr Arg Val Asp Leu Cys Asp Asp Leu Ala Pro Val Ala Arg Gln
                 85                  90                  95
Leu Ala Pro Arg Glu Lys Leu Pro Leu Ser Asn Arg Arg Pro Ala Ala
            100                 105                 110
Val Gly Ala Gly Leu Gln Asn Met Gly Asn Thr Cys Tyr Val Asn Ala
        115                 120                 125
Ser Leu Gln Cys Leu Thr Tyr Thr Pro Pro Leu Ala Asn Tyr Met Leu
    130                 135                 140
Ser Arg Glu His Ser Gln Thr Cys His Arg His Lys Gly Cys Met Leu
145                 150                 155                 160
Cys Thr Met Gln Ala His Ile Thr Arg Ala Leu His Asn Pro Gly His
                165                 170                 175
Val Ile Gln Pro Ser Gln Ala Leu Ala Ala Gly Phe His Arg Gly Lys
            180                 185                 190
Gln Glu Asp Ala His Glu Phe Leu Met Phe Thr Val Asp Ala Met Lys
        195                 200                 205
Lys Ala Cys Leu Pro Gly His Lys Gln Val Asp His His Ser Lys Asp
    210                 215                 220
Thr Thr Leu Ile His Gln Ile Phe Gly Gly Tyr Trp Arg Ser Gln Ile
225                 230                 235                 240
Lys Cys Leu His Cys His Gly Ile Ser Asp Thr Phe Asp Pro Tyr Leu
                245                 250                 255
Asp Ile Ala Leu Asp Ile Gln Ala Ala Gln Ser Val Gln Gln Ala Leu
            260                 265                 270
Glu Gln Leu Val Lys Pro Glu Glu Leu Asn Gly Glu Asn Ala Tyr His
        275                 280                 285
Cys Gly Val Cys Leu Gln Arg Ala Pro Ala Ser Lys Thr Leu Thr Leu
    290                 295                 300
His Thr Ser Ala Lys Val Leu Ile Leu Val Leu Lys Arg Phe Ser Asp
305                 310                 315                 320
Val Thr Gly Asn Lys Ile Asp Lys Asn Val Gln Tyr Pro Glu Cys Leu
                325                 330                 335
Asp Met Lys Leu Tyr Met Ser Gln Thr Asn Ser Gly Pro Leu Val Tyr
            340                 345                 350
Val Leu Tyr Ala Val Leu Val His Ala Gly Trp Ser Cys His Asn Gly
        355                 360                 365
His Tyr Phe Ser Tyr Val Lys Ala Gln Glu Gly Gln Trp Tyr Lys Met
    370                 375                 380
Asp Asp Ala Glu Val Thr Ala Ser Ser Ile Thr Ser Val Leu Ser Gln
385                 390                 395                 400
Gln Ala Tyr Val Leu Phe Tyr Ile Gln Lys Ser Glu Trp Glu Arg His
                405                 410                 415
Ser Glu Ser Val Ser Arg Gly Arg Glu Pro Arg Ala Leu Gly Ala Glu
            420                 425                 430
Asp Thr Asp Arg Arg Ala Thr Gln Gly Glu Leu Lys Arg Asp His Pro
        435                 440                 445
Cys Leu Gln Ala Pro Glu Leu Asp Glu His Leu Val Glu Arg Ala Thr
    450                 455                 460
Gln Glu Ser Thr Leu Asp His Trp Lys Phe Leu Gln Glu Gln Asn Lys
465                 470                 475                 480
Thr Lys Pro Glu Phe Asn Val Arg Lys Val Glu Gly Thr Leu Pro Pro
                485                 490                 495
```

```
Asp Val Leu Val Ile His Gln Ser Lys Tyr Lys Cys Gly Met Lys Asn
                500                 505                 510
His His Pro Glu Gln Gln Ser Ser Leu Leu Asn Leu Ser Ser Thr Thr
            515                 520                 525
Pro Thr His Gln Glu Ser Met Asn Thr Gly Thr Leu Ala Ser Leu Arg
        530                 535                 540
Gly Arg Ala Arg Arg Ser Lys Gly Lys Asn Lys His Ser Lys Arg Ala
545                 550                 555                 560
Leu Leu Val Cys Gln Trp Ser Gln Trp Lys Tyr Arg Pro Thr
                565                 570
```

<210> SEQ ID NO 15
<211> LENGTH: 1593
<212> TYPE: DNA
<213> ORGANISM: Homo sapiens
<220> FEATURE:
<221> NAME/KEY: misc_feature
<223> OTHER INFORMATION: human DUB4.6

<400> SEQUENCE: 15

```
atggaggacg actcactcta cttgggaggt gagtggcagt tcaaccactt ttcaaaactc      60
acatcttctc ggcccgatgc agcttttgct gaaatccagc ggacttctct ccctgagaag     120
tcaccactct catgtgagac ccgtgtcgac ctctgtgatg atttggctcc tgtggcaaga     180
cagcttgctc ccaggagaaa gcttcctctg agtagcagga gacctgctgc ggtgggggct     240
gggctccaga atatgggaaa tacctgctac gtgaacgctt ccttgcagtg cctgacatac     300
acaccgcccc ttgccaacta catgctgtcc cgggagcact ctcaaacgtg tcatcgtcac     360
aagggctgta tgctctgtac gatgcaagct cacatcacac gggccctcca caatcctggc     420
cacgtcatcc agccctcaca ggcattggct gctggcttcc atagaggcaa gcaggaagat     480
gcccatgaat ttctcatgtt cactgtggat gccatgaaaa aggcatgcct tcccgggcac     540
aagcaggtgg atcatcactc taaggacacc accctcatcc accaaatatt tggaggctac     600
tggagatctc aaatcaagtg tctccactgc cacggcattt cagacacttt tgacccttac     660
ctggacatcg ccctggatat ccaggcagct cagagtgtcc agcaagcttt ggaacagttg     720
gtgaagcccg aagaactcaa tggagagaat gcctatcatt gtggtgtttg tctccagagg     780
gcgccggcct ccaagacgtt aactttacac acctctgcca aggtcctcat ccttgtattg     840
aagagattct ccgatgtcac aggcaacaag attgccaaga atgtgcaata tcctgagtgc     900
cttgacatgc agccatacat gtctcagacg aacacaggac ctctcgtcta tgtcctctat     960
gctgtgctgg tccacgctgg gtggagttgt cacaacggac attacttctc ttatgtcaaa    1020
gctcaagaag gccagtggta taaaatggat gatgccgagg tcaccgcctc tagcatcact    1080
tctgtcctga gtcaacaggc ctacgtcctc ttttacatcc agaagagtga atgggaaaga    1140
cacagtgaga gtgtgtcaag aggcagggaa ccaagagccc ttggcgcaga agacacagac    1200
aggcgagcaa cgcaaggaga gctcaagaga gaccacccct gcctccaggc ccccgagttg    1260
gacgagcact ggtggaaaag agccactcag gaaagcacct tagaccactg gaaattcctt    1320
caagagcaaa acaaaacgaa gcctgagttc aacgtcagaa aagtcgaagg taccctgcct    1380
cccgacgtac ttgtgattca tcaatcaaaa tacaagtgtg ggatgaagaa ccatcatcct    1440
gaacagcaaa gctccctgct aaacctctct tcgacgaccc cgacacatca ggagtccatg    1500
aacactggca cactcgcttc cctgcgaggg agggccagga gatccaaagg gaagaacaaa    1560
cacagcaaga gggctctgct tgtgtgccag tga                                 1593
```

<210> SEQ ID NO 16
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB4.6

<400> SEQUENCE: 16

```
Met Glu Asp Asp Ser Leu Tyr Leu Gly Gly Glu Trp Gln Phe Asn His
1               5                   10                  15

Phe Ser Lys Leu Thr Ser Ser Arg Pro Asp Ala Ala Phe Ala Glu Ile
            20                  25                  30

Gln Arg Thr Ser Leu Pro Glu Lys Ser Pro Leu Ser Cys Glu Thr Arg
        35                  40                  45

Val Asp Leu Cys Asp Asp Leu Ala Pro Val Ala Arg Gln Leu Ala Pro
    50                  55                  60

Arg Glu Lys Leu Pro Leu Ser Ser Arg Arg Pro Ala Ala Val Gly Ala
65                  70                  75                  80

Gly Leu Gln Asn Met Gly Asn Thr Cys Tyr Val Asn Ala Ser Leu Gln
                85                  90                  95

Cys Leu Thr Tyr Thr Pro Pro Leu Ala Asn Tyr Met Leu Ser Arg Glu
            100                 105                 110

His Ser Gln Thr Cys His Arg His Lys Gly Cys Met Leu Cys Thr Met
        115                 120                 125

Gln Ala His Ile Thr Arg Ala Leu His Asn Pro Gly His Val Ile Gln
    130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His His Ser Lys Asp Thr Thr Leu
            180                 185                 190

Ile His Gln Ile Phe Gly Gly Tyr Trp Arg Ser Gln Ile Lys Cys Leu
        195                 200                 205

His Cys His Gly Ile Ser Asp Thr Phe Asp Pro Tyr Leu Asp Ile Ala
    210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Cys Gly Val
                245                 250                 255

Cys Leu Gln Arg Ala Pro Ala Ser Lys Thr Leu Thr Leu His Thr Ser
            260                 265                 270

Ala Lys Val Leu Ile Leu Val Leu Lys Arg Phe Ser Asp Val Thr Gly
        275                 280                 285

Asn Lys Ile Ala Lys Asn Val Gln Tyr Pro Glu Cys Leu Asp Met Gln
    290                 295                 300

Pro Tyr Met Ser Gln Thr Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Met Asp Asp Ala
            340                 345                 350

Glu Val Thr Ala Ser Ser Ile Thr Ser Val Leu Ser Gln Gln Ala Tyr
```

```
                355                 360                 365
Val Leu Phe Tyr Ile Gln Lys Ser Glu Trp Glu Arg His Ser Glu Ser
    370                 375                 380

Val Ser Arg Gly Arg Glu Pro Arg Ala Leu Gly Ala Glu Asp Thr Asp
385                 390                 395                 400

Arg Arg Ala Thr Gln Gly Glu Leu Lys Arg Asp His Pro Cys Leu Gln
                405                 410                 415

Ala Pro Glu Leu Asp Glu His Leu Val Glu Arg Ala Thr Gln Glu Ser
                420                 425                 430

Thr Leu Asp His Trp Lys Phe Leu Gln Glu Gln Asn Lys Thr Lys Pro
                435                 440                 445

Glu Phe Asn Val Arg Lys Val Glu Gly Thr Leu Pro Pro Asp Val Leu
    450                 455                 460

Val Ile His Gln Ser Lys Tyr Lys Cys Gly Met Lys Asn His His Pro
465                 470                 475                 480

Glu Gln Gln Ser Ser Leu Leu Asn Leu Ser Ser Thr Thr Pro Thr His
                485                 490                 495

Gln Glu Ser Met Asn Thr Gly Thr Leu Ala Ser Leu Arg Gly Arg Ala
            500                 505                 510

Arg Arg Ser Lys Gly Lys Asn Lys His Ser Lys Arg Ala Leu Leu Val
        515                 520                 525

Cys Gln
    530

<210> SEQ ID NO 17
<211> LENGTH: 1593
<212> TYPE: DNA
<213> ORGANISM: Homo sapiens
<220> FEATURE:
<221> NAME/KEY: misc_feature
<223> OTHER INFORMATION: human DUB4.7

<400> SEQUENCE: 17
atggaggacg actcactcta cttgggtggt gagtggcagt tcaaccactt ttcaaaactc      60
acatcttctc ggcccgatgc agcttttgct gaaatccagc ggacttctct ccctgagaag     120
tcaccactct catgtgagac ccgtgtcgac ctctgtgatg atttggctcc tgtggcaaga     180
cagcttgctc ccagggagaa gcttcctctg agtagcagga gacctgctgc ggtgggggct     240
gggctccaga atatgggaaa tacctgctac gtgaacgctt ccttgcagtg cctgacatac     300
acaccgcccc ttgccaacta catgctgtcc cgggagcact ctcaaacgtg tcatcgtcac     360
aagggctgca tgctctgtac tatgcaagct cacatcacac gggccctcca caatcctggc     420
cacgtcatcc agccctcaca ggcattggct gctggcttcc atagaggcaa gcaggaagat     480
gcccatgaat ttctcatgtt cactgtggat gccatgaaaa aggcatgcct tcccgggcac     540
aagcaggtag atcatcactc taaggacacc accctcatcc accaaatatt tggaggctac     600
tggagatctc aaatcaactg tctccactgc acggcattt cagacacttt tgacccttac      660
ctggacatcg ccctggatat ccaggcagct cagagtgtcc agcaagcttt ggaacagttg     720
gtgaagcccg aagaactcaa tggagagaat gcctatcatt gtggtgtttg tctccagagg     780
gcgccggcct ccaagacgtt aactttacac acctctgcca aggtcctcat ccttgtattg     840
aagagattct ccgatgtcac aggcaacaag attgccaaga atgtgcaata tcctgagtgc     900
cttgacatgc agccatacat gtctcagcag aacacaggac tcttgtctca tgtcctctat     960
gctgtgctgg tccacgctgg gtggagttgt cacaacggac attacttctc ttatgtcaaa    1020
```

-continued

```
gctcaagaag gccagtggta taaaatggat gatgccgagg tcaccgccgc tagcatcact    1080
tctgtcctga gtcaacaggc ctacgtcctc ttttacatcc agaagagtga atgggaaaga    1140
cacagtgaga gtgtgtcaag aggcagggaa ccaagagccc ttggcgcaga agacacagac    1200
aggcgagcaa cgcaaggaga gctcaagaga gaccacccct gcctccaggc ccccgagttg    1260
gacgagcact tggtggaaag agccactcag gaaagcacct tagaccactg gaaattcctt    1320
caagagcaaa acaaaacgaa gcctgagttc aacgtcagaa aagtcgaagg taccctgcct    1380
cccgacgtac ttgtgattca tcaatcaaaa tacaagtgtg ggatgaagaa ccatcatcct    1440
gaacagcaaa gctccctgct aaacctctct tcgtcgaccc cgacacatca ggaggccatg    1500
aacactggca cactcgcttc cctgcgaggg aggaccagga gatccaaagg gaagaacaaa    1560
cacagcaaga gggctctgct tgtgtgccag tga                                 1593
```

<210> SEQ ID NO 18
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB4.7

<400> SEQUENCE: 18

```
Met Glu Asp Asp Ser Leu Tyr Leu Gly Gly Glu Trp Gln Phe Asn His
1               5                   10                  15

Phe Ser Lys Leu Thr Ser Ser Arg Pro Asp Ala Ala Phe Ala Glu Ile
            20                  25                  30

Gln Arg Thr Ser Leu Pro Glu Lys Ser Pro Leu Ser Cys Glu Thr Arg
        35                  40                  45

Val Asp Leu Cys Asp Asp Leu Ala Pro Val Ala Arg Gln Leu Ala Pro
    50                  55                  60

Arg Glu Lys Leu Pro Leu Ser Ser Arg Arg Pro Ala Ala Val Gly Ala
65                  70                  75                  80

Gly Leu Gln Asn Met Gly Asn Thr Cys Tyr Val Asn Ala Ser Leu Gln
                85                  90                  95

Cys Leu Thr Tyr Thr Pro Pro Leu Ala Asn Tyr Met Leu Ser Arg Glu
            100                 105                 110

His Ser Gln Thr Cys His Arg His Lys Gly Cys Met Leu Cys Thr Met
        115                 120                 125

Gln Ala His Ile Thr Arg Ala Leu His Asn Pro Gly His Val Ile Gln
    130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His His Ser Lys Asp Thr Thr Leu
            180                 185                 190

Ile His Gln Ile Phe Gly Gly Tyr Trp Arg Ser Gln Ile Asn Cys Leu
        195                 200                 205

His Cys His Gly Ile Ser Asp Thr Phe Asp Pro Tyr Leu Asp Ile Ala
    210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Cys Gly Val
                245                 250                 255
```

```
Cys Leu Gln Arg Ala Pro Ala Ser Lys Thr Leu Thr Leu His Thr Ser
            260                 265                 270
Ala Lys Val Leu Ile Leu Val Leu Lys Arg Phe Ser Asp Val Thr Gly
        275                 280                 285
Asn Lys Ile Ala Lys Asn Val Gln Tyr Pro Glu Cys Leu Asp Met Gln
    290                 295                 300
Pro Tyr Met Ser Gln Gln Asn Thr Gly Pro Leu Val Tyr Val Leu Tyr
305                 310                 315                 320
Ala Val Leu Val His Ala Gly Trp Ser Cys His Asn Gly His Tyr Phe
                325                 330                 335
Ser Tyr Val Lys Ala Gln Glu Gly Gln Trp Tyr Lys Met Asp Asp Ala
            340                 345                 350
Glu Val Thr Ala Ala Ser Ile Thr Ser Val Leu Ser Gln Gln Ala Tyr
        355                 360                 365
Val Leu Phe Tyr Ile Gln Lys Ser Glu Trp Glu Arg His Ser Glu Ser
    370                 375                 380
Val Ser Arg Gly Arg Glu Pro Arg Ala Leu Gly Ala Glu Asp Thr Asp
385                 390                 395                 400
Arg Arg Ala Thr Gln Gly Glu Leu Lys Arg Asp His Pro Cys Leu Gln
                405                 410                 415
Ala Pro Glu Leu Asp Glu His Leu Val Glu Arg Ala Thr Gln Glu Ser
            420                 425                 430
Thr Leu Asp His Trp Lys Phe Leu Gln Glu Gln Asn Lys Thr Lys Pro
        435                 440                 445
Glu Phe Asn Val Arg Lys Val Glu Gly Thr Leu Pro Pro Asp Val Leu
    450                 455                 460
Val Ile His Gln Ser Lys Tyr Lys Cys Gly Met Lys Asn His His Pro
465                 470                 475                 480
Glu Gln Gln Ser Ser Leu Leu Asn Leu Ser Ser Ser Thr Pro Thr His
                485                 490                 495
Gln Glu Ala Met Asn Thr Gly Thr Leu Ala Ser Leu Arg Gly Arg Thr
            500                 505                 510
Arg Arg Ser Lys Gly Lys Asn Lys His Ser Lys Arg Ala Leu Leu Val
        515                 520                 525
Cys Gln
    530

<210> SEQ ID NO 19
<211> LENGTH: 1698
<212> TYPE: DNA
<213> ORGANISM: Homo sapiens
<220> FEATURE:
<221> NAME/KEY: misc_feature
<223> OTHER INFORMATION: human DUB4.8

<400> SEQUENCE: 19
atgcgccaga gagctcgtca tttgaagact ctctcggaag ggatagcgtc ttgctgcaaa      60
ctgcggtccc agcagaaaaa ccttgtgatc cttgttccag tcgacatgga ggacgactca     120
ctctacttgg gaggtgagtg gcagttcaac cacttttcaa aactcacatc ttctcggccc     180
gatgcagctt tgctgaaat ccagcggact tctctcccctg agaagtcacc actctcatgt     240
gagacccgtg tcgacctctg tgatgatttg gctcctgtgg caagacagct tgctcccagg     300
gagaagcttc ctctgagtag caggagacct gctgcggtgg gggctgggct ccagaatatg     360 ggaaataccct gctacgtgaa cgcttccttg cagtgcctga catacacacc gccccttgcc     420
```

-continued

```
aactacatgc tgtcccggga gcactctcaa acgtgtcatc gtcacaaggg ctgcatgctc    480
tgtacgatgc aagctcacat cacacgggcc ctccacaatc ctggccacgt catccagccc    540
tcacaggcat tggctgctgg cttccataga ggcaagcagg aagatgccca tgaatttctc    600
atgttcactg tggatgccat gaaaaaggca tgccttcccg ggcacaagca ggtagatcat    660
cactctaagg acaccaccct catccaccaa atatttggag gctactggag atctcaaatc    720
aagtgtctcc actgccacgg catttcagac acttttgacc cttacctgga catcgccctg    780
gatatccagg cagctcagag tgtccagcaa gctttggaac agttggtgaa gcccgaagaa    840
ctcaatggag agaatgccta tcattgtggt gtttgtctcc agagggcgcc ggcctccaag    900
acgttaactt tacacacctc tgccaaggtc ctcatccttg tattgaagag attctccgat    960
gtgacaggca acaagattgc caagaatgtg caatatcctg agtgccttga catgcagcca   1020
tacatgtctc agcagaacac aggacctctt gtctatgtcc tctatgctgt gctggtccac   1080
gctgggtgga gttgtcacaa cggacattac ttctcttatg tcaaagctca agaaggccaa   1140
tggtataaaa tggatgatgc cgaggtcacc gccgctagca tcacttctgt cctgagtcaa   1200
caggcctacg tcctctttta catccagaag agtgaatggg aaagacacag tgagagtgtg   1260
tcaagaggca gggaaccaag agcccttggc gcagaagaca cagacaggcg agcaacgcaa   1320
ggagagctca agagagacca cccctgcctc caggccccccg agttggacga gcacttggtg   1380
gaaagagcca ctcaggaaag caccttagac cactggaaat tccttcaaga gcaaaacaaa   1440
acgaagcctg agttcaacgt cagaaaagtc gaaggtaccc tgcctcccga cgtacttgtg   1500
attcatcaat caaaatacaa gtgtgggatg aagaaccatc atcctgaaca gcaaagctcc   1560
ctgctaaacc tctcttcgtc gaccccgaca catcaggagt ccatgaacac tggcacactc   1620
gcttccctgc gagggagggc caggagatcc aaagggaaga caaacacag caagagggct   1680
ctgcttgtgt gccagtga                                                 1698
```

<210> SEQ ID NO 20
<211> LENGTH: 565
<212> TYPE: PRT
<213> ORGANISM: Homo sapiens
<220> FEATURE:
<221> NAME/KEY: MISC_FEATURE
<223> OTHER INFORMATION: human DUB4.8

<400> SEQUENCE: 20

```
Met Arg Gln Arg Ala Arg His Leu Lys Thr Leu Ser Glu Gly Ile Ala
1               5                   10                  15

Ser Cys Cys Lys Leu Arg Ser Gln Gln Lys Asn Leu Val Ile Leu Val
            20                  25                  30

Pro Val Asp Met Glu Asp Ser Leu Tyr Leu Gly Gly Glu Trp Gln
        35                  40                  45

Phe Asn His Phe Ser Lys Leu Thr Ser Ser Arg Pro Asp Ala Ala Phe
    50                  55                  60

Ala Glu Ile Gln Arg Thr Ser Leu Pro Glu Lys Ser Pro Leu Ser Cys
65                  70                  75                  80

Glu Thr Arg Val Asp Leu Cys Asp Asp Leu Ala Pro Val Ala Arg Gln
                85                  90                  95

Leu Ala Pro Arg Glu Lys Leu Pro Leu Ser Ser Arg Arg Pro Ala Ala
            100                 105                 110

Val Gly Ala Gly Leu Gln Asn Met Gly Asn Thr Cys Tyr Val Asn Ala
        115                 120                 125
```

```
Ser Leu Gln Cys Leu Thr Tyr Thr Pro Pro Leu Ala Asn Tyr Met Leu
    130                 135                 140

Ser Arg Glu His Ser Gln Thr Cys His Arg His Lys Gly Cys Met Leu
145                 150                 155                 160

Cys Thr Met Gln Ala His Ile Thr Arg Ala Leu His Asn Pro Gly His
                165                 170                 175

Val Ile Gln Pro Ser Gln Ala Leu Ala Ala Gly Phe His Arg Gly Lys
            180                 185                 190

Gln Glu Asp Ala His Glu Phe Leu Met Phe Thr Val Asp Ala Met Lys
        195                 200                 205

Lys Ala Cys Leu Pro Gly His Lys Gln Val Asp His Ser Lys Asp
210                 215                 220

Thr Thr Leu Ile His Gln Ile Phe Gly Gly Tyr Trp Arg Ser Gln Ile
225                 230                 235                 240

Lys Cys Leu His Cys His Gly Ile Ser Asp Thr Phe Asp Pro Tyr Leu
                245                 250                 255

Asp Ile Ala Leu Asp Ile Gln Ala Ala Gln Ser Val Gln Gln Ala Leu
            260                 265                 270

Glu Gln Leu Val Lys Pro Glu Glu Leu Asn Gly Glu Asn Ala Tyr His
        275                 280                 285

Cys Gly Val Cys Leu Gln Arg Ala Pro Ala Ser Lys Thr Leu Thr Leu
290                 295                 300

His Thr Ser Ala Lys Val Leu Ile Leu Val Leu Lys Arg Phe Ser Asp
305                 310                 315                 320

Val Thr Gly Asn Lys Ile Ala Lys Asn Val Gln Tyr Pro Glu Cys Leu
                325                 330                 335

Asp Met Gln Pro Tyr Met Ser Gln Gln Asn Thr Gly Pro Leu Val Tyr
            340                 345                 350

Val Leu Tyr Ala Val Leu Val His Ala Gly Trp Ser Cys His Asn Gly
        355                 360                 365

His Tyr Phe Ser Tyr Val Lys Ala Gln Glu Gly Gln Trp Tyr Lys Met
    370                 375                 380

Asp Asp Ala Glu Val Thr Ala Ala Ser Ile Thr Ser Val Leu Ser Gln
385                 390                 395                 400

Gln Ala Tyr Val Leu Phe Tyr Ile Gln Lys Ser Glu Trp Glu Arg His
                405                 410                 415

Ser Glu Ser Val Ser Arg Gly Arg Glu Pro Arg Ala Leu Gly Ala Glu
            420                 425                 430

Asp Thr Asp Arg Arg Ala Thr Gln Gly Glu Leu Lys Arg Asp His Pro
        435                 440                 445

Cys Leu Gln Ala Pro Glu Leu Asp Glu His Leu Val Glu Arg Ala Thr
450                 455                 460

Gln Glu Ser Thr Leu Asp His Trp Lys Phe Leu Gln Glu Gln Asn Lys
465                 470                 475                 480

Thr Lys Pro Glu Phe Asn Val Arg Lys Val Glu Gly Thr Leu Pro Pro
                485                 490                 495

Asp Val Leu Val Ile His Gln Ser Lys Tyr Lys Cys Gly Met Lys Asn
            500                 505                 510

His His Pro Glu Gln Gln Ser Ser Leu Leu Asn Leu Ser Ser Ser Thr
        515                 520                 525

Pro Thr His Gln Glu Ser Met Asn Thr Gly Thr Leu Ala Ser Leu Arg
530                 535                 540
```

```
Gly Arg Ala Arg Arg Ser Lys Gly Lys Asn Lys His Ser Lys Arg Ala
545                 550                 555                 560

Leu Leu Val Cys Gln
                565

<210> SEQ ID NO 21
<211> LENGTH: 2148
<212> TYPE: DNA
<213> ORGANISM: Homo sapiens
<220> FEATURE:
<221> NAME/KEY: misc_feature
<223> OTHER INFORMATION: human DUB4.10

<400> SEQUENCE: 21
atgtgcatac gaacagggtc tccgtgtgac gtgtgtgaaa actacagtgt gatgagcatg      60
actggcagac agcttatcga ttgggctccc ctcaaaatcg ttatgagca ttcaagcaca      120 ccgatgccca gggaacatgt ccactttcgg cagcattaca attttggcac caaatgtgct     180
aactgcaatt ccaccataca atgcgtaact ggaaatggag gcaacatcgc cgatcctgaa     240
cgatcgatgc gagaatccag gatatgcacg gcttattttg ccttttccc actgaaacaa      300 gggccagtat taaaaatggt aatttcactc ggacagagaa tcaataggct caacgtggaa     360
aggttatcgc tggaagggaa gaaaatacgc tgtgctaaat actatacttc attgactatt     420
ctcaggtcag aaagcgcact ttcgacttct tgtccttccg tcgctgagag gatgatggca     480
gctgccaaaa ggatagcgtc tttctgcaac ctgcggtccc agcagaaaaa ccttgtgatc     540
ctcgttccag tcgacatgga ggacgactca ctctacttgg gaggtgagtg gcagttcaac     600
cacttttcaa aactcacatc ttctcggccc gatgcagctt ttgctgaaat ccagcggact     660
tctctccctg agaagtcacc actctcatgt gagacccgtg tcgacctctg tgatgatttg     720
gctcctgtgg caagacagct tgctcccagg gagaagcttc ctctgagtag caggagacct     780
gctgcggtgg gggctgggct ccagaatatg gaaatacct gctacgtgaa cgcttccttg      840
cagtgcctga catacacaac gccccttgcc aactacatgc tgtcccggga gcactctcaa     900
acgtgtcatc gtcacaaggg ctgcatgctc tgtactatgc aagctcacat cacacgggcc     960
ctccacaatc ctggccacgt catccagccc tcacaggcat tggctgctgg cttccataga     1020
ggcaagcagg aagatgccca tgaatttctc atgttcactg tggatgccat gaaaaaggca     1080
tgccttcccg ggcacaagca ggtagatcat cactctaagg acaccaccct catccaccaa     1140
atatttggag ctactggag atctcaaatc aagtgtctcc actgccacgg catttcagac      1200
acttttgacc cttacctgga catcgcccta gatatccagg cagctcagag tgtccagcaa     1260
gctttggaac agttggtgaa gcccgaagaa ctcaatggag agaatgccta tcattctggt     1320
gtttgtctcc agagggcgcc ggcctccaag acgttaactt tacacacctc tgccaaggtc     1380
ctcatccttg tattgaagag attctccgat gtcacaggca acaagattgc caagaatgtg     1440
caatatcctg agtgccttga catgcagcca tacatgtctc agcagaacac aggacctctt     1500
gtctatgtcc tctatgctgt gctggtccac gctgggtgga gttgtcacaa cggacattac     1560
ttctcttatg tcaaagctca agaaggccag tggtataaaa tggatgatgc cgaggtcacc     1620
gccgctagca tcacttctgc cctgagtcaa caggcctacg tcctctttta catccagaag     1680
agtgaatggg aaagacacag tgagagtgtg tcaagaggca gggaaccaag agcccttggc     1740
acagaagaca cagacaggcg agcaacgcaa ggagagctca agagagacca cccctgcctc     1800 caggccccg agttggacga gcacttggtg gaaagagcca ctcaggaaag caccttagac     1860
```

```
cactggaaat tccttcaaga gcaaaacaaa acgaagcctg agttcaacgt cagaaaagtc    1920
gaaggtaccc tgcctcccga cgtacttgtg attcatcaat caaaatacaa gtgtgggatg    1980
aagaaccatc atcctgaaca gcaaagctcc ctgctaaacc tctcttcgtc gaccccgaca    2040
catcaggagt ccatgaacac tggcacactc gcttccctgc agggagggc caggagatcc    2100 aaagggaaga acaaacacag caagagggct ctgcttgtgt gccagtga                2148
```

```
<210> SEQ ID NO 22
<211> LENGTH: 715
<212> TYPE: PRT
<213> ORGANISM: Homo sapiens
<220> FEATURE:
<221> NAME/KEY: MISC_FEATURE
<223> OTHER INFORMATION: human DUB4.10

<400> SEQUENCE: 22

Met Cys Ile Arg Thr Gly Ser Pro Cys Asp Val Cys Glu Asn Tyr Ser
1               5                   10                  15

Val Met Ser Met Thr Gly Arg Gln Leu Ile Asp Trp Ala Pro Leu Lys
            20                  25                  30

Ile Gly Tyr Glu His Ser Ser Thr Pro Met Pro Arg Glu His Val His
        35                  40                  45

Phe Arg Gln His Tyr Asn Phe Gly Thr Lys Cys Ala Asn Cys Asn Ser
    50                  55                  60

Thr Ile Gln Cys Val Thr Gly Asn Gly Gly Asn Ile Ala Asp Pro Glu
65                  70                  75                  80

Arg Ser Met Arg Glu Ser Arg Ile Cys Thr Ala Tyr Phe Gly Leu Phe
                85                  90                  95

Pro Leu Lys Gln Gly Pro Val Leu Lys Met Val Ile Ser Leu Gly Gln
            100                 105                 110

Arg Ile Asn Arg Leu Asn Val Glu Arg Leu Ser Leu Glu Gly Lys Lys
        115                 120                 125

Ile Arg Cys Ala Lys Tyr Tyr Thr Ser Leu Thr Ile Leu Arg Ser Glu
    130                 135                 140

Ser Ala Leu Ser Thr Ser Cys Pro Ser Val Ala Glu Arg Met Met Ala
145                 150                 155                 160

Ala Ala Lys Arg Ile Ala Ser Phe Cys Asn Leu Arg Ser Gln Gln Lys
                165                 170                 175

Asn Leu Val Ile Leu Val Pro Val Asp Met Glu Asp Asp Ser Leu Tyr
            180                 185                 190

Leu Gly Gly Glu Trp Gln Phe Asn His Phe Ser Lys Leu Thr Ser Ser
        195                 200                 205

Arg Pro Asp Ala Ala Phe Ala Glu Ile Gln Arg Thr Ser Leu Pro Glu
    210                 215                 220

Lys Ser Pro Leu Ser Cys Glu Thr Arg Val Asp Leu Cys Asp Asp Leu
225                 230                 235                 240

Ala Pro Val Ala Arg Gln Leu Ala Pro Arg Glu Lys Leu Pro Leu Ser
                245                 250                 255

Ser Arg Arg Pro Ala Ala Val Gly Ala Gly Leu Gln Asn Met Gly Asn
            260                 265                 270

Thr Cys Tyr Val Asn Ala Ser Leu Gln Cys Leu Thr Tyr Thr Thr Pro
        275                 280                 285

Leu Ala Asn Tyr Met Leu Ser Arg Glu His Ser Gln Thr Cys His Arg
    290                 295                 300

His Lys Gly Cys Met Leu Cys Thr Met Gln Ala His Ile Thr Arg Ala
```

```
            305                 310                 315                 320
Leu His Asn Pro Gly His Val Ile Gln Pro Ser Gln Ala Leu Ala Ala
                325                 330                 335

Gly Phe His Arg Gly Lys Gln Glu Asp Ala His Glu Phe Leu Met Phe
                340                 345                 350

Thr Val Asp Ala Met Lys Lys Ala Cys Leu Pro Gly His Lys Gln Val
                355                 360                 365

Asp His His Ser Lys Asp Thr Thr Leu Ile His Gln Ile Phe Gly Gly
                370                 375                 380

Tyr Trp Arg Ser Gln Ile Lys Cys Leu His Cys His Gly Ile Ser Asp
385                 390                 395                 400

Thr Phe Asp Pro Tyr Leu Asp Ile Ala Leu Asp Ile Gln Ala Ala Gln
                405                 410                 415

Ser Val Gln Gln Ala Leu Glu Gln Leu Val Lys Pro Glu Glu Leu Asn
                420                 425                 430

Gly Glu Asn Ala Tyr His Ser Gly Val Cys Leu Gln Arg Ala Pro Ala
                435                 440                 445

Ser Lys Thr Leu Thr Leu His Thr Ser Ala Lys Val Leu Ile Leu Val
                450                 455                 460

Leu Lys Arg Phe Ser Asp Val Thr Gly Asn Lys Ile Ala Lys Asn Val
465                 470                 475                 480

Gln Tyr Pro Glu Cys Leu Asp Met Gln Pro Tyr Met Ser Gln Gln Asn
                485                 490                 495

Thr Gly Pro Leu Val Tyr Val Leu Tyr Ala Val Leu Val His Ala Gly
                500                 505                 510

Trp Ser Cys His Asn Gly His Tyr Phe Ser Tyr Val Lys Ala Gln Glu
                515                 520                 525

Gly Gln Trp Tyr Lys Met Asp Asp Ala Glu Val Thr Ala Ala Ser Ile
                530                 535                 540

Thr Ser Ala Leu Ser Gln Gln Ala Tyr Val Leu Phe Tyr Ile Gln Lys
545                 550                 555                 560

Ser Glu Trp Glu Arg His Ser Glu Ser Val Ser Arg Gly Arg Glu Pro
                565                 570                 575

Arg Ala Leu Gly Thr Glu Asp Thr Asp Arg Arg Ala Thr Gln Gly Glu
                580                 585                 590

Leu Lys Arg Asp His Pro Cys Leu Gln Ala Pro Glu Leu Asp Glu His
                595                 600                 605

Leu Val Glu Arg Ala Thr Gln Glu Ser Thr Leu Asp His Trp Lys Phe
                610                 615                 620

Leu Gln Glu Gln Asn Lys Thr Lys Pro Glu Phe Asn Val Arg Lys Val
625                 630                 635                 640

Glu Gly Thr Leu Pro Pro Asp Val Leu Val Ile His Gln Ser Lys Tyr
                645                 650                 655

Lys Cys Gly Met Lys Asn His His Pro Glu Gln Ser Ser Leu Leu
                660                 665                 670

Asn Leu Ser Ser Thr Pro Thr His Gln Glu Ser Met Asn Thr Gly
                675                 680                 685

Thr Leu Ala Ser Leu Arg Gly Arg Ala Arg Ser Lys Gly Lys Asn
                690                 695                 700

Lys His Ser Lys Arg Ala Leu Leu Val Cys Gln
705                 710                 715

<210> SEQ ID NO 23
```

<211> LENGTH: 1902
<212> TYPE: DNA
<213> ORGANISM: Homo sapiens
<220> FEATURE:
<221> NAME/KEY: misc_feature
<223> OTHER INFORMATION: human DUB4.11

<400> SEQUENCE: 23

| | | | | | |
|---|---|---|---|---|---|
| atgtgcatac | gaacagggtc | tccgtgtgac | gtgtgtgaaa | actacagtgt | gatgagcatg | 60 |
| actggcagac | agcttatcga | ttgggctccc | ctcaaaatcg | gttatgagca | ttcaagcaca | 120 |
| ccgatgccca | ggacacttta | catccggcac | aggaagcctt | ctgatggagc | acacctggcc | 180 |
| catgaaaaga | caagggaaag | aaacggggcc | aaagggaaga | aaatacgctg | tgctaaatac | 240 |
| tatacttcat | tgactattct | caggtcagaa | agcgcacttt | cgtcttcttg | tccttccgtc | 300 |
| gcggagagga | tgatggcagc | tgccaaaatc | gacatggagg | acgactcact | ctacttggga | 360 |
| ggtgagtggc | agttcaacca | cttttcaaaa | ctcacatctt | ctcggccaga | tgcagctttt | 420 |
| gctgaaatcc | agcggacttc | tctccctgag | aagtcaccac | tctcatatga | tttggctcct | 480 |
| gtggcaagac | agcttgctcc | cagggagaag | cttcctctga | gtagcaggag | acctgctgcg | 540 |
| gtggggggctg | ggctccagaa | tatgggaaat | acctgctacg | tgaacgcttc | cttgcagtgc | 600 |
| ctgacataca | caccgcccct | tgccaactac | atgctgtccc | gggagcactc | tcaaacgtgt | 660 |
| catcgtcaca | agggctgcat | gctctgtact | atgcaagctc | acatcacacg | ggccctccac | 720 |
| aatcctggcc | acgtcatcca | gccctcacag | gcattggctg | ctggcttcca | tagaggcaag | 780 |
| caggaagatg | cccatgaatt | tctcatgttc | actgtggatg | ccatgaaaaa | ggcatgcctt | 840 |
| cccaggcaca | agcaggtaga | tcatcactct | aaggacacca | ccctcatcca | ccaaatattt | 900 |
| ggaggctact | ggagatctca | aatcaagtgt | ctccactgcc | acggcatttc | agacactttt | 960 |
| gacccttacc | tggacatcgc | cctggatatc | caggcagctc | agagtgtcca | gcaagctttg | 1020 |
| gaacagttgg | tgaagcccga | agaactcaat | ggagagaatg | cctatcattg | tggtgttttgt | 1080 |
| ctccagaggg | cgccggcctc | caagacgtta | actttacaca | cctctgccaa | ggtcctcatc | 1140 |
| cttgtattga | agagattctc | cgatgtcaca | ggcaacaaga | ttgccaagaa | tgtgcaatat | 1200 |
| cctgagtgcc | ttgacatgca | gccatacatg | tctcagcaga | acacaggacc | tcttgtctat | 1260 |
| gtcctctatg | ctgtgctggt | ccacgctgag | tggagttgtc | acaacggaca | ttacttctct | 1320 |
| tatgtcaaag | ctcaagaagg | ccagtggtat | aaaatggatg | atgccgaggt | caccgccgct | 1380 |
| agcatcactt | ctgtcctgag | tcaacaggcc | tacgtcctct | tttacatcca | gaagagtgaa | 1440 |
| tgggaaagac | atagtgagag | tgtgtcaaga | ggcagggaac | caagagccct | tggcgcagaa | 1500 |
| gacacagaca | ggcgagcaac | gcaaggagag | ctcaagagag | accacccctg | cctccaggcc | 1560 |
| cccgagttgg | acgagcactt | ggtggaaaga | gccactcagg | aaagcacctt | agaccactgg | 1620 |
| aaattccttc | aagagcaaaa | caaaacgaag | cctgagttca | acgtcagaaa | agtcaaaggt | 1680 |
| accctgcctc | ccgacgtact | tgtgattcat | caatcaaaat | acaagtgtgg | gatgaagaac | 1740 |
| catcatcctg | aacagcaaag | ctccctgcta | aacctctctt | cgtcgacccc | gacacatcag | 1800 |
| gagtccatga | acactggcac | actcgcttcc | ctgcgaggga | gggccaggag | atccaaaggg | 1860 |
| aagaacaaac | acagcaagag | ggctctgctt | gtgtgccagt | ga | | 1902 |

<210> SEQ ID NO 24
<211> LENGTH: 633
<212> TYPE: PRT
<213> ORGANISM: Homo sapiens
<220> FEATURE:

<221> NAME/KEY: MISC_FEATURE
<223> OTHER INFORMATION: human DUB4.11

<400> SEQUENCE: 24

```
Met Cys Ile Arg Thr Gly Ser Pro Cys Asp Val Cys Glu Asn Tyr Ser
1               5                   10                  15
Val Met Ser Met Thr Gly Arg Gln Leu Ile Asp Trp Ala Pro Leu Lys
            20                  25                  30
Ile Gly Tyr Glu His Ser Ser Thr Pro Met Pro Arg Thr Leu Tyr Ile
        35                  40                  45
Arg His Arg Lys Pro Ser Asp Gly Ala His Leu Ala His Glu Lys Thr
    50                  55                  60
Arg Glu Arg Asn Gly Ala Lys Gly Lys Ile Arg Cys Ala Lys Tyr
65                  70                  75                  80
Tyr Thr Ser Leu Thr Ile Leu Arg Ser Glu Ser Ala Leu Ser Ser Ser
                85                  90                  95
Cys Pro Ser Val Ala Glu Arg Met Met Ala Ala Lys Ile Asp Met
            100                 105                 110
Glu Asp Asp Ser Leu Tyr Leu Gly Gly Glu Trp Gln Phe Asn His Phe
        115                 120                 125
Ser Lys Leu Thr Ser Ser Arg Pro Asp Ala Ala Phe Ala Glu Ile Gln
    130                 135                 140
Arg Thr Ser Leu Pro Glu Lys Ser Pro Leu Ser Tyr Asp Leu Ala Pro
145                 150                 155                 160
Val Ala Arg Gln Leu Ala Pro Arg Glu Lys Leu Pro Leu Ser Ser Arg
                165                 170                 175
Arg Pro Ala Ala Val Gly Ala Gly Leu Gln Asn Met Gly Asn Thr Cys
            180                 185                 190
Tyr Val Asn Ala Ser Leu Gln Cys Leu Thr Tyr Thr Pro Pro Leu Ala
        195                 200                 205
Asn Tyr Met Leu Ser Arg Glu His Ser Gln Thr Cys His Arg His Lys
    210                 215                 220
Gly Cys Met Leu Cys Thr Met Gln Ala His Ile Thr Arg Ala Leu His
225                 230                 235                 240
Asn Pro Gly His Val Ile Gln Pro Ser Gln Ala Leu Ala Ala Gly Phe
                245                 250                 255
His Arg Gly Lys Gln Glu Asp Ala His Glu Phe Leu Met Phe Thr Val
            260                 265                 270
Asp Ala Met Lys Lys Ala Cys Leu Pro Arg His Lys Gln Val Asp His
        275                 280                 285
His Ser Lys Asp Thr Thr Leu Ile His Gln Ile Phe Gly Gly Tyr Trp
    290                 295                 300
Arg Ser Gln Ile Lys Cys Leu His Cys His Gly Ile Ser Asp Thr Phe
305                 310                 315                 320
Asp Pro Tyr Leu Asp Ile Ala Leu Asp Ile Gln Ala Ala Gln Ser Val
                325                 330                 335
Gln Gln Ala Leu Glu Gln Leu Val Lys Pro Glu Glu Leu Asn Gly Glu
            340                 345                 350
Asn Ala Tyr His Cys Gly Val Cys Leu Gln Arg Ala Pro Ala Ser Lys
        355                 360                 365
Thr Leu Thr Leu His Thr Ser Ala Lys Val Leu Ile Leu Val Leu Lys
    370                 375                 380
Arg Phe Ser Asp Val Thr Gly Asn Lys Ile Ala Lys Asn Val Gln Tyr
385                 390                 395                 400
```

-continued

```
Pro Glu Cys Leu Asp Met Gln Pro Tyr Met Ser Gln Gln Asn Thr Gly
                405                 410                 415
Pro Leu Val Tyr Val Leu Tyr Ala Val Leu Val His Ala Glu Trp Ser
            420                 425                 430
Cys His Asn Gly His Tyr Phe Ser Tyr Val Lys Ala Gln Glu Gly Gln
        435                 440                 445
Trp Tyr Lys Met Asp Asp Ala Glu Val Thr Ala Ser Ile Thr Ser
    450                 455                 460
Val Leu Ser Gln Gln Ala Tyr Val Leu Phe Tyr Ile Gln Lys Ser Glu
465                 470                 475                 480
Trp Glu Arg His Ser Glu Ser Val Ser Arg Gly Arg Glu Pro Arg Ala
                485                 490                 495
Leu Gly Ala Glu Asp Thr Asp Arg Ala Thr Gln Gly Glu Leu Lys
            500                 505                 510
Arg Asp His Pro Cys Leu Gln Ala Pro Glu Leu Asp Glu His Leu Val
        515                 520                 525
Glu Arg Ala Thr Gln Glu Ser Thr Leu Asp His Trp Lys Phe Leu Gln
    530                 535                 540
Glu Gln Asn Lys Thr Lys Pro Glu Phe Asn Val Arg Lys Val Lys Gly
545                 550                 555                 560
Thr Leu Pro Pro Asp Val Leu Val Ile His Gln Ser Lys Tyr Lys Cys
                565                 570                 575
Gly Met Lys Asn His His Pro Glu Gln Gln Ser Ser Leu Leu Asn Leu
            580                 585                 590
Ser Ser Ser Thr Pro Thr His Gln Glu Ser Met Asn Thr Gly Thr Leu
        595                 600                 605
Ala Ser Leu Arg Gly Arg Ala Arg Arg Ser Lys Gly Lys Asn Lys His
    610                 615                 620
Ser Lys Arg Ala Leu Leu Val Cys Gln
625                 630
```

<210> SEQ ID NO 25
<211> LENGTH: 1593
<212> TYPE: DNA
<213> ORGANISM: Homo sapiens
<220> FEATURE:
<221> NAME/KEY: misc_feature
<223> OTHER INFORMATION: human DUB8.1

<400> SEQUENCE: 25

```
atgggggacg actcactcta cttgggaggt gagtggcagt tcaaccactt ttcaaaactc      60
acatcttctc ggccagatgc agcttttgct gaaatccagc ggacttctct ccctgagaag     120
tcaccactct catctgagac ccgtgtcgac ctctgtgatg atttggctcc tgtgcaaga     180
cagctcgctc ccaggagaaa gcttcctctg agtagcagga gacctgctgc ggtgggggct     240
gggctccaga atatgggaaa tacctgctac gagaacgctt ccctgcagtg cctgacatac     300
acactgcccc ttgccaacta catgctgtcc cgggagcact ctcaaacatg tcagcgtccc     360
aagtgctgca tgctctgtac tatgcaagct cacatcacat gggccctcca cagtcctggc     420
catgtcatcc agccctcaca ggcattggct gctggcttcc atagaggcaa gcaggaagat     480
gtccatgaat ttctcatgtt cactgtggat gccatgaaaa aggcatgcct tcccggccac     540
aagcaggtag atcatcactg caaggacacc accctcatcc accaaatatt tggaggctgc     600
tggagatctc aaatcaagtg tctccactgc acgggattt cagacacttt tgacccttac     660
```

-continued

```
ctggacatcg ccctggatat ccaggcagct cagagtgtca agcaagcttt ggaacagttg      720
gtgaagcccg aagaactcaa tggagagaat gcctatcatt gcggtctttg tctccagagg      780
gcgccggcct ccaacacgtt aactttacac acttctgcca aggtcctcat ccttgtcttg      840
aagagattct ccgatgtcgc aggcaacaaa cttgccaaga atgtgcaata tcctgagtgc      900
cttgacatgc agccatacat gtctcagcag aacacaggac ctcttgtcta tgtcctctat      960
gctgtgctgg tccacgctgg gtggagttgt cacgacggac attacttctc ctatgtcaaa     1020
gctcaagaag tccagtggta taaaatggat gatgccgagg tcactgtctg tagcatcatt     1080
tctgtcctga gtcaacaggc ctatgtcctc ttttacatcc agaagagtga atgggaaaga     1140
cacagtgaga gtgtgtcaag aggcagggaa ccaagagccc tcggcgctga agacacagac     1200
aggcgagcaa agcaaggaga gctcaagaga gaccacccct gcctccaggc acccgagttg     1260
gacgagcact tggtggaaag agccactcag gaaagcacct tagaccactg gaaattcctg     1320
caagagcaaa acaaaacgaa gcctgagttc aacgtcggaa aagtcgaagg taccctgcct     1380
cccaacgcac ttgtgattca tcaatcaaaa tacaagtgtg ggatgaaaaa ccatcatcct     1440
gaacagcaaa gctccctgct aaacctctct tcgacgaccc ggacagatca ggagtccatg     1500
aacactggca cactcgcttc tctgcaaggg aggaccagga gagccaaagg gaagaacaaa     1560
cacagcaaga gggctctgct tgtgtgccag tga                                 1593
```

<210> SEQ ID NO 26
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB8.1

<400> SEQUENCE: 26

```
Met Gly Asp Asp Ser Leu Tyr Leu Gly Gly Glu Trp Gln Phe Asn His
1               5                   10                  15

Phe Ser Lys Leu Thr Ser Ser Arg Pro Asp Ala Ala Phe Ala Glu Ile
            20                  25                  30

Gln Arg Thr Ser Leu Pro Glu Lys Ser Pro Leu Ser Ser Glu Thr Arg
        35                  40                  45

Val Asp Leu Cys Asp Asp Leu Ala Pro Val Ala Arg Gln Leu Ala Pro
    50                  55                  60

Arg Glu Lys Leu Pro Leu Ser Ser Arg Arg Pro Ala Ala Val Gly Ala
65                  70                  75                  80

Gly Leu Gln Asn Met Gly Asn Thr Cys Tyr Glu Asn Ala Ser Leu Gln
                85                  90                  95

Cys Leu Thr Tyr Thr Leu Pro Leu Ala Asn Tyr Met Leu Ser Arg Glu
            100                 105                 110

His Ser Gln Thr Cys Gln Arg Pro Lys Cys Cys Met Leu Cys Thr Met
        115                 120                 125

Gln Ala His Ile Thr Trp Ala Leu His Ser Pro Gly His Val Ile Gln
    130                 135                 140

Pro Ser Gln Ala Leu Ala Ala Gly Phe His Arg Gly Lys Gln Glu Asp
145                 150                 155                 160

Val His Glu Phe Leu Met Phe Thr Val Asp Ala Met Lys Lys Ala Cys
                165                 170                 175

Leu Pro Gly His Lys Gln Val Asp His His Cys Lys Asp Thr Thr Leu
            180                 185                 190
```

```
Ile His Gln Ile Phe Gly Gly Cys Trp Arg Ser Gln Ile Lys Cys Leu
        195                 200                 205

His Cys His Gly Ile Ser Asp Thr Phe Asp Pro Tyr Leu Asp Ile Ala
        210                 215                 220

Leu Asp Ile Gln Ala Ala Gln Ser Val Lys Gln Ala Leu Glu Gln Leu
225                 230                 235                 240

Val Lys Pro Glu Glu Leu Asn Gly Glu Asn Ala Tyr His Cys Gly Leu
                245                 250                 255

Cys Leu Gln Arg Ala Pro Ala Ser Asn Thr Leu Thr Leu His Thr Ser
            260                 265                 270

Ala Lys Val Leu Ile Leu Val Leu Lys Arg Phe Ser Asp Val Ala Gly
        275                 280                 285

Asn Lys Leu Ala Lys Asn Val Gln Tyr Pro Glu Cys Leu Asp Met Gln
    290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asp Gly His Tyr Phe
                325                 330                 335

Ser Tyr Val Lys Ala Gln Glu Val Gln Trp Tyr Lys Met Asp Asp Ala
            340                 345                 350

Glu Val Thr Val Cys Ser Ile Ile Ser Val Leu Ser Gln Gln Ala Tyr
        355                 360                 365

Val Leu Phe Tyr Ile Gln Lys Ser Glu Trp Glu Arg His Ser Glu Ser
    370                 375                 380

Val Ser Arg Gly Arg Glu Pro Arg Ala Leu Gly Ala Glu Asp Thr Asp
385                 390                 395                 400

Arg Arg Ala Lys Gln Gly Glu Leu Lys Arg Asp His Pro Cys Leu Gln
                405                 410                 415

Ala Pro Glu Leu Asp Glu His Leu Val Glu Arg Ala Thr Gln Glu Ser
            420                 425                 430

Thr Leu Asp His Trp Lys Phe Leu Gln Glu Gln Asn Lys Thr Lys Pro
        435                 440                 445

Glu Phe Asn Val Gly Lys Val Glu Gly Thr Leu Pro Pro Asn Ala Leu
    450                 455                 460

Val Ile His Gln Ser Lys Tyr Lys Cys Gly Met Lys Asn His His Pro
465                 470                 475                 480

Glu Gln Gln Ser Ser Leu Leu Asn Leu Ser Ser Thr Thr Arg Thr Asp
                485                 490                 495

Gln Glu Ser Met Asn Thr Gly Thr Leu Ala Ser Leu Gln Gly Arg Thr
            500                 505                 510

Arg Arg Ala Lys Gly Lys Asn Lys His Ser Lys Arg Ala Leu Leu Val
        515                 520                 525

Cys Gln
    530

<210> SEQ ID NO 27
<211> LENGTH: 1494
<212> TYPE: DNA
<213> ORGANISM: Homo sapiens
<220> FEATURE:
<221> NAME/KEY: misc_feature
<223> OTHER INFORMATION: human DUB8.3

<400> SEQUENCE: 27
atggaggacg actcactcta cttgggaggt gagtggcagt tcaaccactt ttcaaaactc      60
```

-continued

```
acatcttctc ggccagatgc agcctttgct gaaatccagc ggacttctct ccctgagaag      120
tcacaactct caactgagac ccgcgtcgac ttctgcgatg atttggcgcc tgtggcaaga      180
cagcttgctc ccagggagaa gcttcctctg agtagcagga gacctgctgc ggtgggggct      240
gggctccaga atatgggaaa tacctgctac gtgaacgctt cccagcagtg tctgacatac      300
acaccgcccc ttgccaacta catgctgtcc cgggagcact ctcaaacatg tcatcgtcac      360
aagtgctgca tgctctgtac catggaagct cacatcacat ggcccctcca cattcctggc      420
catgtcatcc agccctcaca ggcattggct gctggcttcc atagaggcaa gcaggaagct      480
gcccttgaat ttctcatgtt cactgtggat gccatgaaaa aggcatgcct tcccgggcac      540
aagcaggtag atcatcactc caaggacacc accctcatcc accaaatatt tggagggtac      600
tggagatctc aaatcaagtg tctccactgc acggcattt cagacacttt tggcccttac       660
ctggacatcg ccctggatat ccaggaagct cagagtgtca agcaagcttt ggaacagttg      720
gtgaagcccg aagaactcaa tggagagaat gcctatcatt gtggcaacaa aattgccaag      780
aatgtgcaat atcctgagtg ccttgacatg cagccataca tgtctcagca gaacacagga      840
cctcttgtct atgtcctcta tgctgtgctg gtccacgccg ggtggagttg tcacaacgga      900
cattacttct cttatgtcaa agttcaagaa ggccagtggt ataaaatgga tgatgccgag      960
gtcactgcct ctggcatcac ctctgtcctg agtcaacagg cctatgtcct cttttacatc     1020
cacaagagtg aatgggaaag acacagtgag agtgtgtcaa gaggcaggga accaagagcc     1080
ctcggcgctg aagacacaga caggcgagca acgcaaggag agctcaagag agactacccc     1140
tgcctccagg tacccgagtt ggacgagcac ttggtggaaa gagccactca ggaaagcacc     1200
ttagaccact ggaaattcct ccaagagcaa acaaaacga agcctgagtt caacgtcaga       1260
aaacttgaag gtaccctgcc tcccaacgta cttgtgattc atcaatcaaa atacaagtgt     1320
gggatgaaaa accatcatcc tgaacagcaa agctccctgc taaacctctc ttcgacgaac     1380
ccgacagatc aggagtccat gaacactggc acactcgctt ctctgcaagg gaggaccagg     1440
agagccaaag ggaagaacaa acactgcaag agggctctgc ttgtgtgcca gtga           1494
```

<210> SEQ ID NO 28
<211> LENGTH: 497
<212> TYPE: PRT
<213> ORGANISM: Homo sapiens
<220> FEATURE:
<221> NAME/KEY: MISC_FEATURE
<223> OTHER INFORMATION: human DUB8.3

<400> SEQUENCE: 28

```
Met Glu Asp Asp Ser Leu Tyr Leu Gly Gly Glu Trp Gln Phe Asn His
1               5                   10                  15

Phe Ser Lys Leu Thr Ser Ser Arg Pro Asp Ala Ala Phe Ala Glu Ile
                20                  25                  30

Gln Arg Thr Ser Leu Pro Glu Lys Ser Gln Leu Ser Thr Glu Thr Arg
            35                  40                  45

Val Asp Phe Cys Asp Asp Leu Ala Pro Val Ala Arg Gln Leu Ala Pro
        50                  55                  60

Arg Glu Lys Leu Pro Leu Ser Ser Arg Pro Ala Ala Val Gly Ala
65                  70                  75                  80

Gly Leu Gln Asn Met Gly Asn Thr Cys Tyr Val Asn Ala Ser Gln Gln
                85                  90                  95

Cys Leu Thr Tyr Thr Pro Pro Leu Ala Asn Tyr Met Leu Ser Arg Glu
                100                 105                 110
```

```
His Ser Gln Thr Cys His Arg His Lys Cys Cys Met Leu Cys Thr Met
        115                 120                 125
Glu Ala His Ile Thr Trp Pro Leu His Ile Pro Gly His Val Ile Gln
130                 135                 140
Pro Ser Gln Ala Leu Ala Ala Gly Phe His Arg Gly Lys Gln Glu Ala
145                 150                 155                 160
Ala Leu Glu Phe Leu Met Phe Thr Val Asp Ala Met Lys Lys Ala Cys
                165                 170                 175
Leu Pro Gly His Lys Gln Val Asp His His Ser Lys Asp Thr Thr Leu
            180                 185                 190
Ile His Gln Ile Phe Gly Gly Tyr Trp Arg Ser Gln Ile Lys Cys Leu
        195                 200                 205
His Cys His Gly Ile Ser Asp Thr Phe Gly Pro Tyr Leu Asp Ile Ala
    210                 215                 220
Leu Asp Ile Gln Glu Ala Gln Ser Val Lys Gln Ala Leu Glu Gln Leu
225                 230                 235                 240
Val Lys Pro Glu Glu Leu Asn Gly Glu Asn Ala Tyr His Cys Gly Asn
                245                 250                 255
Lys Ile Ala Lys Asn Val Gln Tyr Pro Glu Cys Leu Asp Met Gln Pro
            260                 265                 270
Tyr Met Ser Gln Gln Asn Thr Gly Pro Leu Val Tyr Val Leu Tyr Ala
        275                 280                 285
Val Leu Val His Ala Gly Trp Ser Cys His Asn Gly His Tyr Phe Ser
    290                 295                 300
Tyr Val Lys Val Gln Glu Gly Gln Trp Tyr Lys Met Asp Asp Ala Glu
305                 310                 315                 320
Val Thr Ala Ser Gly Ile Thr Ser Val Leu Ser Gln Gln Ala Tyr Val
                325                 330                 335
Leu Phe Tyr Ile His Lys Ser Glu Trp Glu Arg His Ser Glu Ser Val
        340                 345                 350
Ser Arg Gly Arg Glu Pro Arg Ala Leu Gly Ala Glu Asp Thr Asp Arg
    355                 360                 365
Arg Ala Thr Gln Gly Glu Leu Lys Arg Asp Tyr Pro Cys Leu Gln Val
370                 375                 380
Pro Glu Leu Asp Glu His Leu Val Glu Arg Ala Thr Gln Glu Ser Thr
385                 390                 395                 400
Leu Asp His Trp Lys Phe Leu Gln Glu Gln Asn Lys Thr Lys Pro Glu
                405                 410                 415
Phe Asn Val Arg Lys Leu Glu Gly Thr Leu Pro Pro Asn Val Leu Val
            420                 425                 430
Ile His Gln Ser Lys Tyr Lys Cys Gly Met Lys Asn His Pro Glu
        435                 440                 445
Gln Gln Ser Ser Leu Leu Asn Leu Ser Ser Thr Asn Pro Thr Asp Gln
    450                 455                 460
Glu Ser Met Asn Thr Gly Thr Leu Ala Ser Leu Gln Gly Arg Thr Arg
465                 470                 475                 480
Arg Ala Lys Gly Lys Asn Lys His Cys Lys Arg Ala Leu Leu Val Cys
                485                 490                 495
Gln

<210> SEQ ID NO 29
<211> LENGTH: 1593
<212> TYPE: DNA
```

-continued

```
<213> ORGANISM: Homo sapiens
<220> FEATURE:
<221> NAME/KEY: misc_feature
<223> OTHER INFORMATION: human DUB8.5

<400> SEQUENCE: 29
atggaggacg actcactcta cttgggaggt gagtggcagt tcaaccactt ttcaaaactc      60
acatcttctc ggccagatgc agcttttgct gaaatccagc ggacttctct ccctgagaag     120
tcaccactct catctgaggc ccgtgtcgac ctctgtgatg atttggctcc tgtggcaaga     180
cagcttgctc ccaggaagaa gcttcctctg agtagcagga gacctgctgc ggtgggggct     240
gggctccaga atatgggaaa tacctgctac agaaacgctt ccctgcagtg cctgacatac     300
acaccgcccc ttgccaacta catgctgtcc cgggagcact ctcaaacatg tcagcgtccc     360
aagtgctgca tgctctgtac tatgcaagct cacatcacat gggccctcca cagtcctggt     420
catgtcatcc agccctcaca ggcattggct gctggcttcc atagaggcaa gcaggaagat     480
gcccatgaat ttctcatgtt cactgtggat gccatgaaaa aggcatgcct tcccggccac     540
aagcaggtag atcatcactc taaggacacc accctcatcc accaaatatt tggaggctgc     600
tggagatctc aaatcaagtg tctccactgc acgggatttc agacactttt tgacccttac     660
ctggacatcg ccctggatat ccaggcagct cagagtgtca agcaagcttt ggaacagttg     720
gtgaagcccg aagaactcaa tggagagaat gcctatcatt gcggtctttg tcttcagagg     780
gcgccagtct ccaagacgtt aactttacac acttttgcca aggaacgcat acttgaaacg     840
cagagaccat gggtggtcac acgccacaaa ctagccaaga gtgtgcaata tgctgagagc     900
cttgacatgc agccatacat gtctcagcag aacacaggac tcttgtcta tgtcctctat     960
gctgtgctgg tccacgctgg gtggagttgt cacgatggca attacttctc ttatgtcaaa    1020
gctcaagaag gccagtggta taaaatggat gatgccaagg tcactgcctg tagcatcact    1080
tctgtcctga gtcaacaggc ctatgtcctc ttttacatcc agaagagtga atgggaagaa    1140
cacagtgaga gtgtgtcaag aggcagggaa ccaagagccc tcggcgctga agacacagac    1200
aggcgagcaa cgcaaggaga gctcaagaga gaccacccct gcctccaggc acccgagttg    1260
gacgagcgct tggtggaaag agccactcag gaaagcacct tagaccactg gagattcccc    1320
caagagcaaa acaaaacgaa gcctgagttc aacgtcagaa aagtcgaagg taccctgcct    1380
cccaacgtac ttgtgattca tcaatcgaaa tacaagtgtg ggatgaaaaa ccatcatcct    1440
gaacagcaaa gctccctgct aaacctctct tcgacgaccc ggacagatca ggagtccgtg    1500
aacactggca ccctcgcttc tctgcaaggg aggaccagga gatccaaagg gaagaacaaa    1560
cacagcaaga gggctctgct tgtgtgccag tga                                 1593

<210> SEQ ID NO 30
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB8.5

<400> SEQUENCE: 30

Met Glu Asp Asp Ser Leu Tyr Leu Gly Gly Glu Trp Gln Phe Asn His
  1               5                  10                  15

Phe Ser Lys Leu Thr Ser Ser Arg Pro Asp Ala Ala Phe Ala Glu Ile
                 20                  25                  30

Gln Arg Thr Ser Leu Pro Glu Lys Ser Pro Leu Ser Ser Glu Ala Arg
```

-continued

```
                35                  40                  45
Val Asp Leu Cys Asp Asp Leu Ala Pro Val Ala Arg Gln Leu Ala Pro
 50                  55                  60
Arg Lys Leu Pro Leu Ser Ser Arg Arg Pro Ala Ala Val Gly Ala
 65                  70                  75                  80
Gly Leu Gln Asn Met Gly Asn Thr Cys Tyr Glu Asn Ala Ser Leu Gln
                 85                  90                  95
Cys Leu Thr Tyr Thr Pro Pro Leu Ala Asn Tyr Met Leu Ser Arg Glu
                100                 105                 110
His Ser Gln Thr Cys Gln Arg Pro Lys Cys Cys Met Leu Cys Thr Met
                115                 120                 125
Gln Ala His Ile Thr Trp Ala Leu His Ser Pro Gly His Val Ile Gln
130                 135                 140
Pro Ser Gln Ala Leu Ala Ala Gly Phe His Arg Gly Lys Gln Glu Asp
145                 150                 155                 160
Ala His Glu Phe Leu Met Phe Thr Val Asp Ala Met Lys Lys Ala Cys
                165                 170                 175
Leu Pro Gly His Lys Gln Val Asp His His Ser Lys Asp Thr Thr Leu
                180                 185                 190
Ile His Gln Ile Phe Gly Gly Cys Trp Arg Ser Gln Ile Lys Cys Leu
                195                 200                 205
His Cys His Gly Ile Ser Asp Thr Phe Asp Pro Tyr Leu Asp Ile Ala
                210                 215                 220
Leu Asp Ile Gln Ala Ala Gln Ser Val Lys Gln Ala Leu Glu Gln Leu
225                 230                 235                 240
Val Lys Pro Glu Glu Leu Asn Gly Glu Asn Ala Tyr His Cys Gly Leu
                245                 250                 255
Cys Leu Gln Arg Ala Pro Val Ser Lys Thr Leu Thr Leu His Thr Phe
                260                 265                 270
Ala Lys Glu Arg Ile Leu Glu Thr Gln Arg Pro Trp Val Val Thr Arg
                275                 280                 285
His Lys Leu Ala Lys Ser Val Gln Tyr Ala Glu Ser Leu Asp Met Gln
290                 295                 300
Pro Tyr Met Ser Gln Gln Asn Thr Gly Pro Leu Val Tyr Val Leu Tyr
305                 310                 315                 320
Ala Val Leu Val His Ala Gly Trp Ser Cys His Asp Gly His Tyr Phe
                325                 330                 335
Ser Tyr Val Lys Ala Gln Glu Gly Gln Trp Tyr Lys Met Asp Asp Ala
                340                 345                 350
Lys Val Thr Ala Cys Ser Ile Thr Ser Val Leu Ser Gln Gln Ala Tyr
                355                 360                 365
Val Leu Phe Tyr Ile Gln Lys Ser Glu Trp Glu Arg His Ser Glu Ser
370                 375                 380
Val Ser Arg Gly Arg Glu Pro Arg Ala Leu Gly Ala Glu Asp Thr Asp
385                 390                 395                 400
Arg Arg Ala Thr Gln Gly Glu Leu Lys Arg Asp His Pro Cys Leu Gln
                405                 410                 415
Ala Pro Glu Leu Asp Glu Arg Leu Val Glu Arg Ala Thr Gln Glu Ser
                420                 425                 430
Thr Leu Asp His Trp Arg Phe Pro Gln Glu Gln Asn Lys Thr Lys Pro
                435                 440                 445
Glu Phe Asn Val Arg Lys Val Glu Gly Thr Leu Pro Pro Asn Val Leu
450                 455                 460
```

| Val | Ile | His | Gln | Ser | Lys | Tyr | Lys | Cys | Gly | Met | Lys | Asn | His | His | Pro |
| --- | --- | --- | --- | --- | --- | --- | --- | --- | --- | --- | --- | --- | --- | --- | --- |
| 465 | | | | 470 | | | | 475 | | | | | | | 480 |

| Glu | Gln | Gln | Ser | Ser | Leu | Leu | Asn | Leu | Ser | Ser | Thr | Thr | Arg | Thr | Asp |
| --- | --- | --- | --- | --- | --- | --- | --- | --- | --- | --- | --- | --- | --- | --- | --- |
| | | | | 485 | | | | | 490 | | | | | 495 | |

| Gln | Glu | Ser | Val | Asn | Thr | Gly | Thr | Leu | Ala | Ser | Leu | Gln | Gly | Arg | Thr |
| --- | --- | --- | --- | --- | --- | --- | --- | --- | --- | --- | --- | --- | --- | --- | --- |
| | | | 500 | | | | | 505 | | | | | 510 | | |

| Arg | Arg | Ser | Lys | Gly | Lys | Asn | Lys | His | Ser | Lys | Arg | Ala | Leu | Leu | Val |
| --- | --- | --- | --- | --- | --- | --- | --- | --- | --- | --- | --- | --- | --- | --- | --- |
| | 515 | | | | | 520 | | | | | 525 | | | | |

| Cys | Gln |
| --- | --- |
| | 530 |

<210> SEQ ID NO 31
<211> LENGTH: 1593
<212> TYPE: DNA
<213> ORGANISM: Homo sapiens
<220> FEATURE:
<221> NAME/KEY: misc_feature
<223> OTHER INFORMATION: human DUB8.6

<400> SEQUENCE: 31

```
atggaagacg actcactcta tttgggaggt gactggcagt tcaatcactt ttcaaaactc        60
acatcttctc ggctagatgc agcttttgct gaaatccagc ggacttctct ctctgaaaag       120
tcaccactct catctgagac ccgtttcgac ctctgtgatg atttggctcc tgtggcaaga       180
cagcttgctc ccagggagaa gcttcctctg agtagcagga gacctgctgc ggtggggggct      240
gggctccaga agataggaaa taccttctat gtgaacgttt ccctgcagtg cctgacatac       300
acactgccgc tttccaacta catgctgtcc cgggaggact ctcaaacgtg tcatcttcac       360
aagtgctgca tgttctgtac tatgcaagct cacatcacat gggccctcta ccgtcctggc       420
catgtcatcc agccctcaca ggtattggct gctggcttcc atagaggtga gcaggaggat       480
gcccatgaat ttctcatgtt tactgtggat gccatgaaaa aggcatgcct tcccgggcac       540
aagcagctag atcatcactc caaggacacc accctcatcc accaaatatt tggagcgtat       600
tggagatctc aaatcaagta tctccactgc acggcatttt cagacacctt tgacccttac       660
ctggacatcg ccctggatat ccaggcagct cagagtgtca agcaagcttt ggaacagttg       720
gtgaagccca agaactcaa tggagagaat gcctatcatt gtggtctttg tctccagaag       780
gcgcctgcct ccaagacgtt aactttaccc acttctgcca aggtcctcat tcttgtattg       840
aagagattct ccgatgtcac aggcaacaaa cttgccaaga tgtgcaata tcctaagtgc       900
cgtgacatgc agccatacat gtctcagcag aacacaggac ctcttgtcta tgtcctctat       960
gctgtgctgg tccacgctgg gtggagttgt cacaacggac attacttctc ttatgtcaaa      1020
gctcaagaag gccagtggta taaatggat gatgccgagg tcactgcctc tggcatcacc       1080
tctgtcctga gtcaacaggc ctatgtcctc ttttacatcc agaagagtga atgggaaaga      1140
cacagtgaga gtgtgtcaag aggcagggaa ccaagagccc ttggtgctga agacacagac      1200
aggccagcaa cgcaaggaga gctcaagaga gaccacccctt gcctccaggt acccgagttg      1260
gacgagcact tggtggaaag agccactcag gaaagcacct tagaccactg gaaattcccc      1320
caaaagcaaa acaaaacgaa gcctgagttc aacgtcagaa aagttgaagg taccctgcct      1380
cccaacgtac ttgtgattca tcaatcaaaa tacaagtgtg gtatgaaaaa ccatcatcct      1440
gaacagcaaa gctccctgct aaacctctct tcgacgaaac cgacagatca ggagtccatg      1500
aacactggca cactcgcttc tctgcaaggg agcaccagga gatccaaagg gaataacaaa      1560
```

```
cacagcaaga gatctctgct tgtgtgccag tga                    1593
```

<210> SEQ ID NO 32
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB8.6

<400> SEQUENCE: 32

```
Met Glu Asp Asp Ser Leu Tyr Leu Gly Gly Asp Trp Gln Phe Asn His
 1               5                  10                  15

Phe Ser Lys Leu Thr Ser Ser Arg Leu Asp Ala Ala Phe Ala Glu Ile
             20                  25                  30

Gln Arg Thr Ser Leu Ser Glu Lys Ser Pro Leu Ser Ser Glu Thr Arg
         35                  40                  45

Phe Asp Leu Cys Asp Asp Leu Ala Pro Val Ala Arg Gln Leu Ala Pro
     50                  55                  60

Arg Glu Lys Leu Pro Leu Ser Arg Arg Pro Ala Ala Val Gly Ala
 65                  70                  75                  80

Gly Leu Gln Lys Ile Gly Asn Thr Phe Tyr Val Asn Val Ser Leu Gln
                 85                  90                  95

Cys Leu Thr Tyr Thr Leu Pro Leu Ser Asn Tyr Met Leu Ser Arg Glu
            100                 105                 110

Asp Ser Gln Thr Cys His Leu His Lys Cys Cys Met Phe Cys Thr Met
        115                 120                 125

Gln Ala His Ile Thr Trp Ala Leu Tyr Arg Pro Gly His Val Ile Gln
    130                 135                 140

Pro Ser Gln Val Leu Ala Ala Gly Phe His Arg Gly Glu Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Leu Asp His His Ser Lys Asp Thr Thr Leu
            180                 185                 190

Ile His Gln Ile Phe Gly Ala Tyr Trp Arg Ser Gln Ile Lys Tyr Leu
        195                 200                 205

His Cys His Gly Ile Ser Asp Thr Phe Asp Pro Tyr Leu Asp Ile Ala
    210                 215                 220

Leu Asp Ile Gln Ala Ala Gln Ser Val Lys Gln Ala Leu Glu Gln Leu
225                 230                 235                 240

Val Lys Pro Lys Glu Leu Asn Gly Glu Asn Ala Tyr His Cys Gly Leu
                245                 250                 255

Cys Leu Gln Lys Ala Pro Ala Ser Lys Thr Leu Thr Leu Pro Thr Ser
            260                 265                 270

Ala Lys Val Leu Ile Leu Val Leu Lys Arg Phe Ser Asp Val Thr Gly
        275                 280                 285

Asn Lys Leu Ala Lys Asn Val Gln Tyr Pro Lys Cys Arg Asp Met Gln
    290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Met Asp Asp Ala
            340                 345                 350
```

```
                Glu Val Thr Ala Ser Gly Ile Thr Ser Val Leu Ser Gln Gln Ala Tyr
                            355                 360                 365

Val Leu Phe Tyr Ile Gln Lys Ser Glu Trp Glu Arg His Ser Glu Ser
                    370                 375                 380

Val Ser Arg Gly Arg Glu Pro Arg Ala Leu Gly Ala Glu Asp Thr Asp
                385                 390                 395                 400

Arg Pro Ala Thr Gln Gly Glu Leu Lys Arg Asp His Pro Cys Leu Gln
                                405                 410                 415

Val Pro Glu Leu Asp Glu His Leu Val Glu Arg Ala Thr Gln Glu Ser
                            420                 425                 430

Thr Leu Asp His Trp Lys Phe Pro Gln Lys Gln Asn Lys Thr Lys Pro
                        435                 440                 445

Glu Phe Asn Val Arg Lys Val Glu Gly Thr Leu Pro Pro Asn Val Leu
                    450                 455                 460

Val Ile His Gln Ser Lys Tyr Lys Cys Gly Met Lys Asn His His Pro
                465                 470                 475                 480

Glu Gln Gln Ser Ser Leu Leu Asn Leu Ser Ser Thr Lys Pro Thr Asp
                                485                 490                 495

Gln Glu Ser Met Asn Thr Gly Thr Leu Ala Ser Leu Gln Gly Ser Thr
                            500                 505                 510

Arg Arg Ser Lys Gly Asn Asn Lys His Ser Lys Arg Ser Leu Leu Val
                        515                 520                 525

Cys Gln
                    530

<210> SEQ ID NO 33
<211> LENGTH: 1593
<212> TYPE: DNA
<213> ORGANISM: Homo sapiens
<220> FEATURE:
<221> NAME/KEY: misc_feature
<223> OTHER INFORMATION: human DUB8.7

<400> SEQUENCE: 33
atggaggacg actcactcta cttgggaggt gagtggcagt tcaaccactt ttcaaaactc      60
acatcttctc ggccagatgc agcttttgct gaaatccagc ggacttctct ccctgagaag     120
tcaccactct catctgaggc ccgtgtcgac ctctgtgatg atttggctcc tgtggcaaga     180
cagcttgctc ccaggaagaa gcttcctctg agtagcagga gacctgctgc ggtgggggct     240
gggctccaga atatgggaaa tacctgctac gagaacgctt ccctgcagtg cctgacatac     300
acaccgcccc ttgccaacta catgctgtcc cgggagcact ctcaaacatg tcagcgtccc     360
aagtgctgca tgctctgtac tatgcaagct cacatcacat gggccctcca cagtcctggt     420
catgtcatcc agccctcaca ggcattggct gctggcttcc atagaggcaa gcaggaagat     480
gcccatgaat ttctcatgtt cactgtggat gccatgaaaa aggcatgcct tcccggccac     540
aagcaggtag atcatcactc taaggacacc accctcatcc accaaatatt tggaggctgc     600
tggagatctc aaatcaagtg tctccactgc cacgggattt cagacacttt tgacccttac     660
ctggacatcg ccctggatat ccaggcagct cagagtgtca agcaagcttt ggaacagttg     720
gtgaagcccg aagaactcaa tggagagaat gcctatcatt gcggtctttg tctccagagg     780
gcgccagcct ccaagacgtt aactttacac acttctgcca aggtcctcat ccttgtcttg     840
aagagattct ccgatgtcac aggcaacaaa cttgccaaga atgtgcaata tcctgagtgc     900
cttgacatgc agccatacat gtctcagcag aacacaggac ctcttgtcta tgtcctctat     960
```

```
gctgtgctgg tccacgctgg gtggagttgt cacgatggac attacttctc ttatgtcaaa    1020
gctcaagaag gccagtggta taaaatggat gatgccaagg tcactgcctg tagcatcact    1080
tctgtcctga gtcaacaggc ctatgtcctc ttttacatcc agaagagtga atgggaaaga    1140
cacagtgaga gtgtgtcaag aggcagggaa ccaagagccc tcggcgctga agacacagac    1200
aggcgagcaa cgcaaggaga gctcaagaga gaccacccct gcctccaggc acccgagttg    1260
gacgagcgct tggtggaaag agccactcag gaaagcacct tagaccactg agattcccc    1320 caagagcaaa acaaaacgaa gcctgagttc aacgtcagaa aagtcgaagg taccctgcct    1380
cccaacgtac ttgtgattca tcaatcgaaa tacaagtgtg ggatgaaaaa ccatcatcct    1440
gaacagcaaa gctccctgct aaacctctct tcgacgaccc ggacagatca ggagtccgtg    1500
aacactggca ccctcgcttc tctgcaaggg aggaccagga gatccaaagg gaagaacaaa    1560
cacagcaaga gggctctgct tgtgtgccag tga                                 1593
```

<210> SEQ ID NO 34
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB8.7

<400> SEQUENCE: 34

```
Met Glu Asp Asp Ser Leu Tyr Leu Gly Gly Glu Trp Gln Phe Asn His
1               5                   10                  15

Phe Ser Lys Leu Thr Ser Ser Arg Pro Asp Ala Ala Phe Ala Glu Ile
                20                  25                  30

Gln Arg Thr Ser Leu Pro Glu Lys Ser Pro Leu Ser Ser Glu Ala Arg
            35                  40                  45

Val Asp Leu Cys Asp Asp Leu Ala Pro Val Ala Arg Gln Leu Ala Pro
        50                  55                  60

Arg Lys Lys Leu Pro Leu Ser Ser Arg Arg Pro Ala Ala Val Gly Ala
65                  70                  75                  80

Gly Leu Gln Asn Met Gly Asn Thr Cys Tyr Glu Asn Ala Ser Leu Gln
                85                  90                  95

Cys Leu Thr Tyr Thr Pro Pro Leu Ala Asn Tyr Met Leu Ser Arg Glu
            100                 105                 110

His Ser Gln Thr Cys Gln Arg Pro Lys Cys Cys Met Leu Cys Thr Met
        115                 120                 125

Gln Ala His Ile Thr Trp Ala Leu His Ser Pro Gly His Val Ile Gln
    130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His His Ser Lys Asp Thr Thr Leu
            180                 185                 190

Ile His Gln Ile Phe Gly Gly Cys Trp Arg Ser Gln Ile Lys Cys Leu
        195                 200                 205

His Cys His Gly Ile Ser Asp Thr Phe Asp Pro Tyr Leu Asp Ile Ala
    210                 215                 220

Leu Asp Ile Gln Ala Ala Gln Ser Val Lys Gln Ala Leu Glu Gln Leu
225                 230                 235                 240

Val Lys Pro Glu Glu Leu Asn Gly Glu Asn Ala Tyr His Cys Gly Leu
```

```
                245                 250                 255
Cys Leu Gln Arg Ala Pro Ala Ser Lys Thr Leu Thr Leu His Thr Ser
            260                 265                 270

Ala Lys Val Leu Ile Leu Val Leu Lys Arg Phe Ser Asp Val Thr Gly
        275                 280                 285

Asn Lys Leu Ala Lys Asn Val Gln Tyr Pro Glu Cys Leu Asp Met Gln
    290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asp Gly His Tyr Phe
                325                 330                 335

Ser Tyr Val Lys Ala Gln Glu Gly Gln Trp Tyr Lys Met Asp Asp Ala
            340                 345                 350

Lys Val Thr Ala Cys Ser Ile Thr Ser Val Leu Ser Gln Gln Ala Tyr
        355                 360                 365

Val Leu Phe Tyr Ile Gln Lys Ser Glu Trp Glu Arg His Ser Glu Ser
    370                 375                 380

Val Ser Arg Gly Arg Glu Pro Arg Ala Leu Gly Ala Glu Asp Thr Asp
385                 390                 395                 400

Arg Arg Ala Thr Gln Gly Glu Leu Lys Arg Asp His Pro Cys Leu Gln
                405                 410                 415

Ala Pro Glu Leu Asp Glu Arg Leu Val Glu Arg Ala Thr Gln Glu Ser
            420                 425                 430

Thr Leu Asp His Trp Arg Phe Pro Gln Glu Gln Asn Lys Thr Lys Pro
        435                 440                 445

Glu Phe Asn Val Arg Lys Val Glu Gly Thr Leu Pro Pro Asn Val Leu
    450                 455                 460

Val Ile His Gln Ser Lys Tyr Lys Cys Gly Met Lys Asn His His Pro
465                 470                 475                 480

Glu Gln Gln Ser Ser Leu Leu Asn Leu Ser Thr Thr Arg Thr Asp
                485                 490                 495

Gln Glu Ser Val Asn Thr Gly Thr Leu Ala Ser Leu Gln Gly Arg Thr
            500                 505                 510

Arg Arg Ser Lys Gly Lys Asn Lys His Ser Lys Arg Ala Leu Leu Val
        515                 520                 525

Cys Gln
    530

<210> SEQ ID NO 35
<211> LENGTH: 1593
<212> TYPE: PRT
<213> ORGANISM: Homo sapiens
<220> FEATURE:
<221> NAME/KEY: MISC_FEATURE
<223> OTHER INFORMATION: human DUB8.8

<400> SEQUENCE: 35

Ala Thr Gly Gly Ala Gly Ala Cys Gly Ala Cys Thr Cys Ala Cys
1               5                   10                  15

Thr Cys Thr Ala Thr Thr Gly Gly Gly Ala Gly Gly Thr Gly Ala
            20                  25                  30

Cys Thr Gly Gly Cys Ala Gly Thr Cys Ala Ala Thr Cys Ala Cys
        35                  40                  45

Thr Thr Thr Thr Cys Ala Ala Ala Ala Cys Thr Cys Ala Cys Ala Thr
50                  55                  60
```

-continued

```
Cys Thr Thr Cys Thr Cys Gly Gly Cys Thr Ala Gly Ala Thr Gly Cys
65                  70                  75                  80

Ala Gly Cys Thr Thr Thr Thr Gly Cys Thr Gly Ala Ala Ala Thr Cys
                85                  90                  95

Cys Ala Gly Cys Gly Gly Ala Cys Thr Thr Cys Thr Cys Thr Cys Thr
            100                 105                 110

Cys Thr Gly Ala Ala Ala Ala Gly Thr Cys Ala Cys Cys Ala Cys Thr
        115                 120                 125

Cys Thr Cys Ala Thr Cys Thr Gly Ala Gly Ala Cys Cys Cys Gly Thr
    130                 135                 140

Thr Thr Cys Gly Ala Cys Cys Thr Cys Thr Gly Thr Gly Ala Thr Gly
145                 150                 155                 160

Ala Thr Thr Thr Gly Gly Cys Thr Cys Cys Thr Gly Thr Gly Gly Cys
                165                 170                 175

Ala Ala Gly Ala Cys Ala Gly Cys Thr Thr Gly Cys Thr Cys Cys Cys
            180                 185                 190

Ala Gly Gly Gly Ala Gly Ala Ala Gly Cys Thr Thr Cys Cys Thr Cys
        195                 200                 205

Thr Gly Ala Gly Thr Ala Gly Cys Ala Gly Gly Ala Gly Ala Cys Cys
    210                 215                 220

Thr Gly Cys Thr Gly Cys Gly Gly Thr Gly Gly Gly Gly Gly Cys Thr
225                 230                 235                 240

Gly Gly Gly Cys Thr Cys Cys Ala Gly Ala Ala Gly Ala Thr Ala Gly
                245                 250                 255

Gly Ala Ala Ala Thr Ala Cys Cys Thr Thr Cys Thr Ala Thr Gly Thr
            260                 265                 270

Gly Ala Ala Cys Gly Thr Thr Thr Cys Cys Cys Thr Gly Cys Ala Gly
        275                 280                 285

Thr Gly Cys Cys Thr Gly Ala Cys Ala Thr Ala Cys Ala Cys Ala Cys
    290                 295                 300

Thr Gly Cys Cys Gly Cys Thr Thr Thr Cys Cys Ala Ala Cys Thr Ala
305                 310                 315                 320

Cys Ala Thr Gly Cys Thr Gly Thr Cys Cys Gly Gly Gly Ala Gly
                325                 330                 335

Gly Ala Cys Thr Cys Thr Cys Ala Ala Ala Cys Gly Thr Gly Thr Cys
            340                 345                 350

Ala Thr Cys Thr Thr Cys Ala Cys Ala Ala Gly Thr Gly Cys Thr Gly
        355                 360                 365

Cys Ala Thr Gly Thr Thr Cys Thr Gly Thr Ala Cys Thr Ala Thr Gly
    370                 375                 380

Cys Ala Ala Gly Cys Thr Cys Ala Cys Ala Thr Cys Ala Cys Ala Thr
385                 390                 395                 400

Gly Gly Gly Cys Cys Cys Thr Cys Thr Ala Cys Cys Gly Thr Cys Cys
                405                 410                 415

Thr Gly Gly Cys Cys Ala Thr Gly Thr Cys Ala Thr Cys Cys Ala Gly
            420                 425                 430

Cys Cys Cys Thr Cys Ala Cys Ala Gly Gly Thr Ala Thr Thr Gly Gly
        435                 440                 445

Cys Thr Gly Cys Thr Gly Gly Cys Thr Thr Cys Cys Ala Thr Ala Gly
    450                 455                 460

Ala Gly Gly Thr Gly Ala Gly Cys Ala Gly Gly Ala Gly Gly Ala Thr
465                 470                 475                 480

Gly Cys Cys Cys Ala Thr Gly Ala Ala Thr Thr Thr Cys Thr Cys Ala
```

-continued

```
                485                 490                 495

Thr Gly Thr Thr Thr Ala Cys Thr Gly Thr Gly Gly Ala Thr Gly Cys
            500                 505                 510

Cys Ala Thr Gly Ala Ala Ala Ala Ala Gly Gly Cys Ala Thr Gly Cys
        515                 520                 525

Cys Thr Thr Cys Cys Cys Gly Gly Gly Cys Ala Cys Ala Ala Gly Cys
    530                 535                 540

Ala Gly Cys Thr Ala Gly Ala Thr Cys Ala Thr Cys Ala Cys Thr Cys
545                 550                 555                 560

Cys Ala Ala Gly Gly Ala Cys Ala Cys Cys Ala Cys Cys Cys Thr Cys
                565                 570                 575

Ala Thr Cys Cys Ala Cys Cys Ala Ala Ala Thr Ala Thr Thr Thr Gly
            580                 585                 590

Gly Ala Gly Cys Gly Thr Ala Thr Thr Gly Gly Ala Gly Ala Thr Cys
        595                 600                 605

Thr Cys Ala Ala Ala Thr Cys Ala Ala Gly Thr Ala Thr Cys Thr Cys
    610                 615                 620

Cys Ala Cys Thr Gly Cys Cys Ala Cys Gly Gly Cys Ala Thr Thr Thr
625                 630                 635                 640

Cys Ala Gly Ala Cys Ala Cys Cys Thr Thr Thr Gly Ala Cys Cys Cys
                645                 650                 655

Thr Thr Ala Cys Cys Thr Gly Gly Ala Cys Ala Thr Cys Gly Cys Cys
            660                 665                 670

Cys Thr Gly Gly Ala Thr Ala Thr Cys Cys Ala Gly Gly Cys Ala Gly
        675                 680                 685

Cys Thr Cys Ala Gly Ala Gly Thr Gly Thr Cys Ala Ala Gly Cys Ala
    690                 695                 700

Ala Gly Cys Thr Thr Thr Gly Gly Ala Ala Cys Ala Gly Thr Thr Gly
705                 710                 715                 720

Gly Thr Gly Ala Ala Gly Cys Cys Cys Ala Ala Ala Gly Ala Ala Cys
                725                 730                 735

Thr Cys Ala Ala Thr Gly Gly Ala Gly Ala Gly Ala Ala Thr Gly Cys
            740                 745                 750

Cys Thr Ala Thr Cys Ala Thr Thr Gly Thr Gly Gly Thr Cys Thr Thr
        755                 760                 765

Thr Gly Thr Cys Thr Cys Cys Ala Gly Ala Ala Gly Gly Cys Gly Cys
    770                 775                 780

Cys Thr Gly Cys Cys Thr Cys Cys Ala Ala Gly Ala Cys Gly Thr Thr
785                 790                 795                 800

Ala Ala Cys Thr Thr Thr Ala Cys Cys Cys Ala Cys Thr Thr Cys Thr
                805                 810                 815

Gly Cys Cys Ala Ala Gly Gly Thr Cys Cys Thr Cys Ala Thr Thr Cys
            820                 825                 830

Thr Thr Gly Thr Ala Thr Thr Gly Ala Ala Gly Ala Gly Ala Thr Thr
        835                 840                 845

Cys Thr Cys Cys Gly Ala Thr Gly Thr Cys Ala Cys Ala Gly Gly Cys
    850                 855                 860

Ala Ala Cys Ala Ala Ala Cys Thr Thr Gly Cys Cys Ala Ala Gly Ala
865                 870                 875                 880

Ala Thr Gly Thr Gly Cys Ala Ala Thr Ala Thr Cys Cys Thr Ala Ala
                885                 890                 895

Gly Thr Gly Cys Cys Gly Thr Gly Ala Cys Ala Thr Gly Cys Ala Gly
            900                 905                 910
```

-continued

Cys Cys Ala Thr Ala Cys Ala Thr Gly Thr Cys Thr Cys Ala Gly Cys
        915                 920                 925

Ala Gly Ala Ala Cys Ala Cys Ala Gly Gly Ala Cys Cys Thr Cys Thr
        930                 935                 940

Thr Gly Thr Cys Thr Ala Thr Gly Thr Cys Cys Thr Cys Thr Ala Thr
945                 950                 955                 960

Gly Cys Thr Gly Thr Gly Cys Thr Gly Gly Thr Cys Cys Ala Cys Gly
                965                 970                 975

Cys Thr Gly Gly Gly Thr Gly Gly Ala Gly Thr Thr Gly Thr Cys Ala
            980                 985                 990

Cys Ala Ala Cys Gly Gly Ala Cys  Ala Thr Thr Ala Cys  Thr Thr Cys
        995                 1000                1005

Thr Cys  Thr Thr Ala Thr Gly  Thr Cys Ala Ala Ala  Gly Cys Thr
    1010                1015                1020

Cys Ala  Ala Gly Ala Ala Gly  Gly Cys Cys Ala Gly  Thr Gly Gly
    1025                1030                1035

Thr Ala  Thr Ala Ala Ala Ala  Thr Gly Gly Ala Thr  Gly Ala Thr
    1040                1045                1050

Gly Cys  Cys Gly Ala Gly Gly  Thr Cys Ala Cys Thr  Gly Cys Cys
    1055                1060                1065

Thr Cys  Thr Gly Gly Cys Ala  Thr Cys Ala Cys Cys  Thr Cys Thr
    1070                1075                1080

Gly Thr  Cys Cys Thr Gly Ala  Gly Thr Cys Ala Ala  Cys Ala Gly
    1085                1090                1095

Gly Cys  Cys Thr Ala Thr Gly  Thr Cys Cys Thr Cys  Thr Thr Thr
    1100                1105                1110

Thr Ala  Cys Ala Thr Cys Cys  Ala Gly Ala Ala Gly  Ala Gly Thr
    1115                1120                1125

Gly Ala  Ala Thr Gly Gly Gly  Ala Ala Ala Gly Ala  Cys Ala Cys
    1130                1135                1140

Ala Gly  Thr Gly Ala Gly Ala  Gly Thr Gly Thr Gly  Thr Cys Ala
    1145                1150                1155

Ala Gly  Ala Gly Gly Cys Ala  Gly Gly Gly Ala Ala  Cys Cys Ala
    1160                1165                1170

Ala Gly  Ala Gly Cys Cys Cys  Thr Thr Gly Gly Thr  Gly Cys Thr
    1175                1180                1185

Gly Ala  Ala Gly Ala Cys Ala  Cys Ala Gly Ala Cys  Ala Gly Gly
    1190                1195                1200

Cys Cys  Ala Gly Cys Ala Ala  Cys Gly Cys Ala Ala  Gly Gly Ala
    1205                1210                1215

Gly Ala  Gly Cys Thr Cys Ala  Ala Gly Ala Gly Ala  Gly Ala Cys
    1220                1225                1230

Cys Ala  Cys Cys Cys Thr Thr  Gly Cys Cys Thr Cys  Cys Ala Gly
    1235                1240                1245

Gly Thr  Ala Cys Cys Gly Ala  Gly Thr Thr Gly  Gly Ala Cys
    1250                1255                1260

Gly Ala  Gly Cys Ala Cys Thr  Thr Gly Gly Thr Gly  Gly Ala Ala
    1265                1270                1275

Ala Gly  Ala Gly Cys Cys Ala  Cys Thr Cys Ala Gly  Gly Ala Ala
    1280                1285                1290

Ala Gly  Cys Ala Cys Cys Thr  Ala Gly Ala Cys Cys  Ala Cys
    1295                1300                1305

```
Thr Gly Gly Ala Ala Ala Thr Cys Cys Cys Cys Ala Ala
    1310            1315                1320

Ala Ala Gly Cys Ala Ala Ala Cys Ala Ala Ala Cys Gly
    1325            1330                1335

Ala Ala Gly Cys Cys Thr Gly Ala Gly Thr Thr Cys Ala Ala Cys
    1340            1345                1350

Gly Thr Cys Ala Gly Ala Ala Ala Ala Gly Thr Gly Ala Ala
    1355            1360                1365

Gly Gly Thr Ala Cys Cys Thr Gly Cys Cys Thr Cys Cys
    1370            1375                1380

Ala Ala Cys Gly Thr Ala Cys Thr Thr Gly Thr Gly Ala Thr Thr
    1385            1390                1395

Cys Ala Thr Cys Ala Ala Thr Cys Ala Ala Ala Ala Thr Ala Cys
    1400            1405                1410

Ala Ala Gly Thr Gly Thr Gly Gly Thr Ala Thr Gly Ala Ala Ala
    1415            1420                1425

Ala Ala Cys Cys Ala Thr Cys Ala Thr Cys Cys Thr Gly Ala Ala
    1430            1435                1440

Cys Ala Gly Cys Ala Ala Ala Gly Cys Thr Cys Cys Gly Thr Gly
    1445            1450                1455

Cys Thr Ala Ala Ala Cys Cys Thr Cys Thr Cys Thr Thr Cys Gly
    1460            1465                1470

Ala Cys Gly Ala Ala Ala Cys Cys Gly Ala Cys Ala Gly Ala Thr
    1475            1480                1485

Cys Ala Gly Gly Ala Gly Thr Cys Cys Ala Thr Gly Ala Ala Cys
    1490            1495                1500

Ala Cys Thr Gly Gly Cys Ala Cys Ala Cys Thr Cys Gly Cys Thr
    1505            1510                1515

Thr Cys Thr Cys Thr Gly Cys Ala Ala Gly Gly Gly Ala Gly Cys
    1520            1525                1530

Ala Cys Cys Ala Gly Gly Ala Gly Ala Thr Cys Cys Ala Ala Ala
    1535            1540                1545

Gly Gly Gly Ala Ala Thr Ala Ala Cys Ala Ala Ala Cys Ala Cys
    1550            1555                1560

Ala Gly Cys Ala Ala Gly Ala Gly Ala Thr Cys Thr Cys Thr Gly
    1565            1570                1575

Cys Thr Thr Gly Thr Gly Thr Gly Cys Cys Ala Gly Thr Gly Ala
    1580            1585                1590
```

<210> SEQ ID NO 36
<211> LENGTH: 530
<212> TYPE: PRT
<213> ORGANISM: Homo sapiens
<220> FEATURE:
<221> NAME/KEY: MISC_FEATURE
<223> OTHER INFORMATION: human DUB8.8

<400> SEQUENCE: 36

```
Met Glu Asp Asp Ser Leu Tyr Leu Gly Gly Asp Trp Gln Phe Asn His
1               5                   10                  15

Phe Ser Lys Leu Thr Ser Ser Arg Leu Asp Ala Ala Phe Ala Glu Ile
                20                  25                  30

Gln Arg Thr Ser Leu Ser Glu Lys Ser Pro Leu Ser Ser Glu Thr Arg
            35                  40                  45

Phe Asp Leu Cys Asp Asp Leu Ala Pro Val Ala Arg Gln Leu Ala Pro
        50                  55                  60
```

-continued

```
Arg Glu Lys Leu Pro Leu Ser Ser Arg Arg Pro Ala Ala Val Gly Ala
 65                  70                  75                  80

Gly Leu Gln Lys Ile Gly Asn Thr Phe Tyr Val Asn Val Ser Leu Gln
                 85                  90                  95

Cys Leu Thr Tyr Thr Leu Pro Leu Ser Asn Tyr Met Leu Ser Arg Glu
                100                 105                 110

Asp Ser Gln Thr Cys His Leu His Lys Cys Cys Met Phe Cys Thr Met
            115                 120                 125

Gln Ala His Ile Thr Trp Ala Leu Tyr Arg Pro Gly His Val Ile Gln
130                 135                 140

Pro Ser Gln Val Leu Ala Ala Gly Phe His Arg Gly Glu Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Leu Asp His His Ser Lys Asp Thr Thr Leu
                180                 185                 190

Ile His Gln Ile Phe Gly Ala Tyr Trp Arg Ser Gln Ile Lys Tyr Leu
            195                 200                 205

His Cys His Gly Ile Ser Asp Thr Phe Asp Pro Tyr Leu Asp Ile Ala
210                 215                 220

Leu Asp Ile Gln Ala Ala Gln Ser Val Lys Gln Ala Leu Glu Gln Leu
225                 230                 235                 240

Val Lys Pro Lys Glu Leu Asn Gly Glu Asn Ala Tyr His Cys Gly Leu
                245                 250                 255

Cys Leu Gln Lys Ala Pro Ala Ser Lys Thr Leu Thr Leu Pro Thr Ser
            260                 265                 270

Ala Lys Val Leu Ile Leu Val Leu Lys Arg Phe Ser Asp Val Thr Gly
            275                 280                 285

Asn Lys Leu Ala Lys Asn Val Gln Tyr Pro Lys Cys Arg Asp Met Gln
290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Met Asp Asp Ala
            340                 345                 350

Glu Val Thr Ala Ser Gly Ile Thr Ser Val Leu Ser Gln Gln Ala Tyr
            355                 360                 365

Val Leu Phe Tyr Ile Gln Lys Ser Glu Trp Glu Arg His Ser Glu Ser
            370                 375                 380

Val Ser Arg Gly Arg Glu Pro Arg Ala Leu Gly Ala Glu Asp Thr Asp
385                 390                 395                 400

Arg Pro Ala Thr Gln Gly Glu Leu Lys Arg Asp His Pro Cys Leu Gln
                405                 410                 415

Val Pro Glu Leu Asp Glu His Leu Val Glu Arg Ala Thr Gln Glu Ser
                420                 425                 430

Thr Leu Asp His Trp Lys Phe Pro Gln Lys Gln Asn Lys Thr Lys Pro
            435                 440                 445

Glu Phe Asn Val Arg Lys Val Glu Gly Thr Leu Pro Pro Asn Val Leu
            450                 455                 460

Val Ile His Gln Ser Lys Tyr Lys Cys Gly Met Lys Asn His His Pro
465                 470                 475                 480
```

```
Glu Gln Gln Ser Ser Val Leu Asn Leu Ser Ser Thr Lys Pro Thr Asp
            485                 490                 495

Gln Glu Ser Met Asn Thr Gly Thr Leu Ala Ser Leu Gln Gly Ser Thr
            500                 505                 510

Arg Arg Ser Lys Gly Asn Asn Lys His Ser Lys Arg Ser Leu Leu Val
            515                 520                 525

Cys Gln
    530
```

<210> SEQ ID NO 37
<211> LENGTH: 1254
<212> TYPE: DNA
<213> ORGANISM: Homo sapiens
<220> FEATURE:
<221> NAME/KEY: misc_feature
<223> OTHER INFORMATION: human DUB8.11

<400> SEQUENCE: 37

| | |
|---|---|
| atggaggacg actcactcta cttgggaggt gagtggcagt tcaaccactt ttcaaaactc | 60 |
| acatcttctc ggccagatgc agcctttgct gaaatccagc ggacttctct ccctgagaag | 120 |
| tcacaactct caactgagac ccgcgtcgac ttctgcgatg atttggccgc tgtggcaaga | 180 |
| cagctcgctc ccagggagaa gcttcctctg agtagcagga gacctgctgc ggtgggggct | 240 |
| gggctccaga atatgggaaa tacctgctac gtgaacgctt cccagcagtg tctgacatac | 300 |
| ataccgcccc ttgccaacta catgctgtcc cgggagcact ctcaaacatg tcatcgtcac | 360 |
| aagtgctgca tgctctgtac catggaagct cacatcacat ggcccctcca cattcctggc | 420 |
| catgtcatcc agccctcaca ggcattggct gctggcttcc atagaggcaa gcaggaagct | 480 |
| gcccttgaat ttctcatgtt cactgtggat gccatgaaaa aggcatgcct tcccgggcac | 540 |
| aagcagatcc tcatcctcgt atggaagaga ttctccgatg tcacaggcaa caaaattgcc | 600 |
| aagaatgtgc aatatcctga gtgccttgac atgcagccat acatgtctca gcagaacaca | 660 |
| ggacctcttg tctatgtcct ctatgctgtg ctggtccacg ccgggtggag ttgtcacaac | 720 |
| ggacattact tctcttatgt caaagttcaa gaaggccagt ggtataaaat ggatgatgcc | 780 |
| gagaagagtg aatgggaaag acacagtgag agtgtgtcaa gaggcaggga accaagagcc | 840 |
| ctcggcgctg aagacacaga caggcgagca acgcaaggag agctcaagag agactacccc | 900 |
| tgcctccagg tacccgagtt ggacgagcac ttggtggaaa gagccactca ggaaagcacc | 960 |
| ttagaccact ggaaattcct ccaagagcaa acaaaacga agcctgagtt caacgtcaga | 1020 |
| aaacttgaag gtaccctgcc tcccaacgta cttgtgattc atcaatcaaa atacaagtgt | 1080 |
| gggatgaaaa accatcatcc tgaacagcaa agctccctgc taaacctctc ttcgacgaac | 1140 |
| ccgacagatc aggagtccat gaacactggc acactcgctt ctctgcaagg gaggaccagg | 1200 |
| agatccaaag ggaagaacaa acactgcaag agggctctgc ttgtgtgcca gtga | 1254 |

<210> SEQ ID NO 38
<211> LENGTH: 417
<212> TYPE: PRT
<213> ORGANISM: Homo sapiens
<220> FEATURE:
<221> NAME/KEY: MISC_FEATURE
<223> OTHER INFORMATION: human DUB8.11

<400> SEQUENCE: 38

```
Met Glu Asp Asp Ser Leu Tyr Leu Gly Gly Glu Trp Gln Phe Asn His
1               5                   10                  15
```

-continued

```
Phe Ser Lys Leu Thr Ser Ser Arg Pro Asp Ala Ala Phe Ala Glu Ile
             20                  25                  30

Gln Arg Thr Ser Leu Pro Glu Lys Ser Gln Leu Ser Thr Glu Thr Arg
         35                  40                  45

Val Asp Phe Cys Asp Asp Leu Ala Ala Val Ala Arg Gln Leu Ala Pro
 50                  55                  60

Arg Glu Lys Leu Pro Leu Ser Ser Arg Arg Pro Ala Ala Val Gly Ala
 65                  70                  75                  80

Gly Leu Gln Asn Met Gly Asn Thr Cys Tyr Val Asn Ala Ser Gln Gln
             85                  90                  95

Cys Leu Thr Tyr Ile Pro Pro Leu Ala Asn Tyr Met Leu Ser Arg Glu
            100                 105                 110

His Ser Gln Thr Cys His Arg His Lys Cys Cys Met Leu Cys Thr Met
            115                 120                 125

Glu Ala His Ile Thr Trp Pro Leu His Ile Pro Gly His Val Ile Gln
130                 135                 140

Pro Ser Gln Ala Leu Ala Ala Gly Phe His Arg Gly Lys Gln Glu Ala
145                 150                 155                 160

Ala Leu Glu Phe Leu Met Phe Thr Val Asp Ala Met Lys Lys Ala Cys
                165                 170                 175

Leu Pro Gly His Lys Gln Ile Leu Ile Leu Val Trp Lys Arg Phe Ser
            180                 185                 190

Asp Val Thr Gly Asn Lys Ile Ala Lys Asn Val Gln Tyr Pro Glu Cys
            195                 200                 205

Leu Asp Met Gln Pro Tyr Met Ser Gln Gln Asn Thr Gly Pro Leu Val
210                 215                 220

Tyr Val Leu Tyr Ala Val Leu Val His Ala Gly Trp Ser Cys His Asn
225                 230                 235                 240

Gly His Tyr Phe Ser Tyr Val Lys Val Gln Glu Gly Gln Trp Tyr Lys
                245                 250                 255

Met Asp Asp Ala Glu Lys Ser Glu Trp Glu Arg His Ser Glu Ser Val
            260                 265                 270

Ser Arg Gly Arg Glu Pro Arg Ala Leu Gly Ala Glu Asp Thr Asp Arg
            275                 280                 285

Arg Ala Thr Gln Gly Glu Leu Lys Arg Asp Tyr Pro Cys Leu Gln Val
290                 295                 300

Pro Glu Leu Asp Glu His Leu Val Glu Arg Ala Thr Gln Glu Ser Thr
305                 310                 315                 320

Leu Asp His Trp Lys Phe Leu Gln Glu Gln Asn Lys Thr Lys Pro Glu
                325                 330                 335

Phe Asn Val Arg Lys Leu Glu Gly Thr Leu Pro Pro Asn Val Leu Val
            340                 345                 350

Ile His Gln Ser Lys Tyr Lys Cys Gly Met Lys Asn His His Pro Glu
            355                 360                 365

Gln Gln Ser Ser Leu Leu Asn Leu Ser Ser Thr Asn Pro Thr Asp Gln
370                 375                 380

Glu Ser Met Asn Thr Gly Thr Leu Ala Ser Leu Gln Gly Arg Thr Arg
385                 390                 395                 400

Arg Ser Lys Gly Lys Asn Lys His Cys Lys Arg Ala Leu Leu Val Cys
                405                 410                 415

Gln

<210> SEQ ID NO 39
```

<211> LENGTH: 1594
<212> TYPE: DNA
<213> ORGANISM: Homo sapiens
<220> FEATURE:
<221> NAME/KEY: misc_feature
<223> OTHER INFORMATION: human DUB4.4

<400> SEQUENCE: 39

```
atggaggagg actcactcta cttgggtggt gagtggcagt tcaaccactt ttcaaaactc      60
acatcttctc ggctcgatgc agcttttgct gaaatccagc ggacttctct ccctgagaag     120
tcaccactct catgtgagac ccgtgtcgac ctctgtgatg atttggttcc tgaggcaaga     180
cagcttgctc ccagggagaa gcttcctctg agtagcagga gacctgctgc ggtgggggct     240
gggctccaga atatgggaaa tacctgctac gtgaacgctt ccttgcagtg cctgacatac     300
acaccgcccc ttgccaacta catgctgtcc cgggagcact ctcaaacgtg tcatcgtcac     360
aagggctgca tgtctctgtac tatgcaagct cacatcacac gggccctcca caatcctggc     420
cacgtcatcc agccctcaca ggcattggct gctggcttcc atagaggcaa gcaggaagat     480
gcccatgaat ttctcatgtt cactgtggat gccatgaaaa aggcatgcct tcccgggcac     540
aagcaggtag atcatccctc taaggacacc accctcatcc accaaatatt tggaggctac     600
tggagatctc aaatcaagtg tctccactgc cacggcattt cagacacttt tgacccttac     660
ctggacatcg ccctggatat ccaggcagct cagagtgtcc agcaagcttt ggaacagttg     720
gtgaagcccg aagaactcaa tggagagaat gcctatcatt gtggtgtttg tctccagagg     780
gcgccggcct ccaagacgtt aactttacac acttctgcca aggtcctcat ccttgtattg     840
aagagattct ccgatgtcac aggcaacaag attgccaaga atgtgcaata tcctgagtgc     900
cttgacatgc agccatacat gtctcagcag aacacaggac tcttgtcta tgtcctctat     960
gctgtgctgg tccatgctgg gtggagttgt cacaacggac attacttctc ttatgtcaaa    1020
gctcaagaag gccagtggta taaaatggat gatgccgagg tcaccgcctc ttagcatcac    1080
atctgtcctg agtcaacagg cctacgtcct ctttacatc cagaagagtg aatgggaaag    1140
acacagtgag agtgtgtcaa gaggcaggga ccaagagccc ttggcgcag aagcacaga    1200
caggcgagta acgcaaggag agctcaagag agaccacccc tgactccagg ccccgagtt     1260
ggacgagcac ttggtggaaa gagccactca ggaaagcacc ttagaccact ggaaattcct    1320
tcaagagcaa acaaaacga agcctgagtt caacgtcaga aaagtcgaag gtaccctgcc    1380
tcccgacgta cttgtgattc atcaatcaaa atacaagtgt gggatgaaga accatcatcc    1440
tgaacagcaa agctccctgc taaacctctc ttcgacgacc ccgacacatc agcagtccat    1500
gaacaatggc acactcgctt ccctgcgagg gagggccagg agatccaaag ggaagaacaa    1560
acacagcaag agggctctgc ttgtgtgcca gtga                                1594
```

<210> SEQ ID NO 40
<211> LENGTH: 357
<212> TYPE: PRT
<213> ORGANISM: Homo sapiens
<220> FEATURE:
<221> NAME/KEY: MISC_FEATURE
<223> OTHER INFORMATION: human DUB4.4

<400> SEQUENCE: 40

```
Met Glu Glu Asp Ser Leu Tyr Leu Gly Gly Glu Trp Gln Phe Asn His
1               5                   10                  15
Phe Ser Lys Leu Thr Ser Ser Arg Leu Asp Ala Ala Phe Ala Glu Ile
            20                  25                  30
```

Gln Arg Thr Ser Leu Pro Glu Lys Ser Pro Leu Ser Cys Glu Thr Arg
            35                  40                  45

Val Asp Leu Cys Asp Asp Leu Val Pro Glu Ala Arg Gln Leu Ala Pro
 50                  55                  60

Arg Glu Lys Leu Pro Leu Ser Ser Arg Arg Pro Ala Ala Val Gly Ala
 65                  70                  75                  80

Gly Leu Gln Asn Met Gly Asn Thr Cys Tyr Val Asn Ala Ser Leu Gln
                 85                  90                  95

Cys Leu Thr Tyr Thr Pro Pro Leu Ala Asn Tyr Met Leu Ser Arg Glu
             100                 105                 110

His Ser Gln Thr Cys His Arg His Lys Gly Cys Met Leu Cys Thr Met
         115                 120                 125

Gln Ala His Ile Thr Arg Ala Leu His Asn Pro Gly His Val Ile Gln
    130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His Pro Ser Lys Asp Thr Thr Leu
            180                 185                 190

Ile His Gln Ile Phe Gly Gly Tyr Trp Arg Ser Gln Ile Lys Cys Leu
        195                 200                 205

His Cys His Gly Ile Ser Asp Thr Phe Asp Pro Tyr Leu Asp Ile Ala
    210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Cys Gly Val
                245                 250                 255

Cys Leu Gln Arg Ala Pro Ala Ser Lys Thr Leu Thr Leu His Thr Ser
            260                 265                 270

Ala Lys Val Leu Ile Leu Val Leu Lys Arg Phe Ser Asp Val Thr Gly
        275                 280                 285

Asn Lys Ile Ala Lys Asn Val Gln Tyr Pro Glu Cys Leu Asp Met Gln
    290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Met Asp Asp Ala
            340                 345                 350

Glu Val Thr Ala Ser
        355

<210> SEQ ID NO 41
<211> LENGTH: 1197
<212> TYPE: DNA
<213> ORGANISM: Homo sapiens
<220> FEATURE:
<221> NAME/KEY: misc_feature
<223> OTHER INFORMATION: human DUB4.9

<400> SEQUENCE: 41
atggaggacg actcactcta cttgggaggt gagtggcagt tcaaccactt ttcaaaactc    60
acatctcctc ggcccgatgc agcttttgct gaaatccagc ggacttctct ccctgagaag   120

```
tcaccactct catgtgagac ccgtgtcgac ctctgtgatt atttggctcc tgtggcaaga      180
cagcttgctc ccagggagaa gcttcctctg agtagcagga gacctgctgc ggtgggggct      240
gggctccaga atatgggaaa tacctgctac gtgaacgctt ccttgcagtg cctgacatac      300
acaccgcccc ttgccaacta catgctgtcc cgggagcact ctcaaacgtg tcatcgtcac      360
aagggctgca tgctctgtac tatgcaagct cacatcacac gggccctcca caatcctggc      420
cacgtcatcc agccctcaca ggcattggct gctggcttcc atagaggcaa gcaggaagat      480
gcccatgaat ttctcatgtt cactgtggat gccatgaaaa aggcatgcct tcccgggcac      540
aagcaggtgg atcatcactc taaggacacc accctcatcc accaaatatt tggaggctac      600
tggagatctc aaatcaagtg tctccactgc acggcattt cagacacttt tgacccttac       660
ctggacatcg ccctggatat ccaggcagct cagagtgtcc agcaagcttt ggaacagttg      720
gtgaagcccg aagaactcaa tggagagaat gcctatcatt gtggtgtttg tctccagagg      780
gcgccggcct ccaagacgtt aactttacac acctctgcca aggtcctcat ccttgtattg      840
aagagattct ccgatgtcac aggcaacaag attgccaaga atgtgcaata tcctgagtgc      900
cttgacatgc agccatacat gtctcagcag aacacaggac tcttgtctca tgtcctctat      960
gctgtgctgg tccacgctgg gtggagttgt cacaacggac attacttctc ttatgtcaaa     1020
gctcaagaag gccagtggta taaaattgat gatgccgagg tcaccgcctc tagcatcact     1080
tctgtcctga ctcaacaggc ctacgtcctc ttttacatcc agaagagtga atgggaaaga     1140
cacagtgaga gtgtgtcaag aggcagggaa ccaagagccc ttggctctga agactaa       1197
```

<210> SEQ ID NO 42
<211> LENGTH: 398
<212> TYPE: PRT
<213> ORGANISM: Homo sapiens
<220> FEATURE:
<221> NAME/KEY: MISC_FEATURE
<223> OTHER INFORMATION: human DUB4.9

<400> SEQUENCE: 42

```
Met Glu Asp Asp Ser Leu Tyr Leu Gly Gly Glu Trp Gln Phe Asn His
  1               5                  10                  15

Phe Ser Lys Leu Thr Ser Pro Arg Pro Asp Ala Ala Phe Ala Glu Ile
                 20                  25                  30

Gln Arg Thr Ser Leu Pro Glu Lys Ser Pro Leu Ser Cys Glu Thr Arg
             35                  40                  45

Val Asp Leu Cys Asp Tyr Leu Ala Pro Val Ala Arg Gln Leu Ala Pro
         50                  55                  60

Arg Glu Lys Leu Pro Leu Ser Ser Arg Arg Pro Ala Ala Val Gly Ala
 65                  70                  75                  80

Gly Leu Gln Asn Met Gly Asn Thr Cys Tyr Val Asn Ala Ser Leu Gln
                 85                  90                  95

Cys Leu Thr Tyr Thr Pro Pro Leu Ala Asn Tyr Met Leu Ser Arg Glu
                100                 105                 110

His Ser Gln Thr Cys His Arg His Lys Gly Cys Met Leu Cys Thr Met
            115                 120                 125

Gln Ala His Ile Thr Arg Ala Leu His Asn Pro Gly His Val Ile Gln
        130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175
```

```
Leu Pro Gly His Lys Gln Val Asp His His Ser Lys Asp Thr Thr Leu
            180                 185                 190

Ile His Gln Ile Phe Gly Gly Tyr Trp Arg Ser Gln Ile Lys Cys Leu
            195                 200                 205

His Cys His Gly Ile Ser Asp Thr Phe Asp Pro Tyr Leu Asp Ile Ala
            210                 215                 220

Leu Asp Ile Gln Ala Ala Gln Ser Val Gln Gln Ala Leu Glu Gln Leu
225                 230                 235                 240

Val Lys Pro Glu Glu Leu Asn Gly Glu Asn Ala Tyr His Cys Gly Val
                245                 250                 255

Cys Leu Gln Arg Ala Pro Ala Ser Lys Thr Leu Thr Leu His Thr Ser
            260                 265                 270

Ala Lys Val Leu Ile Leu Val Leu Lys Arg Phe Ser Asp Val Thr Gly
            275                 280                 285

Asn Lys Ile Ala Lys Asn Val Gln Tyr Pro Glu Cys Leu Asp Met Gln
290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Ile Asp Asp Ala
            340                 345                 350

Glu Val Thr Ala Ser Ser Ile Thr Ser Val Leu Thr Gln Gln Ala Tyr
            355                 360                 365

Val Leu Phe Tyr Ile Gln Lys Ser Glu Trp Glu Arg His Ser Glu Ser
            370                 375                 380

Val Ser Arg Gly Arg Glu Pro Arg Ala Leu Gly Ser Glu Asp
385                 390                 395

<210> SEQ ID NO 43
<211> LENGTH: 1706
<212> TYPE: DNA
<213> ORGANISM: Homo sapiens
<220> FEATURE:
<221> NAME/KEY: misc_feature
<223> OTHER INFORMATION: human 8.2

<400> SEQUENCE: 43
atgcggccag agagcccgtc atttgaagac tcggaagaga tagcgtctt  ctgcaacctg      60 cggtcccagc cgaaaaacct tgtgatcctt gttccgggcg acatgaggga cgactcactc     120
tacttgggag gtgagtggca gttcaaccac ttttcaaaac tcacatcttc tcggccagat     180
gcagcttttg ctgaaatcca gcggacttct ctctctgaga agtcatcact ctcatctgag     240
acccgcgtcg acctctgtga tgatttggct cctgtggcaa gacagctcgc tcccagggag     300
aagcttcctc tgagtagcag gagacctgct gcggtggggg ctgggctcca gaatatggga     360
aatacctgct acgtgaacgc ttccctgcag tgcctgacat acacaccgcc ccttgccaac     420
tacatgctgt cccgggagca ctctcaaacg tgtcatcgtc acaagtgctg catgctctgt     480
actatgcaag ctcacatcac atggcccctc acagtcctg  gcatgtcat  ccagccctca     540 caggtgttgg ctgctggctt ccatagaggc gagcaggaag atgccatga  atttctcatg     600 ttcactgtgg atgccatgaa aaaggcattc cttcccgggc acaagcattt agataatcac     660
tctaaggaca ccaccctcat ccaccaaata tttggagggt actggagatc tcacatcaac     720
tgtttccact gccacgggat ttcagacacc tttgacccctt acctggacat cgccctggat     780
```

```
atccaggcag ctcagagtgt caagcaagct ttgtaacagt tggtgaagcc cgaagaactc    840
aatggataaa atgcctatca ttgtggtctt tgtctccaga aggcgcctgc ctccaggacg    900
ttaactttac acacttctgc caaggtcctc atccttgtat tgaagagatt ctctgaggtc    960
acaggcaaca aacttgccaa gaatgtgcaa tatcctgagt gccttgacat gcagccatac   1020
atgtctcagc agaacacagg acctcttgtc tatgtcctct atgctgtgct ggtccacgct   1080
gggtggagtt gtcacaacgg acattactta tcttatgtca aactcaagaa ggccattggt   1140
ataaaatgga tgatgccgag gtcactgcct ccggtatcac ttctgtcctg agtcaacagg   1200
cctatgtcct ctttacatc cagaagaatg aatttggaag acccagttac agtgtgtcca    1260
taggcaggga accaagagct ctttgcgtga aggcaagtga attgtgtgtg aaataaaatg   1320
tcatgaataa atcttgcagt ggagtattta tttgtctcac tttgtaatca gtgaatgagc   1380
tttaaccaat atcaatgcct agtgcctacc ccccagagat aagaacttcc actctcttat   1440
gtgtaaccat ggcctctgga ttgcttatga ctctgaagat aattctcctt ccccccaacg   1500
tttcagaatc acttcaggtg gtggtaacag ataacacatc agtccctttc tctctctttt   1560
ctcttcactc aggaaaactc tcactgagac aaaggaaaat cctatggttt actggggagg   1620
aagaattccc tcaggagtga aattggtggc tccttcctcc ctgtcaagtc tcttcctcag   1680
gattgcccct ttgtctcttc aggact                                         1706
```

<210> SEQ ID NO 44
<211> LENGTH: 271
<212> TYPE: PRT
<213> ORGANISM: Homo sapiens
<220> FEATURE:
<221> NAME/KEY: MISC_FEATURE
<223> OTHER INFORMATION: human DUB8.2

<400> SEQUENCE: 44

```
Met Arg Pro Glu Ser Pro Ser Phe Glu Asp Ser Glu Glu Ile Ala Ser
1               5                   10                  15

Phe Cys Asn Leu Arg Ser Gln Pro Lys Asn Leu Val Ile Leu Val Pro
            20                  25                  30

Gly Asp Met Glu Asp Asp Ser Leu Tyr Leu Gly Gly Glu Trp Gln Phe
        35                  40                  45

Asn His Phe Ser Lys Leu Thr Ser Ser Arg Pro Asp Ala Ala Phe Ala
    50                  55                  60

Glu Ile Gln Arg Thr Ser Leu Ser Glu Lys Ser Ser Leu Ser Ser Glu
65                  70                  75                  80

Thr Arg Val Asp Leu Cys Asp Asp Leu Ala Pro Val Ala Arg Gln Leu
                85                  90                  95

Ala Pro Arg Glu Lys Leu Pro Leu Ser Ser Arg Arg Pro Ala Ala Val
            100                 105                 110

Gly Ala Gly Leu Gln Asn Met Gly Asn Thr Cys Tyr Val Asn Ala Ser
        115                 120                 125

Leu Gln Cys Leu Thr Tyr Thr Pro Pro Leu Ala Asn Tyr Met Leu Ser
    130                 135                 140

Arg Glu His Ser Gln Thr Cys His Arg His Lys Cys Cys Met Leu Cys
145                 150                 155                 160

Thr Met Gln Ala His Ile Thr Trp Pro Leu His Ser Pro Gly His Val
                165                 170                 175

Ile Gln Pro Ser Gln Val Leu Ala Ala Gly Phe His Arg Gly Glu Gln
            180                 185                 190
```

```
Glu Asp Ala His Glu Phe Leu Met Phe Thr Val Asp Ala Met Lys Lys
            195                 200                 205

Ala Phe Leu Pro Gly His Lys His Leu Asp Asn His Ser Lys Asp Thr
        210                 215                 220

Thr Leu Ile His Gln Ile Phe Gly Gly Tyr Trp Arg Ser His Ile Asn
225                 230                 235                 240

Cys Phe His Cys His Gly Ile Ser Asp Thr Phe Asp Pro Tyr Leu Asp
            245                 250                 255

Ile Ala Leu Asp Ile Gln Ala Ala Gln Ser Val Lys Gln Ala Leu
            260                 265                 270
```

<210> SEQ ID NO 45
<211> LENGTH: 1463
<212> TYPE: DNA
<213> ORGANISM: Homo sapiens
<220> FEATURE:
<221> NAME/KEY: misc_feature
<223> OTHER INFORMATION: human DUB8.9

<400> SEQUENCE: 45

| | | | | | |
|---|---|---|---|---|---|
| atggaggaag | actcactcta | cttgggaggt | gagtggcagt | tcaaccactt | ttcaaaactc | 60 |
| acatcttctc | agccagatgc | agcttttcct | gaaatccagc | ggacttctct | ccctgagaag | 120 |
| tcaccactct | catcggagac | ccgtgtcgac | ctctgtgacg | atttggctcc | tgtgacaaga | 180 |
| cagcttgctc | ccagggagaa | gcttcctccg | agtagcagga | gacctgctgc | ggtgggagct | 240 |
| ggtctccaga | atatgggaaa | tacctgccac | ttgaatgctt | ccctgcagtg | cctgacatac | 300 |
| acaccgcccc | ttgccaacta | catgctgtcc | tgggagctct | ctcaaatgtg | tcatcgtccc | 360 |
| aagtgctgca | tgctctgtat | tatggaagct | cacagcacac | gggcacctcc | accgtcctgg | 420 |
| ccatgtcatc | cagccctcac | aggcattggc | tgctgacttc | catagagaca | agcaggaaga | 480 |
| tgcccatgaa | tttctcatat | tcactgtgga | tgccattaga | aaggcatgcc | ttcccgggca | 540 |
| caagcagcta | gatcatcact | gcaaggacac | catcctcatc | caccaaatat | tggagggta | 600 |
| ctagagatct | caaatcaagt | gtctctactt | ccacggcatt | tcagacacct | tcgaccctta | 660 |
| cctggatatc | gccctggata | tccaggcagc | tcagagtgtc | aagcaagctt | ggaacagtt | 720 |
| ggtgaagccc | gaagaactca | atggagagaa | tgcctatcat | tgtggtcttt | gtctccagaa | 780 |
| ggcgcctgcc | gccaagacgt | taactttacc | cacttctgcc | aaggtcctca | tccttgtctt | 840 |
| gaagagattc | tccgatgtca | caggcaacaa | acttgccaag | aatctgcaat | atcctgagtg | 900 |
| cgttgacatg | cagccataca | tgtctcagca | gaacacagga | cctcttttct | atgtcctcta | 960 |
| tgctgttctc | gtcatcaccg | ggtggagttg | tcacaacgga | cattacttct | cttgtgtcaa | 1020 |
| actcaagaag | gccagtggta | taaaatggat | gatgccgagg | tcactgcctc | tggtatcact | 1080 |
| tctccttaga | gtcaacaggc | ctatgtcctc | ttttacatcc | agaagaatga | atttggaaga | 1140 |
| cccagttaca | gggtgtccgc | aggcagagaa | ccaagagctc | tttgtgctga | agacaattga | 1200 |
| attgtggtga | ataatatatgt | catgaataaa | tcttgcagca | gatttatttg | tctcactttg | 1260 |
| taatcagtga | atgagcttta | acgaatatca | atgcctagtg | cctaccccc | agagataaga | 1320 |
| acttccagtt | tctcatgtgt | aatcatggca | tctggattgc | tcatgattct | gaagataatt | 1380 |
| ctcctgtccc | ccaaagtttc | agaatcactt | caggtggtag | aaacagataa | cacatcagtc | 1440 |
| cctttctctc | tcttttctct | tca | | | | 1463 |

<210> SEQ ID NO 46

<211> LENGTH: 248
<212> TYPE: PRT
<213> ORGANISM: Homo sapiens
<220> FEATURE:
<221> NAME/KEY: MISC_FEATURE
<223> OTHER INFORMATION: human DUB8.9

<400> SEQUENCE: 46

```
Met Glu Asp Asp Ser Leu Tyr Leu Gly Gly Glu Trp Gln Phe Asn His
1               5                   10                  15
Phe Ser Lys Leu Thr Ser Ser Arg Pro Asp Ala Ala Phe Ala Glu Ile
            20                  25                  30
Gln Arg Thr Ser Leu Ser Glu Lys Ser Ser Leu Ser Ser Glu Thr Arg
        35                  40                  45
Val Asp Leu Cys Asp Asp Leu Ala Pro Val Ala Arg Gln Leu Ala Pro
    50                  55                  60
Arg Glu Lys Leu Pro Leu Ser Ser Arg Arg Pro Ala Ala Val Gly Ala
65                  70                  75                  80
Gly Leu Gln Asn Met Gly Asn Thr Cys Tyr Val Asn Ala Ser Leu Gln
                85                  90                  95
Cys Leu Thr Tyr Thr Pro Pro Leu Ala Asn Tyr Met Leu Ser Arg Glu
            100                 105                 110
His Ser Gln Thr Cys His Arg His Lys Cys Cys Met Leu Cys Thr Met
        115                 120                 125
Gln Ala His Ile Thr Trp Pro Leu His Ser Pro Gly His Val Ile Gln
    130                 135                 140
Pro Ser Gln Val Leu Ala Ala Gly Phe His Arg Gly Glu Gln Glu Asp
145                 150                 155                 160
Ala His Glu Phe Leu Met Phe Thr Val Asp Ala Met Lys Lys Ala Phe
                165                 170                 175
Leu Pro Gly His Lys His Leu Asp Asn His Ser Lys Asp Thr Thr Leu
            180                 185                 190
Ile His Gln Ile Phe Gly Gly Tyr Trp Arg Ser His Ile Asn Cys Phe
        195                 200                 205
His Cys His Gly Ile Ser Asp Thr Phe Asp Pro Tyr Leu Asp Ile Ala
    210                 215                 220
Leu Asp Ile Gln Ala Ala Gln Ser Val Lys Gln Ala Leu Glu Gln Leu
225                 230                 235                 240
Val Lys Pro Glu Glu Leu Asn Gly
                245
```

SEQ ID NO 47
LENGTH: 1661
TYPE: DNA
ORGANISM: Homo sapiens
FEATURE:
NAME/KEY: misc_feature
OTHER INFORMATION: human DUB 8.10

SEQUENCE: 47

```
atggaggacg actcactcta cttgggaggt gagtggcagt tcaaccactt ttcaaaactc      60
acatcttctc ggccagatgc agcttttgct gaaatccagc ggacttctct ctctgagaag     120
tcatcactct catctgagac ccgcgtcgac ctctgtgatg atttggctcc tgtggcaaga     180
cagctcgctc ccagggagaa gcttcctctg agtagcagga gacctgctgc ggtgggggct     240
gggctccaga atatgggaaa tacctgctac gtgaacgctt ccctgcagtg cctgacatac     300
acaccgcccc ttgccaacta catgctgtcc cgggagcact ctcaaacgtg tcatcgtcac     360
aagtgctgca tgctctgtac tatgcaagct cacatcacat ggcccctcca cagtcctggc     420
catgtcatcc agccttcaca ggtgttggct gctggcttcc atagaggcga gcaggaagat     480
gcccatgaat ttctcatgtt cactgtggat gccatgaaaa agcattcct tcccgggcac     540 aagcatttag ataatcactc taaggacacc accctcatcc accaaatatt tggagggtac     600
tggagatctc acatcaactg tttccactgc atgggatttt cagacacctt tgacccttac     660
ctggacatcg ccctggatat ccaggcagct cagagtgtca agcaagcttt ggaacagttg     720
gtgaagcccg aagaactcaa tggataaaat gcctatcatt gtggtctttg tctccagaag     780
```

```
gcgcctacct ccaggacgtt aactttacac acttctgcca aggtcctcat ccttgtattg    840
aagagattct ctgatgtcac aggcaacaaa cttgccaaga atgtgcaata tcctgagtgc    900
cttgacatgc agccatacat gtctcagcag aacacaggac ctcttgtcta tgtcctctat    960
gctgtgctgg tccacgctgg gtggagttgt cacaacggac attacttatc ttatgtcaaa   1020
ctcaagaagg ccattggtat aaaatggatg atgccgaggt cactgcctcc ggtatcactt   1080
ctgtcctgag tcaacaggcc tatgtcctct tttacatcca gaagaatgaa tttggaagac   1140
ccagttacag tgtgtccata ggcagggaac cgagagctct ttgcgtgaag caagtgaat   1200 tgtgtgtgaa ataaaatgtc atgaataaat cttgcagtgg agtatttatt tgtctcactt   1260
tgtaatcagt gaatgagctt taaccaatat caatgcctag tgcctacccc ccagagataa   1320
gaacttccac tctcttatgt gtaaccatgg cctctggatt gcttatgact ctgaagataa   1380
ttctcctttc ccccaacgtt tcagaatcac ttcaggtggt ggtaacagat aacacatcag   1440
tccctttctc tctcttttct cttcactcag gaaaactctc actgagacaa aggaaaatcc   1500
tatggtttac tggggaggaa gaattccctc aggagtgaaa ttggtggctc cttcctccct   1560
gtcaagtctc ttcctcagga ttgcccctttt gtctcttcag gactctgctc atcaggcccg   1620
agatgccccc tggttgtgca tacctggcct gtgaagaaat a                       1661
```

<210> SEQ ID NO 48
<211> LENGTH: 151
<212> TYPE: PRT
<213> ORGANISM: Homo sapiens
<220> FEATURE:
<221> NAME/KEY: MISC_FEATURE
<223> OTHER INFORMATION: human DUB8.10

<400> SEQUENCE: 48

```
Met Glu Glu Asp Ser Leu Tyr Leu Gly Gly Glu Trp Gln Phe Asn His
1               5                   10                  15

Phe Ser Lys Leu Thr Ser Ser Gln Pro Asp Ala Ala Phe Pro Glu Ile
            20                  25                  30

Gln Arg Thr Ser Leu Pro Glu Lys Ser Pro Leu Ser Ser Glu Thr Arg
        35                  40                  45

Val Asp Leu Cys Asp Asp Leu Ala Pro Val Thr Arg Gln Leu Ala Pro
    50                  55                  60

Arg Glu Lys Leu Pro Pro Ser Ser Arg Arg Pro Ala Ala Val Gly Ala
65                  70                  75                  80

Gly Leu Gln Asn Met Gly Asn Thr Cys His Leu Asn Ala Ser Leu Gln
                85                  90                  95

Cys Leu Thr Tyr Thr Pro Pro Leu Ala Asn Tyr Met Leu Ser Trp Glu
            100                 105                 110

Leu Ser Gln Met Cys His Arg Pro Lys Cys Cys Met Leu Cys Ile Met
        115                 120                 125

Glu Ala His Ser Thr Arg Ala Pro Pro Ser Trp Pro Cys His Pro
    130                 135                 140

Ala Leu Thr Gly Ile Gly Cys
145                 150
```

<210> SEQ ID NO 49
<211> LENGTH: 2001
<212> TYPE: DNA
<213> ORGANISM: Homo sapiens
<220> FEATURE:
<221> NAME/KEY: misc_feature
<223> OTHER INFORMATION: promoter sequence for human DUB4.6

```
<400> SEQUENCE: 49
gcatgactgg cagacagctt atcgattggg ctcccctcaa aatcggttat gagcattcaa      60
gcacaccgat gcccaggtcc cggctgcagg aataagaccc tccagggtct tgtgtgaagc     120
ctcggcatct gcattgctca tgcttctggg gatcattctc ctgaaaatgg tggctccttt     180
ctccctgtgg agcatctttc taagcagtgc tcttttcttc ccccaggaca ctttacatcc     240
ggcacaggaa gccttctgat ggagcacacc tggcccatga aaagacaagg gaaagaaacg     300
gggccaaagg tcacagtcct ctcatcccat catcctcctt aaaatcatcc taatttcatg     360
ggccctgaag ccagggctgt ttcttttacac ctagaggcct tggcgccggg cctcaattcc     420
gccctgttcc ttaccgtcta agacatgttg gaaaatccc tagagccagg atcttcattc      480
ctgctaagcc agacagccgg aagacacacc caaattctgt ccctcttact tcagggaaca    540
tgtccacttt cggcagcatt acaattttgg caccaaatgt gctaactgca attccaccat    600
acaatgcgta actggaaatg gaggcaacat ctccgatcct gaacgatcga tgcgagaatc    660
caggatatgc acggcttatt ttggcctttt cccactgaaa caaggccag tattaaaaat     720
ggcacgctat cctctgtttc actccctgct tttaaacgtc tccgatgttt ctccctgaga    780
cagggcctca cttccgtcag ccgggctttt ccacggtata attttccttg tttgcttttg    840
tccaaattag aactttttat ttcacctcta ggaaacgttg atccattatc acatcgtat     900
ggaaatatta tcacacatgc tgtgagatac gttgttttta ttttcatcaa ttctttaata    960
aacaaacggt tatagctggg ataccttctg agttctcaag tttttttgttt cgtgtttct   1020
taaactgccg tcgcacgtcc gaaaccgctc actatgcagt gtcatgaccg tctctctttt   1080
ctggcaaaca taaatttggg gattgtcatc aattagtctc tcggggattg catgatttcc   1140
ccaaaggctt tcacagtcta ctttgtgcac tgagtatctc ttcaaacttc agtgcatgtt   1200
tctaccattt catgctttct tatttggcaa tctagcttcc acaagagcat ttcatgcaaa   1260
gacttgtctt gttctccact ggcaggtaat ttcactcaga tagagaatca ataggctcaa   1320
cgtggaaagg ttatcgctgg aaggtctgtt tgattccacg gatctctcct ttctcattag   1380
ggaagaaaat acgctgtgct aaatactata cttcattgac tattctcagg tcagaaagcg   1440
cactttcgac ttcttgtctt tccgtcgctg agaggatgat ggcagctgcc aaaagtacat   1500
acttggaagt tcatcgcaga aaaacacac acacacacgc gccccccccca cacacacaca   1560
cacgaacaca atcacacaca cacacactca cacggtttcc tacgtaaaga tttcttccct   1620
gccattgctt tacctaaaat aaggcaactg tgtggccact gtcccaaccc ggttacactc   1680
ctattatatg tgcctatcat cctgaggagt aatttgattc aggtgttctg gaagtcatgc   1740
tgtgggctgt gtctgttgaa ttcccagcga tgcaagggga cacacctgt gactccttcc    1800
tgaattgagt gctgatattt gattggctta tcgcgcacct gatgagtggg tgtggtgttc   1860
gcggttggag ggggtgactt acagaagggc tgatgcggcc agagagctcg tcatttgaag   1920
actctctcgg aagggatagc gtctttctgc aacctgcggt cccagcagaa aaaccttgtg   1980
atccttgttc cagtcgacat g                                              2001

<210> SEQ ID NO 50
<211> LENGTH: 1901
<212> TYPE: DNA
<213> ORGANISM: Homo sapiens
<220> FEATURE:
<221> NAME/KEY: misc_feature
<223> OTHER INFORMATION: promoter sequence for human DUB4.7
```

<400> SEQUENCE: 50

```
tcctcagcgt cggtttttag gcctggcata agctgtttga acccaggaa cgtaccccac      60
ccatcatctt tggcctagtt aacacctccc ctccgtgtgt ggtggtttgg agaacctgct     120
ttttcctcat cccactgatc ccaaacccag dacaccctac agctgctgac caggattaaa     180
cctaatggag atttaatgcc attaaatcag aagaaattct gattctcagg gactgacatt     240
cattcactta catacttgca gagtcggcca ggtgtgttgg ctcacacctg taatcccagc     300
actttgggaa gccgaggtgg gtggatcacg aggtcaagaa ttcgagacca tcctggccaa     360
catggtgaaa ccccgtctct actaaaaata caaaaattaa ctggtgtagc tgtgcgtgcc     420
tgtaatccca gctactcagg aggctgaggc aggcgatttg cttgaacctg ggaggtggag     480
gttgcagtga gccaagatta tgccattgca ctccagcctg gcaacagag cgagactctc      540
agaaaacaaa aacccaaaa acttgcagag tgaatttagg aaaccatgaa gtacacagtt      600
tgatccaatg ccttccttt tctctttctc aaatattttg agccaggtac tatcctagac      660
tgtcttgtga tatttacaat ctaggagaag gcaggagaga gaactaagaa cagagagcat     720
gttctgagat gtctgctgtg tttgcaggta ccttccctca atttccctac tcactggcca     780
tgctggaaag caggtcttgg cgctatattt ataccatggt acttcccctc cctatactca     840
attggttggc cagaagccca attgtcactc tctctctctg tctccctctc gctccctccc     900
tccctccctc cctccctccc tctccaagat atccagtaac tgactgatca gctggggtg      960
ggctctgctg gctgccaaga tgggccacca gcaaaaaggg aaaattggtt gtgagtgaga    1020
agaagagata agaaattcca cagggctgat aagaaagacc atgggcttcc aggcgcggtg    1080
tttcacgcct gtaatcccag cacttgggag gccaggatgg tcggatttgg caatctagct    1140
tccacaagag catttcacgc aaagacttgt cttgttctcc actggcaggt aatttcactc    1200
ggatagagaa tcaataggct caacgtggaa aggttatcgc tggaaggtct gtttaattcc    1260
acggatctct cctttctcat tagggaagaa aatacgctgt gctaaatact atacttcatt    1320
gactattctc aggtcagaaa gcgcactttt gacttcttgt ccttccgtcg ctgagaggat    1380
gatggcagct gccaaaagta catacttgga agttcatccc agcacaaaca cacacacaca    1440
cacgccccc cacacacaca cacacaaaca cactcacaca cacacgca cacggtttcc       1500
taggtaaaga tttcttccct gccattgctt tacctaaaat aaggcaactg tgaggccact    1560
gtcccaaccc ggttacgctc ctattatatg tgcctatcat cctgaggagt aatttgattc    1620
aggtgttctg gaagtcatgt tgtgggctgt gtctgttgaa ttcccagcga tgccagggga    1680
cacaccctgt gactccttcc tgaattgagt gctgatattt gattggctta tcgcgcacct    1740
gatgagtggg tgggtgttc gcggttggtg gggtgactt acagaagggc tgatgcggcc     1800
agagagctcg tcatttgaag actctctcgg aagggatagc gtccttctgc aacctgcggt    1860
cccagcagac aaaccttgtg atccttgttc cagtcgacat g                        1901
```

<210> SEQ ID NO 51
<211> LENGTH: 2001
<212> TYPE: DNA
<213> ORGANISM: Homo sapiens
<220> FEATURE:
<221> NAME/KEY: misc_feature
<223> OTHER INFORMATION: promoter sequence for human DUB4.8

<400> SEQUENCE: 51

```
cagggctccg tagaaccaca gaatcttggg cgcaaccctg ctcaagcacc caaatgtgca      60
```

-continued

```
tacgaacagg gtctccgtgt gacgtgtgtg aaaactacag tgtgatgagc atgactggca    120
gacagcttat cgattgggct cccctcaaaa tcggttatga gcattcaagc acaccgatgc    180
ccaggtcccg gctgcaggaa taagaccctc agggtcttg tgtgaagcct cggcatctgc    240
attgctcatg cttctgggga tcattctcct gaaaatggtg gctcctttct ccctgtggag    300
catctttcta agcagtgctc ttttcttccc ccaggacact ttacatccgg cacaggaagc    360
cttctgatgg agcacacctg gcccatgaaa agacaaggga agaaacggg gccaaaggtc    420 acagtcctct catcccatca tcctccttaa aatcatccta atttcatggg ccctgaagcc    480
agggctgttt ctttacacct agaggccttg gcgccgggcc tcaattccgc cctgttcctt    540
accgtctaag acatgttggg aaaatcccta gagccaggat cttcattcct gctaagccag    600
acagccggaa gacacaccca aattctgtcc ctcttacttc agggaacatg tccactttcg    660
gcagcattac aattttggca ccaaatgtgc taactgcaat tccaccatac aatgcgtaac    720
tggaaatgga ggcaacatct ccgatcctga acgatcgatg cgagaatcca ggatatgcac    780
ggcttatttt ggccttttcc cactgaaaca agggccagta ttaaaaatgg cacgctatcc    840
tctgtttcac tccctgcttt taaacgtctc cgatgtttct ccctgagaca gggcctcact    900
tccgtcagcc gggcttttct acggtataat tttccttgtt tgcttttgtc caaattagaa    960 cttttatt cacctctagg aaacgttgat ccattatcac atacgtatgg aaatattatc   1020
acacatgctg tgagatacgt tgttttatt ttcatcaatt ctttaataaa caaacggtta   1080
tagctgggat accttctgag ttctcaagtt ttttgtttcg tgttttctta aactgccgtc   1140
gcacgtccga aaccgctcac tatgcagtgt catgaccgtc tctctttttct ggcaaacata   1200 aatttgggga ttgtcatcaa ttagtctctc ggggattgca tgatttcccc aaaggctttc   1260
acagtctact tgtgcactg agtatctctt caaacttcag tgcatgtttc taccatttga   1320
tgctttatta tttggcaatc tagcttccac aagagcattt catgcaaaga cttgtcttct   1380
tctccactgg caggtaattt cacttggaca gagaatcaat aggctcaacg tggaaaggtt   1440
atcgctggaa ggtctgtttg attccacgga tctctccttt ctcattaggg aagaaaatac   1500
gctgtgctaa atactatact tcattgacta ttctcaggtc agaaagcgca ctttcgactt   1560
cttgtccttc cgtcgctgag aggatgatgg cagctgccaa aagtacatac ttggaggttc   1620
atcccagcac aaacacacac acacacgcgc cccccccaca cacacacaca cgaacacaat   1680
cacacacaca cactcacacg gtttcctacg taaagatttc ttccctgcca ttgctttacc   1740
taaaataagg caactgtgtg gccactgtcc caacccggtt acactcctat tatatgtgcc   1800
tatcatcctg aggagtaatt tgattcaggt gttctggaag tcatgctgtg ggctgtgtct   1860
gttgaatacc cagcgatgca aggggacaca ccctgtgact ccttcctgaa ttgagtgctg   1920
atatttgatt ggcttatcgc gcacctgatg agtgggtggg gtgttcgcgg ttggtggggg   1980
tgacttacag aagggctgat g                                             2001
```

<210> SEQ ID NO 52
<211> LENGTH: 1805
<212> TYPE: DNA
<213> ORGANISM: Homo sapiens
<220> FEATURE:
<221> NAME/KEY: misc_feature
<223> OTHER INFORMATION: promoter sequence for human DUB4.9

<400> SEQUENCE: 52

```
gcatctttct agtcagcgct cttttcttcg cccaggacac tttacatccg gcacacgaag     60
```

-continued

```
ccttctgatg gagcacacct ggcccatgaa aagccaaggg aaagaaacgg ggccaaaggt        120
cacagtcctc tcctcccatc atcctcctta aaatcatcct aatttcctgg ccctgaagcc        180
agggctgttt ctttacacct agaggccttg gcgccgggcc tcaattccgc cctgttcctt        240
accgtctaag acatgttggg aaaatcccta gagccaggat cttcattcct gctaagccag        300
acagccggaa gacacaccca aattctgtcc ctcttacttc agggaacatg tccactttcg        360
gcagcattac aattttggca ccaaatgtgc taactgcaat tccaccatac aatgcctaac        420
tggaaatgga ggcaacatct ccgatcctga acgatcgatg cgagaatcca ggatatgcac        480
ggcttatttt ggccttttcc cactgaaaca agggccagta ttaaaaatgg cacgctatcc        540
tctgtttcac tccctgcttt taaacgtctc cgatgttgct ccctgagaca ggacctcact        600
tccgtcagcc gggcttttct acggtataat tttccttgtt tgcttttgtc caaattagaa        660
cttttatttt catctctagg aaacgttgat ccattatcac atacgtatgg aaatattatc        720
acacatgctg tgagatacgt tgtttttatt ttcatcaatt ctttaataaa caaaaggtta        780
tagctgggat accttctgag ttctcaagtt ttttgtttcg tgttttctta aactgccgtc        840
gcacgtccga aaccgctcac tatgcagtgt catgaccgtc tctcttttct ggcaaacata        900
aatttgggga ttgtcatcaa ttagtctctc ggggattgca tgatttcccc aaaggctttc        960
acagtctact ttgtgcactg agtatctctt caaacttcag tgcatgtttc tacaatttga       1020
tgctttatta tttggcaatc tagcttccac aagagcattt catgcaaaga cttgtcttgt       1080
tctccactgg caggtacttt cactcggaca gagaatcaat aggctcaacg tggaaaggtt       1140
ttcgctggaa ggtctgtttg attccacgga tctctccttt ctcattaggg aagaaaatac       1200
actgtgctaa atactatact tcattgacta ttctcaggtc agaaagcgca ctttcgactt       1260
cttgtccttc cgtcgctgag aggatgatgg cagctgccaa agtacatac ttggaagttc       1320
atcccagcac aaacacacac acgcgcgccc ccccacacac acacaaaac acaatcacac        1380
acacacacaa tcacacggtt cctaggtaa agatttcttc cctgccatgg ctttacctaa        1440
aataaggcaa ctgtgtgacc actgtcccaa cccggttaca ctcctattat atgtgcctat       1500
catcctgagg agtaatttga ttcaggtgtt ctggaagtca tgctgtggga tgtgtctgtt       1560
gaattcccag cgatgccagg gggacacacc ctgtgactcc ttcctgaatt gagtgctgat       1620
atttgattgg cttatcgcgc acctgatgag tgggtggggt gttcgcggtt ggtggggtg        1680
acttacagaa gggctgatgc ggccagagag ctcgtcattt gaagactctc tcggaaggga       1740
tagcgtcttt ctgcaacctg cggtcccagc agaaaaacct tgtgatcctt gttccagtcg       1800
acatg                                                                  1805
```

<210> SEQ ID NO 53
<211> LENGTH: 2001
<212> TYPE: DNA
<213> ORGANISM: Homo sapiens
<220> FEATURE:
<221> NAME/KEY: misc_feature
<223> OTHER INFORMATION: promoter sequence for human DUB4.10

<400> SEQUENCE: 53

```
agcaagcttt ggaacagttg gtgaagcccg aagaactcaa tggagagaat gcctatcatt         60
gtggtgtttg tctccagagg gcgccggcct ccaagacgtt aactttacac acctctgcca        120
aggtcctcat ccttgtattg aagagattct ccgatgtcac aggcaacaag attgccaaga        180
atgtgcaata tcctgagtgc cttgacatgc agccatacat gtctcagcag aacacaggac        240
```

```
ctcttgtcta tgtcctctat gctgtgctgg tccacgctga gtggagttgt cacaacggac     300
attacttctc ttatgtcaaa gctcaagaag gccagtggta taaaatggat gatgccgagg     360
tcaccgccgc tagcatcact tctgtcctga gtcaacaggc ctacgtcctc ttttacatcc     420
agaagagtga atgggaaaga catagtgaga gtgtgtcaag aggcagggaa ccaagagccc     480
ttggcgcaga agacacagac aggcgagcaa cgcaaggaga gctcaagaga gaccaccccct    540 gcctccaggc ccccgagttg gacgagcact tggtggaaag agccactcag gaaagcacct     600
tagaccactg gaaattcctt caagagcaaa acaaaacgaa gcctgagttc aacgtcagaa     660
aagtcaaagg taccctgcct cccgacgtac ttgtgattca tcaatcaaaa tacaagtgtg     720
ggatgaagaa ccatcatcct gaacagcaaa gctccctgct aaacctctct tcgtcgaccc     780
cgacacatca ggagtccatg aacactggca cactcgcttc cctgcgaggg agggccagga     840
gatccaaagg gaagaacaaa cacagcaaga gggctctgct tgtgtgccag tgatctcagt     900
ggaagtaccg acccacacgt aggggtgcac acacacacgc acacacacag acacacacat     960
aactacaccc agaagcgcgc acgcaaaaac acacacaccc acacaaacac gaacaccgtc    1020
aatcctacat aaactaatga ggagcccaag tttctgtctc tacaacaggg acaactggat    1080
agtgatggct acatctcagg atgagcccgc atatgggaaa catcaagttt tggggtcgtg    1140
agtcttccga acctctggag ggactgtctg agtgtttgtg ttcatgatag gtgacattca    1200
gtgtgtattt ctgaatatga cctaccgacg tgtaggtttg cgtgtgaggt aattgcaggg    1260
gactcggttt cgtatttttct cttggggtgt gtttcattcg tcagttgttg gtcggcatga    1320
gaaggtgaaa tgtggctcat gtgggacatc cgtggatcat tctcgccacc ttgaatagtg    1380
gaaactggaa tgcatttgga agagaagaac ggtgctcttc tttcttcccc gggctcgccg    1440 ttttttacact ggttcctgaa tggacctcag gcgccctggg acttgtgctc ttgctggaac    1500
ccacataacg ccggaagcgg acagaccgac ttgcctgttt cacggtgccc gcttcccatg    1560
agtccaaacg gaaaattttc ccacgggcat gtaagtcatc tggaagtaag ctgtattgat    1620
aataaaggaa agcaaacaca ggagtgtgtg tattcaactg aaataaattc agaaagccct    1680
gaaatcaatc tcactgggtg tgtttaaaaa tggcatttgg ggaatttctg ggtcatttgt    1740
ccagctgcga aagctgcatc tctgaagcac agtccctgtc ccgcagtgag acttattgat    1800
ccgacgtggt gtttccgtgg aaatgattgt gggaaatggc cccttccttt tctctatttg    1860
ctgattagac ttcatggtcc ctttctcgtc aggtacagta atcaaagttg accagcccca    1920
gaggaaagct gcccagggca caactcaggg ctccgtagaa ccacagaatc ttgggcgcaa    1980
ccctgctcaa gcacccaaat g                                              2001
```

<210> SEQ ID NO 54
<211> LENGTH: 2002
<212> TYPE: DNA
<213> ORGANISM: Homo sapiens
<220> FEATURE:
<221> NAME/KEY: misc_feature
<223> OTHER INFORMATION: promoter sequence for human DUB4.11

<400> SEQUENCE: 54

```
cagcaagctt tggaacagtt ggtgaagccc gaagaactca atggagagaa tgcctatcat      60
tgtggtgttt gtctccagag ggcgccggcc tccaagacgt taactttaca caactctgcc     120 aaggtccctca tccttgtatt gaagagattc ccgatgtca caggcaacaa aattgccaag     180
aatgtgcaat atcctgagtg ccttgacatg cagccataca tgtctcagca gaacacagga     240
```

```
cctctcgtct atgtcctcta tgctgtgctg gtccacgctg ggtggagttg tcacaacgga    300
cattactcct cttatgtcaa agctcaagaa ggccagtggt ataaaatgga tgatgccgag    360
gtcaccgcct ctagcatcac ttctgtcctg agtcaacagg cctacgtcct cttttacatc    420
cagaagagtg aatgggaaag acacagtgag agtgtgtcaa gaggcaggga accaagagcc    480
cttggcgtag aagacacaga caggcgagca acgcaaggag agctcaagag agaccacccc    540
tgcctccagg cccccgagtt ggacgagcac ttggtggaaa gagccactca ggaaagcacc    600
ttagaccact ggaaattcct tcaagagcaa acaaaaacga agcctgagtt caacgtcaga    660
agagtcgaag gtacggtgcc tcccgacgta cttgtgattc atcaatcaaa atacaagtgt    720
cggatgaaga accatcatcc tgaacagcaa agctccctgc taaacctctc ttcgacgacc    780
ccgacagatc aggagtccat gaacactggc acactcgctt ccctacgagg gaggaccagg    840
agatccaaag ggaagaacaa acacagcaag agggctctgc ttgtgtgcca gtgatctcag    900
tggaagtacc gacccacacg tagggggtgca tacacacaca cacacacaca cacacacaca    960
taactacacc cagaagcgcg cacgcaaaca cacacacacc cacacaaaca cgaacaccgt   1020
caatcctaca taaactaatg aggagcccaa gtttctgtct gtacaacagg acaactgga   1080
tagagatggc tacatctcag gatgagcccg catatgggaa acatcaagtt ttggggtcgt   1140
gagtcttccg aacctctgga gggactgtct gagtgtttgt gttcatgata ggtgacattc   1200
agtgtgtatt tatgaatatg acctaccgac gtgtaggttt gcgtgtgagg taattgcagg   1260
ggactcggtt tcgtattttc tcttggggtg tgtttcattc gacagttgtt ggtcggcacg   1320
agaaggtgaa atttggctca tgtgggacat ccgtggatca ttctcgccac cttgaatagt   1380
ggaaactgga atgcatttgg aagagaagaa cggtgctctt ctttcttccc cgggctcgcc   1440
gtttttacac tagttcctga atggacctca ggcgccctgg gacttgtgct cttgctggaa   1500
cccacataac gccggaagca gacagaccga cttgcctgtt tcacggtgcc cgcttcccat   1560
gagtccaaac ggaaaatttt cccacgggca tgtaagtcat ctggaagtaa gctgtattga   1620
taataaagga aagcaaacac aggagtgtgt gtattcaaca gaaataaatt cagaaagccc   1680
tgaaatcaat ctcactgggt gtgtttaaaa atggcatttg gggaatttct gggtcatttg   1740
tccagctgcg aaagctgcat ctctgaagca cagtccctgt cccgcagtga gacttattta   1800
tccgacgtgg tgtttccgtg gaaatgattg tgggaaatgg ccccttcctt ttctctattt   1860
gctgactaga cttcatggtc cctttctcgt caggtacagt gatcaaagtt gaccaacccc   1920
agaggaaagc tgcccagggc acaactcagg gctccataga accacagaat cttgggagca   1980
accctgctca agcacccaaa tg                                            2002
```